US012642203B2

(12) United States Patent
Lindbo

(10) Patent No.: US 12,642,203 B2
(45) Date of Patent: Jun. 2, 2026

(54) TOMATO PLANTS RESISTANT TO ToBRFV, TMV, ToMV AND ToMMV AND CORRESPONDING RESISTANCE GENES

(71) Applicant: VILMORIN & CIE, Paris (FR)

(72) Inventor: John Lindbo, Davis, CA (US)

(73) Assignee: VILMORIN & CIE, Paris (FR)

( * ) Notice: Subject to any disclaimer, the term of this patent is extended or adjusted under 35 U.S.C. 154(b) by 255 days.

(21) Appl. No.: 18/255,916

(22) PCT Filed: Dec. 3, 2021

(86) PCT No.: PCT/EP2021/084289
§ 371 (c)(1),
(2) Date: Jun. 5, 2023

(87) PCT Pub. No.: WO2022/117884
PCT Pub. Date: Jun. 9, 2022

(65) Prior Publication Data
US 2024/0049668 A1 Feb. 15, 2024

(30) Foreign Application Priority Data

Dec. 3, 2020 (EP) ..................................... 20306496
Aug. 2, 2021 (EP) ..................................... 21306078

(51) Int. Cl.
C07K 14/415 (2006.01)
A01H 1/00 (2006.01)
C12N 15/82 (2006.01)

(52) U.S. Cl.
CPC ........... *A01H 1/126* (2021.01); *C07K 14/415* (2013.01); *C12N 15/8283* (2013.01)

(58) Field of Classification Search
None
See application file for complete search history.

(56) References Cited

U.S. PATENT DOCUMENTS

2021/0238627 A1* 8/2021 Ykema ................... A01H 6/825

FOREIGN PATENT DOCUMENTS

| EP | 3 409 106 A1 | 12/2018 |
|----|--------------|---------|
| WO | 2018/219941 A1 | 12/2018 |
| WO | 2019/110130 A1 | 6/2019 |
| WO | 2020/148021 A1 | 7/2020 |

OTHER PUBLICATIONS

Kobayashi et al., Identification of an amino acid residue required for differential recognition of a viral movement protein by the Tomato mosaic virus resistance gene Tm-22, 2011, Journal of Plant Physiology, 168:1142-1145 (Year: 2011).*

Matsushima et al., Leucine-Rich Repeat (LRR) Domains Containing Intervening Motifs in Plants, 2012, Biomolecules, 2:288-311 (Year: 2012).*
Structure and domain analysis of Tomato TM-2-2 protein (Accession No. Q71BG9), UniProt (Year: 2025).*
Banerjee et al., Compensatory Mutations Occur Within the Electrostatic Interaction Range of Deleterious Mutations in Protein Structure, 2015, J. Mol. Evol., 80:10-12 (Year: 2015).*
Melero et al., Host developmental stages shape the evolution of a plant RNA virus, 2023, Phil. Trans. R. Soc. B., 378:20220005 (Year: 2023).*
Davino et al., Tomato Brown Rugose Fruit Virus: Seed Transmission Rate and Efficacy of Different Seed Disinfection Treatments, 2020, Plants, 9:1615 (Year: 2020).*
Ullah et al., Characterization of tomato mosaic virus and search for its resistance in *Solanum* species, 2019, Eur. J. Plant Pathol., 155:1195-1209 (Year: 2019).*
Maayanet al., Using genomic analysis to identify tomato Tm-2 resistance-breaking mutations and their underlying evolutionary path in a new and emerging tobamovirus, 2018, Archives of Virology, 163: 1863-1875 (Year: 2018).*
Wang et al., Genome of Solanum pimpinellifolium provides insights into structural variants during tomato breeding, 2020, Nat. Commun., 11:5817 (Year: 2020).*
Oladokun et al., Tomato brown rugose fruit disease: current distribution, knowledge and future prospects, 2019, Plant Pathology, 68:1579-1586 (Year: 2019).*
Lee et al., Screening a cDNA Library for Protein-Protein Interactions Directly in Planta, 2012, The Plant Cell, 24: 1746-1759 (Year: 2012).*
Jaiswal et al., Evaluation of Tomato Germplasm against Tomato Brown Rugose Fruit Virus and Identification of Resistance in Solanum pimpinellifolium, 2024, Plants, 13:581 (Year: 2024).*
Lanfermeijer, F. C., Warmink, J., and Hille, J. 2005. "The products of the broken Tm-2 and the durable Tm-2(2) resistance genes from tomato differ in four amino acids." J Exp Bot 56:2925-2933.
Luria N. et al. 2017. "A New Israeli Tobamovirus Isolate Infects Tomato Plants Harboring Tm-22 Resistance Genes." PLoS One.; 12(1): e0170429.
Le Cong et al. 2013. "Multiplex Genome Engineering Using CRIPSR/Cas Systems." Science 339(6121):819-823.
Weber, H., Schultze, S., and Pfitzner, A. J. 1993. Two Amino Acid Substitutions in the Tomato Mosaic Virus 30-Kilodalton Movement Protein Confer the Ability to Overcome the Tm-2(2) Resistance Gene in the Tomato. J Virol 67:6432-6438.

(Continued)

*Primary Examiner* — Bratislav Stankovic
*Assistant Examiner* — Jay Chatterjee
(74) *Attorney, Agent, or Firm* — Oliff PLC

(57) ABSTRACT
A variants of the TM-2-2 protein, conferring recognition of the Movement Protein (MP) of the Tomato Brown Rugose Fruit Virus (ToBRFV), and wherein said variant comprises a tyrosine (Y), a phenylalanine (F) or a tryptophan (W) at the position corresponding to tyrosine 767 of the TM-2-2 protein and at least one of the following mutations: C848R, N822C, N822F, N822M, N822Y, N822W, N825H, N825K and N825T with respect to the TM-2-2 protein, potentially in combination with a F655L mutation. The present invention also relates to genetic sequences encoding such a variant protein, preferably to a mutated Tm-2-2 gene, and to plants, especially *Solanum lycopersicum* plants comprising in their genome the mutated gene conferring resistance to ToBRFV. The invention is also directed to parts of these plants, as well as progeny, and to the use of these sequences for providing ToBRFV resistance.

19 Claims, 6 Drawing Sheets

Figure 1:
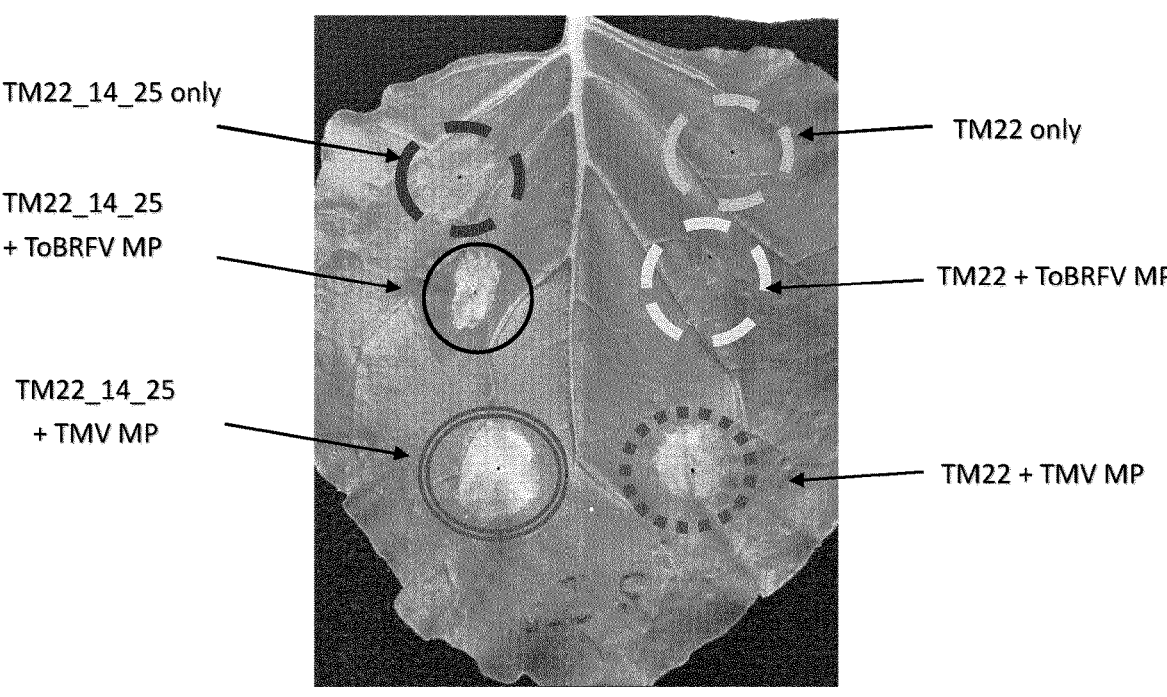

Specification includes a Sequence Listing.

(56) References Cited

OTHER PUBLICATIONS

Kobayashi, M., Yamamoto-Katou, A., Katou, S., Hirai, K., Meshi, T., Ohashi, Y., and Mitsuhara, I. 2011. "Identification of an amino acid residue required for differential recognition of a viral movement protein by the Tomato mosaic virus resistance gene Tm-2(2)." J Plant Physiol 168:1142-1145.

Nagai, A., Duarte M. L.L., Chaves A. LR., Peres L. EP. , dos Santos D. Y.A.C. 2019. "Tomato mottle mosaic virus in Brazil and its relationship with Tm-22 gene." Eur J Plant Pathol 155, 353-359.

Sui, X. et al., 2017. "Molecular and Biological Characterization of Tomato mottle mosaic virus and Development of RT-PCR Detection." Plant Disease 101, 704-711.

Calder, V. L., and Palukaitis, P. 1992. "Nucleotide sequence analysis of the movement genes of resistance breaking strains of tomato mosaic virus." J Gen Virol 73 ( Pt 1):165-168.

Meshi, T., Motoyoshi, F., Maeda, T., Yoshiwoka, S., Watanabe, H., and Okada, Y. 1989. "Mutations in the Tobacco Mosaic Virus 30-kD Protein Gene Overcome Tm-2 Resistance in Tomato." Plant Cell 1:515-522.

Weber, H., and Pfitzner, A. J. 1998. "Tm-2(2) Resistance in Tomato Requires Recognition of the Carboxy Terminus of the Movement Protein of Tomato Mosaic Virus." Mol Plant Microbe Interact 11:498-503.

Lanfermeijer, F. C., Dijkhuis, J., Sturre, M. J., de Haan, P., and Hille, J. 2003. "Cloning and characterization of the durable tomato mosaic virus resistance gene Tm-2(2) from Lycopersicon esculentum." Plant Mol Biol 52:1037-1049.

Baggs, E., Dagdas, G., and Krasileva, K. V. 2017. "NLR diversity, helpers and integrated domains: making sense of the NLR IDentity." Curr Opin Plant Biol 38:59-67.

Kapos, P., Devendrakumar, K. T., and Li, X. 2019. "Plant NLRs: From discovery to application." Plant Sci 279:3-18.

Wang, J., Chen, T., Han, M., Qian, L., Li, J., Wu, M., Han, T., Cao, J., Nagalakshmi, U., Rathjen, J. P., Hong, Y., and Liu, Y. 2020. "Plant NLR immune receptor Tm-22 activation requires NB-ARC domain-mediated self-association of CC domain." PLoS Pathog 16:e1008475.

Mondragon-Palomino, M., Meyers, B. C., Michelmore, R. W., and Gaut, B. S. 2002. "Patterns of Positive Selection in the Complete NBS-LRR Gene Family of *Arabidopsis thaliana*." Genome Res 12:1305-1315.

Slootweg, E., Koropacka, K., Roosien, J., Dees, R., Overmars, H., Lankhorst, R. K., van Schaik, C., Pomp, R., Bouwman, L., Helder, J., Schots, A., Bakker, J., Smant, G., and Goverse, A. 2017. "Sequence Exchange between Homologous NB-LRR Genes Converts Virus Resistance into Nematode Resistance, and Vice Versa." Plant Physiol 175:498-510.

Ishibashi et al, 2007. "An inhibitor of viral RNA replication is encoded by a plant resistance gene." PNAS 104 (34) 13833-13838.

Lanfermeirjer, F., Jiang,G, Ferwerda, MA, Kijkhuis,J, de Haan, P, Yang, R, Hille, J. 2004. "The durable resistance gene Tm-22 from tomato confers resistance against ToMV in tobacco and preserves its viral specificity." Plant Science 167:687-692.

Ma, L., Lukasik, E, Gawehns F, Takken F LW. 2012. "The Use of Agroinfiltration for Transient Expression of Plant Resistance and Fungal Effector Proteins in Nicotiana benthamiana Leaves." Methods Mol Biol 835:61-74.

Weber, H., Ohnesorge, S., Silber, M. V., and Pfitzner, A. J. 2004. "The Tomato mosaic virus 30 kDa movement protein Interacts differentially with the resistance genes Tm-2 and Tm-2(2)." Arch Virol 149:1499-1514.

Mar. 14, 2022 International Search Report issued in International Patent Application No. PCT/EP2021/084289.

Mar. 14, 2022 Written Opinion of the International Searching Authority issued in International Patent Application No. PCT/EP2021/084289.

* cited by examiner

TM22_14_25 only

TM22_14_25
+ ToBRFV MP

TM22_14_25
+ TMV MP

TM22 only

TM22 + ToBRFV MP

TM22 + TMV MP

50 DO plant Leaf 6 from top (younger)

43 DO plant Leaf 5 from top (younger)

TM22 + TMV MP

TM22 + ToBRFV MP

TM22_14_25 + ToBRFV MP

```
TM22_PROTEIN    MAEILLTSVINKSVEIAGNLLIQEGKRLYWLKEDIDWLQREMRHIRSYVDNAKAKEAGGD    60
TM2_1425        MAEILLTSVINKSVEIAGNLLIQEGKRLYWLKEDIDWLQREMRHIRSYVDNAKAKEAGGD    60
TM2_467         MAEILLTSVINKSVEIAGNLLIQEGKRLYWLKEDIDWLQREMRHIRSYVDNAKAKEAGGD    60
                ************************************************************

TM22_PROTEIN    SRVKNLLKDIQELAGDVEDLLDDFLPKIQQSNKFNYCLKRSSFADEFAMEIEKIKRRVVD   120
TM2_1425        SRVKNLLKDIQELAGDVEDLLDDFLPKIQQSNKFNYCLKRSSFADEFAMEIEKIKRRVVD   120
TM2_467         SRVKNLLKDIQELAGDVEDLLDDFLPKIQQSNKFNYCLKRSSFADEFAMEIEKIKRRVVD   120
                ************************************************************

TM22_PROTEIN    IDRIRKTYNIIDTDNNNDDCVLLDRRRLFLHADETEIIGLDDDFNMLQAKLLNQDLHYGV   180
TM2_1425        IDRIRKTYNIIDTDNNNDDCVLLDRRRLFLHADETEIIGLDDDFNMLQAKLLNQDLHYGV   180
TM2_467         IDRIRKTYNIIDTDNNNDDCVLLDRRRLFLHADETEIIGLDDDFNMLQAKLLNQDLHYGV   180
                ************************************************************

TM22_PROTEIN    VSIVGMPGLGKTTLAKKLYRLIRDQFECSGLVYVSQQPRASEILLDIAKQIGLTEQKMKE   240
TM2_1425        VSIVGMPGLGKTTLAKKLYRLIRDQFECSGLVYVSQQPRASEILLDIAKQIGLTEQKMKE   240
TM2_467         VSIVGMPGLGKTTLAKKLYRLIRDQFECSGLVYVSQQPRASEILLDIAKQIGLTEQKMKE   240
                ************************************************************

TM22_PROTEIN    NLEDNLRSLLKIKRYVILLDDIWDVEIWDDLKLVLPECDSKVGSRMIITSRNSNVGRYIG   300
TM2_1425        NLEDNLRSLLKIKRYVILLDDIWDVEIWDDLKLVLPECDSKVGSRMIITSRNSNVGRYIG   300
TM2_467         NLEDNLRSLLKIKRYVILLDDIWDVEIWDDLKLVLPECDSKVGSRMIITSRNSNVGRYIG   300
                ************************************************************

TM22_PROTEIN    GESSLHALQPLESEKSFELFTKKIFNFDDNNSWANASPDLVNIGRNIVGRCGGIPLAIVV   360
TM2_1425        GESSLHALQPLESEKSFELFTKKIFNFDDNNSWANASPDLVNIGRNIVGRCGGIPLAIVV   360
TM2_467         GESSLHALQPLESEKSFELFTKKIFNFDDNNSWANASPDLVNIGRNIVGRCGGIPLAIVV   360
                ************************************************************

TM22_PROTEIN    TAGMLRARERTEHAWNRVLESMGHKVQDGCAKVLALSYNDLPIASRPCFLYFGLYPEDHE   420
TM2_1425        TAGMLRARERTEHAWNRVLESMGHKVQDGCAKVLALSYNDLPIASRPCFLYFGLYPEDHE   420
TM2_467         TAGMLRARERTEHAWNRVLESMGHKVQDGCAKVLALSYNDLPIASRPCFLYFGLYPEDHE   420
                ************************************************************

TM22_PROTEIN    IRAFDLINMWIAEKFIVVNSGNRREAEDLAEDVLNDLVSRNLIQLAKRTYNGRISSCRIH   480
TM2_1425        IRAFDLINMWIAEKFIVVNSGNRREAEDLAEDVLNDLVSRNLIQLAKRTYNGRISSCRIH   480
TM2_467         IRAFDLINMWIAEKFIVVNSGNRREAEDLAEDVLNDLVSRNLIQLAKRTYNGRISSCRIH   480
                ************************************************************

TM22_PROTEIN    DLLHSLCVDLAKESNFFHTAHDAFGDPGNVARLRRITFYSDNVMIEFFRSNPKLEKLRVL   540
TM2_1425        DLLHSLCVDLAKESNFFHTAHDAFGDPGNVARLRRITFYSDNVMIEFFRSNPKLEKLRVL   540
TM2_467         DLLHSLCVDLAKESNFFHTAHDAFGDPGNVARLRRITFYSDNVMIEFFRSNPKLEKLRVL   540
                ************************************************************

TM22_PROTEIN    FCFAKDPSIFSHMAYFDFKLLHTLVVVMSQSFQAYVTIPSKFGNMTCLRYLRLEGNICGK   600
TM2_1425        FCFAKDPSIFSHMAYFDFKLLHTLVVVMSQSFQAYVTIPSKFGNMTCLRYLRLEGNICGK   600
TM2_467         FCFAKDPSIFSHMAYFDFKLLHTLVVVMSQSFQAYVTIPSKFGNMTCLRYLRLEGNICGK   600
                ************************************************************

TM22_PROTEIN    LPNSIVKLTRLETIDIDRRSLIQPPSGVWESKHLRHLCYRDYGQACNSCFSISSFYPNIY   660
TM2_1425        LPNSIVKLTRLETIDIDRRSLIQPPSGVWESKHLRHLCYRDYGQACNSCFSISSLYPNIY   660
TM2_467         LPNSIVKLTRLETIDIDRRSLIQPPSGVWESKHLRHLCYRDYGQACNSCFSISSFYPNIY   660
                ******************************************************:*****

TM22_PROTEIN    SLHPNNLQTLMWIPDKFFEPRLLHRLINLRKLGILGVSNSTVKMLSIFSPVLKALEVLKL   720
TM2_1425        SLHPNNLQTLMWIPDKFFEPRLLHRLINLRKLGILGVSNSTVKMLSIFSPVLKALEVLKL   720
TM2_467         SLHPNNLQTLMWIPDKFFEPRLLHRLINLRKLGILGVSNSTVKMLSIFSPVLKALEVLKL   720
                ************************************************************

TM22_PROTEIN    SFSSDPSEQIKLSSYPHIAKLHLNVNRTMALNSQSFPPNLIKLTLAYFSVDRYILAVLKT   780
TM2_1425        SFSSDPSEQIKLSSYPHIAKLHLNVNRTMALNSQSFPPNLIKLTLAYFSVDRYILAVLKT   780
TM2_467         SFSSDPSEQIKLSSYPHIAKLHLNVNRTMALNSQSFPPNLIKLTLAYFSVDRYILAVLKT   780
                ************************************************************

TM22_PROTEIN    FPKLRKLKMFICKYNEEKMDLSGEANGYSFPQLEVLHIHSPNGLSEVTCTDDVSMPKLKK   840
TM2_1425        FPKLRKLKMFICKYNEEKMDLSGEANGYSFPQLEVLHIHSPNGLSEVTCTDDVSMPKLKK   840
TM2_467         FPKLRKLKMFICKYNEEKMDLSGEANGYSFPQLEVLHIHSPNGLSEVTCTDDVSMPKLKK   840
                ************************************************************

TM22_PROTEIN    LLLTGFHCRISLSERLKKLSK-      861
TM2_1425        LLLTGFHRRISLSERLKKLSK*      861
TM2_467         LLLTGFHRRISLSERLKKLSK*      861
                ******* ************
```

FIG. 4

SEQUENCE LISTING

<160> NUMBER OF SEQ ID NOS: 46

<210> SEQ ID NO 1
<211> LENGTH: 2820
<212> TYPE: DNA
<213> ORGANISM: Lycopersicon esculentum

<400> SEQUENCE: 1

```
atagaaaaaa gaaatttctc ctttttcatt aatgtgcagc tgccccacgt tgtcactccc      60
cttcttcttt ataatttcct tcttgacaat tattaggaga cttggccgag gactccatct     120
accactaaaa agctaaagcc atcagtatac tcattttttg gtagctactg aaaaagagag     180
aaaaaaaaat ggctgaaatt cttcttacat cagtaatcaa taaatctgta gaaatagctg     240
gaaatttact gattcaagaa ggaaagcgtt tatattggtt gaaagaggat atcgattggc     300
```

```
tccagagaga aatgagacac attcgatctt atgttgacaa cgcaaaggcc aaggaagctg    360
gaggtgattc aagggtcaaa aacttattga aagatattca agaattggca ggtgatgtgg    420
aggatctctt agatgacttc cttccaaaaa ttcaacgatc caataagttc aattattgcc    480
ttaagacgag ttctttttgcg gatgagtttg ctatggagat tgagaagata aagagaaggg    540
ttgttgacat tgaccgaata aggaaaactt acaacatcat agatacagat aacaataatg    600
atgattgtgt tttgctggat cggagaagat tattcctaca tgctgatgaa acagagatca    660
tcggtttgga tgatgacttc aatatgctac aagccaaatt actcaatcaa gatttgcatt    720
atggagttgt ttccatagtt ggcatgcccg gtctggggaa aacaactctt gccaagaaac    780
tttataggct cattcgtgat caatttgagt gttctggact ggtctacgtt tcacaacagc    840
caagagcggt tgaaatctta cttgacattg ccaaacaaat tggactgacg gaacagaaaa    900
ttaaggaaaa tttggaggac aacctgcgat cactcttgaa aataaaaagg tatgttatcc    960
tcctagatga catttgggat gttgaaattt gggatgatct gaaacttgtc cttcctgaat   1020
gtgactcaaa agtcggcagt agaatgataa tcacgtctcg aaatagtaat gtaggcagat   1080
acataggagg ggaatcctcc ctccatgcat tgcaacccct agaatccgag aaaagctttg   1140
aactctttac caagaaaatc tttaattttg atgataataa tagttgggcc aatgcttcac   1200
ctgacttggt gaatattggt agaaatatag ctgggagatg tggaggtata ccgctagcca   1260
tagtggtgac tgcaggcatg ttaagggcaa gagaaagaac agaacatgcg tggaacagag   1320
tacttgagag tatgggccat aaagttcaag atggatgtgc taaggtattg gctctcagtt   1380
acaatgattt accgattgcc tcaaggccat gtttcttgta ctttagcctt tacccccgagg   1440 accatgaaat tcgtgctttt gatttgataa atatgtggat tgctgagaag tttattgtag   1500
taaatagtgg taataggcga gaggctgagg atttggcgga ggacgtccta aatgatttgg   1560
tttctagaaa cttgattcaa cttgccaaaa ggacatataa tggaagaatt tcaagttgtc   1620
gcatacatga cttgttacat agtttgtgtg tggacttggc taaggaaagt aacttctttc   1680
acaccgcgca tgatgtattt ggtgatcccg gcaatgtcgc taggcttcga aggattacat   1740
tctactctga caatgtcatg attgagttct tcggttctaa tcctaagctt gagaagcttc   1800
gtgtactttt ctgtttcaca aaagacccctt ccatattttc tcatatggct tgttttgact   1860
tcaaattgtt gcacacattg gttgtagtca tgtctcaaag ttttcaagca tatgtcacta   1920
tcccaagcaa atttgggaac atgacttgct tacgctatct gaaattggag gggaatattt   1980
gtggaaaact gccaaatagt attgtcaagc tcacacgtct agagaccata gacattgatc   2040
gacgtagcct cattcaactt ccttctggtg tttgggagtc taaacatttg agacatcttt   2100
gttatagaga ttatggacaa gcatgtaaca gttgcttttc tataagctca tttttacccaa   2160 acatttactc attgcatcct aacaatctac aaaccttgat gtggatacct gataaatttt   2220
ttgaaccgag gttgttgcac cgattgatca atttaagaaa actgggtata ctgggagtgt   2280
ccaattcaac cgttaagata ttatcaacat gtcgccctgt gccaaaggcg ctaaaggttc   2340
tgaagctcag gttttttcagt gatccgagtg agcaaataaa cttgtcatcc tatccaaaaa   2400
ttgttaagtt gcatttgaat gttgacagaa caatagcctt gaactctgaa gcattccctc   2460
caaatattat caagcttact cttgtctgct ttatggtaga cagttgtcta ctggcagtgc   2520
ttaagacatt acccaaatta agaaaactta aaatggtcat ctgcaagtat aatgaagaaa   2580
agatggctct ctcgggcgag gcaaatggtt atagctttcc gcaacttgaa gttttgcata   2640
```

-continued

```
ttcatagccc gaatgggttg tctgaagtaa catgcacgga tgatgtcagt atgcccaaat    2700
tgaaaaagct gttacttaca ggattccatt gcggaatcag tttatcggaa cggcttaaaa    2760
agctgagtaa atgaacatct caacaggtca gtttgctagt ataactattt acgtacaggg    2820

<210> SEQ ID NO 2
<211> LENGTH: 2819
<212> TYPE: DNA
<213> ORGANISM: Lycopersicon esculentum

<400> SEQUENCE: 2
atagaaaaaa gaaatttctc cttttttcatt aatgtgcagc tgccccacgt tgtcactccc     60
cttcttcttt atcatttcct tcttgacatt attaggagac ttggccgtgg actccatcta    120
ccactaaaaa gctaaagcca tcagtatact cattttttgg tagctactga aaaagagaga    180
aaaaaaaatg gctgaaattc ttcttacatc agtaatcaat aaatctgtag aaatagctgg    240
aaatttactg attcaagaag gaaagcgttt atattggttg aaagaggata tcgattggct    300
ccagagagaa atgagacaca ttcgatctta tgttgacaac gcaaaggcca aggaagctgg    360
aggtgattca agggtcaaaa acttattgaa agatattcaa gaattggcag gtgatgtgga    420
ggatctctta gatgacttcc ttccaaaaat tcaacaatcc aataagttca attattgcct    480
taagaggagt tcttttgcgg atgagtttgc tatggagatt gagaagataa agagaagggt    540
tgttgacatt gaccgaataa ggaaaactta caacatcata gatacagata acaataatga    600
tgattgtgtt ctgctggatc ggagaagatt attcctacat gctgatgaaa cagagatcat    660
cggtttggat gatgacttca atatgctaca agccaaatta cttaatcaag atttgcatta    720
tggagttgtt tccatagttg gcatgcccgg tctgggaaa acaactcttg ccaagaaact     780
ttataggctc attcgtgatc aatttgagtg ttctggactg gtctacgttt cacaacagcc    840
aagagcgagt gaaatcttac ttgacattgc caaacaaatt ggactgacgg aacagaaaat    900
gaaggaaaat ttggaggaca acctgcgatc actcttgaaa ataaaaaggt atgttttcct    960
cctagatgac atttgggatg tggaaatttg ggatgatctg aaacttgtcc ttcctgaatg   1020
tgattcaaaa gtcggcagta gaattataat cacgtctcga aatagtaatg taggcagata   1080
cataggaggg gaatcctccc tccatgcatt gcaacccctt gaatccgaga aaagctttga   1140
actctttacc aagaaaatct ttaattttga tgataataat agttgggcca atgcttcacc   1200
tgacttggtg aatattggta gaaatatagt tgggagatgt ggaggtatac cgctagccat   1260
agtggtgact gcaggcatgt taagggcaag agaaagaaca gaacatgcgt ggaacagagt   1320
acttgagagt atgggccata aagttcaaga tggatgtgct aaggtattgg ctctcagtta   1380
caatgattta cctattgcct caaggccatg tttcttgtac tttggccttt accccgagga   1440
ccatgaaatt cgtgctttg atttgataaa tatgtggatt gctgagaagt ttatagtagt   1500
aaatagtggt aataggcgag aggctgagga tttggcggag gacgtcctaa atgatttggt   1560
ttctagaaac ttgattcaac ttgccaaaag gacatataat ggaagaattt caagttgtcg   1620
catacatgac ttgttacata gtttgtgtgt ggacttggct aaggaaagta acttctttca   1680
caccgcgcat gatgcatttg gtgatcccgg caatgttgct aggctccgaa ggattacatt   1740
ctactctgac aatgtcatga ttgagttctt ccgttcaaat cctaagcttg agaagcttcg   1800 tgtactttc tgtttcgcaa aagacccttc catattttct catatggctt attttgactt   1860
caaattgttg cacacattgg ttgtagtcat gtctcaaagt tttcaagcat atgtcactat   1920
cccaagcaaa tttgggaaca tgacttgctt acgctatctg agattggagg ggaatatttg   1980
```

```
tggaaaactg ccaaatagta ttgtcaagct cacacgtcta gagaccatag acattgatcg      2040
acgtagcctc attcaacctc cttctggtgt ttgggagtct aaacatttga gacatctttg      2100
ttatagagat tatggacaag catgtaacag ttgctttct ataagctcat tttacccaaa       2160
tatttactca ttgcatccta acaatctaca aaccttgatg tggatacctg ataaattttt      2220
tgaaccgagg ttgttgcacc gattgatcaa tttaagaaaa ctgggtatac tgggagtgtc      2280
caattctacc gttaagatgt tatcaatatt tagccctgtg ctcaaggcgc tggaggttct      2340
gaagctcagt ttttccagtg acccgagtga acaaataaag ttgtcatcgt atccacatat      2400
tgctaagttg catttgaatg ttaacagaac aatggccttg aactctcaat catttcctcc      2460
aaatctcatc aagcttactc tagccaactt tacggtagac cgttatatac tggcagtact      2520
taagacattt cccaaattaa gaaaacttaa aatgttcatc tgcaagtata atgaagaaaa      2580
gatggatctc tcgggcgagg caaatggtta tagctttccg caacttgaag ttttgcatat      2640
tcatagcccg aatgggttgt ctgaagtaac gtgcacggat gatgtcagta tgcccaaatt      2700
gaaaaagctg ttacttacag gattccattg ccgaatcagt ttatcggaac ggcttaaaaa      2760
gctgagtaaa tgaacatctc aacaggtcag tttgctagta taactattta cgtacaggg      2819
```

```
<210> SEQ ID NO 3
<211> LENGTH: 2586
<212> TYPE: DNA
<213> ORGANISM: Lycopersicon esculentum

<400> SEQUENCE: 3
```

```
atggctgaaa ttcttcttac atcagtaatc aataaatctg tagaaatagc tggaaattta        60
ctgattcaag aaggaaagcg tttatattgg ttgaaagagg atatcgattg gctccagaga       120
gaaatgagac acattcgatc ttatgttgac aacgcaaagg ccaaggaagc tggaggtgat       180
tcaagggtca aaacttatt gaaagatatt caagaattgg caggtgatgt ggaggatctc        240
ttagatgact tccttccaaa aattcaacaa tccaataagt tcaattattg ccttaagagg       300
agttcttttg cagatgagtt tgctatggag attgagaaga taaagagaag ggttgttgac       360
attgaccgaa taaggaaaac ttacaacatc atagatacag ataacaataa tgatgattgt       420
gttctgctgg atcggagaag attattccta catgctgatg aaacagagat catcggtttg       480
gatgatgact tcaatatgct acaagccaaa ttacttaatc aagatttgca ttatggagtt       540
gtttccatag ttggcatgcc cggtctgggg aaaacaactc ttgccaagaa actttatagg       600
ctcattcgtg atcaatttga gtgttctgga ctggtctacg tttcacaaca gccaagagcg       660
agtgaaatct tacttgacat tgccaaacaa attggactga cggaacagaa aatgaaggaa       720
aatttggagg acaacctgcg atcactcttg aaaataaaaa ggtatgttat cctcctagat       780
gacatttggg atgtggaaat ttgggatgat ctgaaacttg tccttcctga atgtgattca       840
aaagtcggca gtagaatgat aatcacgtct cgaaatagta atgtaggcag atacatagga       900
ggggaatcct ccctccatgc attgcaaccc ctagaatccg agaaaagctt tgaactcttt       960
accaagaaaa tctttaattt tgatgataat aatagttggg ccaatgcttc acctgacttg      1020
gtgaatattg gtagaaatat agttgggaga tgtggaggta taccgctagc catagtggtg      1080
actgcaggca tgttaagggc aagagaaaga acagaacatg cgtggaacag agtacttgag      1140
agtatgggcc ataaagttca agatggatgt gctaaggtat tggctctcag ttacaatgat      1200
ttacctattg cctcaaggcc atgtttcttg tactttggcc tttaccccga ggaccatgaa      1260
```

```
attcgtgctt ttgatttgat aaatatgtgg attgctgaga agtttatagt agtaaatagt    1320
ggtaataggc gagaggctga ggatttggcg gaggacgtcc taaatgattt ggtttctaga    1380
aacttgattc aacttgccaa aaggacatat aatggaagaa tttcaagttg tcgcatacat    1440
gacttgttac atagtttgtg tgtggacttg gctaaggaaa gtaacttctt tcacaccgcg    1500
catgatgcat ttggtgatcc cggcaatgtt gctaggctcc gaaggattac attctactct    1560
gacaatgtca tgattgagtt cttccgttca aatcctaagc ttgagaagct tcgtgtactt    1620
ttctgtttcg caaaagaccc ttccatattt tctcatatgg cttattttga cttcaaattg    1680
ttgcacacat tggttgtagt catgtctcaa agttttcaag catatgtcac tatcccaagc    1740
aaatttggga acatgacttg cttacgctat ctgagattgg aggggaatat ttgtggaaaa    1800
ctgccaaata gtattgtcaa gctcacacgt ctagagacca tagacattga tcgacgtagc    1860
ctcattcaac ctccttctgg tgtttgggag tctaaacatt tgagacatct ttgttataga    1920
gattatggac aagcatgtaa cagttgcttt tctataagct cattttaccc aaatatttac    1980
tcattgcatc ctaacaatct acaaaccttg atgtggatac ctgataaatt ttttgaaccg    2040
aggttgttgc accgattgat caatttaaga aaactgggta tactgggagt gtccaattct    2100
accgttaaga tgttatcaat atttagccct gtgcttaagg cgctggaggt tctgaagctc    2160
agtttttcca gtgacccgag tgaacaaata aagttgtcat cgtatccaca tattgctaag    2220
ttgcatttga atgttaacag aacaatggcc ttgaactctc aatcatttcc tccaaatctc    2280
atcaagctta ctctagccta ctttagtgta gaccgttata tactggcagt acttaagaca    2340
tttcccaaat taagaaaact taaaatgttc atctgcaagt ataatgaaga aaagatggat    2400
ctctcgggcg aggcaaatgg ttatagcttt ccgcaacttg aagttttgca tattcatagc    2460
ccgaatgggt tgtctgaagt aacgtgcacg gatgatgtca gtatgcccaa attgaaaaag    2520
ctgttactta caggattcca ttgccgaatc agtttatcgg aacggcttaa aaagctgagt    2580
aaatga                                                                2586

<210> SEQ ID NO 4
<211> LENGTH: 2586
<212> TYPE: DNA
<213> ORGANISM: artificial
<220> FEATURE:
<223> OTHER INFORMATION: mutant

<400> SEQUENCE: 4
atggctgaaa ttcttcttac atcagtaatc aataaatctg tagaaatagc tggaaattta     60
ctgattcaag aaggaaagcg tttatattgg ttgaaagagg atatcgattg gctccagaga    120
gaaatgagac acattcgatc ttatgttgac aacgcaaagg ccaaggaagc tggaggtgat    180
tcaagggtca aaaacttatt gaaagatatt caagaattgg caggtgatgt ggaggatctc    240
ttagatgact tccttccaaa aattcaacaa tccaataagt tcaattattg ccttaagagg    300
agttcttttg cagatgagtt tgctatggag attgagaaga taaagagaag ggttgttgac    360
attgaccgaa taaggaaaac ttacaacatc atagatacag ataacaataa tgatgattgt    420
gttctgctgg atcggagaag attattccta catgctgatg aaacagagat catcggtttg    480
gatgatgact tcaatatgct acaagccaaa ttacttaatc aagatttgca ttatggagtt    540
gtttccatag ttggcatgcc cggtctgggg aaaacaactc ttgccaagaa actttatagg    600
ctcattcgtg atcaatttga gtgttctgga ctggtctacg tttcacaaca gccaagagcg    660
agtgaaatct tacttgacat tgccaaacaa attggactga cggaacagaa aatgaaggaa    720
```

```
aatttggagg acaacctgcg atcactcttg aaaataaaaa ggtatgttat cctcctagat      780
gacatttggg atgtggaaat ttgggatgat ctgaaacttg tccttcctga atgtgattca      840
aaagtcggca gtagaatgat aatcacgtct cgaaatagta atgtaggcag atacatagga      900
ggggaatcct ccctccatgc attgcaaccc ctagaatccg agaaaagctt tgaactcttt      960
accaagaaaa tctttaattt tgatgataat aatagttggg ccaatgcttc acctgacttg     1020
gtgaatattg gtagaaatat agttgggaga tgtggaggta taccgctagc catagtggtg     1080
actgcaggca tgttaagggc aagagaaaga acagaacatg cgtggaacag agtacttgag     1140
agtatgggcc ataaagttca agatggatgt gctaaggtat tggctctcag ttacaatgat     1200
ttacctattg cctcaaggcc atgtttcttg tactttggcc tttaccccga ggaccatgaa     1260
attcgtgctt ttgatttgat aaatatgtgg attgctgaga agtttatagt agtaaatagt     1320
ggtaataggc gagaggctga ggatttggcg gaggacgtcc taaatgattt ggtttctaga     1380
aacttgattc aacttgccaa aaggacatat aatggaagaa tttcaagttg tcgcatacat     1440
gacttgttac atagtttgtg tgtggacttg gctaaggaaa gtaacttctt tcacaccgcg     1500
catgatgcat ttggtgatcc cggcaatgtt gctaggctcc gaaggattac attctactct     1560
gacaatgtca tgattgagtt cttccgttca aatcctaagc ttgagaagct tcgtgtactt     1620
ttctgtttcg caaaagaccc ttccatattt tctcatatgg cttattttga cttcaaattg     1680
ttgcacacat tggttgtagt catgtctcaa agttttcaag catatgtcac tatcccaagc     1740
aaatttggga acatgacttg cttacgctat ctgagattgg aggggaatat ttgtggaaaa     1800
ctgccaaata gtattgtcaa gctcacacgt ctagaaacca tagacattga tcgacgtagc     1860
ctcattcaac ctccttctgg tgtttgggag tctaaacatt tgagacatct ttgttataga     1920
gattatggac aagcatgtaa cagttgcttt tctataagct cattataccc aaatatttac     1980
tcattgcatc ctaacaatct acaaaccttg atgtggatac ctgataaatt ttttgaaccg     2040
aggttgttgc accgattgat caatttaaga aaactgggta tactgggagt gtccaattct     2100
accgttaaga tgttatcaat atttagccct gtgcttaagg cgctggaggt tctgaagctc     2160 agttttttcca gtgacccgag tgaacaaata aagttgtcat cgtatccaca tattgctaag     2220
ttgcatttga atgttaacag aacaatggcc ttgaactctc aatcatttcc tccaaatctc     2280
atcaagctta ctctagccta ctttagtgta gaccgttata tactggcagt acttaagaca     2340
tttcccaaat taagaaaact taaaatgttc atctgcaagt ataatgaaga aaagatggat     2400
ctctcgggcg aggcaaatgg ttatagcttt ccgcaacttg aagttttgca tattcatagc     2460
ccgaatgggt tgtctgaagt aacgtgcacg gatgatgtca gtatgcccaa attgaaaaag     2520
ctgttactta caggattcca tcgccgaatc agtttatcgg aacggcttaa aaagctgagt     2580
aaatga                                                                 2586
```

```
<210> SEQ ID NO 5
<211> LENGTH: 2586
<212> TYPE: DNA
<213> ORGANISM: artificial
<220> FEATURE:
<223> OTHER INFORMATION: mutant

<400> SEQUENCE: 5
atggctgaaa ttcttcttac atcagtaatc aataaatctg tagaaatagc tggaaattta       60
ctgattcaag aaggaaagcg tttatattgg ttgaaagagg atatcgattg gctccagaga      120
```

-continued

```
gaaatgagac acattcgatc ttatgttgac aacgcaaagg ccaaggaagc tggaggtgat      180
tcaagggtca aaaacttatt gaaagatatt caagaattgg caggtgatgt ggaggatctc      240
ttagatgact tccttccaaa aattcaacaa tccaataagt tcaattattg ccttaagagg      300
agttcttttg cagatgagtt tgctatggag attgagaaga taaagagaag ggttgttgac      360
attgaccgaa taaggaaaac ttacaacatc atagatacag ataacaataa tgatgattgt      420
gttctgctgg atcggagaag attattccta catgctgatg aaacagagat catcggtttg      480
gatgatgact tcaatatgct acaagccaaa ttacttaatc aagatttgca ttatggagtt      540
gtttccatag ttggcatgcc cggtctgggg aaaacaactc ttgccaagaa actttatagg      600
ctcattcgtg atcaatttga gtgttctgga ctggtctacg tttcacaaca gccaagagcg      660
agtgaaatct tacttgacat tgccaaacaa attggactga cggaacagaa aatgaaggaa      720
aatttggagg acaacctgcg atcactcttg aaaataaaaa ggtatgttat cctcctagat      780
gacatttggg atgtgaaat ttgggatgat ctgaaacttg tccttcctga atgtgattca      840
aaagtcggca gtagaatgat aatcacgtct cgaaatagta atgtaggcag atacatagga      900
ggggaatcct ccctccatgc attgcaaccc ctagaatccg agaaaagctt tgaactcttt      960
accaagaaaa tctttaattt tgatgataat aatagttggg ccaatgcttc acctgacttg     1020
gtgaatattg gtagaaatat agttgggaga tgtggaggta taccgctagc catagtggtg     1080
actgcaggca tgttaagggc aagagaaaga acagaacatg cgtggaacag agtacttgag     1140
agtatgggcc ataaagttca agatggatgt gctaaggtat tggctctcag ttacaatgat     1200
ttacctattg cctcaaggcc atgtttcttg tactttggcc tttaccccga ggaccatgaa     1260
attcgtgctt ttgatttgat aaatatgtgg attgctgaga gtttatagt agtaaatagt     1320 ggtaataggc gagaggctga ggatttggcg gaggacgtcc taaatgattt ggtttctaga     1380
aacttgattc aacttgccaa aaggacatat aatggaagaa tttcaagttg tcgcatacat     1440
gacttgttac atagtttgtg tgtggacttg gctaaggaaa gtaacttctt tcacaccgcg     1500
catgatgcat ttggtgatcc cggcaatgtt gctaggctcc gaaggattac attctactct     1560
gacaatgtca tgattgagtt cttccgttca aatcctaagc ttgagaagct tcgtgtactt     1620
ttctgtttcg caaaagaccc ttccatattt tctcatatgg cttattttga cttcaaattg     1680
ttgcacacat tggttgtagt catgtctcaa agtttcaag catatgtcac tatcccaagc     1740
aaatttggga acatgacttg cttacgctat ctgagattgg aggggaatat ttgtggaaaa     1800
ctgccaaata gtattgtcaa gctcacacgt ctagaaacca tagacattga tcgacgtagc     1860
ctcattcaac ctccttctgg tgtttgggag tctaaacatt tgagacatct ttgttataga     1920
gattatggac aagcatgtaa cagttgcttt tctataagct cattttaccc aaatatttac     1980
tcattgcatc ctaacaatct acaaaccttg atgtggatac ctgataaatt ttttgaaccg     2040
aggttgttgc accgattgat caatttaaga aaactgggta tactgggagt gtccaattct     2100
accgttaaga tgttatcaat atttagccct gtgcttaagg cgctggaggt tctgaagctc     2160 agttttttcca gtgacccgag tgaacaaata aagttgtcat cgtatccaca tattgctaag     2220
ttgcatttga atgttaacag aacaatggcc ttgaactctc aatcatttcc tccaaatctc     2280
atcaagctta ctctagccta ctttagtgta gaccgttata tactggcagt acttaagaca     2340
tttcccaaat taagaaaact taaaatgttc atctgcaagt ataatgaaga aaagatggat     2400
ctctcgggcg aggcaaatgg ttatagcttt ccgcaacttg aagttttgca tattcatagc     2460
ccgaatgggt tgtctgaagt aacgtgcacg gatgatgtca gtatgcccaa attgaaaaag     2520
```

-continued

```
ctgttactta caggattcca tcgccgaatc agtttatcgg aacggcttaa aaagctgagt    2580
aaatga                                                                2586
```

<210> SEQ ID NO 6
<211> LENGTH: 861
<212> TYPE: PRT
<213> ORGANISM: Lycopersicon esculentum

<400> SEQUENCE: 6

```
Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Ala Gly Gly Asp Ser Arg Val Lys
    50                  55                  60

Asn Leu Leu Lys Asp Ile Gln Glu Leu Ala Gly Asp Val Glu Asp Leu
65                  70                  75                  80

Leu Asp Asp Phe Leu Pro Lys Ile Gln Arg Ser Asn Lys Phe Asn Tyr
                85                  90                  95

Cys Leu Lys Thr Ser Ser Phe Ala Asp Glu Phe Ala Met Glu Ile Glu
            100                 105                 110

Lys Ile Lys Arg Arg Val Val Asp Ile Asp Arg Ile Arg Lys Thr Tyr
        115                 120                 125

Asn Ile Ile Asp Thr Asp Asn Asn Asn Asp Asp Cys Val Leu Leu Asp
    130                 135                 140

Arg Arg Arg Leu Phe Leu His Ala Asp Glu Thr Glu Ile Ile Gly Leu
145                 150                 155                 160

Asp Asp Asp Phe Asn Met Leu Gln Ala Lys Leu Leu Asn Gln Asp Leu
                165                 170                 175

His Tyr Gly Val Val Ser Ile Val Gly Met Pro Gly Leu Gly Lys Thr
            180                 185                 190

Thr Leu Ala Lys Lys Leu Tyr Arg Leu Ile Arg Asp Gln Phe Glu Cys
        195                 200                 205

Ser Gly Leu Val Tyr Val Ser Gln Gln Pro Arg Ala Gly Glu Ile Leu
    210                 215                 220

Leu Asp Ile Ala Lys Gln Ile Gly Leu Thr Glu Gln Lys Ile Lys Glu
225                 230                 235                 240

Asn Leu Glu Asp Asn Leu Arg Ser Leu Leu Lys Ile Lys Arg Tyr Val
                245                 250                 255

Ile Leu Leu Asp Asp Ile Trp Asp Val Glu Ile Trp Asp Asp Leu Lys
            260                 265                 270

Leu Val Leu Pro Glu Cys Asp Ser Lys Val Gly Ser Arg Met Ile Ile
        275                 280                 285

Thr Ser Arg Asn Ser Asn Val Gly Arg Tyr Ile Gly Gly Glu Ser Ser
    290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Asn Ser Trp Ala Asn Ala
                325                 330                 335

Ser Pro Asp Leu Val Asn Ile Gly Arg Asn Ile Ala Gly Arg Cys Gly
            340                 345                 350
```

```
Gly Ile Pro Leu Ala Ile Val Val Thr Ala Gly Met Leu Arg Ala Arg
    355             360             365

Glu Arg Thr Glu His Ala Trp Asn Arg Val Leu Glu Ser Met Gly His
    370             375             380

Lys Val Gln Asp Gly Cys Ala Lys Val Leu Ala Leu Ser Tyr Asn Asp
385             390             395             400

Leu Pro Ile Ala Ser Arg Pro Cys Phe Leu Tyr Phe Ser Leu Tyr Pro
            405             410             415

Glu Asp His Glu Ile Arg Ala Phe Asp Leu Ile Asn Met Trp Ile Ala
            420             425             430

Glu Lys Phe Ile Val Val Asn Ser Gly Asn Arg Arg Glu Ala Glu Asp
            435             440             445

Leu Ala Glu Asp Val Leu Asn Asp Leu Val Ser Arg Asn Leu Ile Gln
    450             455             460

Leu Ala Lys Arg Thr Tyr Asn Gly Arg Ile Ser Ser Cys Arg Ile His
465             470             475             480

Asp Leu Leu His Ser Leu Cys Val Asp Leu Ala Lys Glu Ser Asn Phe
                485             490             495

Phe His Thr Ala His Asp Val Phe Gly Asp Pro Gly Asn Val Ala Arg
            500             505             510

Leu Arg Arg Ile Thr Phe Tyr Ser Asp Asn Val Met Ile Glu Phe Phe
            515             520             525

Gly Ser Asn Pro Lys Leu Glu Lys Leu Arg Val Leu Phe Cys Phe Thr
    530             535             540

Lys Asp Pro Ser Ile Phe Ser His Met Ala Cys Phe Asp Phe Lys Leu
545             550             555             560

Leu His Thr Leu Val Val Val Met Ser Gln Ser Phe Gln Ala Tyr Val
                565             570             575

Thr Ile Pro Ser Lys Phe Gly Asn Met Thr Cys Leu Arg Tyr Leu Lys
            580             585             590

Leu Glu Gly Asn Ile Cys Gly Lys Leu Pro Asn Ser Ile Val Lys Leu
    595             600             605

Thr Arg Leu Glu Thr Ile Asp Ile Asp Arg Arg Ser Leu Ile Gln Leu
    610             615             620

Pro Ser Gly Val Trp Glu Ser Lys His Leu Arg His Leu Cys Tyr Arg
625             630             635             640

Asp Tyr Gly Gln Ala Cys Asn Ser Cys Phe Ser Ile Ser Ser Phe Tyr
            645             650             655

Pro Asn Ile Tyr Ser Leu His Pro Asn Asn Leu Gln Thr Leu Met Trp
            660             665             670

Ile Pro Asp Lys Phe Phe Glu Pro Arg Leu Leu His Arg Leu Ile Asn
            675             680             685

Leu Arg Lys Leu Gly Ile Leu Gly Val Ser Asn Ser Thr Val Lys Ile
    690             695             700

Leu Ser Thr Cys Arg Pro Val Pro Lys Ala Leu Lys Val Leu Lys Leu
705             710             715             720

Arg Phe Phe Ser Asp Pro Ser Glu Gln Ile Asn Leu Ser Ser Tyr Pro
            725             730             735

Lys Ile Val Lys Leu His Leu Asn Val Asp Arg Thr Ile Ala Leu Asn
            740             745             750

Ser Glu Ala Phe Pro Pro Asn Ile Ile Lys Leu Thr Leu Val Cys Phe
    755             760             765

Met Val Asp Ser Cys Leu Leu Ala Val Leu Lys Thr Leu Pro Lys Leu
```

-continued

```
          770                 775                 780

Arg Lys Leu Lys Met Val Ile Cys Lys Tyr Asn Glu Glu Lys Met Ala
785                 790                 795                 800

Leu Ser Gly Glu Ala Asn Gly Tyr Ser Phe Pro Gln Leu Glu Val Leu
                805                 810                 815

His Ile His Ser Pro Asn Gly Leu Ser Glu Val Thr Cys Thr Asp Asp
                820                 825                 830

Val Ser Met Pro Lys Leu Lys Lys Leu Leu Leu Thr Gly Phe His Cys
                835                 840                 845

Gly Ile Ser Leu Ser Glu Arg Leu Lys Lys Leu Ser Lys
        850                 855                 860

<210> SEQ ID NO 7
<211> LENGTH: 861
<212> TYPE: PRT
<213> ORGANISM: Lycopersicon esculentum

<400> SEQUENCE: 7

Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
                20                  25                  30

Glu Asp Ile Asp Trp Leu Gln Arg Glu Met Arg His Ile Arg Ser Tyr
                35                  40                  45

Val Asp Asn Ala Lys Ala Lys Glu Ala Gly Gly Asp Ser Arg Val Lys
        50                  55                  60

Asn Leu Leu Lys Asp Ile Gln Glu Leu Ala Gly Asp Val Glu Asp Leu
65                  70                  75                  80

Leu Asp Asp Phe Leu Pro Lys Ile Gln Gln Ser Asn Lys Phe Asn Tyr
                85                  90                  95

Cys Leu Lys Arg Ser Ser Phe Ala Asp Glu Phe Ala Met Glu Ile Glu
                100                 105                 110

Lys Ile Lys Arg Arg Val Val Asp Ile Asp Arg Ile Arg Lys Thr Tyr
                115                 120                 125

Asn Ile Ile Asp Thr Asp Asn Asn Asn Asp Asp Cys Val Leu Leu Asp
        130                 135                 140

Arg Arg Arg Leu Phe Leu His Ala Asp Glu Thr Glu Ile Ile Gly Leu
145                 150                 155                 160

Asp Asp Asp Phe Asn Met Leu Gln Ala Lys Leu Leu Asn Gln Asp Leu
                165                 170                 175

His Tyr Gly Val Val Ser Ile Val Gly Met Pro Gly Leu Gly Lys Thr
                180                 185                 190

Thr Leu Ala Lys Lys Leu Tyr Arg Leu Ile Arg Asp Gln Phe Glu Cys
                195                 200                 205

Ser Gly Leu Val Tyr Val Ser Gln Gln Pro Arg Ala Ser Glu Ile Leu
        210                 215                 220

Leu Asp Ile Ala Lys Gln Ile Gly Leu Thr Glu Gln Lys Met Lys Glu
225                 230                 235                 240

Asn Leu Glu Asp Asn Leu Arg Ser Leu Leu Lys Ile Lys Arg Tyr Val
                245                 250                 255

Phe Leu Leu Asp Asp Ile Trp Asp Val Glu Ile Trp Asp Asp Leu Lys
                260                 265                 270

Leu Val Leu Pro Glu Cys Asp Ser Lys Val Gly Ser Arg Ile Ile Ile
                275                 280                 285
```

```
Thr Ser Arg Asn Ser Asn Val Gly Arg Tyr Ile Gly Gly Glu Ser Ser
290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Asn Ser Trp Ala Asn Ala
                325                 330                 335

Ser Pro Asp Leu Val Asn Ile Gly Arg Asn Ile Val Gly Arg Cys Gly
                340                 345                 350

Gly Ile Pro Leu Ala Ile Val Val Thr Ala Gly Met Leu Arg Ala Arg
                355                 360                 365

Glu Arg Thr Glu His Ala Trp Asn Arg Val Leu Glu Ser Met Gly His
370                 375                 380

Lys Val Gln Asp Gly Cys Ala Lys Val Leu Ala Leu Ser Tyr Asn Asp
385                 390                 395                 400

Leu Pro Ile Ala Ser Arg Pro Cys Phe Leu Tyr Phe Gly Leu Tyr Pro
                405                 410                 415

Glu Asp His Glu Ile Arg Ala Phe Asp Leu Ile Asn Met Trp Ile Ala
                420                 425                 430

Glu Lys Phe Ile Val Val Asn Ser Gly Asn Arg Arg Glu Ala Glu Asp
                435                 440                 445

Leu Ala Glu Asp Val Leu Asn Asp Leu Val Ser Arg Asn Leu Ile Gln
                450                 455                 460

Leu Ala Lys Arg Thr Tyr Asn Gly Arg Ile Ser Ser Cys Arg Ile His
465                 470                 475                 480

Asp Leu Leu His Ser Leu Cys Val Asp Leu Ala Lys Glu Ser Asn Phe
                485                 490                 495

Phe His Thr Ala His Asp Ala Phe Gly Asp Pro Gly Asn Val Ala Arg
                500                 505                 510

Leu Arg Arg Ile Thr Phe Tyr Ser Asp Asn Val Met Ile Glu Phe Phe
                515                 520                 525

Arg Ser Asn Pro Lys Leu Glu Lys Leu Arg Val Leu Phe Cys Phe Ala
530                 535                 540

Lys Asp Pro Ser Ile Phe Ser His Met Ala Tyr Phe Asp Phe Lys Leu
545                 550                 555                 560

Leu His Thr Leu Val Val Val Met Ser Gln Ser Phe Gln Ala Tyr Val
                565                 570                 575

Thr Ile Pro Ser Lys Phe Gly Asn Met Thr Cys Leu Arg Tyr Leu Arg
                580                 585                 590

Leu Glu Gly Asn Ile Cys Gly Lys Leu Pro Asn Ser Ile Val Lys Leu
                595                 600                 605

Thr Arg Leu Glu Thr Ile Asp Ile Asp Arg Arg Ser Leu Ile Gln Pro
                610                 615                 620

Pro Ser Gly Val Trp Glu Ser Lys His Leu Arg His Leu Cys Tyr Arg
625                 630                 635                 640

Asp Tyr Gly Gln Ala Cys Asn Ser Cys Phe Ser Ile Ser Ser Phe Tyr
                645                 650                 655

Pro Asn Ile Tyr Ser Leu His Pro Asn Asn Leu Gln Thr Leu Met Trp
                660                 665                 670

Ile Pro Asp Lys Phe Phe Glu Pro Arg Leu Leu His Arg Leu Ile Asn
                675                 680                 685

Leu Arg Lys Leu Gly Ile Leu Gly Val Ser Asn Ser Thr Val Lys Met
                690                 695                 700

Leu Ser Ile Phe Ser Pro Val Leu Lys Ala Leu Glu Val Leu Lys Leu
```

-continued

```
705              710              715              720

Ser Phe Ser Ser Asp Pro Ser Glu Gln Ile Lys Leu Ser Ser Tyr Pro
                725              730              735

His Ile Ala Lys Leu His Leu Asn Val Asn Arg Thr Met Ala Leu Asn
            740              745              750

Ser Gln Ser Phe Pro Pro Asn Leu Ile Lys Leu Thr Leu Ala Asn Phe
            755              760              765

Thr Val Asp Arg Tyr Ile Leu Ala Val Leu Lys Thr Phe Pro Lys Leu
        770              775              780

Arg Lys Leu Lys Met Phe Ile Cys Lys Tyr Asn Glu Glu Lys Met Asp
785              790              795              800

Leu Ser Gly Glu Ala Asn Gly Tyr Ser Phe Pro Gln Leu Glu Val Leu
            805              810              815

His Ile His Ser Pro Asn Gly Leu Ser Glu Val Thr Cys Thr Asp Asp
            820              825              830

Val Ser Met Pro Lys Leu Lys Lys Leu Leu Leu Thr Gly Phe His Cys
            835              840              845

Arg Ile Ser Leu Ser Glu Arg Leu Lys Lys Leu Ser Lys
    850              855              860

<210> SEQ ID NO 8
<211> LENGTH: 861
<212> TYPE: PRT
<213> ORGANISM: Lycopersicon esculentum

<400> SEQUENCE: 8

Met Ala Glu Ile Leu Leu Thr Ser Val Ile Asn Lys Ser Val Glu Ile
1               5               10              15

Ala Gly Asn Leu Leu Ile Gln Glu Gly Lys Arg Leu Tyr Trp Leu Lys
            20              25              30

Glu Asp Ile Asp Trp Leu Gln Arg Glu Met Arg His Ile Arg Ser Tyr
        35              40              45

Val Asp Asn Ala Lys Ala Lys Glu Ala Gly Gly Asp Ser Arg Val Lys
    50              55              60

Asn Leu Leu Lys Asp Ile Gln Glu Leu Ala Gly Asp Val Glu Asp Leu
65              70              75              80

Leu Asp Asp Phe Leu Pro Lys Ile Gln Gln Ser Asn Lys Phe Asn Tyr
            85              90              95

Cys Leu Lys Arg Ser Ser Phe Ala Asp Glu Phe Ala Met Glu Ile Glu
            100             105             110

Lys Ile Lys Arg Arg Val Val Asp Ile Asp Arg Ile Arg Lys Thr Tyr
            115             120             125

Asn Ile Ile Asp Thr Asp Asn Asn Asp Asp Cys Val Leu Leu Asp
        130             135             140

Arg Arg Arg Leu Phe Leu His Ala Asp Glu Thr Glu Ile Ile Gly Leu
145             150             155             160

Asp Asp Asp Phe Asn Met Leu Gln Ala Lys Leu Leu Asn Gln Asp Leu
            165             170             175

His Tyr Gly Val Val Ser Ile Val Gly Met Pro Gly Leu Gly Lys Thr
            180             185             190

Thr Leu Ala Lys Lys Leu Tyr Arg Leu Ile Arg Asp Gln Phe Glu Cys
            195             200             205

Ser Gly Leu Val Tyr Val Ser Gln Gln Pro Arg Ala Ser Glu Ile Leu
    210             215             220
```

-continued

```
Leu Asp Ile Ala Lys Gln Ile Gly Leu Thr Glu Gln Lys Met Lys Glu
225             230             235             240

Asn Leu Glu Asp Asn Leu Arg Ser Leu Leu Lys Ile Lys Arg Tyr Val
            245             250             255

Ile Leu Leu Asp Asp Ile Trp Asp Val Glu Ile Trp Asp Asp Leu Lys
            260             265             270

Leu Val Leu Pro Glu Cys Asp Ser Lys Val Gly Ser Arg Met Ile Ile
        275             280             285

Thr Ser Arg Asn Ser Asn Val Gly Arg Tyr Ile Gly Gly Glu Ser Ser
        290             295             300

Leu His Ala Leu Gln Pro Leu Glu Ser Glu Lys Ser Phe Glu Leu Phe
305             310             315             320

Thr Lys Lys Ile Phe Asn Phe Asp Asp Asn Asn Ser Trp Ala Asn Ala
                325             330             335

Ser Pro Asp Leu Val Asn Ile Gly Arg Asn Ile Val Gly Arg Cys Gly
            340             345             350

Gly Ile Pro Leu Ala Ile Val Val Thr Ala Gly Met Leu Arg Ala Arg
            355             360             365

Glu Arg Thr Glu His Ala Trp Asn Arg Val Leu Glu Ser Met Gly His
    370             375             380

Lys Val Gln Asp Gly Cys Ala Lys Val Leu Ala Leu Ser Tyr Asn Asp
385             390             395             400

Leu Pro Ile Ala Ser Arg Pro Cys Phe Leu Tyr Phe Gly Leu Tyr Pro
            405             410             415

Glu Asp His Glu Ile Arg Ala Phe Asp Leu Ile Asn Met Trp Ile Ala
            420             425             430

Glu Lys Phe Ile Val Val Asn Ser Gly Asn Arg Arg Glu Ala Glu Asp
        435             440             445

Leu Ala Glu Asp Val Leu Asn Asp Leu Val Ser Arg Asn Leu Ile Gln
    450             455             460

Leu Ala Lys Arg Thr Tyr Asn Gly Arg Ile Ser Ser Cys Arg Ile His
465             470             475             480

Asp Leu Leu His Ser Leu Cys Val Asp Leu Ala Lys Glu Ser Asn Phe
            485             490             495

Phe His Thr Ala His Asp Ala Phe Gly Asp Pro Gly Asn Val Ala Arg
            500             505             510

Leu Arg Arg Ile Thr Phe Tyr Ser Asp Asn Val Met Ile Glu Phe Phe
            515             520             525

Arg Ser Asn Pro Lys Leu Glu Lys Leu Arg Val Leu Phe Cys Phe Ala
        530             535             540

Lys Asp Pro Ser Ile Phe Ser His Met Ala Tyr Phe Asp Phe Lys Leu
545             550             555             560

Leu His Thr Leu Val Val Val Met Ser Gln Ser Phe Gln Ala Tyr Val
            565             570             575

Thr Ile Pro Ser Lys Phe Gly Asn Met Thr Cys Leu Arg Tyr Leu Arg
            580             585             590

Leu Glu Gly Asn Ile Cys Gly Lys Leu Pro Asn Ser Ile Val Lys Leu
        595             600             605

Thr Arg Leu Glu Thr Ile Asp Ile Asp Arg Arg Ser Leu Ile Gln Pro
    610             615             620

Pro Ser Gly Val Trp Glu Ser Lys His Leu Arg His Leu Cys Tyr Arg
625             630             635             640

Asp Tyr Gly Gln Ala Cys Asn Ser Cys Phe Ser Ile Ser Ser Phe Tyr
```

-continued

```
                 645              650              655
Pro Asn Ile Tyr Ser Leu His Pro Asn Asn Leu Gln Thr Leu Met Trp
             660              665              670

Ile Pro Asp Lys Phe Phe Glu Pro Arg Leu Leu His Arg Leu Ile Asn
             675              680              685

Leu Arg Lys Leu Gly Ile Leu Gly Val Ser Asn Ser Thr Val Lys Met
    690              695              700

Leu Ser Ile Phe Ser Pro Val Leu Lys Ala Leu Glu Val Leu Lys Leu
705              710              715              720

Ser Phe Ser Ser Asp Pro Ser Glu Gln Ile Lys Leu Ser Ser Tyr Pro
             725              730              735

His Ile Ala Lys Leu His Leu Asn Val Asn Arg Thr Met Ala Leu Asn
             740              745              750

Ser Gln Ser Phe Pro Pro Asn Leu Ile Lys Leu Thr Leu Ala Tyr Phe
             755              760              765

Ser Val Asp Arg Tyr Ile Leu Ala Val Leu Lys Thr Phe Pro Lys Leu
    770              775              780

Arg Lys Leu Lys Met Phe Ile Cys Lys Tyr Asn Glu Glu Lys Met Asp
785              790              795              800

Leu Ser Gly Glu Ala Asn Gly Tyr Ser Phe Pro Gln Leu Glu Val Leu
             805              810              815

His Ile His Ser Pro Asn Gly Leu Ser Glu Val Thr Cys Thr Asp Asp
             820              825              830

Val Ser Met Pro Lys Leu Lys Lys Leu Leu Leu Thr Gly Phe His Cys
             835              840              845

Arg Ile Ser Leu Ser Glu Arg Leu Lys Lys Leu Ser Lys
    850              855              860
```

```
<210> SEQ ID NO 9
<211> LENGTH: 861
<212> TYPE: PRT
<213> ORGANISM: artificial
<220> FEATURE:
<223> OTHER INFORMATION: mutant

<400> SEQUENCE: 9

Met Ala Glu Ile Leu Leu Thr Ser Val Ile Asn Lys Ser Val Glu Ile
1               5               10               15

Ala Gly Asn Leu Leu Ile Gln Glu Gly Lys Arg Leu Tyr Trp Leu Lys
             20               25               30

Glu Asp Ile Asp Trp Leu Gln Arg Glu Met Arg His Ile Arg Ser Tyr
             35               40               45

Val Asp Asn Ala Lys Ala Lys Glu Ala Gly Gly Asp Ser Arg Val Lys
    50               55               60

Asn Leu Leu Lys Asp Ile Gln Glu Leu Ala Gly Asp Val Glu Asp Leu
65               70               75               80

Leu Asp Asp Phe Leu Pro Lys Ile Gln Gln Ser Asn Lys Phe Asn Tyr
             85               90               95

Cys Leu Lys Arg Ser Ser Phe Ala Asp Glu Phe Ala Met Glu Ile Glu
             100              105              110

Lys Ile Lys Arg Arg Val Val Asp Ile Asp Arg Ile Arg Lys Thr Tyr
             115              120              125

Asn Ile Ile Asp Thr Asp Asn Asn Asp Asp Cys Val Leu Leu Asp
             130              135              140

Arg Arg Arg Leu Phe Leu His Ala Asp Glu Thr Glu Ile Ile Gly Leu
```

-continued

```
145              150              155              160

Asp Asp Asp Phe Asn Met Leu Gln Ala Lys Leu Leu Asn Gln Asp Leu
             165              170              175

His Tyr Gly Val Val Ser Ile Val Gly Met Pro Gly Leu Gly Lys Thr
             180              185              190

Thr Leu Ala Lys Lys Leu Tyr Arg Leu Ile Arg Asp Gln Phe Glu Cys
         195              200              205

Ser Gly Leu Val Tyr Val Ser Gln Gln Pro Arg Ala Ser Glu Ile Leu
         210              215              220

Leu Asp Ile Ala Lys Gln Ile Gly Leu Thr Glu Gln Lys Met Lys Glu
225              230              235              240

Asn Leu Glu Asp Asn Leu Arg Ser Leu Leu Lys Ile Lys Arg Tyr Val
             245              250              255

Ile Leu Leu Asp Asp Ile Trp Asp Val Glu Ile Trp Asp Asp Leu Lys
             260              265              270

Leu Val Leu Pro Glu Cys Asp Ser Lys Val Gly Ser Arg Met Ile Ile
         275              280              285

Thr Ser Arg Asn Ser Asn Val Gly Arg Tyr Ile Gly Gly Glu Ser Ser
         290              295              300

Leu His Ala Leu Gln Pro Leu Glu Ser Glu Lys Ser Phe Glu Leu Phe
305              310              315              320

Thr Lys Lys Ile Phe Asn Phe Asp Asp Asn Asn Ser Trp Ala Asn Ala
             325              330              335

Ser Pro Asp Leu Val Asn Ile Gly Arg Asn Ile Val Gly Arg Cys Gly
         340              345              350

Gly Ile Pro Leu Ala Ile Val Val Thr Ala Gly Met Leu Arg Ala Arg
         355              360              365

Glu Arg Thr Glu His Ala Trp Asn Arg Val Leu Glu Ser Met Gly His
         370              375              380

Lys Val Gln Asp Gly Cys Ala Lys Val Leu Ala Leu Ser Tyr Asn Asp
385              390              395              400

Leu Pro Ile Ala Ser Arg Pro Cys Phe Leu Tyr Phe Gly Leu Tyr Pro
             405              410              415

Glu Asp His Glu Ile Arg Ala Phe Asp Leu Ile Asn Met Trp Ile Ala
             420              425              430

Glu Lys Phe Ile Val Val Asn Ser Gly Asn Arg Arg Glu Ala Glu Asp
         435              440              445

Leu Ala Glu Asp Val Leu Asn Asp Leu Val Ser Arg Asn Leu Ile Gln
         450              455              460

Leu Ala Lys Arg Thr Tyr Asn Gly Arg Ile Ser Ser Cys Arg Ile His
465              470              475              480

Asp Leu Leu His Ser Leu Cys Val Asp Leu Ala Lys Glu Ser Asn Phe
             485              490              495

Phe His Thr Ala His Asp Ala Phe Gly Asp Pro Gly Asn Val Ala Arg
         500              505              510

Leu Arg Arg Ile Thr Phe Tyr Ser Asp Asn Val Met Ile Glu Phe Phe
         515              520              525

Arg Ser Asn Pro Lys Leu Glu Lys Leu Arg Val Leu Phe Cys Phe Ala
         530              535              540

Lys Asp Pro Ser Ile Phe Ser His Met Ala Tyr Phe Asp Phe Lys Leu
545              550              555              560

Leu His Thr Leu Val Val Val Met Ser Gln Ser Phe Gln Ala Tyr Val
             565              570              575
```

-continued

```
Thr Ile Pro Ser Lys Phe Gly Asn Met Thr Cys Leu Arg Tyr Leu Arg
        580                 585                 590

Leu Glu Gly Asn Ile Cys Gly Lys Leu Pro Asn Ser Ile Val Lys Leu
        595                 600                 605

Thr Arg Leu Glu Thr Ile Asp Ile Asp Arg Arg Ser Leu Ile Gln Pro
        610                 615                 620

Pro Ser Gly Val Trp Glu Ser Lys His Leu Arg His Leu Cys Tyr Arg
625                 630                 635                 640

Asp Tyr Gly Gln Ala Cys Asn Ser Cys Phe Ser Ile Ser Ser Leu Tyr
                645                 650                 655

Pro Asn Ile Tyr Ser Leu His Pro Asn Asn Leu Gln Thr Leu Met Trp
                660                 665                 670

Ile Pro Asp Lys Phe Phe Glu Pro Arg Leu Leu His Arg Leu Ile Asn
                675                 680                 685

Leu Arg Lys Leu Gly Ile Leu Gly Val Ser Asn Ser Thr Val Lys Met
        690                 695                 700

Leu Ser Ile Phe Ser Pro Val Leu Lys Ala Leu Glu Val Leu Lys Leu
705                 710                 715                 720

Ser Phe Ser Ser Asp Pro Ser Glu Gln Ile Lys Leu Ser Ser Tyr Pro
                725                 730                 735

His Ile Ala Lys Leu His Leu Asn Val Asn Arg Thr Met Ala Leu Asn
                740                 745                 750

Ser Gln Ser Phe Pro Pro Asn Leu Ile Lys Leu Thr Leu Ala Tyr Phe
                755                 760                 765

Ser Val Asp Arg Tyr Ile Leu Ala Val Leu Lys Thr Phe Pro Lys Leu
        770                 775                 780

Arg Lys Leu Lys Met Phe Ile Cys Lys Tyr Asn Glu Glu Lys Met Asp
785                 790                 795                 800

Leu Ser Gly Glu Ala Asn Gly Tyr Ser Phe Pro Gln Leu Glu Val Leu
                805                 810                 815

His Ile His Ser Pro Asn Gly Leu Ser Glu Val Thr Cys Thr Asp Asp
                820                 825                 830

Val Ser Met Pro Lys Leu Lys Lys Leu Leu Leu Thr Gly Phe His Arg
        835                 840                 845

Arg Ile Ser Leu Ser Glu Arg Leu Lys Lys Leu Ser Lys
    850                 855                 860
```

```
<210> SEQ ID NO 10
<211> LENGTH: 861
<212> TYPE: PRT
<213> ORGANISM: artificial
<220> FEATURE:
<223> OTHER INFORMATION: mutant

<400> SEQUENCE: 10

Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
            20                  25                  30

Glu Asp Ile Asp Trp Leu Gln Arg Glu Met Arg His Ile Arg Ser Tyr
            35                  40                  45

Val Asp Asn Ala Lys Ala Lys Glu Ala Gly Gly Asp Ser Arg Val Lys
        50                  55                  60

Asn Leu Leu Lys Asp Ile Gln Glu Leu Ala Gly Asp Val Glu Asp Leu
65                  70                  75                  80
```

-continued

```
Leu Asp Asp Phe Leu Pro Lys Ile Gln Gln Ser Asn Lys Phe Asn Tyr
             85                  90                  95

Cys Leu Lys Arg Ser Ser Phe Ala Asp Glu Phe Ala Met Glu Ile Glu
            100                 105                 110

Lys Ile Lys Arg Arg Val Val Asp Ile Asp Arg Ile Arg Lys Thr Tyr
            115                 120                 125

Asn Ile Ile Asp Thr Asp Asn Asn Asp Asp Cys Val Leu Leu Asp
        130                 135                 140

Arg Arg Arg Leu Phe Leu His Ala Asp Glu Thr Glu Ile Ile Gly Leu
145                 150                 155                 160

Asp Asp Asp Phe Asn Met Leu Gln Ala Lys Leu Leu Asn Gln Asp Leu
                165                 170                 175

His Tyr Gly Val Val Ser Ile Val Gly Met Pro Gly Leu Gly Lys Thr
            180                 185                 190

Thr Leu Ala Lys Lys Leu Tyr Arg Leu Ile Arg Asp Gln Phe Glu Cys
            195                 200                 205

Ser Gly Leu Val Tyr Val Ser Gln Gln Pro Arg Ala Ser Glu Ile Leu
            210                 215                 220

Leu Asp Ile Ala Lys Gln Ile Gly Leu Thr Glu Gln Lys Met Lys Glu
225                 230                 235                 240

Asn Leu Glu Asp Asn Leu Arg Ser Leu Leu Lys Ile Lys Arg Tyr Val
                245                 250                 255

Ile Leu Leu Asp Asp Ile Trp Asp Val Glu Ile Trp Asp Asp Leu Lys
                260                 265                 270

Leu Val Leu Pro Glu Cys Asp Ser Lys Val Gly Ser Arg Met Ile Ile
            275                 280                 285

Thr Ser Arg Asn Ser Asn Val Gly Arg Tyr Ile Gly Gly Glu Ser Ser
            290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Asn Ser Trp Ala Asn Ala
                325                 330                 335

Ser Pro Asp Leu Val Asn Ile Gly Arg Asn Ile Val Gly Arg Cys Gly
            340                 345                 350

Gly Ile Pro Leu Ala Ile Val Val Thr Ala Gly Met Leu Arg Ala Arg
            355                 360                 365

Glu Arg Thr Glu His Ala Trp Asn Arg Val Leu Glu Ser Met Gly His
            370                 375                 380

Lys Val Gln Asp Gly Cys Ala Lys Val Leu Ala Leu Ser Tyr Asn Asp
385                 390                 395                 400

Leu Pro Ile Ala Ser Arg Pro Cys Phe Leu Tyr Phe Gly Leu Tyr Pro
                405                 410                 415

Glu Asp His Glu Ile Arg Ala Phe Asp Leu Ile Asn Met Trp Ile Ala
            420                 425                 430

Glu Lys Phe Ile Val Val Asn Ser Gly Asn Arg Arg Glu Ala Glu Asp
            435                 440                 445

Leu Ala Glu Asp Val Leu Asn Asp Leu Val Ser Arg Asn Leu Ile Gln
    450                 455                 460

Leu Ala Lys Arg Thr Tyr Asn Gly Arg Ile Ser Ser Cys Arg Ile His
465                 470                 475                 480

Asp Leu Leu His Ser Leu Cys Val Asp Leu Ala Lys Glu Ser Asn Phe
                485                 490                 495
```

-continued

```
Phe His Thr Ala His Asp Ala Phe Gly Asp Pro Gly Asn Val Ala Arg
            500                 505                 510

Leu Arg Arg Ile Thr Phe Tyr Ser Asp Asn Val Met Ile Glu Phe Phe
            515                 520                 525

Arg Ser Asn Pro Lys Leu Glu Lys Leu Arg Val Leu Phe Cys Phe Ala
            530                 535                 540

Lys Asp Pro Ser Ile Phe Ser His Met Ala Tyr Phe Asp Phe Lys Leu
545                 550                 555                 560

Leu His Thr Leu Val Val Met Ser Gln Ser Phe Gln Ala Tyr Val
            565                 570                 575

Thr Ile Pro Ser Lys Phe Gly Asn Met Thr Cys Leu Arg Tyr Leu Arg
            580                 585                 590

Leu Glu Gly Asn Ile Cys Gly Lys Leu Pro Asn Ser Ile Val Lys Leu
            595                 600                 605

Thr Arg Leu Glu Thr Ile Asp Ile Asp Arg Arg Ser Leu Ile Gln Pro
            610                 615                 620

Pro Ser Gly Val Trp Glu Ser Lys His Leu Arg His Leu Cys Tyr Arg
625                 630                 635                 640

Asp Tyr Gly Gln Ala Cys Asn Ser Cys Phe Ser Ile Ser Ser Phe Tyr
                645                 650                 655

Pro Asn Ile Tyr Ser Leu His Pro Asn Asn Leu Gln Thr Leu Met Trp
                660                 665                 670

Ile Pro Asp Lys Phe Phe Glu Pro Arg Leu Leu His Arg Leu Ile Asn
            675                 680                 685

Leu Arg Lys Leu Gly Ile Leu Gly Val Ser Asn Ser Thr Val Lys Met
            690                 695                 700

Leu Ser Ile Phe Ser Pro Val Leu Lys Ala Leu Glu Val Leu Lys Leu
705                 710                 715                 720

Ser Phe Ser Ser Asp Pro Ser Glu Gln Ile Lys Leu Ser Ser Tyr Pro
                725                 730                 735

His Ile Ala Lys Leu His Leu Asn Val Asn Arg Thr Met Ala Leu Asn
            740                 745                 750

Ser Gln Ser Phe Pro Pro Asn Leu Ile Lys Leu Thr Leu Ala Tyr Phe
            755                 760                 765

Ser Val Asp Arg Tyr Ile Leu Ala Val Leu Lys Thr Phe Pro Lys Leu
            770                 775                 780

Arg Lys Leu Lys Met Phe Ile Cys Lys Tyr Asn Glu Glu Lys Met Asp
785                 790                 795                 800

Leu Ser Gly Glu Ala Asn Gly Tyr Ser Phe Pro Gln Leu Glu Val Leu
                805                 810                 815

His Ile His Ser Pro Asn Gly Leu Ser Glu Val Thr Cys Thr Asp Asp
            820                 825                 830

Val Ser Met Pro Lys Leu Lys Lys Leu Leu Leu Thr Gly Phe His Arg
            835                 840                 845

Arg Ile Ser Leu Ser Glu Arg Leu Lys Lys Leu Ser Lys
    850                 855                 860
```

<210> SEQ ID NO 11
<211> LENGTH: 385
<212> TYPE: PRT
<213> ORGANISM: Lycopersicon esculentum

<400> SEQUENCE: 11

```
Cys Arg Ile His Asp Leu Leu His Ser Leu Cys Val Asp Leu Ala Lys
1               5                   10                  15
```

```
Glu Ser Asn Phe Phe His Thr Ala His Asp Ala Phe Gly Asp Pro Gly
            20              25              30

Asn Val Ala Arg Leu Arg Arg Ile Thr Phe Tyr Ser Asp Asn Val Met
            35              40              45

Ile Glu Phe Phe Arg Ser Asn Pro Lys Leu Glu Lys Leu Arg Val Leu
    50              55              60

Phe Cys Phe Ala Lys Asp Pro Ser Ile Phe Ser His Met Ala Tyr Phe
65              70              75              80

Asp Phe Lys Leu Leu His Thr Leu Val Val Val Met Ser Gln Ser Phe
            85              90              95

Gln Ala Tyr Val Thr Ile Pro Ser Lys Phe Gly Asn Met Thr Cys Leu
            100             105             110

Arg Tyr Leu Arg Leu Glu Gly Asn Ile Cys Gly Lys Leu Pro Asn Ser
            115             120             125

Ile Val Lys Leu Thr Arg Leu Glu Thr Ile Asp Ile Asp Arg Arg Ser
    130             135             140

Leu Ile Gln Pro Pro Ser Gly Val Trp Glu Ser Lys His Leu Arg His
145             150             155             160

Leu Cys Tyr Arg Asp Tyr Gly Gln Ala Cys Asn Ser Cys Phe Ser Ile
            165             170             175

Ser Ser Phe Tyr Pro Asn Ile Tyr Ser Leu His Pro Asn Asn Leu Gln
            180             185             190

Thr Leu Met Trp Ile Pro Asp Lys Phe Phe Glu Pro Arg Leu Leu His
            195             200             205

Arg Leu Ile Asn Leu Arg Lys Leu Gly Ile Leu Gly Val Ser Asn Ser
    210             215             220

Thr Val Lys Met Leu Ser Ile Phe Ser Pro Val Leu Lys Ala Leu Glu
225             230             235             240

Val Leu Lys Leu Ser Phe Ser Ser Asp Pro Ser Glu Gln Ile Lys Leu
            245             250             255

Ser Ser Tyr Pro His Ile Ala Lys Leu His Leu Asn Val Asn Arg Thr
            260             265             270

Met Ala Leu Asn Ser Gln Ser Phe Pro Pro Asn Leu Ile Lys Leu Thr
            275             280             285

Leu Ala Tyr Phe Ser Val Asp Arg Tyr Ile Leu Ala Val Leu Lys Thr
    290             295             300

Phe Pro Lys Leu Arg Lys Leu Lys Met Phe Ile Cys Lys Tyr Asn Glu
305             310             315             320

Glu Lys Met Asp Leu Ser Gly Glu Ala Asn Gly Tyr Ser Phe Pro Gln
            325             330             335

Leu Glu Val Leu His Ile His Ser Pro Asn Gly Leu Ser Glu Val Thr
            340             345             350

Cys Thr Asp Asp Val Ser Met Pro Lys Leu Lys Lys Leu Leu Leu Thr
            355             360             365

Gly Phe His Arg Arg Ile Ser Leu Ser Glu Arg Leu Lys Lys Leu Ser
    370             375             380

Lys
385
```

<210> SEQ ID NO 12
<211> LENGTH: 1158
<212> TYPE: DNA
<213> ORGANISM: Lycopersicon esculentum -continued

```
<400> SEQUENCE: 12
tgtcgcatac atgacttgtt acatagtttg tgtgtggact tggctaagga aagtaacttc        60
tttcacaccg cgcatgatgc atttggtgat cccggcaatg ttgctaggct ccgaaggatt       120
acattctact ctgacaatgt catgattgag ttcttccgtt caaatcctaa gcttgagaag       180
cttcgtgtac ttttctgttt cgcaaaagac ccttccatat tttctcatat ggcttatttt       240
gacttcaaat tgttgcacac attggttgta gtcatgtctc aaagtttttca agcatatgtc       300 actatcccaa gcaaatttgg aacatgact tgcttacgct atctgagatt ggaggggaat        360
atttgtggaa aactgccaaa tagtattgtc aagctcacac gtctagagac catagacatt       420
gatcgacgta gcctcattca acctccttct ggtgtttggg agtctaaaca tttgagacat       480
ctttgttata gagattatgg acaagcatgt aacagttgct tttctataag ctcattttac       540
ccaaatattt actcattgca tcctaacaat ctacaaacct tgatgtggat acctgataaa       600 tttttttgaac cgaggttgtt gcaccgattg atcaatttaa gaaaactggg tatactggga       660
gtgtccaatt ctaccgttaa gatgttatca atatttagcc ctgtgcttaa ggcgctggag       720
gttctgaagc tcagttttc cagtgacccg agtgaacaaa taaagttgtc atcgtatcca       780
catattgcta agttgcattt gaatgttaac agaacaatgg ccttgaactc tcaatcattt       840
cctccaaatc tcatcaagct tactctagcc tactttagtg tagaccgtta tatactggca       900
gtacttaaga catttcccaa attaagaaaa cttaaaatgt tcatctgcaa gtataatgaa       960
gaaaagatgg atctctcggg cgaggcaaat ggttatagct ttccgcaact tgaagttttg      1020
catattcata gcccgaatgg gttgtctgaa gtaacgtgca cggatgatgt cagtatgccc      1080
aaattgaaaa agctgttact tacaggattc cattgccgaa tcagtttatc ggaacggctt      1140
aaaaagctga gtaaatga                                                    1158

<210> SEQ ID NO 13
<211> LENGTH: 268
<212> TYPE: PRT
<213> ORGANISM: Tobacco mosaic virus

<400> SEQUENCE: 13

Met Ala Leu Val Val Lys Gly Lys Val Asn Ile Asn Glu Phe Ile Asp
1               5                   10                  15

Leu Thr Lys Met Glu Lys Ile Leu Pro Ser Met Phe Thr Pro Val Lys
            20                  25                  30

Ser Val Met Cys Ser Lys Val Asp Lys Ile Met Val His Glu Asn Glu
        35                  40                  45

Ser Leu Ser Gly Val Asn Leu Leu Lys Gly Val Lys Leu Ile Asp Ser
    50                  55                  60

Gly Tyr Val Cys Leu Ala Gly Leu Val Val Thr Gly Glu Trp Asn Leu
65                  70                  75                  80

Pro Asp Asn Cys Arg Gly Gly Val Ser Val Cys Leu Val Asp Lys Arg
                85                  90                  95

Met Glu Arg Ala Asp Glu Ala Thr Leu Gly Ser Tyr Tyr Thr Ala Ala
            100                 105                 110

Ala Lys Lys Arg Phe Gln Phe Lys Val Val Pro Asn Tyr Ala Ile Thr
        115                 120                 125

Thr Gln Asp Ala Met Lys Asn Val Trp Gln Val Leu Val Asn Ile Arg
    130                 135                 140

Asn Val Lys Met Ser Ala Gly Phe Cys Pro Leu Ser Leu Glu Phe Val
145                 150                 155                 160
```

-continued

```
Ser Val Cys Ile Val Tyr Arg Asn Asn Ile Lys Leu Gly Leu Arg Glu
              165                 170                 175

Lys Ile Thr Asn Val Arg Asp Gly Gly Pro Met Glu Leu Thr Glu Glu
              180                 185                 190

Val Val Asp Glu Phe Met Glu Asp Val Pro Met Ser Ile Arg Leu Ala
              195                 200                 205

Lys Phe Arg Ser Arg Thr Gly Lys Lys Ser Asp Val Arg Lys Gly Lys
              210                 215                 220

Asn Ser Ser Ser Asp Arg Ser Val Pro Asn Lys Asn Tyr Arg Asn Val
225                 230                 235                 240

Lys Asp Phe Gly Gly Met Ser Phe Lys Lys Asn Asn Leu Ile Asp Asp
              245                 250                 255

Asp Ser Glu Ala Thr Val Ala Glu Ser Asp Ser Phe
              260                 265

<210> SEQ ID NO 14
<211> LENGTH: 264
<212> TYPE: PRT
<213> ORGANISM: Tomato mosaic virus

<400> SEQUENCE: 14

Met Ala Leu Val Val Lys Gly Lys Val Asn Ile Asn Glu Phe Ile Asp
1                 5                   10                  15

Leu Ser Lys Ser Glu Lys Leu Leu Pro Ser Met Phe Thr Pro Val Lys
              20                  25                  30

Ser Val Met Val Ser Lys Val Asp Lys Ile Met Val His Glu Asn Glu
              35                  40                  45

Ser Leu Ser Glu Val Asn Leu Leu Lys Gly Val Lys Leu Ile Glu Gly
              50                  55                  60

Gly Tyr Val Cys Leu Val Gly Leu Val Val Ser Gly Glu Trp Asn Leu
65                  70                  75                  80

Pro Asp Asn Cys Arg Gly Gly Val Ser Val Cys Met Val Asp Lys Arg
              85                  90                  95

Met Glu Arg Ala Asp Glu Ala Thr Leu Gly Ser Tyr Tyr Thr Ala Ala
              100                 105                 110

Ala Lys Lys Arg Phe Gln Phe Lys Val Val Pro Asn Tyr Gly Ile Thr
              115                 120                 125

Thr Lys Asp Ala Glu Lys Asn Ile Trp Gln Val Leu Val Asn Ile Lys
              130                 135                 140

Asn Val Lys Met Ser Ala Gly Tyr Cys Pro Leu Ser Leu Glu Phe Val
145                 150                 155                 160

Ser Val Cys Ile Val Tyr Lys Asn Asn Ile Lys Leu Gly Leu Arg Glu
              165                 170                 175

Lys Val Thr Ser Val Asn Asp Gly Gly Pro Met Glu Leu Ser Glu Glu
              180                 185                 190

Val Val Asp Glu Phe Met Glu Asn Val Pro Met Ser Val Arg Leu Ala
              195                 200                 205

Lys Phe Arg Thr Lys Ser Ser Lys Arg Gly Pro Lys Asn Asn Asn Asn
              210                 215                 220

Leu Gly Lys Gly Arg Ser Gly Gly Arg Ser Lys Pro Lys Ser Phe Asp
225                 230                 235                 240

Glu Val Glu Lys Glu Phe Asp Asn Leu Ile Glu Asp Glu Ala Glu Thr
              245                 250                 255

Ser Val Ala Asp Ser Asp Ser Tyr
```

US 12,642,203 B2

89                                                                90

-continued

260

<210> SEQ ID NO 15
<211> LENGTH: 266
<212> TYPE: PRT
<213> ORGANISM: Tomato brown rugose fruit virus

<400> SEQUENCE: 15

Met Ala Leu Val Lys Gly Lys Val Asn Ile Asn Glu Phe Ile Asp Leu
1               5                   10                  15

Ser Lys Ser Glu Lys Phe Leu Pro Ser Met Phe Thr Pro Val Lys Ser
                20                  25                  30

Val Met Ile Ser Lys Val Asp Lys Ile Leu Val His Glu Asp Glu Ser
            35                  40                  45

Leu Ser Glu Val Asn Leu Leu Lys Gly Val Lys Leu Ile Asp Gly Gly
        50                  55                  60

Tyr Val His Leu Ala Gly Leu Val Val Thr Gly Glu Trp Asn Leu Pro
65                  70                  75                  80

Asp Asn Cys Arg Gly Gly Val Ser Val Cys Leu Val Asp Lys Arg Met
                85                  90                  95

Glu Arg Ala Asp Glu Ala Thr Leu Ala Ser Tyr Tyr Thr Ala Ala Ala
            100                 105                 110

Lys Lys Arg Phe Gln Phe Lys Val Val Pro Asn Tyr Asn Ile Thr Thr
        115                 120                 125

Lys Asp Ala Glu Lys Ala Val Trp Gln Val Leu Val Asn Ile Arg Asn
    130                 135                 140

Val Lys Ile Ala Ala Gly Tyr Cys Pro Leu Ser Leu Glu Phe Val Ser
145                 150                 155                 160

Val Cys Ile Val Tyr Lys Asn Ile Ile Lys Leu Gly Leu Arg Glu Lys
                165                 170                 175

Ile Thr Ser Val Thr Asp Gly Gly Pro Met Glu Leu Ser Glu Glu Val
            180                 185                 190

Val Asp Glu Phe Met Glu Glu Val Pro Met Ser Val Arg Leu Ala Lys
        195                 200                 205

Phe Arg Ser Lys Thr Gly Lys Lys Phe Ser Ser Lys Ser Glu Asn Asn
    210                 215                 220

Ser Gly Asn Asn Arg Pro Lys Pro Asn Lys Asn Gln Arg Lys Glu Lys
225                 230                 235                 240

Gly Leu Lys Val Arg Val Glu Lys Asp Asn Leu Ile Asp Asn Glu Leu
                245                 250                 255

Glu Thr Tyr Val Ala Asp Ser Asp Ser Tyr
            260                 265

<210> SEQ ID NO 16
<211> LENGTH: 268
<212> TYPE: PRT
<213> ORGANISM: Tomato mottle virus

<400> SEQUENCE: 16

Met Ala Leu Thr Val Ser Gly Lys Val Arg Ile Ser Glu Phe Ile Asp
1               5                   10                  15

Leu Ser Lys Ser Glu Arg Leu Leu Pro Ser Met Phe Thr His Val Lys
                20                  25                  30

Ser Val Ser Val Ser Lys Val Asp Lys Val Met Val Asn Glu Glu Asp
            35                  40                  45

Ser Leu Ser Glu Val Asn Leu Leu Lys Gly Val Lys Leu Ile Asp Gly

-continued

```
            50                  55                  60
Gly Tyr Val Cys Leu Ala Gly Leu Val Val Ser Gly Glu Trp Asn Leu
65                  70                  75                  80

Pro Asp Asn Cys Arg Gly Gly Val Ser Ile Cys Leu Val Asp Lys Arg
                85                  90                  95

Met Gln Arg Ala Asp Glu Ala Thr Leu Gly Ser Tyr Tyr Thr Gly Ala
                100                 105                 110

Ala Lys Lys Arg Phe Gln Phe Lys Ile Val Pro Asn Tyr Ala Ile Thr
                115                 120                 125

Thr Lys Asp Ala Glu Lys Asn Ile Trp Gln Val Leu Val Asn Ile Arg
                130                 135                 140

Asn Val Lys Met Ala Gly Gly Phe Cys Pro Leu Ser Leu Glu Phe Val
145                 150                 155                 160

Ser Val Cys Ile Val Tyr Lys Asn Asn Ile Lys Leu Gly Leu Arg Glu
                165                 170                 175

Lys Ile Thr Arg Val Asp Asp Ala Gly Pro Ile Glu Leu Thr Glu Glu
                180                 185                 190

Val Val Asp Glu Phe Met Glu Ser Val Pro Met Ser Val Arg Leu Ala
                195                 200                 205

Lys Phe Arg Thr Lys Ser Ser Lys Arg Gly Pro Lys His Asn Ser Asn
                210                 215                 220

Asn Thr Asn Asp Arg Lys Gly Arg Ser Asn Phe Arg Lys Lys Gln Asp
225                 230                 235                 240

Gln Glu Ser Tyr Gly Val Ser Asp Ser Leu Asp Asn Leu Ile Glu Asp
                245                 250                 255

Asp Thr Glu Thr Ser Val Ala Gly Ser Asp Ser Tyr
                260                 265

<210> SEQ ID NO 17
<211> LENGTH: 861
<212> TYPE: PRT
<213> ORGANISM: artificial
<220> FEATURE:
<223> OTHER INFORMATION: mutant

<400> SEQUENCE: 17

Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
                20                  25                  30

Glu Asp Ile Asp Trp Leu Gln Arg Glu Met Arg His Ile Arg Ser Tyr
                35                  40                  45

Val Asp Asn Ala Lys Ala Lys Glu Ala Gly Gly Asp Ser Arg Val Lys
                50                  55                  60

Asn Leu Leu Lys Asp Ile Gln Glu Leu Ala Gly Asp Val Glu Asp Leu
65                  70                  75                  80

Leu Asp Asp Phe Leu Pro Lys Ile Gln Gln Ser Asn Lys Phe Asn Tyr
                85                  90                  95

Cys Leu Lys Arg Ser Ser Phe Ala Asp Glu Phe Ala Met Glu Ile Glu
                100                 105                 110

Lys Ile Lys Arg Arg Val Val Asp Ile Asp Arg Ile Arg Lys Thr Tyr
                115                 120                 125

Asn Ile Ile Asp Thr Asp Asn Asn Asp Asp Cys Val Leu Leu Asp
                130                 135                 140

Arg Arg Arg Leu Phe Leu His Ala Asp Glu Thr Glu Ile Ile Gly Leu
```

-continued

```
145               150               155               160

Asp Asp Asp Phe Asn Met Leu Gln Ala Lys Leu Leu Asn Gln Asp Leu
             165               170               175

His Tyr Gly Val Val Ser Ile Val Gly Met Pro Gly Leu Gly Lys Thr
             180               185               190

Thr Leu Ala Lys Lys Leu Tyr Arg Leu Ile Arg Asp Gln Phe Glu Cys
         195               200               205

Ser Gly Leu Val Tyr Val Ser Gln Gln Pro Arg Ala Ser Glu Ile Leu
     210               215               220

Leu Asp Ile Ala Lys Gln Ile Gly Leu Thr Glu Gln Lys Met Lys Glu
225               230               235               240

Asn Leu Glu Asp Asn Leu Arg Ser Leu Leu Lys Ile Lys Arg Tyr Val
             245               250               255

Ile Leu Leu Asp Asp Ile Trp Asp Val Glu Ile Trp Asp Asp Leu Lys
             260               265               270

Leu Val Leu Pro Glu Cys Asp Ser Lys Val Gly Ser Arg Met Ile Ile
         275               280               285

Thr Ser Arg Asn Ser Asn Val Gly Arg Tyr Ile Gly Gly Glu Ser Ser
     290               295               300

Leu His Ala Leu Gln Pro Leu Glu Ser Glu Lys Ser Phe Glu Leu Phe
305               310               315               320

Thr Lys Lys Ile Phe Asn Phe Asp Asp Asn Asn Ser Trp Ala Asn Ala
             325               330               335

Ser Pro Asp Leu Val Asn Ile Gly Arg Asn Ile Val Gly Arg Cys Gly
         340               345               350

Gly Ile Pro Leu Ala Ile Val Val Thr Ala Gly Met Leu Arg Ala Arg
         355               360               365

Glu Arg Thr Glu His Ala Trp Asn Arg Val Leu Glu Ser Met Gly His
     370               375               380

Lys Val Gln Asp Gly Cys Ala Lys Val Leu Ala Leu Ser Tyr Asn Asp
385               390               395               400

Leu Pro Ile Ala Ser Arg Pro Cys Phe Leu Tyr Phe Gly Leu Tyr Pro
             405               410               415

Glu Asp His Glu Ile Arg Ala Phe Asp Leu Ile Asn Met Trp Ile Ala
             420               425               430

Glu Lys Phe Ile Val Val Asn Ser Gly Asn Arg Arg Glu Ala Glu Asp
         435               440               445

Leu Ala Glu Asp Val Leu Asn Asp Leu Val Ser Arg Asn Leu Ile Gln
     450               455               460

Leu Ala Lys Arg Thr Tyr Asn Gly Arg Ile Ser Ser Cys Arg Ile His
465               470               475               480

Asp Leu Leu His Ser Leu Cys Val Asp Leu Ala Lys Glu Ser Asn Phe
             485               490               495

Phe His Thr Ala His Asp Ala Phe Gly Asp Pro Gly Asn Val Ala Arg
         500               505               510

Leu Arg Arg Ile Thr Phe Tyr Ser Asp Asn Val Met Ile Glu Phe Phe
         515               520               525

Arg Ser Asn Pro Lys Leu Glu Lys Leu Arg Val Leu Phe Cys Phe Ala
     530               535               540

Lys Asp Pro Ser Ile Phe Ser His Met Ala Tyr Phe Asp Phe Lys Leu
545               550               555               560

Leu His Thr Leu Val Val Val Met Ser Gln Ser Phe Gln Ala Tyr Val
             565               570               575
```

-continued

```
Thr Ile Pro Ser Lys Phe Gly Asn Met Thr Cys Leu Arg Tyr Leu Arg
        580                 585                 590

Leu Glu Gly Asn Ile Cys Gly Lys Leu Pro Asn Ser Ile Val Lys Leu
        595                 600                 605

Thr Arg Leu Glu Thr Ile Asp Ile Asp Arg Arg Ser Leu Ile Gln Pro
        610                 615                 620

Pro Ser Gly Val Trp Glu Ser Lys His Leu Arg His Leu Cys Tyr Arg
625                 630                 635                 640

Asp Tyr Gly Gln Ala Cys Asn Ser Cys Phe Ser Ile Ser Ser Phe Tyr
                645                 650                 655

Pro Asn Ile Tyr Ser Leu His Pro Asn Asn Leu Gln Thr Leu Met Trp
                660                 665                 670

Ile Pro Asp Lys Phe Phe Glu Pro Arg Leu Leu His Arg Leu Ile Asn
                675                 680                 685

Leu Arg Lys Leu Gly Ile Leu Gly Val Ser Asn Ser Thr Val Lys Met
        690                 695                 700

Leu Ser Ile Phe Ser Pro Val Leu Lys Ala Leu Glu Val Leu Lys Leu
705                 710                 715                 720

Ser Phe Ser Ser Asp Pro Ser Glu Gln Ile Lys Leu Ser Ser Tyr Pro
                725                 730                 735

His Ile Ala Lys Leu His Leu Asn Val Asn Arg Thr Met Ala Leu Asn
                740                 745                 750

Ser Gln Ser Phe Pro Pro Asn Leu Ile Lys Leu Thr Leu Ala Phe Phe
                755                 760                 765

Ser Val Asp Arg Tyr Ile Leu Ala Val Leu Lys Thr Phe Pro Lys Leu
        770                 775                 780

Arg Lys Leu Lys Met Phe Ile Cys Lys Tyr Asn Glu Glu Lys Met Asp
785                 790                 795                 800

Leu Ser Gly Glu Ala Asn Gly Tyr Ser Phe Pro Gln Leu Glu Val Leu
                805                 810                 815

His Ile His Ser Pro Asn Gly Leu Ser Glu Val Thr Cys Thr Asp Asp
                820                 825                 830

Val Ser Met Pro Lys Leu Lys Lys Leu Leu Leu Thr Gly Phe His Arg
        835                 840                 845

Arg Ile Ser Leu Ser Glu Arg Leu Lys Lys Leu Ser Lys
        850                 855                 860
```

```
<210> SEQ ID NO 18
<211> LENGTH: 861
<212> TYPE: PRT
<213> ORGANISM: artificial
<220> FEATURE:
<223> OTHER INFORMATION: mutant

<400> SEQUENCE: 18
```

```
Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
                20                  25                  30

Glu Asp Ile Asp Trp Leu Gln Arg Glu Met Arg His Ile Arg Ser Tyr
        35                  40                  45

Val Asp Asn Ala Lys Ala Lys Glu Ala Gly Gly Asp Ser Arg Val Lys
        50                  55                  60

Asn Leu Leu Lys Asp Ile Gln Glu Leu Ala Gly Asp Val Glu Asp Leu
65                  70                  75                  80
```

-continued

```
Leu Asp Asp Phe Leu Pro Lys Ile Gln Gln Ser Asn Lys Phe Asn Tyr
            85              90              95

Cys Leu Lys Arg Ser Ser Phe Ala Asp Glu Phe Ala Met Glu Ile Glu
            100             105             110

Lys Ile Lys Arg Arg Val Val Asp Ile Asp Arg Ile Arg Lys Thr Tyr
            115             120             125

Asn Ile Ile Asp Thr Asp Asn Asn Asp Asp Cys Val Leu Leu Asp
        130             135             140

Arg Arg Arg Leu Phe Leu His Ala Asp Glu Thr Glu Ile Ile Gly Leu
145             150             155             160

Asp Asp Asp Phe Asn Met Leu Gln Ala Lys Leu Leu Asn Gln Asp Leu
            165             170             175

His Tyr Gly Val Val Ser Ile Val Gly Met Pro Gly Leu Gly Lys Thr
            180             185             190

Thr Leu Ala Lys Lys Leu Tyr Arg Leu Ile Arg Asp Gln Phe Glu Cys
            195             200             205

Ser Gly Leu Val Tyr Val Ser Gln Gln Pro Arg Ala Ser Glu Ile Leu
            210             215             220

Leu Asp Ile Ala Lys Gln Ile Gly Leu Thr Glu Gln Lys Met Lys Glu
225             230             235             240

Asn Leu Glu Asp Asn Leu Arg Ser Leu Leu Lys Ile Lys Arg Tyr Val
            245             250             255

Ile Leu Leu Asp Asp Ile Trp Asp Val Glu Ile Trp Asp Asp Leu Lys
            260             265             270

Leu Val Leu Pro Glu Cys Asp Ser Lys Val Gly Ser Arg Met Ile Ile
            275             280             285

Thr Ser Arg Asn Ser Asn Val Gly Arg Tyr Ile Gly Gly Glu Ser Ser
            290             295             300

Leu His Ala Leu Gln Pro Leu Glu Ser Glu Lys Ser Phe Glu Leu Phe
305             310             315             320

Thr Lys Lys Ile Phe Asn Phe Asp Asp Asn Asn Ser Trp Ala Asn Ala
            325             330             335

Ser Pro Asp Leu Val Asn Ile Gly Arg Asn Ile Val Gly Arg Cys Gly
            340             345             350

Gly Ile Pro Leu Ala Ile Val Val Thr Ala Gly Met Leu Arg Ala Arg
            355             360             365

Glu Arg Thr Glu His Ala Trp Asn Arg Val Leu Glu Ser Met Gly His
            370             375             380

Lys Val Gln Asp Gly Cys Ala Lys Val Leu Ala Leu Ser Tyr Asn Asp
385             390             395             400

Leu Pro Ile Ala Ser Arg Pro Cys Phe Leu Tyr Phe Gly Leu Tyr Pro
            405             410             415

Glu Asp His Glu Ile Arg Ala Phe Asp Leu Ile Asn Met Trp Ile Ala
            420             425             430

Glu Lys Phe Ile Val Val Asn Ser Gly Asn Arg Arg Glu Ala Glu Asp
            435             440             445

Leu Ala Glu Asp Val Leu Asn Asp Leu Val Ser Arg Asn Leu Ile Gln
            450             455             460

Leu Ala Lys Arg Thr Tyr Asn Gly Arg Ile Ser Ser Cys Arg Ile His
465             470             475             480

Asp Leu Leu His Ser Leu Cys Val Asp Leu Ala Lys Glu Ser Asn Phe
            485             490             495
```

-continued

```
Phe His Thr Ala His Asp Ala Phe Gly Asp Pro Gly Asn Val Ala Arg
            500                 505                 510

Leu Arg Arg Ile Thr Phe Tyr Ser Asp Asn Val Met Ile Glu Phe Phe
            515                 520                 525

Arg Ser Asn Pro Lys Leu Glu Lys Leu Arg Val Leu Phe Cys Phe Ala
            530                 535                 540

Lys Asp Pro Ser Ile Phe Ser His Met Ala Tyr Phe Asp Phe Lys Leu
545                 550                 555                 560

Leu His Thr Leu Val Val Val Met Ser Gln Ser Phe Gln Ala Tyr Val
                565                 570                 575

Thr Ile Pro Ser Lys Phe Gly Asn Met Thr Cys Leu Arg Tyr Leu Arg
            580                 585                 590

Leu Glu Gly Asn Ile Cys Gly Lys Leu Pro Asn Ser Ile Val Lys Leu
            595                 600                 605

Thr Arg Leu Glu Thr Ile Asp Ile Asp Arg Arg Ser Leu Ile Gln Pro
    610                 615                 620

Pro Ser Gly Val Trp Glu Ser Lys His Leu Arg His Leu Cys Tyr Arg
625                 630                 635                 640

Asp Tyr Gly Gln Ala Cys Asn Ser Cys Phe Ser Ile Ser Ser Phe Tyr
                645                 650                 655

Pro Asn Ile Tyr Ser Leu His Pro Asn Asn Leu Gln Thr Leu Met Trp
            660                 665                 670

Ile Pro Asp Lys Phe Phe Glu Pro Arg Leu Leu His Arg Leu Ile Asn
            675                 680                 685

Leu Arg Lys Leu Gly Ile Leu Gly Val Ser Asn Ser Thr Val Lys Met
    690                 695                 700

Leu Ser Ile Phe Ser Pro Val Leu Lys Ala Leu Glu Val Leu Lys Leu
705                 710                 715                 720

Ser Phe Ser Ser Asp Pro Ser Glu Gln Ile Lys Leu Ser Ser Tyr Pro
                725                 730                 735

His Ile Ala Lys Leu His Leu Asn Val Asn Arg Thr Met Ala Leu Asn
            740                 745                 750

Ser Gln Ser Phe Pro Pro Asn Leu Ile Lys Leu Thr Leu Ala Trp Phe
            755                 760                 765

Ser Val Asp Arg Tyr Ile Leu Ala Val Leu Lys Thr Phe Pro Lys Leu
    770                 775                 780

Arg Lys Leu Lys Met Phe Ile Cys Lys Tyr Asn Glu Glu Lys Met Asp
785                 790                 795                 800

Leu Ser Gly Glu Ala Asn Gly Tyr Ser Phe Pro Gln Leu Glu Val Leu
                805                 810                 815

His Ile His Ser Pro Asn Gly Leu Ser Glu Val Thr Cys Thr Asp Asp
            820                 825                 830

Val Ser Met Pro Lys Leu Lys Lys Leu Leu Leu Thr Gly Phe His Arg
            835                 840                 845

Arg Ile Ser Leu Ser Glu Arg Leu Lys Lys Leu Ser Lys
    850                 855                 860
```

```
<210> SEQ ID NO 19
<211> LENGTH: 861
<212> TYPE: PRT
<213> ORGANISM: artificial
<220> FEATURE:
<223> OTHER INFORMATION: mutant

<400> SEQUENCE: 19
```

```
Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
            20                  25                  30

Glu Asp Ile Asp Trp Leu Gln Arg Glu Met Arg His Ile Arg Ser Tyr
            35                  40                  45

Val Asp Asn Ala Lys Ala Lys Glu Ala Gly Gly Asp Ser Arg Val Lys
        50                  55                  60

Asn Leu Leu Lys Asp Ile Gln Glu Leu Ala Gly Asp Val Glu Asp Leu
65                  70                  75                  80

Leu Asp Asp Phe Leu Pro Lys Ile Gln Gln Ser Asn Lys Phe Asn Tyr
                85                  90                  95

Cys Leu Lys Arg Ser Ser Phe Ala Asp Glu Phe Ala Met Glu Ile Glu
            100                 105                 110

Lys Ile Lys Arg Arg Val Val Asp Ile Asp Arg Ile Arg Lys Thr Tyr
            115                 120                 125

Asn Ile Ile Asp Thr Asp Asn Asn Asp Asp Cys Val Leu Leu Asp
        130                 135                 140

Arg Arg Arg Leu Phe Leu His Ala Asp Glu Thr Glu Ile Ile Gly Leu
145                 150                 155                 160

Asp Asp Asp Phe Asn Met Leu Gln Ala Lys Leu Leu Asn Gln Asp Leu
                165                 170                 175

His Tyr Gly Val Val Ser Ile Val Gly Met Pro Gly Leu Gly Lys Thr
            180                 185                 190

Thr Leu Ala Lys Lys Leu Tyr Arg Leu Ile Arg Asp Gln Phe Glu Cys
            195                 200                 205

Ser Gly Leu Val Tyr Val Ser Gln Gln Pro Arg Ala Ser Glu Ile Leu
        210                 215                 220

Leu Asp Ile Ala Lys Gln Ile Gly Leu Thr Glu Gln Lys Met Lys Glu
225                 230                 235                 240

Asn Leu Glu Asp Asn Leu Arg Ser Leu Leu Lys Ile Lys Arg Tyr Val
                245                 250                 255

Ile Leu Leu Asp Asp Ile Trp Asp Val Glu Ile Trp Asp Asp Leu Lys
                260                 265                 270

Leu Val Leu Pro Glu Cys Asp Ser Lys Val Gly Ser Arg Met Ile Ile
            275                 280                 285

Thr Ser Arg Asn Ser Asn Val Gly Arg Tyr Ile Gly Gly Glu Ser Ser
        290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Asn Ser Trp Ala Asn Ala
                325                 330                 335

Ser Pro Asp Leu Val Asn Ile Gly Arg Asn Ile Val Gly Arg Cys Gly
                340                 345                 350

Gly Ile Pro Leu Ala Ile Val Val Thr Ala Gly Met Leu Arg Ala Arg
            355                 360                 365

Glu Arg Thr Glu His Ala Trp Asn Arg Val Leu Glu Ser Met Gly His
        370                 375                 380

Lys Val Gln Asp Gly Cys Ala Lys Val Leu Ala Leu Ser Tyr Asn Asp
385                 390                 395                 400

Leu Pro Ile Ala Ser Arg Pro Cys Phe Leu Tyr Phe Gly Leu Tyr Pro
                405                 410                 415

Glu Asp His Glu Ile Arg Ala Phe Asp Leu Ile Asn Met Trp Ile Ala
```

-continued

```
            420                 425                 430
Glu Lys Phe Ile Val Val Asn Ser Gly Asn Arg Arg Glu Ala Glu Asp
        435                 440                 445

Leu Ala Glu Asp Val Leu Asn Asp Leu Val Ser Arg Asn Leu Ile Gln
        450                 455                 460

Leu Ala Lys Arg Thr Tyr Asn Gly Arg Ile Ser Ser Cys Arg Ile His
465                 470                 475                 480

Asp Leu Leu His Ser Leu Cys Val Asp Leu Ala Lys Glu Ser Asn Phe
                485                 490                 495

Phe His Thr Ala His Asp Ala Phe Gly Asp Pro Gly Asn Val Ala Arg
            500                 505                 510

Leu Arg Arg Ile Thr Phe Tyr Ser Asp Asn Val Met Ile Glu Phe Phe
            515                 520                 525

Arg Ser Asn Pro Lys Leu Glu Lys Leu Arg Val Leu Phe Cys Phe Ala
            530                 535                 540

Lys Asp Pro Ser Ile Phe Ser His Met Ala Tyr Phe Asp Phe Lys Leu
545                 550                 555                 560

Leu His Thr Leu Val Val Val Met Ser Gln Ser Phe Gln Ala Tyr Val
                565                 570                 575

Thr Ile Pro Ser Lys Phe Gly Asn Met Thr Cys Leu Arg Tyr Leu Arg
            580                 585                 590

Leu Glu Gly Asn Ile Cys Gly Lys Leu Pro Asn Ser Ile Val Lys Leu
            595                 600                 605

Thr Arg Leu Glu Thr Ile Asp Ile Asp Arg Arg Ser Leu Ile Gln Pro
        610                 615                 620

Pro Ser Gly Val Trp Glu Ser Lys His Leu Arg His Leu Cys Tyr Arg
625                 630                 635                 640

Asp Tyr Gly Gln Ala Cys Asn Ser Cys Phe Ser Ile Ser Ser Phe Tyr
                645                 650                 655

Pro Asn Ile Tyr Ser Leu His Pro Asn Asn Leu Gln Thr Leu Met Trp
            660                 665                 670

Ile Pro Asp Lys Phe Phe Glu Pro Arg Leu Leu His Arg Leu Ile Asn
            675                 680                 685

Leu Arg Lys Leu Gly Ile Leu Gly Val Ser Asn Ser Thr Val Lys Met
        690                 695                 700

Leu Ser Ile Phe Ser Pro Val Leu Lys Ala Leu Glu Val Leu Lys Leu
705                 710                 715                 720

Ser Phe Ser Ser Asp Pro Ser Glu Gln Ile Lys Leu Ser Ser Tyr Pro
                725                 730                 735

His Ile Ala Lys Leu His Leu Asn Val Asn Arg Thr Met Ala Leu Asn
            740                 745                 750

Ser Gln Ser Phe Pro Pro Asn Leu Ile Lys Leu Thr Leu Ala Tyr Phe
            755                 760                 765

Ser Val Asp Arg Tyr Ile Leu Ala Val Leu Lys Thr Phe Pro Lys Leu
        770                 775                 780

Arg Lys Leu Lys Met Phe Ile Cys Lys Tyr Asn Glu Glu Lys Met Asp
785                 790                 795                 800

Leu Ser Gly Glu Ala Asn Gly Tyr Ser Phe Pro Gln Leu Glu Val Leu
                805                 810                 815

His Ile His Ser Pro Asn Gly Leu His Glu Val Thr Cys Thr Asp Asp
            820                 825                 830

Val Ser Met Pro Lys Leu Lys Lys Leu Leu Leu Thr Gly Phe His Cys
            835                 840                 845
```

-continued

```
Arg Ile Ser Leu Ser Glu Arg Leu Lys Lys Leu Ser Lys
    850                 855                 860

<210> SEQ ID NO 20
<211> LENGTH: 861
<212> TYPE: PRT
<213> ORGANISM: Lycopersicon esculentum

<400> SEQUENCE: 20

Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Ala Gly Gly Asp Ser Arg Val Lys
    50                  55                  60

Asn Leu Leu Lys Asp Ile Gln Glu Leu Ala Gly Asp Val Glu Asp Leu
65                  70                  75                  80

Leu Asp Asp Phe Leu Pro Lys Ile Gln Gln Ser Asn Lys Phe Asn Tyr
                85                  90                  95

Cys Leu Lys Arg Ser Ser Phe Ala Asp Glu Phe Ala Met Glu Ile Glu
            100                 105                 110

Lys Ile Lys Arg Arg Val Val Asp Ile Asp Arg Ile Arg Lys Thr Tyr
            115                 120                 125

Asn Ile Ile Asp Thr Asp Asn Asn Asp Asp Cys Val Leu Leu Asp
    130                 135                 140

Arg Arg Arg Leu Phe Leu His Ala Asp Glu Thr Glu Ile Ile Gly Leu
145                 150                 155                 160

Asp Asp Asp Phe Asn Met Leu Gln Ala Lys Leu Leu Asn Gln Asp Leu
                165                 170                 175

His Tyr Gly Val Val Ser Ile Val Gly Met Pro Gly Leu Gly Lys Thr
            180                 185                 190

Thr Leu Ala Lys Lys Leu Tyr Arg Leu Ile Arg Asp Gln Phe Glu Cys
            195                 200                 205

Ser Gly Leu Val Tyr Val Ser Gln Gln Pro Arg Ala Ser Glu Ile Leu
    210                 215                 220

Leu Asp Ile Ala Lys Gln Ile Gly Leu Thr Glu Gln Lys Met Lys Glu
225                 230                 235                 240

Asn Leu Glu Asp Asn Leu Arg Ser Leu Leu Lys Ile Lys Arg Tyr Val
                245                 250                 255

Ile Leu Leu Asp Asp Ile Trp Asp Val Glu Ile Trp Asp Asp Leu Lys
            260                 265                 270

Leu Val Leu Pro Glu Cys Asp Ser Lys Val Gly Ser Arg Met Ile Ile
            275                 280                 285

Thr Ser Arg Asn Ser Asn Val Gly Arg Tyr Ile Gly Gly Glu Ser Ser
    290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Asn Ser Trp Ala Asn Ala
                325                 330                 335

Ser Pro Asp Leu Val Asn Ile Gly Arg Asn Ile Val Gly Arg Cys Gly
            340                 345                 350

Gly Ile Pro Leu Ala Ile Val Val Thr Ala Gly Met Leu Arg Ala Arg
```

-continued

```
          355                 360                 365

Glu Arg Thr Glu His Ala Trp Asn Arg Val Leu Glu Ser Met Gly His
    370                 375                 380

Lys Val Gln Asp Gly Cys Ala Lys Val Leu Ala Leu Ser Tyr Asn Asp
385                 390                 395                 400

Leu Pro Ile Ala Ser Arg Pro Cys Phe Leu Tyr Phe Gly Leu Tyr Pro
                405                 410                 415

Glu Asp His Glu Ile Arg Ala Phe Asp Leu Ile Asn Met Trp Ile Ala
                420                 425                 430

Glu Lys Phe Ile Val Val Asn Ser Gly Asn Arg Arg Glu Ala Glu Asp
                435                 440                 445

Leu Ala Glu Asp Val Leu Asn Asp Leu Val Ser Arg Asn Leu Ile Gln
    450                 455                 460

Leu Ala Lys Arg Thr Tyr Asn Gly Arg Ile Ser Ser Cys Arg Ile His
465                 470                 475                 480

Asp Leu Leu His Ser Leu Cys Val Asp Leu Ala Lys Glu Ser Asn Phe
                485                 490                 495

Phe His Thr Ala His Asp Ala Phe Gly Asp Pro Gly Asn Val Ala Arg
                500                 505                 510

Leu Arg Arg Ile Thr Phe Tyr Ser Asp Asn Val Met Ile Glu Phe Phe
                515                 520                 525

Arg Ser Asn Pro Lys Leu Glu Lys Leu Arg Val Leu Phe Cys Phe Ala
    530                 535                 540

Lys Asp Pro Ser Ile Phe Ser His Met Ala Tyr Phe Asp Phe Lys Leu
545                 550                 555                 560

Leu His Thr Leu Val Val Val Met Ser Gln Ser Phe Gln Ala Tyr Val
                565                 570                 575

Thr Ile Pro Ser Lys Phe Gly Asn Met Thr Cys Leu Arg Tyr Leu Arg
                580                 585                 590

Leu Glu Gly Asn Ile Cys Gly Lys Leu Pro Asn Ser Ile Val Lys Leu
                595                 600                 605

Thr Arg Leu Glu Thr Ile Asp Ile Asp Arg Arg Ser Leu Ile Gln Pro
    610                 615                 620

Pro Ser Gly Val Trp Glu Ser Lys His Leu Arg His Leu Cys Tyr Arg
625                 630                 635                 640

Asp Tyr Gly Gln Ala Cys Asn Ser Cys Phe Ser Ile Ser Ser Phe Tyr
                645                 650                 655

Pro Asn Ile Tyr Ser Leu His Pro Asn Asn Leu Gln Thr Leu Met Trp
                660                 665                 670

Ile Pro Asp Lys Phe Phe Glu Pro Arg Leu Leu His Arg Leu Ile Asn
                675                 680                 685

Leu Arg Lys Leu Gly Ile Leu Gly Val Ser Asn Ser Thr Val Lys Met
    690                 695                 700

Leu Ser Ile Phe Ser Pro Val Leu Lys Ala Leu Glu Val Leu Lys Leu
705                 710                 715                 720

Ser Phe Ser Ser Asp Pro Ser Glu Gln Ile Lys Leu Ser Ser Tyr Pro
                725                 730                 735

His Ile Ala Lys Leu His Leu Asn Val Asn Arg Thr Met Ala Leu Asn
                740                 745                 750

Ser Gln Ser Phe Pro Pro Asn Leu Ile Lys Leu Thr Leu Ala Tyr Phe
                755                 760                 765

Ser Val Asp Arg Tyr Ile Leu Ala Val Leu Lys Thr Phe Pro Lys Leu
770                 775                 780
```

-continued

Arg Lys Leu Lys Met Phe Ile Cys Lys Tyr Asn Glu Glu Lys Met Asp
785                 790                 795                 800

Leu Ser Gly Glu Ala Asn Gly Tyr Ser Phe Pro Gln Leu Glu Val Leu
                805                 810                 815

His Ile His Ser Pro Asn Gly Leu Lys Glu Val Thr Cys Thr Asp Asp
            820                 825                 830

Val Ser Met Pro Lys Leu Lys Lys Leu Leu Leu Thr Gly Phe His Cys
            835                 840                 845

Arg Ile Ser Leu Ser Glu Arg Leu Lys Lys Leu Ser Lys
        850                 855                 860

<210> SEQ ID NO 21
<211> LENGTH: 861
<212> TYPE: PRT
<213> ORGANISM: artificial
<220> FEATURE:
<223> OTHER INFORMATION: mutant

<400> SEQUENCE: 21

Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
                20                  25                  30

Glu Asp Ile Asp Trp Leu Gln Arg Glu Met Arg His Ile Arg Ser Tyr
            35                  40                  45

Val Asp Asn Ala Lys Ala Lys Glu Ala Gly Gly Asp Ser Arg Val Lys
        50                  55                  60

Asn Leu Leu Lys Asp Ile Gln Glu Leu Ala Gly Asp Val Glu Asp Leu
65                  70                  75                  80

Leu Asp Asp Phe Leu Pro Lys Ile Gln Gln Ser Asn Lys Phe Asn Tyr
                85                  90                  95

Cys Leu Lys Arg Ser Ser Phe Ala Asp Glu Phe Ala Met Glu Ile Glu
            100                 105                 110

Lys Ile Lys Arg Arg Val Val Asp Ile Asp Arg Ile Arg Lys Thr Tyr
            115                 120                 125

Asn Ile Ile Asp Thr Asp Asn Asn Asn Asp Asp Cys Val Leu Leu Asp
        130                 135                 140

Arg Arg Arg Leu Phe Leu His Ala Asp Glu Thr Glu Ile Ile Gly Leu
145                 150                 155                 160

Asp Asp Asp Phe Asn Met Leu Gln Ala Lys Leu Leu Asn Gln Asp Leu
                165                 170                 175

His Tyr Gly Val Val Ser Ile Val Gly Met Pro Gly Leu Gly Lys Thr
            180                 185                 190

Thr Leu Ala Lys Lys Leu Tyr Arg Leu Ile Arg Asp Gln Phe Glu Cys
            195                 200                 205

Ser Gly Leu Val Tyr Val Ser Gln Gln Pro Arg Ala Ser Glu Ile Leu
        210                 215                 220

Leu Asp Ile Ala Lys Gln Ile Gly Leu Thr Glu Gln Lys Met Lys Glu
225                 230                 235                 240

Asn Leu Glu Asp Asn Leu Arg Ser Leu Leu Lys Ile Lys Arg Tyr Val
                245                 250                 255

Ile Leu Leu Asp Asp Ile Trp Asp Val Glu Ile Trp Asp Asp Leu Lys
            260                 265                 270

Leu Val Leu Pro Glu Cys Asp Ser Lys Val Gly Ser Arg Met Ile Ile
            275                 280                 285

```
Thr Ser Arg Asn Ser Asn Val Gly Arg Tyr Ile Gly Gly Glu Ser Ser
    290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Asn Ser Trp Ala Asn Ala
            325                 330                 335

Ser Pro Asp Leu Val Asn Ile Gly Arg Asn Ile Val Gly Arg Cys Gly
            340                 345                 350

Gly Ile Pro Leu Ala Ile Val Val Thr Ala Gly Met Leu Arg Ala Arg
            355                 360                 365

Glu Arg Thr Glu His Ala Trp Asn Arg Val Leu Glu Ser Met Gly His
    370                 375                 380

Lys Val Gln Asp Gly Cys Ala Lys Val Leu Ala Leu Ser Tyr Asn Asp
385                 390                 395                 400

Leu Pro Ile Ala Ser Arg Pro Cys Phe Leu Tyr Phe Gly Leu Tyr Pro
            405                 410                 415

Glu Asp His Glu Ile Arg Ala Phe Asp Leu Ile Asn Met Trp Ile Ala
            420                 425                 430

Glu Lys Phe Ile Val Val Asn Ser Gly Asn Arg Arg Glu Ala Glu Asp
            435                 440                 445

Leu Ala Glu Asp Val Leu Asn Asp Leu Val Ser Arg Asn Leu Ile Gln
    450                 455                 460

Leu Ala Lys Arg Thr Tyr Asn Gly Arg Ile Ser Ser Cys Arg Ile His
465                 470                 475                 480

Asp Leu Leu His Ser Leu Cys Val Asp Leu Ala Lys Glu Ser Asn Phe
                485                 490                 495

Phe His Thr Ala His Asp Ala Phe Gly Asp Pro Gly Asn Val Ala Arg
            500                 505                 510

Leu Arg Arg Ile Thr Phe Tyr Ser Asp Asn Val Met Ile Glu Phe Phe
    515                 520                 525

Arg Ser Asn Pro Lys Leu Glu Lys Leu Arg Val Leu Phe Cys Phe Ala
    530                 535                 540

Lys Asp Pro Ser Ile Phe Ser His Met Ala Tyr Phe Asp Phe Lys Leu
545                 550                 555                 560

Leu His Thr Leu Val Val Val Met Ser Gln Ser Phe Gln Ala Tyr Val
            565                 570                 575

Thr Ile Pro Ser Lys Phe Gly Asn Met Thr Cys Leu Arg Tyr Leu Arg
            580                 585                 590

Leu Glu Gly Asn Ile Cys Gly Lys Leu Pro Asn Ser Ile Val Lys Leu
            595                 600                 605

Thr Arg Leu Glu Thr Ile Asp Ile Asp Arg Arg Ser Leu Ile Gln Pro
    610                 615                 620

Pro Ser Gly Val Trp Glu Ser Lys His Leu Arg His Leu Cys Tyr Arg
625                 630                 635                 640

Asp Tyr Gly Gln Ala Cys Asn Ser Cys Phe Ser Ile Ser Ser Phe Tyr
            645                 650                 655

Pro Asn Ile Tyr Ser Leu His Pro Asn Asn Leu Gln Thr Leu Met Trp
            660                 665                 670

Ile Pro Asp Lys Phe Phe Glu Pro Arg Leu Leu His Arg Leu Ile Asn
            675                 680                 685

Leu Arg Lys Leu Gly Ile Leu Gly Val Ser Asn Ser Thr Val Lys Met
    690                 695                 700
```

-continued

```
Leu Ser Ile Phe Ser Pro Val Leu Lys Ala Leu Glu Val Leu Lys Leu
705             710             715             720

Ser Phe Ser Ser Asp Pro Ser Glu Gln Ile Lys Leu Ser Ser Tyr Pro
                725             730             735

His Ile Ala Lys Leu His Leu Asn Val Asn Arg Thr Met Ala Leu Asn
            740             745             750

Ser Gln Ser Phe Pro Pro Asn Leu Ile Lys Leu Thr Leu Ala Tyr Phe
            755             760             765

Ser Val Asp Arg Tyr Ile Leu Ala Val Leu Lys Thr Phe Pro Lys Leu
        770             775             780

Arg Lys Leu Lys Met Phe Ile Cys Lys Tyr Asn Glu Glu Lys Met Asp
785             790             795             800

Leu Ser Gly Glu Ala Asn Gly Tyr Ser Phe Pro Gln Leu Glu Val Leu
            805             810             815

His Ile His Ser Pro Asn Gly Leu Thr Glu Val Thr Cys Thr Asp Asp
            820             825             830

Val Ser Met Pro Lys Leu Lys Lys Leu Leu Leu Thr Gly Phe His Cys
            835             840             845

Arg Ile Ser Leu Ser Glu Arg Leu Lys Lys Leu Ser Lys
        850             855             860

<210> SEQ ID NO 22
<211> LENGTH: 861
<212> TYPE: PRT
<213> ORGANISM: artificial
<220> FEATURE:
<223> OTHER INFORMATION: mutant

<400> SEQUENCE: 22

Met Ala Glu Ile Leu Leu Thr Ser Val Ile Asn Lys Ser Val Glu Ile
1               5               10              15

Ala Gly Asn Leu Leu Ile Gln Glu Gly Lys Arg Leu Tyr Trp Leu Lys
            20              25              30

Glu Asp Ile Asp Trp Leu Gln Arg Glu Met Arg His Ile Arg Ser Tyr
            35              40              45

Val Asp Asn Ala Lys Ala Lys Glu Ala Gly Gly Asp Ser Arg Val Lys
        50              55              60

Asn Leu Leu Lys Asp Ile Gln Glu Leu Ala Gly Asp Val Glu Asp Leu
65              70              75              80

Leu Asp Asp Phe Leu Pro Lys Ile Gln Gln Ser Asn Lys Phe Asn Tyr
            85              90              95

Cys Leu Lys Arg Ser Ser Phe Ala Asp Glu Phe Ala Met Glu Ile Glu
            100             105             110

Lys Ile Lys Arg Arg Val Val Asp Ile Asp Arg Ile Arg Lys Thr Tyr
            115             120             125

Asn Ile Ile Asp Thr Asp Asn Asn Asp Asp Cys Val Leu Leu Asp
        130             135             140

Arg Arg Arg Leu Phe Leu His Ala Asp Glu Thr Glu Ile Ile Gly Leu
145             150             155             160

Asp Asp Asp Phe Asn Met Leu Gln Ala Lys Leu Leu Asn Gln Asp Leu
            165             170             175

His Tyr Gly Val Val Ser Ile Val Gly Met Pro Gly Leu Gly Lys Thr
            180             185             190

Thr Leu Ala Lys Lys Leu Tyr Arg Leu Ile Arg Asp Gln Phe Glu Cys
            195             200             205
```

-continued

```
Ser Gly Leu Val Tyr Val Ser Gln Gln Pro Arg Ala Ser Glu Ile Leu
    210                 215                 220

Leu Asp Ile Ala Lys Gln Ile Gly Leu Thr Glu Gln Lys Met Lys Glu
225                 230                 235                 240

Asn Leu Glu Asp Asn Leu Arg Ser Leu Leu Lys Ile Lys Arg Tyr Val
                245                 250                 255

Ile Leu Leu Asp Asp Ile Trp Asp Val Glu Ile Trp Asp Asp Leu Lys
                260                 265                 270

Leu Val Leu Pro Glu Cys Asp Ser Lys Val Gly Ser Arg Met Ile Ile
        275                 280                 285

Thr Ser Arg Asn Ser Asn Val Gly Arg Tyr Ile Gly Gly Glu Ser Ser
    290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Asn Ser Trp Ala Asn Ala
                325                 330                 335

Ser Pro Asp Leu Val Asn Ile Gly Arg Asn Ile Val Gly Arg Cys Gly
                340                 345                 350

Gly Ile Pro Leu Ala Ile Val Val Thr Ala Gly Met Leu Arg Ala Arg
        355                 360                 365

Glu Arg Thr Glu His Ala Trp Asn Arg Val Leu Glu Ser Met Gly His
    370                 375                 380

Lys Val Gln Asp Gly Cys Ala Lys Val Leu Ala Leu Ser Tyr Asn Asp
385                 390                 395                 400

Leu Pro Ile Ala Ser Arg Pro Cys Phe Leu Tyr Phe Gly Leu Tyr Pro
                405                 410                 415

Glu Asp His Glu Ile Arg Ala Phe Asp Leu Ile Asn Met Trp Ile Ala
                420                 425                 430

Glu Lys Phe Ile Val Val Asn Ser Gly Asn Arg Arg Glu Ala Glu Asp
        435                 440                 445

Leu Ala Glu Asp Val Leu Asn Asp Leu Val Ser Arg Asn Leu Ile Gln
    450                 455                 460

Leu Ala Lys Arg Thr Tyr Asn Gly Arg Ile Ser Ser Cys Arg Ile His
465                 470                 475                 480

Asp Leu Leu His Ser Leu Cys Val Asp Leu Ala Lys Glu Ser Asn Phe
                485                 490                 495

Phe His Thr Ala His Asp Ala Phe Gly Asp Pro Gly Asn Val Ala Arg
                500                 505                 510

Leu Arg Arg Ile Thr Phe Tyr Ser Asp Asn Val Met Ile Glu Phe Phe
        515                 520                 525

Arg Ser Asn Pro Lys Leu Glu Lys Leu Arg Val Leu Phe Cys Phe Ala
    530                 535                 540

Lys Asp Pro Ser Ile Phe Ser His Met Ala Tyr Phe Asp Phe Lys Leu
545                 550                 555                 560

Leu His Thr Leu Val Val Val Met Ser Gln Ser Phe Gln Ala Tyr Val
                565                 570                 575

Thr Ile Pro Ser Lys Phe Gly Asn Met Thr Cys Leu Arg Tyr Leu Arg
                580                 585                 590

Leu Glu Gly Asn Ile Cys Gly Lys Leu Pro Asn Ser Ile Val Lys Leu
                595                 600                 605

Thr Arg Leu Glu Thr Ile Asp Ile Asp Arg Arg Ser Leu Ile Gln Pro
    610                 615                 620

Pro Ser Gly Val Trp Glu Ser Lys His Leu Arg His Leu Cys Tyr Arg
```

```
625                630                635                640

Asp Tyr Gly Gln Ala Cys Asn Ser Cys Phe Ser Ile Ser Ser Phe Tyr
            645                650                655

Pro Asn Ile Tyr Ser Leu His Pro Asn Asn Leu Gln Thr Leu Met Trp
            660                665                670

Ile Pro Asp Lys Phe Phe Glu Pro Arg Leu Leu His Arg Leu Ile Asn
            675                680                685

Leu Arg Lys Leu Gly Ile Leu Gly Val Ser Asn Ser Thr Val Lys Met
    690                695                700

Leu Ser Ile Phe Ser Pro Val Leu Lys Ala Leu Glu Val Leu Lys Leu
705                710                715                720

Ser Phe Ser Ser Asp Pro Ser Glu Gln Ile Lys Leu Ser Ser Tyr Pro
                725                730                735

His Ile Ala Lys Leu His Leu Asn Val Asn Arg Thr Met Ala Leu Asn
            740                745                750

Ser Gln Ser Phe Pro Pro Asn Leu Ile Lys Leu Thr Leu Ala Tyr Phe
            755                760                765

Ser Val Asp Arg Tyr Ile Leu Ala Val Leu Lys Thr Phe Pro Lys Leu
    770                775                780

Arg Lys Leu Lys Met Phe Ile Cys Lys Tyr Asn Glu Glu Lys Met Asp
785                790                795                800

Leu Ser Gly Glu Ala Asn Gly Tyr Ser Phe Pro Gln Leu Glu Val Leu
                805                810                815

His Ile His Ser Pro Cys Gly Leu Ser Glu Val Thr Cys Thr Asp Asp
                820                825                830

Val Ser Met Pro Lys Leu Lys Lys Leu Leu Leu Thr Gly Phe His Cys
            835                840                845

Arg Ile Ser Leu Ser Glu Arg Leu Lys Lys Leu Ser Lys
    850                855                860

<210> SEQ ID NO 23
<211> LENGTH: 861
<212> TYPE: PRT
<213> ORGANISM: artificial
<220> FEATURE:
<223> OTHER INFORMATION: mutant

<400> SEQUENCE: 23

Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
            20                  25                  30

Glu Asp Ile Asp Trp Leu Gln Arg Glu Met Arg His Ile Arg Ser Tyr
            35                  40                  45

Val Asp Asn Ala Lys Ala Lys Glu Ala Gly Gly Asp Ser Arg Val Lys
    50                  55                  60

Asn Leu Leu Lys Asp Ile Gln Glu Leu Ala Gly Asp Val Glu Asp Leu
65                  70                  75                  80

Leu Asp Asp Phe Leu Pro Lys Ile Gln Gln Ser Asn Lys Phe Asn Tyr
                85                  90                  95

Cys Leu Lys Arg Ser Ser Phe Ala Asp Glu Phe Ala Met Glu Ile Glu
            100                 105                 110

Lys Ile Lys Arg Arg Val Val Asp Ile Asp Arg Ile Arg Lys Thr Tyr
            115                 120                 125

Asn Ile Ile Asp Thr Asp Asn Asn Asn Asp Asp Cys Val Leu Leu Asp
```

-continued

```
           130                   135                   140

Arg Arg Arg Leu Phe Leu His Ala Asp Glu Thr Glu Ile Ile Gly Leu
145                 150                 155                 160

Asp Asp Asp Phe Asn Met Leu Gln Ala Lys Leu Leu Asn Gln Asp Leu
                    165                 170                 175

His Tyr Gly Val Val Ser Ile Val Gly Met Pro Gly Leu Gly Lys Thr
                180                 185                 190

Thr Leu Ala Lys Lys Leu Tyr Arg Leu Ile Arg Asp Gln Phe Glu Cys
                195                 200                 205

Ser Gly Leu Val Tyr Val Ser Gln Gln Pro Arg Ala Ser Glu Ile Leu
            210                 215                 220

Leu Asp Ile Ala Lys Gln Ile Gly Leu Thr Glu Gln Lys Met Lys Glu
225                 230                 235                 240

Asn Leu Glu Asp Asn Leu Arg Ser Leu Leu Lys Ile Lys Arg Tyr Val
                    245                 250                 255

Ile Leu Leu Asp Asp Ile Trp Asp Val Glu Ile Trp Asp Asp Leu Lys
                260                 265                 270

Leu Val Leu Pro Glu Cys Asp Ser Lys Val Gly Ser Arg Met Ile Ile
            275                 280                 285

Thr Ser Arg Asn Ser Asn Val Gly Arg Tyr Ile Gly Gly Glu Ser Ser
    290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Asn Ser Trp Ala Asn Ala
                325                 330                 335

Ser Pro Asp Leu Val Asn Ile Gly Arg Asn Ile Val Gly Arg Cys Gly
                340                 345                 350

Gly Ile Pro Leu Ala Ile Val Val Thr Ala Gly Met Leu Arg Ala Arg
                355                 360                 365

Glu Arg Thr Glu His Ala Trp Asn Arg Val Leu Glu Ser Met Gly His
            370                 375                 380

Lys Val Gln Asp Gly Cys Ala Lys Val Leu Ala Leu Ser Tyr Asn Asp
385                 390                 395                 400

Leu Pro Ile Ala Ser Arg Pro Cys Phe Leu Tyr Phe Gly Leu Tyr Pro
                405                 410                 415

Glu Asp His Glu Ile Arg Ala Phe Asp Leu Ile Asn Met Trp Ile Ala
                420                 425                 430

Glu Lys Phe Ile Val Val Asn Ser Gly Asn Arg Arg Glu Ala Glu Asp
            435                 440                 445

Leu Ala Glu Asp Val Leu Asn Asp Leu Val Ser Arg Asn Leu Ile Gln
    450                 455                 460

Leu Ala Lys Arg Thr Tyr Asn Gly Arg Ile Ser Ser Cys Arg Ile His
465                 470                 475                 480

Asp Leu Leu His Ser Leu Cys Val Asp Leu Ala Lys Glu Ser Asn Phe
                485                 490                 495

Phe His Thr Ala His Asp Ala Phe Gly Asp Pro Gly Asn Val Ala Arg
                500                 505                 510

Leu Arg Arg Ile Thr Phe Tyr Ser Asp Asn Val Met Ile Glu Phe Phe
            515                 520                 525

Arg Ser Asn Pro Lys Leu Glu Lys Leu Arg Val Leu Phe Cys Phe Ala
    530                 535                 540

Lys Asp Pro Ser Ile Phe Ser His Met Ala Tyr Phe Asp Phe Lys Leu
545                 550                 555                 560
```

-continued

```
Leu His Thr Leu Val Val Val Met Ser Gln Ser Phe Gln Ala Tyr Val
            565             570             575

Thr Ile Pro Ser Lys Phe Gly Asn Met Thr Cys Leu Arg Tyr Leu Arg
            580             585             590

Leu Glu Gly Asn Ile Cys Gly Lys Leu Pro Asn Ser Ile Val Lys Leu
            595             600             605

Thr Arg Leu Glu Thr Ile Asp Ile Asp Arg Arg Ser Leu Ile Gln Pro
    610             615             620

Pro Ser Gly Val Trp Glu Ser Lys His Leu Arg His Leu Cys Tyr Arg
625             630             635             640

Asp Tyr Gly Gln Ala Cys Asn Ser Cys Phe Ser Ile Ser Ser Phe Tyr
            645             650             655

Pro Asn Ile Tyr Ser Leu His Pro Asn Asn Leu Gln Thr Leu Met Trp
            660             665             670

Ile Pro Asp Lys Phe Phe Glu Pro Arg Leu Leu His Arg Leu Ile Asn
            675             680             685

Leu Arg Lys Leu Gly Ile Leu Gly Val Ser Asn Ser Thr Val Lys Met
    690             695             700

Leu Ser Ile Phe Ser Pro Val Leu Lys Ala Leu Glu Val Leu Lys Leu
705             710             715             720

Ser Phe Ser Ser Asp Pro Ser Glu Gln Ile Lys Leu Ser Ser Tyr Pro
            725             730             735

His Ile Ala Lys Leu His Leu Asn Val Asn Arg Thr Met Ala Leu Asn
            740             745             750

Ser Gln Ser Phe Pro Pro Asn Leu Ile Lys Leu Thr Leu Ala Tyr Phe
            755             760             765

Ser Val Asp Arg Tyr Ile Leu Ala Val Leu Lys Thr Phe Pro Lys Leu
    770             775             780

Arg Lys Leu Lys Met Phe Ile Cys Lys Tyr Asn Glu Glu Lys Met Asp
785             790             795             800

Leu Ser Gly Glu Ala Asn Gly Tyr Ser Phe Pro Gln Leu Glu Val Leu
            805             810             815

His Ile His Ser Pro Phe Gly Leu Ser Glu Val Thr Cys Thr Asp Asp
            820             825             830

Val Ser Met Pro Lys Leu Lys Lys Leu Leu Leu Thr Gly Phe His Cys
            835             840             845

Arg Ile Ser Leu Ser Glu Arg Leu Lys Lys Leu Ser Lys
    850             855             860
```

```
<210> SEQ ID NO 24
<211> LENGTH: 861
<212> TYPE: PRT
<213> ORGANISM: artificial
<220> FEATURE:
<223> OTHER INFORMATION: mutant

<400> SEQUENCE: 24

Met Ala Glu Ile Leu Leu Thr Ser Val Ile Asn Lys Ser Val Glu Ile
1               5               10              15

Ala Gly Asn Leu Leu Ile Gln Glu Gly Lys Arg Leu Tyr Trp Leu Lys
            20              25              30

Glu Asp Ile Asp Trp Leu Gln Arg Glu Met Arg His Ile Arg Ser Tyr
        35              40              45

Val Asp Asn Ala Lys Ala Lys Glu Ala Gly Gly Asp Ser Arg Val Lys
    50              55              60
```

-continued

```
Asn Leu Leu Lys Asp Ile Gln Glu Leu Ala Gly Asp Val Glu Asp Leu
65              70              75              80

Leu Asp Asp Phe Leu Pro Lys Ile Gln Gln Ser Asn Lys Phe Asn Tyr
            85              90              95

Cys Leu Lys Arg Ser Ser Phe Ala Asp Glu Phe Ala Met Glu Ile Glu
            100             105             110

Lys Ile Lys Arg Arg Val Val Asp Ile Asp Arg Ile Arg Lys Thr Tyr
            115             120             125

Asn Ile Ile Asp Thr Asp Asn Asn Asp Asp Cys Val Leu Leu Asp
    130             135             140

Arg Arg Arg Leu Phe Leu His Ala Asp Glu Thr Glu Ile Ile Gly Leu
145             150             155             160

Asp Asp Asp Phe Asn Met Leu Gln Ala Lys Leu Leu Asn Gln Asp Leu
            165             170             175

His Tyr Gly Val Val Ser Ile Val Gly Met Pro Gly Leu Gly Lys Thr
            180             185             190

Thr Leu Ala Lys Lys Leu Tyr Arg Leu Ile Arg Asp Gln Phe Glu Cys
            195             200             205

Ser Gly Leu Val Tyr Val Ser Gln Gln Pro Arg Ala Ser Glu Ile Leu
    210             215             220

Leu Asp Ile Ala Lys Gln Ile Gly Leu Thr Glu Gln Lys Met Lys Glu
225             230             235             240

Asn Leu Glu Asp Asn Leu Arg Ser Leu Leu Lys Ile Lys Arg Tyr Val
            245             250             255

Ile Leu Leu Asp Asp Ile Trp Asp Val Glu Ile Trp Asp Asp Leu Lys
            260             265             270

Leu Val Leu Pro Glu Cys Asp Ser Lys Val Gly Ser Arg Met Ile Ile
            275             280             285

Thr Ser Arg Asn Ser Asn Val Gly Arg Tyr Ile Gly Gly Glu Ser Ser
    290             295             300

Leu His Ala Leu Gln Pro Leu Glu Ser Glu Lys Ser Phe Glu Leu Phe
305             310             315             320

Thr Lys Lys Ile Phe Asn Phe Asp Asp Asn Asn Ser Trp Ala Asn Ala
            325             330             335

Ser Pro Asp Leu Val Asn Ile Gly Arg Asn Ile Val Gly Arg Cys Gly
            340             345             350

Gly Ile Pro Leu Ala Ile Val Val Thr Ala Gly Met Leu Arg Ala Arg
            355             360             365

Glu Arg Thr Glu His Ala Trp Asn Arg Val Leu Glu Ser Met Gly His
    370             375             380

Lys Val Gln Asp Gly Cys Ala Lys Val Leu Ala Leu Ser Tyr Asn Asp
385             390             395             400

Leu Pro Ile Ala Ser Arg Pro Cys Phe Leu Tyr Phe Gly Leu Tyr Pro
            405             410             415

Glu Asp His Glu Ile Arg Ala Phe Asp Leu Ile Asn Met Trp Ile Ala
            420             425             430

Glu Lys Phe Ile Val Val Asn Ser Gly Asn Arg Arg Glu Ala Glu Asp
            435             440             445

Leu Ala Glu Asp Val Leu Asn Asp Leu Val Ser Arg Asn Leu Ile Gln
    450             455             460

Leu Ala Lys Arg Thr Tyr Asn Gly Arg Ile Ser Ser Cys Arg Ile His
465             470             475             480
```

-continued

```
Asp Leu Leu His Ser Leu Cys Val Asp Leu Ala Lys Glu Ser Asn Phe
            485             490             495

Phe His Thr Ala His Asp Ala Phe Gly Asp Pro Gly Asn Val Ala Arg
            500             505             510

Leu Arg Arg Ile Thr Phe Tyr Ser Asp Asn Val Met Ile Glu Phe Phe
            515             520             525

Arg Ser Asn Pro Lys Leu Glu Lys Leu Arg Val Leu Phe Cys Phe Ala
    530             535             540

Lys Asp Pro Ser Ile Phe Ser His Met Ala Tyr Phe Asp Phe Lys Leu
545             550             555             560

Leu His Thr Leu Val Val Val Met Ser Gln Ser Phe Gln Ala Tyr Val
            565             570             575

Thr Ile Pro Ser Lys Phe Gly Asn Met Thr Cys Leu Arg Tyr Leu Arg
            580             585             590

Leu Glu Gly Asn Ile Cys Gly Lys Leu Pro Asn Ser Ile Val Lys Leu
            595             600             605

Thr Arg Leu Glu Thr Ile Asp Ile Asp Arg Arg Ser Leu Ile Gln Pro
    610             615             620

Pro Ser Gly Val Trp Glu Ser Lys His Leu Arg His Leu Cys Tyr Arg
625             630             635             640

Asp Tyr Gly Gln Ala Cys Asn Ser Cys Phe Ser Ile Ser Ser Phe Tyr
            645             650             655

Pro Asn Ile Tyr Ser Leu His Pro Asn Asn Leu Gln Thr Leu Met Trp
            660             665             670

Ile Pro Asp Lys Phe Phe Glu Pro Arg Leu Leu His Arg Leu Ile Asn
            675             680             685

Leu Arg Lys Leu Gly Ile Leu Gly Val Ser Asn Ser Thr Val Lys Met
    690             695             700

Leu Ser Ile Phe Ser Pro Val Leu Lys Ala Leu Glu Val Leu Lys Leu
705             710             715             720

Ser Phe Ser Ser Asp Pro Ser Glu Gln Ile Lys Leu Ser Ser Tyr Pro
            725             730             735

His Ile Ala Lys Leu His Leu Asn Val Asn Arg Thr Met Ala Leu Asn
            740             745             750

Ser Gln Ser Phe Pro Pro Asn Leu Ile Lys Leu Thr Leu Ala Tyr Phe
            755             760             765

Ser Val Asp Arg Tyr Ile Leu Ala Val Leu Lys Thr Phe Pro Lys Leu
    770             775             780

Arg Lys Leu Lys Met Phe Ile Cys Lys Tyr Asn Glu Glu Lys Met Asp
785             790             795             800

Leu Ser Gly Glu Ala Asn Gly Tyr Ser Phe Pro Gln Leu Glu Val Leu
            805             810             815

His Ile His Ser Pro Met Gly Leu Ser Glu Val Thr Cys Thr Asp Asp
            820             825             830

Val Ser Met Pro Lys Leu Lys Lys Leu Leu Leu Thr Gly Phe His Cys
            835             840             845

Arg Ile Ser Leu Ser Glu Arg Leu Lys Lys Leu Ser Lys
    850             855             860
```

<210> SEQ ID NO 25
<211> LENGTH: 861
<212> TYPE: PRT
<213> ORGANISM: artificial
<220> FEATURE:
<223> OTHER INFORMATION: mutant -continued

```
<400> SEQUENCE: 25

Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Ala Gly Gly Asp Ser Arg Val Lys
    50                  55                  60

Asn Leu Leu Lys Asp Ile Gln Glu Leu Ala Gly Asp Val Glu Asp Leu
65                  70                  75                  80

Leu Asp Asp Phe Leu Pro Lys Ile Gln Gln Ser Asn Lys Phe Asn Tyr
                85                  90                  95

Cys Leu Lys Arg Ser Ser Phe Ala Asp Glu Phe Ala Met Glu Ile Glu
            100                 105                 110

Lys Ile Lys Arg Arg Val Val Asp Ile Asp Arg Ile Arg Lys Thr Tyr
            115                 120                 125

Asn Ile Ile Asp Thr Asp Asn Asn Asp Asp Cys Val Leu Leu Asp
        130                 135                 140

Arg Arg Arg Leu Phe Leu His Ala Asp Glu Thr Glu Ile Ile Gly Leu
145                 150                 155                 160

Asp Asp Asp Phe Asn Met Leu Gln Ala Lys Leu Leu Asn Gln Asp Leu
                165                 170                 175

His Tyr Gly Val Val Ser Ile Val Gly Met Pro Gly Leu Gly Lys Thr
            180                 185                 190

Thr Leu Ala Lys Lys Leu Tyr Arg Leu Ile Arg Asp Gln Phe Glu Cys
            195                 200                 205

Ser Gly Leu Val Tyr Val Ser Gln Gln Pro Arg Ala Ser Glu Ile Leu
    210                 215                 220

Leu Asp Ile Ala Lys Gln Ile Gly Leu Thr Glu Gln Lys Met Lys Glu
225                 230                 235                 240

Asn Leu Glu Asp Asn Leu Arg Ser Leu Leu Lys Ile Lys Arg Tyr Val
                245                 250                 255

Ile Leu Leu Asp Asp Ile Trp Asp Val Glu Ile Trp Asp Asp Leu Lys
                260                 265                 270

Leu Val Leu Pro Glu Cys Asp Ser Lys Val Gly Ser Arg Met Ile Ile
            275                 280                 285

Thr Ser Arg Asn Ser Asn Val Gly Arg Tyr Ile Gly Gly Glu Ser Ser
    290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Asn Ser Trp Ala Asn Ala
                325                 330                 335

Ser Pro Asp Leu Val Asn Ile Gly Arg Asn Ile Val Gly Arg Cys Gly
            340                 345                 350

Gly Ile Pro Leu Ala Ile Val Val Thr Ala Gly Met Leu Arg Ala Arg
            355                 360                 365

Glu Arg Thr Glu His Ala Trp Asn Arg Val Leu Glu Ser Met Gly His
    370                 375                 380

Lys Val Gln Asp Gly Cys Ala Lys Val Leu Ala Leu Ser Tyr Asn Asp
385                 390                 395                 400

Leu Pro Ile Ala Ser Arg Pro Cys Phe Leu Tyr Phe Gly Leu Tyr Pro
```

```
                    405                 410                 415

Glu Asp His Glu Ile Arg Ala Phe Asp Leu Ile Asn Met Trp Ile Ala
            420                 425                 430

Glu Lys Phe Ile Val Val Asn Ser Gly Asn Arg Arg Glu Ala Glu Asp
            435                 440                 445

Leu Ala Glu Asp Val Leu Asn Asp Leu Val Ser Arg Asn Leu Ile Gln
            450                 455                 460

Leu Ala Lys Arg Thr Tyr Asn Gly Arg Ile Ser Ser Cys Arg Ile His
465                 470                 475                 480

Asp Leu Leu His Ser Leu Cys Val Asp Leu Ala Lys Glu Ser Asn Phe
                485                 490                 495

Phe His Thr Ala His Asp Ala Phe Gly Asp Pro Gly Asn Val Ala Arg
            500                 505                 510

Leu Arg Arg Ile Thr Phe Tyr Ser Asp Asn Val Met Ile Glu Phe Phe
            515                 520                 525

Arg Ser Asn Pro Lys Leu Glu Lys Leu Arg Val Leu Phe Cys Phe Ala
            530                 535                 540

Lys Asp Pro Ser Ile Phe Ser His Met Ala Tyr Phe Asp Phe Lys Leu
545                 550                 555                 560

Leu His Thr Leu Val Val Val Met Ser Gln Ser Phe Gln Ala Tyr Val
                565                 570                 575

Thr Ile Pro Ser Lys Phe Gly Asn Met Thr Cys Leu Arg Tyr Leu Arg
            580                 585                 590

Leu Glu Gly Asn Ile Cys Gly Lys Leu Pro Asn Ser Ile Val Lys Leu
            595                 600                 605

Thr Arg Leu Glu Thr Ile Asp Ile Asp Arg Arg Ser Leu Ile Gln Pro
            610                 615                 620

Pro Ser Gly Val Trp Glu Ser Lys His Leu Arg His Leu Cys Tyr Arg
625                 630                 635                 640

Asp Tyr Gly Gln Ala Cys Asn Ser Cys Phe Ser Ile Ser Ser Phe Tyr
                645                 650                 655

Pro Asn Ile Tyr Ser Leu His Pro Asn Asn Leu Gln Thr Leu Met Trp
                660                 665                 670

Ile Pro Asp Lys Phe Phe Glu Pro Arg Leu Leu His Arg Leu Ile Asn
            675                 680                 685

Leu Arg Lys Leu Gly Ile Leu Gly Val Ser Asn Ser Thr Val Lys Met
            690                 695                 700

Leu Ser Ile Phe Ser Pro Val Leu Lys Ala Leu Glu Val Leu Lys Leu
705                 710                 715                 720

Ser Phe Ser Ser Asp Pro Ser Glu Gln Ile Lys Leu Ser Ser Tyr Pro
                725                 730                 735

His Ile Ala Lys Leu His Leu Asn Val Asn Arg Thr Met Ala Leu Asn
            740                 745                 750

Ser Gln Ser Phe Pro Pro Asn Leu Ile Lys Leu Thr Leu Ala Tyr Phe
            755                 760                 765

Ser Val Asp Arg Tyr Ile Leu Ala Val Leu Lys Thr Phe Pro Lys Leu
            770                 775                 780

Arg Lys Leu Lys Met Phe Ile Cys Lys Tyr Asn Glu Glu Lys Met Asp
785                 790                 795                 800

Leu Ser Gly Glu Ala Asn Gly Tyr Ser Phe Pro Gln Leu Glu Val Leu
                805                 810                 815

His Ile His Ser Pro Tyr Gly Leu Ser Glu Val Thr Cys Thr Asp Asp
                820                 825                 830
```

-continued

```
Val Ser Met Pro Lys Leu Lys Lys Leu Leu Leu Thr Gly Phe His Cys
        835             840             845

Arg Ile Ser Leu Ser Glu Arg Leu Lys Lys Leu Ser Lys
    850             855             860

<210> SEQ ID NO 26
<211> LENGTH: 861
<212> TYPE: PRT
<213> ORGANISM: artificial
<220> FEATURE:
<223> OTHER INFORMATION: mutant

<400> SEQUENCE: 26

Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Ala Gly Gly Asp Ser Arg Val Lys
    50                  55                  60

Asn Leu Leu Lys Asp Ile Gln Glu Leu Ala Gly Asp Val Glu Asp Leu
65                  70                  75                  80

Leu Asp Asp Phe Leu Pro Lys Ile Gln Gln Ser Asn Lys Phe Asn Tyr
                85                  90                  95

Cys Leu Lys Arg Ser Ser Phe Ala Asp Glu Phe Ala Met Glu Ile Glu
            100                 105                 110

Lys Ile Lys Arg Arg Val Val Asp Ile Asp Arg Ile Arg Lys Thr Tyr
            115                 120                 125

Asn Ile Ile Asp Thr Asp Asn Asn Asn Asp Asp Cys Val Leu Leu Asp
    130                 135                 140

Arg Arg Arg Leu Phe Leu His Ala Asp Glu Thr Glu Ile Ile Gly Leu
145                 150                 155                 160

Asp Asp Asp Phe Asn Met Leu Gln Ala Lys Leu Leu Asn Gln Asp Leu
                165                 170                 175

His Tyr Gly Val Val Ser Ile Val Gly Met Pro Gly Leu Gly Lys Thr
            180                 185                 190

Thr Leu Ala Lys Lys Leu Tyr Arg Leu Ile Arg Asp Gln Phe Glu Cys
            195                 200                 205

Ser Gly Leu Val Tyr Val Ser Gln Gln Pro Arg Ala Ser Glu Ile Leu
    210                 215                 220

Leu Asp Ile Ala Lys Gln Ile Gly Leu Thr Glu Gln Lys Met Lys Glu
225                 230                 235                 240

Asn Leu Glu Asp Asn Leu Arg Ser Leu Leu Lys Ile Lys Arg Tyr Val
                245                 250                 255

Ile Leu Leu Asp Asp Ile Trp Asp Val Glu Ile Trp Asp Asp Leu Lys
            260                 265                 270

Leu Val Leu Pro Glu Cys Asp Ser Lys Val Gly Ser Arg Met Ile Ile
            275                 280                 285

Thr Ser Arg Asn Ser Asn Val Gly Arg Tyr Ile Gly Gly Glu Ser Ser
    290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Asn Ser Trp Ala Asn Ala
                325                 330                 335
```

```
Ser Pro Asp Leu Val Asn Ile Gly Arg Asn Ile Val Gly Arg Cys Gly
        340                 345                 350

Gly Ile Pro Leu Ala Ile Val Val Thr Ala Gly Met Leu Arg Ala Arg
        355                 360                 365

Glu Arg Thr Glu His Ala Trp Asn Arg Val Leu Glu Ser Met Gly His
        370                 375                 380

Lys Val Gln Asp Gly Cys Ala Lys Val Leu Ala Leu Ser Tyr Asn Asp
385                 390                 395                 400

Leu Pro Ile Ala Ser Arg Pro Cys Phe Leu Tyr Phe Gly Leu Tyr Pro
                405                 410                 415

Glu Asp His Glu Ile Arg Ala Phe Asp Leu Ile Asn Met Trp Ile Ala
        420                 425                 430

Glu Lys Phe Ile Val Val Asn Ser Gly Asn Arg Arg Glu Ala Glu Asp
        435                 440                 445

Leu Ala Glu Asp Val Leu Asn Asp Leu Val Ser Arg Asn Leu Ile Gln
    450                 455                 460

Leu Ala Lys Arg Thr Tyr Asn Gly Arg Ile Ser Ser Cys Arg Ile His
465                 470                 475                 480

Asp Leu Leu His Ser Leu Cys Val Asp Leu Ala Lys Glu Ser Asn Phe
                485                 490                 495

Phe His Thr Ala His Asp Ala Phe Gly Asp Pro Gly Asn Val Ala Arg
            500                 505                 510

Leu Arg Arg Ile Thr Phe Tyr Ser Asp Asn Val Met Ile Glu Phe Phe
            515                 520                 525

Arg Ser Asn Pro Lys Leu Glu Lys Leu Arg Val Leu Phe Cys Phe Ala
    530                 535                 540

Lys Asp Pro Ser Ile Phe Ser His Met Ala Tyr Phe Asp Phe Lys Leu
545                 550                 555                 560

Leu His Thr Leu Val Val Val Met Ser Gln Ser Phe Gln Ala Tyr Val
                565                 570                 575

Thr Ile Pro Ser Lys Phe Gly Asn Met Thr Cys Leu Arg Tyr Leu Arg
            580                 585                 590

Leu Glu Gly Asn Ile Cys Gly Lys Leu Pro Asn Ser Ile Val Lys Leu
        595                 600                 605

Thr Arg Leu Glu Thr Ile Asp Ile Asp Arg Arg Ser Leu Ile Gln Pro
    610                 615                 620

Pro Ser Gly Val Trp Glu Ser Lys His Leu Arg His Leu Cys Tyr Arg
625                 630                 635                 640

Asp Tyr Gly Gln Ala Cys Asn Ser Cys Phe Ser Ile Ser Ser Phe Tyr
                645                 650                 655

Pro Asn Ile Tyr Ser Leu His Pro Asn Asn Leu Gln Thr Leu Met Trp
                660                 665                 670

Ile Pro Asp Lys Phe Phe Glu Pro Arg Leu Leu His Arg Leu Ile Asn
            675                 680                 685

Leu Arg Lys Leu Gly Ile Leu Gly Val Ser Asn Ser Thr Val Lys Met
        690                 695                 700

Leu Ser Ile Phe Ser Pro Val Leu Lys Ala Leu Glu Val Leu Lys Leu
705                 710                 715                 720

Ser Phe Ser Ser Asp Pro Ser Glu Gln Ile Lys Leu Ser Ser Tyr Pro
                725                 730                 735

His Ile Ala Lys Leu His Leu Asn Val Asn Arg Thr Met Ala Leu Asn
            740                 745                 750
```

-continued

Ser Gln Ser Phe Pro Pro Asn Leu Ile Lys Leu Thr Leu Ala Tyr Phe
        755                 760                 765

Ser Val Asp Arg Tyr Ile Leu Ala Val Leu Lys Thr Phe Pro Lys Leu
        770                 775                 780

Arg Lys Leu Lys Met Phe Ile Cys Lys Tyr Asn Glu Glu Lys Met Asp
785                 790                 795                 800

Leu Ser Gly Glu Ala Asn Gly Tyr Ser Phe Pro Gln Leu Glu Val Leu
                805                 810                 815

His Ile His Ser Pro Trp Gly Leu Ser Glu Val Thr Cys Thr Asp Asp
                820                 825                 830

Val Ser Met Pro Lys Leu Lys Lys Leu Leu Leu Thr Gly Phe His Cys
        835                 840                 845

Arg Ile Ser Leu Ser Glu Arg Leu Lys Lys Leu Ser Lys
    850                 855                 860

<210> SEQ ID NO 27
<211> LENGTH: 2586
<212> TYPE: DNA
<213> ORGANISM: artificial
<220> FEATURE:
<223> OTHER INFORMATION: mutant

<400> SEQUENCE: 27
atggctgaaa ttcttcttac atcagtaatc aataaatctg tagaaatagc tggaaattta      60
ctgattcaag aaggaaagcg tttatattgg ttgaaagagg atatcgattg gctccagaga     120
gaaatgagac acattcgatc ttatgttgac aacgcaaagg ccaaggaagc tggaggtgat     180
tcaagggtca aaaacttatt gaaagatatt caagaattgg caggtgatgt ggaggatctc     240
ttagatgact ccttccaaa aattcaacaa tccaataagt tcaattattg ccttaagagg     300 agttctttg cagatgagtt tgctatggag attgagaaga taaagagaag ggttgttgac     360
attgaccgaa taaggaaaac ttacaacatc atagatacag ataacaataa tgatgattgt     420
gttctgctgg atcggagaag attattccta catgctgatg aaacagagat catcggtttg     480
gatgatgact tcaatatgct acaagccaaa ttacttaatc aagatttgca ttatggagtt     540
gtttccatag ttggcatgcc cggtctgggg aaaacaactc ttgccaagaa actttatagg     600
ctcattcgtg atcaatttga gtgttctgga ctggtctacg tttcacaaca gccaagagcg     660
agtgaaatct tacttgacat tgccaaacaa attggactga cggaacagaa aatgaaggaa     720
aatttggagg acaacctgcg atcactcttg aaaataaaaa ggtatgttat cctcctagat     780
gacatttggg atgtggaaat ttgggatgat ctgaaacttg tccttcctga atgtgattca     840
aaagtcggca gtagaatgat aatcacgtct cgaaatagta atgtaggcag atacatagga     900
ggggaatcct ccctccatgc attgcaaccc ctagaatccg agaaaagctt tgaactcttt     960
accaagaaaa tctttaattt tgatgataat aatagttggg ccaatgcttc acctgacttg    1020
gtgaatattg gtagaaatat agttgggaga tgtggaggta taccgctagc catagtggtg    1080
actgcaggca tgttaagggc aagagaaaga acagaacatg cgtggaacag agtacttgag    1140
agtatgggcc ataaagttca agatggatgt gctaaggtat tggctctcag ttacaatgat    1200
ttacctattg cctcaaggcc atgtttcttg tactttggcc tttaccccga ggaccatgaa    1260
attcgtgctt ttgatttgat aaatatgtgg attgctgaga gtttatagt agtaaatagt    1320 ggtaataggc gagaggctga ggattttggcg gaggacgtcc taaatgattt ggtttctaga    1380
aacttgattc aacttgccaa aaggacatat aatggaagaa tttcaagttg tcgcatacat    1440

-continued

```
gacttgttac atagtttgtg tgtggacttg gctaaggaaa gtaacttctt tcacaccgcg      1500
catgatgcat ttggtgatcc cggcaatgtt gctaggctcc gaaggattac attctactct      1560
gacaatgtca tgattgagtt cttccgttca aatcctaagc ttgagaagct tcgtgtactt      1620
ttctgtttcg caaaagaccc ttccatattt tctcatatgg cttattttga cttcaaattg      1680
ttgcacacat tggttgtagt catgtctcaa agttttcaag catatgtcac tatcccaagc      1740
aaatttggga acatgacttg cttacgctat ctgagattgg aggggaatat ttgtggaaaa      1800
ctgccaaata gtattgtcaa gctcacacgt ctagagacca tagacattga tcgacgtagc      1860
ctcattcaac ctccttctgg tgtttgggag tctaaacatt tgagacatct ttgttataga      1920
gattatggac aagcatgtaa cagttgcttt tctataagct cattttaccc aaatatttac      1980
tcattgcatc ctaacaatct acaaaccttg atgtggatac ctgataaatt tttttgaaccg      2040 aggttgttgc accgattgat caatttaaga aaactgggta tactgggagt gtccaattct      2100
accgttaaga tgttatcaat atttagccct gtgcttaagg cgctggaggt tctgaagctc      2160 agttttttcca gtgacccgag tgaacaaata aagttgtcat cgtatccaca tattgctaag      2220
ttgcatttga atgttaacag aacaatggcc ttgaactctc aatcatttcc tccaaatctc      2280
atcaagctta ctctagcctt ttttagtgta gaccgttata tactggcagt acttaagaca      2340
tttcccaaat taagaaaact taaaatgttc atctgcaagt ataatgaaga aaagatggat      2400
ctctcgggcg aggcaaatgg ttatagcttt ccgcaacttg aagttttgca tattcatagc      2460
ccgaatgggt tgtctgaagt aacgtgcacg gatgatgtca gtatgcccaa attgaaaaag      2520
ctgttactta caggattcca tcgccgaatc agtttatcgg aacggcttaa aaagctgagt      2580
aaatga                                                                  2586
```

<210> SEQ ID NO 28
<211> LENGTH: 2586
<212> TYPE: DNA
<213> ORGANISM: artificial
<220> FEATURE:
<223> OTHER INFORMATION: mutant

<400> SEQUENCE: 28

```
atggctgaaa ttcttcttac atcagtaatc aataaatctg tagaaatagc tggaaattta        60
ctgattcaag aaggaaagcg tttatattgg ttgaaagagg atatcgattg gctccagaga       120
gaaatgagac acattcgatc ttatgttgac aacgcaaagg ccaaggaagc tggaggtgat       180
tcaagggtca aaaacttatt gaaagatatt caagaattgg caggtgatgt ggaggatctc       240
ttagatgact tccttccaaa aattcaacaa tccaataagt tcaattattg ccttaagagg       300
agttcttttg cagatgagtt tgctatggag attgagaaga taaagagaag ggttgttgac       360
attgaccgaa taaggaaaac ttacaacatc atagatacag ataacaataa tgatgattgt       420
gttctgctgg atcggagaag attattccta catgctgatg aaacagagat catcggtttg       480
gatgatgact tcaatatgct acaagccaaa ttacttaatc aagatttgca ttatggagtt       540
gtttccatag ttggcatgcc cggtctgggg aaaacaactc ttgccaagaa actttatagg       600
ctcattcgtg atcaatttga gtgttctgga ctggtctacg tttcacaaca gccaagagcg       660
agtgaaatct tacttgacat tgccaaacaa attggactga cggaacagaa aatgaaggaa       720
aatttggagg acaacctgcg atcactcttg aaaataaaaa ggtatgttat cctcctagat       780
gacatttggg atgtggaaat ttgggatgat ctgaacttg tccttcctga atgtgattca       840
aaagtcggca gtagaatgat aatcacgtct cgaaatagta atgtaggcag atacatagga       900
```

-continued

```
ggggaatcct ccctccatgc attgcaaccc ctagaatccg agaaaagctt tgaactcttt      960
accaagaaaa tctttaattt tgatgataat aatagttggg ccaatgcttc acctgacttg     1020
gtgaatattg gtagaaatat agttgggaga tgtggaggta taccgctagc catagtggtg     1080
actgcaggca tgttaagggc aagagaaaga acagaacatg cgtggaacag agtacttgag     1140
agtatgggcc ataaagttca agatggatgt gctaaggtat tggctctcag ttacaatgat     1200
ttacctattg cctcaaggcc atgtttcttg tactttggcc tttaccccga ggaccatgaa     1260
attcgtgctt ttgatttgat aaatatgtgg attgctgaga agtttatagt agtaaatagt     1320
ggtaataggc gagaggctga ggatttggcg gaggacgtcc taaatgattt ggtttctaga     1380
aacttgattc aacttgccaa aaggacatat aatggaagaa tttcaagttg tcgcatacat     1440
gacttgttac atagtttgtg tgtggacttg gctaaggaaa gtaacttctt tcacaccgcg     1500
catgatgcat ttggtgatcc cggcaatgtt gctaggctcc gaaggattac attctactct     1560
gacaatgtca tgattgagtt cttccgttca aatcctaagc ttgagaagct tcgtgtactt     1620
ttctgtttcg caaaagaccc ttccatattt tctcatatgg cttattttga cttcaaattg     1680
ttgcacacat tggttgtagt catgtctcaa agttttcaag catatgtcac tatcccaagc     1740
aaatttggga acatgacttg cttacgctat ctgagattgg aggggaatat ttgtggaaaa     1800
ctgccaaata gtattgtcaa gctcacacgt ctagagacca tagacattga tcgacgtagc     1860
ctcattcaac ctccttctgg tgtttgggag tctaaacatt tgagacatct ttgttataga     1920
gattatggac aagcatgtaa cagttgcttt tctataagct cattttaccc aaatatttac     1980
tcattgcatc ctaacaatct acaaaccttg atgtggatac ctgataaatt ttttgaaccg     2040
aggttgttgc accgattgat caatttaaga aaactgggta tactgggagt gtccaattct     2100
accgttaaga tgttatcaat atttagccct gtgcttaagg cgctggaggt tctgaagctc     2160 agttttttcca gtgacccgag tgaacaaata aagttgtcat cgtatccaca tattgctaag     2220
ttgcatttga atgttaacag aacaatggcc ttgaactctc aatcatttcc tccaaatctc     2280
atcaagctta ctctagcctg gtttagtgta gaccgttata tactggcagt acttaagaca     2340
tttcccaaat taagaaaact taaaatgttc atctgcaagt ataatgaaga aaagatggat     2400
ctctcgggcg aggcaaatgg ttatagcttt ccgcaacttg aagttttgca tattcatagc     2460
ccgaatgggt tgtctgaagt aacgtgcacg gatgatgtca gtatgcccaa attgaaaaag     2520
ctgttactta caggattcca tcgccgaatc agtttatcgg aacggcttaa aaagctgagt     2580
aaatga                                                                2586
```

<210> SEQ ID NO 29
<211> LENGTH: 2586
<212> TYPE: DNA
<213> ORGANISM: artificial
<220> FEATURE:
<223> OTHER INFORMATION: mutant

<400> SEQUENCE: 29

```
atggctgaaa ttcttcttac atcagtaatc aataaatctg tagaaatagc tggaaattta       60
ctgattcaag aaggaaagcg tttatattgg ttgaaagagg atatcgattg gctccagaga      120
gaaatgagac acattcgatc ttatgttgac aacgcaaagg ccaaggaagc tggaggtgat      180
tcaagggtca aaaacttatt gaagatatt caagaattgg caggtgatgt ggaggatctc      240
ttagatgact tccttccaaa aattcaacaa tccaataagt tcaattattg ccttaagagg      300
```

-continued

```
agttcttttg cagatgagtt tgctatggag attgagaaga taaagagaag ggttgttgac     360
attgaccgaa taaggaaaac ttacaacatc atagatacag ataacaataa tgatgattgt     420
gttctgctgg atcggagaag attattccta catgctgatg aaacagagat catcggtttg     480
gatgatgact tcaatatgct acaagccaaa ttacttaatc aagatttgca ttatggagtt     540
gtttccatag ttggcatgcc cggtctgggg aaaacaactc ttgccaagaa actttatagg     600
ctcattcgtg atcaatttga gtgttctgga ctggtctacg tttcacaaca gccaagagcg     660
agtgaaatct tacttgacat tgccaaacaa attggactga cggaacagaa aatgaaggaa     720
aatttggagg acaacctgcg atcactcttg aaaataaaaa ggtatgttat cctcctagat     780
gacatttggg atgtggaaat ttgggatgat ctgaaacttg tccttcctga atgtgattca     840
aaagtcggca gtagaatgat aatcacgtct cgaaatagta atgtaggcag atacatagga     900
ggggaatcct ccctccatgc attgcaaccc ctagaatccg agaaaagctt tgaactcttt     960
accaagaaaa tctttaattt tgatgataat aatagttggg ccaatgcttc acctgacttg    1020
gtgaatattg gtagaaatat agttgggaga tgtggaggta taccgctagc catagtggtg    1080
actgcaggca tgttaagggc aagagaaaga acagaacatg cgtggaacag agtacttgag    1140
agtatgggcc ataaagttca agatggatgt gctaaggtat tggctctcag ttacaatgat    1200
ttacctattg cctcaaggcc atgtttcttg tactttggcc tttaccccga ggaccatgaa    1260
attcgtgctt ttgatttgat aaatatgtgg attgctgaga agtttatagt agtaaatagt    1320
ggtaataggc gagaggctga ggatttggcg gaggacgtcc taaatgattt ggtttctaga    1380
aacttgattc aacttgccaa aaggacatat aatggaagaa tttcaagttg tcgcatacat    1440
gacttgttac atagtttgtg tgtggacttg gctaaggaaa gtaacttctt tcacaccgcg    1500
catgatgcat ttggtgatcc cggcaatgtt gctaggctcc gaaggattac attctactct    1560
gacaatgtca tgattgagtt cttccgttca aatcctaagc ttgagaagct tcgtgtactt    1620
ttctgtttcg caaaagaccc ttccatattt tctcatatgg cttattttga cttcaaattg    1680
ttgcacacat tggttgtagt catgtctcaa agttttcaag catatgtcac tatcccaagc    1740
aaatttggga acatgacttg cttacgctat ctgagattgg aggggaatat ttgtggaaaa    1800
ctgccaaata gtattgtcaa gctcacacgt ctagagacca tagacattga tcgacgtagc    1860
ctcattcaac ctccttctgg tgtttgggag tctaaacatt tgagacatct ttgttataga    1920
gattatggac aagcatgtaa cagttgcttt tctataagct cattttaccc aaatatttac    1980
tcattgcatc ctaacaatct acaaaccttg atgtggatac ctgataaatt ttttgaaccg    2040
aggttgttgc accgattgat caatttaaga aaactgggta tactgggagt gtccaattct    2100
accgttaaga tgttatcaat atttagccct gtgcttaagg cgctggaggt tctgaagctc    2160 agttttttcca gtgacccgag tgaacaaata aagttgtcat cgtatccaca tattgctaag    2220
ttgcatttga atgttaacag aacaatggcc ttgaactctc aatcatttcc tccaaatctc    2280
atcaagctta ctctagccta ctttagtgta gaccgttata tactggcagt acttaagaca    2340
tttcccaaat taagaaaact taaaatgttc atctgcaagt ataatgaaga aaagatggat    2400
ctctcgggcg aggcaaatgg ttatagcttt ccgcaacttg aagttttgca tattcatagc    2460
ccgaatgggt tgcatgaagt aacgtgcacg gatgatgtca gtatgcccaa attgaaaaag    2520
ctgttactta caggattcca ttgccgaatc agtttatcgg aacggcttaa aaagctgagt    2580
aaatga                                                               2586
```

<210> SEQ ID NO 30
<211> LENGTH: 2586
<212> TYPE: DNA
<213> ORGANISM: artificial
<220> FEATURE:
<223> OTHER INFORMATION: mutant

<400> SEQUENCE: 30

```
atggctgaaa ttcttcttac atcagtaatc aataaatctg tagaaatagc tggaaattta      60
ctgattcaag aaggaaagcg tttatattgg ttgaaagagg atatcgattg gctccagaga     120
gaaatgagac acattcgatc ttatgttgac aacgcaaagg ccaaggaagc tggaggtgat     180
tcaagggtca aaaacttatt gaaagatatt caagaattgg caggtgatgt ggaggatctc     240
ttagatgact tccttccaaa aattcaacaa tccaataagt tcaattattg ccttaagagg     300
agttcttttg cagatgagtt tgctatggag attgagaaga taaagagaag ggttgttgac     360
attgaccgaa taaggaaaac ttacaacatc atagatacag ataacaataa tgatgattgt     420
gttctgctgg atcggagaag attattccta catgctgatg aaacagagat catcggtttg     480
gatgatgact tcaatatgct acaagccaaa ttacttaatc aagatttgca ttatggagtt     540
gtttccatag ttggcatgcc cggtctgggg aaaacaactc ttgccaagaa actttatagg     600
ctcattcgtg atcaatttga gtgttctgga ctggtctacg tttcacaaca gccaagagcg     660
agtgaaatct tacttgacat tgccaaacaa attggactga cggaacagaa aatgaaggaa     720
aatttggagg acaacctgcg atcactcttg aaaataaaaa ggtatgttat cctcctagat     780
gacatttggg atgtggaaat ttgggatgat ctgaaacttg tccttcctga atgtgattca     840
aaagtcggca gtagaatgat aatcacgtct cgaaatagta atgtaggcag atacatagga     900
ggggaatcct ccctccatgc attgcaaccc ctagaatccg agaaaagctt tgaactcttt     960
accaagaaaa tctttaattt tgatgataat aatagttggg ccaatgcttc acctgacttg    1020
gtgaatattg gtagaaatat agttgggaga tgtggaggta taccgctagc catagtggtg    1080
actgcaggca tgttaagggc aagagaaaga acagaacatg cgtggaacag agtacttgag    1140
agtatgggcc ataaagttca agatggatgt gctaaggtat tggctctcag ttacaatgat    1200
ttacctattg cctcaaggcc atgtttcttg tactttggcc tttaccccga ggaccatgaa    1260
attcgtgctt ttgatttgat aaatatgtgg attgctgaga gtttatagt agtaaatagt    1320 ggtaataggc gagaggctga ggattggcg gaggacgtcc taaatgattt ggtttctaga    1380
aacttgattc aacttgccaa aaggacatat aatggaagaa tttcaagttg tcgcatacat    1440
gacttgttac atagtttgtg tgtggacttg gctaaggaaa gtaacttctt tcacaccgcg    1500
catgatgcat ttggtgatcc cggcaatgtt gctaggctcc gaaggattac attctactct    1560
gacaatgtca tgattgagtt cttccgttca aatcctaagc ttgagaagct tcgtgtactt    1620
ttctgtttcg caaaagaccc ttccatattt tctcatatgg cttattttga cttcaaattg    1680
ttgcacacat tggttgtagt catgtctcaa agttttcaag catatgtcac tatcccaagc    1740
aaatttggga acatgacttg cttacgctat ctgagattgg aggggaatat ttgtggaaaa    1800
ctgccaaata gtattgtcaa gctcacacgt ctagagacca tagacattga tcgacgtagc    1860
ctcattcaac ctccttctgg tgtttgggag tctaaacatt tgagacatct ttgttataga    1920
gattatggac aagcatgtaa cagttgcttt tctataagct cattttaccc aaatatttac    1980
tcattgcatc ctaacaatct acaaaccttg atgtggatac ctgataaatt ttttgaaccg    2040
aggttgttgc accgattgat caatttaaga aaactgggta tactgggagt gtccaattct    2100
```

```
accgttaaga tgttatcaat atttagccct gtgcttaagg cgctggaggt tctgaagctc      2160 agttttttcca gtgacccgag tgaacaaata aagttgtcat cgtatccaca tattgctaag      2220
ttgcatttga atgttaacag aacaatggcc ttgaactctc aatcatttcc tccaaatctc      2280
atcaagctta ctctagccta ctttagtgta gaccgttata tactggcagt acttaagaca      2340
tttcccaaat taagaaaact taaaatgttc atctgcaagt ataatgaaga aaagatggat      2400
ctctcgggcg aggcaaatgg ttatagcttt ccgcaacttg aagttttgca tattcatagc      2460
ccgaatgggt tgaaggaagt aacgtgcacg gatgatgtca gtatgcccaa attgaaaaag      2520
ctgttactta caggattcca ttgccgaatc agtttatcgg aacggcttaa aaagctgagt      2580
aaatga                                                                 2586
```

```
<210> SEQ ID NO 31
<211> LENGTH: 2586
<212> TYPE: DNA
<213> ORGANISM: artificial
<220> FEATURE:
<223> OTHER INFORMATION: mutant

<400> SEQUENCE: 31
atggctgaaa ttcttcttac atcagtaatc aataaatctg tagaaatagc tggaaattta        60
ctgattcaag aaggaaagcg tttatattgg ttgaaagagg atatcgattg gctccagaga       120
gaaatgagac acattcgatc ttatgttgac aacgcaaagg ccaaggaagc tggaggtgat       180
tcaagggtca aaaacttatt gaaagatatt caagaattgg caggtgatgt ggaggatctc       240
ttagatgact tccttccaaa aattcaacaa tccaataagt tcaattattg ccttaagagg       300
agttcttttg cagatgagtt tgctatggag attgagaaga taaagagaag ggttgttgac       360
attgaccgaa taaggaaaac ttacaacatc atagatacag ataacaataa tgatgattgt       420
gttctgctgg atcggagaag attattccta catgctgatg aaacagagat catcggtttg       480
gatgatgact tcaatatgct acaagccaaa ttacttaatc aagatttgca ttatggagtt       540
gtttccatag ttggcatgcc cggtctgggg aaaacaactc ttgccaagaa actttatagg       600
ctcattcgtg atcaatttga gtgttctgga ctggtctacg tttcacaaca gccaagagcg       660
agtgaaatct tacttgacat tgccaaacaa attggactga cggaacagaa aatgaaggaa       720
aatttggagg acaacctgcg atcactcttg aaaataaaaa ggtatgttat cctcctagat       780
gacatttggg atgtggaaat ttgggatgat ctgaaacttg tccttcctga atgtgattca       840
aaagtcggca gtagaatgat aatcacgtct cgaaatagta atgtaggcag atacatagga       900
ggggaatcct ccctccatgc attgcaaccc ctagaatccg agaaaagctt tgaactcttt       960
accaagaaaa tctttaattt tgatgataat aatagttggg ccaatgcttc acctgacttg      1020
gtgaatattg gtagaaatat agttgggaga tgtggaggta taccgctagc catagtggtg      1080
actgcaggca tgttaagggc aagagaaaga acagaacatg cgtggaacag agtacttgag      1140
agtatgggcc ataaagttca agatggatgt gctaaggtat tggctctcag ttacaatgat      1200
ttacctattg cctcaaggcc atgtttcttg tactttggcc tttaccccga ggaccatgaa      1260
attcgtgctt ttgatttgat aaatatgtgg attgctgaga gtttatagt agtaaatagt       1320 ggtaataggc gagaggctga ggatttggcg gaggacgtcc taaatgattt ggtttctaga      1380
aacttgattc aacttgccaa aaggacatat aatggaagaa tttcaagttg tcgcatacat      1440
gacttgttac atagtttgtg tgtggacttg gctaaggaaa gtaacttctt tcacaccgcg      1500
catgatgcat ttggtgatcc cggcaatgtt gctaggctcc gaaggattac attctactct      1560
```

```
gacaatgtca tgattgagtt cttccgttca aatcctaagc ttgagaagct tcgtgtactt      1620
ttctgtttcg caaaagaccc ttccatattt tctcatatgg cttattttga cttcaaattg      1680
ttgcacacat tggttgtagt catgtctcaa agttttcaag catatgtcac tatcccaagc      1740
aaatttggga acatgacttg cttacgctat ctgagattgg aggggaatat ttgtggaaaa      1800
ctgccaaata gtattgtcaa gctcacacgt ctagagacca tagacattga tcgacgtagc      1860
ctcattcaac ctccttctgg tgtttgggag tctaaacatt tgagacatct ttgttataga      1920
gattatggac aagcatgtaa cagttgcttt tctataagct cattttaccc aaatatttac      1980
tcattgcatc ctaacaatct acaaaccttg atgtggatac ctgataaatt ttttgaaccg      2040
aggttgttgc accgattgat caatttaaga aaactgggta tactgggagt gtccaattct      2100
accgttaaga tgttatcaat atttagccct gtgcttaagg cgctggaggt tctgaagctc      2160 agttttttcca gtgacccgag tgaacaaata aagttgtcat cgtatccaca tattgctaag      2220
ttgcatttga atgttaacag aacaatggcc ttgaactctc aatcatttcc tccaaatctc      2280
atcaagctta ctctagccta ctttagtgta gaccgttata tactggcagt acttaagaca      2340
tttcccaaat taagaaaact taaaatgttc atctgcaagt ataatgaaga aaagatggat      2400
ctctcgggcg aggcaaatgg ttatagcttt ccgcaacttg aagttttgca tattcatagc      2460
ccgaatgggt tgactgaagt aacgtgcacg gatgatgtca gtatgcccaa attgaaaaag      2520
ctgttactta caggattcca ttgccgaatc agtttatcgg aacggcttaa aaagctgagt      2580
aaatga                                                                  2586

<210> SEQ ID NO 32
<211> LENGTH: 2586
<212> TYPE: DNA
<213> ORGANISM: artificial
<220> FEATURE:
<223> OTHER INFORMATION: mutant

<400> SEQUENCE: 32
atggctgaaa ttcttcttac atcagtaatc aataaatctg tagaaatagc tggaaattta       60
ctgattcaag aaggaaagcg tttatattgg ttgaaagagg atatcgattg gctccagaga      120
gaaatgagac acattcgatc ttatgttgac aacgcaaagg ccaaggaagc tggaggtgat      180
tcaagggtca aaacttatt gaaagatatt caagaattgg caggtgatgt ggaggatctc      240
ttagatgact tccttccaaa aattcaacaa tccaataagt tcaattattg ccttaagagg      300
agttcttttg cagatgagtt tgctatggag attgagaaga taaagagaag ggttgttgac      360
attgaccgaa taaggaaaac ttacaacatc atagatacag ataacaataa tgatgattgt      420
gttctgctgg atcggagaag attattccta catgctgatg aaacagagat catcggtttg      480
gatgatgact tcaatatgct acaagccaaa ttacttaatc aagatttgca ttatggagtt      540
gtttccatag ttggcatgcc cggtctgggg aaaacaactc ttgccaagaa acttatagg       600 ctcattcgtg atcaatttga gtgttctgga ctggtctacg tttcacaaca gccaagagcg      660
agtgaaatct tacttgacat tgccaaacaa attggactga cggaacgaaa aatgaaggaa      720
aatttggagg acaacctgcg atcactcttg aaaataaaaa ggtatgttat cctcctagat      780
gacatttggg atgtggaaat ttgggatgat ctgaaacttg tccttcctga atgtgattca      840
aaagtcggca gtagaatgat aatcacgtct cgaaatagta atgtaggcag atacatagga      900
ggggaatcct ccctccatgc attgcaaccc ctagaatccg agaaaagctt tgaactcttt      960
```

-continued

```
accaagaaaa tctttaattt tgatgataat aatagttggg ccaatgcttc acctgacttg     1020
gtgaatattg gtagaaatat agttgggaga tgtggaggta taccgctagc catagtggtg     1080
actgcaggca tgttaagggc aagagaaaga acagaacatg cgtggaacag agtacttgag     1140
agtatgggcc ataaagttca agatggatgt gctaaggtat tggctctcag ttacaatgat     1200
ttacctattg cctcaaggcc atgtttcttg tactttggcc tttaccccga ggaccatgaa     1260
attcgtgctt ttgatttgat aaatatgtgg attgctgaga agtttatagt agtaaatagt     1320
ggtaataggc gagaggctga ggatttggcg gaggacgtcc taaatgattt ggtttctaga     1380
aacttgattc aacttgccaa aaggacatat aatggaagaa tttcaagttg tcgcatacat     1440
gacttgttac atagtttgtg tgtggacttg gctaaggaaa gtaacttctt tcacaccgcg     1500
catgatgcat ttggtgatcc cggcaatgtt gctaggctcc gaaggattac attctactct     1560
gacaatgtca tgattgagtt cttccgttca aatcctaagc ttgagaagct tcgtgtactt     1620
ttctgtttcg caaaagaccc ttccatattt tctcatatgg cttatttga cttcaaattg      1680 ttgcacacat tggttgtagt catgtctcaa agttttcaag catatgtcac tatcccaagc     1740
aaatttggga acatgacttg cttacgctat ctgagattgg aggggaatat ttgtggaaaa     1800
ctgccaaata gtattgtcaa gctcacacgt ctagagacca tagacattga tcgacgtagc     1860
ctcattcaac ctccttctgg tgtttgggag tctaaacatt tgagacatct ttgttataga     1920
gattatggac aagcatgtaa cagttgcttt tctataagct cattttaccc aaatatttac     1980
tcattgcatc ctaacaatct acaaaccttg atgtggatac ctgataaatt ttttgaaccg     2040
aggttgttgc accgattgat caatttaaga aaactgggta tactgggagt gtccaattct     2100
accgttaaga tgttatcaat atttagccct gtgcttaagg cgctggaggt tctgaagctc     2160 agttttttcca gtgacccgag tgaacaaata aagttgtcat cgtatccaca tattgctaag     2220
ttgcatttga atgttaacag aacaatggcc ttgaactctc aatcatttcc tccaaatctc     2280
atcaagctta ctctagccta ctttagtgta gaccgttata tactggcagt acttaagaca     2340
tttcccaaat taagaaaact taaaatgttc atctgcaagt ataatgaaga aaagatggat     2400
ctctcgggcg aggcaaatgg ttatagcttt ccgcaacttg aagttttgca tattcatagc     2460
ccgtgtgggt tgtctgaagt aacgtgcacg gatgatgtca gtatgcccaa attgaaaaag     2520
ctgttactta caggattcca ttgccgaatc agtttatcgg aacggcttaa aaagctgagt     2580
aaatga                                                                 2586
```

<210> SEQ ID NO 33
<211> LENGTH: 2586
<212> TYPE: DNA
<213> ORGANISM: artificial
<220> FEATURE:
<223> OTHER INFORMATION: mutant

<400> SEQUENCE: 33

```
atggctgaaa ttcttcttac atcagtaatc aataaatctg tagaaatagc tggaaattta       60
ctgattcaag aaggaaagcg tttatattgg ttgaaagagg atatcgattg gctccagaga      120
gaaatgagac acattcgatc ttatgttgac aacgcaaagg ccaaggaagc tggaggtgat      180
tcaagggtca aaaacttatt gaaagatatt caagaattgg caggtgatgt ggaggatctc      240
ttagatgact ccttccaaa aattcaacaa tccaataagt tcaattattg ccttaagagg        300
agttcttttg cagatgagtt tgctatggag attgagaaga taaagagaag ggttgttgac      360
attgaccgaa taaggaaaac ttacaacatc atagatacag ataacaataa tgatgattgt      420
```

-continued

```
gttctgctgg atcggagaag attattccta catgctgatg aaacagagat catcggtttg      480
gatgatgact tcaatatgct acaagccaaa ttacttaatc aagatttgca ttatggagtt      540
gtttccatag ttggcatgcc cggtctgggg aaaacaactc ttgccaagaa actttatagg      600
ctcattcgtg atcaatttga gtgttctgga ctggtctacg tttcacaaca gccaagagcg      660
agtgaaatct tacttgacat tgccaaacaa attggactga cggaacagaa aatgaaggaa      720
aatttggagg acaacctgcg atcactcttg aaaataaaaa ggtatgttat cctcctagat      780
gacatttggg atgtggaaat ttgggatgat ctgaaacttg tccttcctga atgtgattca      840
aaagtcggca gtagaatgat aatcacgtct cgaaatagta atgtaggcag atacatagga      900
ggggaatcct ccctccatgc attgcaaccc ctagaatccg agaaaagctt tgaactcttt      960
accaagaaaa tctttaattt tgatgataat aatagttggg ccaatgcttc acctgacttg     1020
gtgaatattg gtagaaatat agttgggaga tgtggaggta taccgctagc catagtggtg     1080
actgcaggca tgttaagggc aagagaaaga acagaacatg cgtggaacag agtacttgag     1140
agtatgggcc ataaagttca agatggatgt gctaaggtat tggctctcag ttacaatgat     1200
ttacctattg cctcaaggcc atgtttcttg tactttggcc tttaccccga ggaccatgaa     1260
attcgtgctt ttgatttgat aaatatgtgg attgctgaga agtttatagt agtaaatagt     1320
ggtaataggc gagaggctga ggatttggcg gaggacgtcc taaatgattt ggtttctaga     1380
aacttgattc aacttgccaa aaggacatat aatggaagaa tttcaagttg tcgcatacat     1440
gacttgttac atagtttgtg tgtggacttg gctaaggaaa gtaacttctt tcacaccgcg     1500
catgatgcat ttggtgatcc cggcaatgtt gctaggctcc gaaggattac attctactct     1560
gacaatgtca tgattgagtt cttccgttca aatcctaagc ttgagaagct tcgtgtactt     1620
ttctgtttcg caaaagaccc ttccatattt tctcatatgg cttattttga cttcaaattg     1680
ttgcacacat tggttgtagt catgtctcaa agttttcaag catatgtcac tatcccaagc     1740
aaatttggga acatgacttg cttacgctat ctgagattgg aggggaatat ttgtggaaaa     1800
ctgccaaata gtattgtcaa gctcacacgt ctagagacca tagacattga tcgacgtagc     1860
ctcattcaac ctccttctgg tgtttgggag tctaaacatt tgagacatct ttgttataga     1920
gattatggac aagcatgtaa cagttgcttt tctataagct cattttaccc aaatatttac     1980
tcattgcatc ctaacaatct acaaaccttg atgtggatac ctgataaatt ttttgaaccg     2040
aggttgttgc accgattgat caatttaaga aaactgggta tactgggagt gtccaattct     2100
accgttaaga tgttatcaat atttagccct gtgcttaagg cgctggaggt tctgaagctc     2160
agtttttcca gtgacccgag tgaacaaata aagttgtcat cgtatccaca tattgctaag     2220
ttgcatttga atgttaacag aacaatggcc ttgaactctc aatcatttcc tccaaatctc     2280
atcaagctta ctctagccta ctttagtgta gaccgttata tactggcagt acttaagaca     2340
tttcccaaat taagaaaact aaaatgttc atctgcaagt ataatgaaga aaagatggat     2400
ctctcgggcg aggcaaatgg ttatagcttt ccgcaacttg aagttttgca tattcatagc     2460
ccgtttgggt tgtctgaagt aacgtgcacg gatgatgtca gtatgcccaa attgaaaaag     2520
ctgttactta caggattcca ttgccgaatc agtttatcgg aacggcttaa aaagctgagt     2580
aaatga                                                                  2586
```

<210> SEQ ID NO 34
<211> LENGTH: 2586
<212> TYPE: DNA

-continued

```
<213> ORGANISM: artificial
<220> FEATURE:
<223> OTHER INFORMATION: mutant

<400> SEQUENCE: 34
atggctgaaa ttcttcttac atcagtaatc aataaatctg tagaaatagc tggaaattta     60
ctgattcaag aaggaaagcg tttatattgg ttgaaagagg atatcgattg gctccagaga    120
gaaatgagac acattcgatc ttatgttgac aacgcaaagg ccaaggaagc tggaggtgat    180
tcaagggtca aaaacttatt gaaagatatt caagaattgg caggtgatgt ggaggatctc    240
ttagatgact tccttccaaa aattcaacaa tccaataagt tcaattattg ccttaagagg    300
agttcttttg cagatgagtt tgctatggag attgagaaga taaagagaag ggttgttgac    360
attgaccgaa taaggaaaac ttacaacatc atagatacag ataacaataa tgatgattgt    420
gttctgctgg atcggagaag attattccta catgctgatg aaacagagat catcggtttg    480
gatgatgact tcaatatgct acaagccaaa ttacttaatc aagatttgca ttatggagtt    540
gtttccatag ttggcatgcc cggtctgggg aaaacaactc ttgccaagaa actttatagg    600
ctcattcgtg atcaatttga gtgttctgga ctggtctacg tttcacaaca gccaagagcg    660
agtgaaatct tacttgacat tgccaaacaa attggactga cggaacagaa aatgaaggaa    720
aatttggagg acaacctgcg atcactcttg aaaataaaaa ggtatgttat cctcctagat    780
gacatttggg atgtggaaat ttgggatgat ctgaaacttg tccttcctga atgtgattca    840
aaagtcggca gtagaatgat aatcacgtct cgaaatagta atgtaggcag atacatagga    900
ggggaatcct ccctccatgc attgcaaccc ctagaatccg agaaaagctt tgaactcttt    960
accaagaaaa tctttaattt tgatgataat aatagttggg ccaatgcttc acctgacttg   1020
gtgaatattg gtagaaatat agttgggaga tgtggaggta taccgctagc catagtggtg   1080
actgcaggca tgttaagggc aagagaaaga acagaacatg cgtggaacag agtacttgag   1140
agtatgggcc ataaagttca agatggatgt gctaaggtat tggctctcag ttacaatgat   1200
ttacctattg cctcaaggcc atgtttcttg tactttggcc tttaccccga ggaccatgaa   1260
attcgtgctt ttgatttgat aaatatgtgg attgctgaga gtttatagt agtaaatagt   1320 ggtaataggc gagaggctga ggatttggcg gaggacgtcc taaatgattt ggtttctaga   1380
aacttgattc aacttgccaa aaggacatat aatggaagaa tttcaagttg tcgcatacat   1440
gacttgttac atagtttgtg tgtggacttg gctaaggaaa gtaacttctt tcacaccgcg   1500
catgatgcat ttggtgatcc cggcaatgtt gctaggctcc gaaggattac attctactct   1560
gacaatgtca tgattgagtt cttccgttca aatcctaagc ttgagaagct tcgtgtactt   1620
ttctgtttcg caaaagaccc ttccatattt tctcatatgg cttattttga cttcaaattg   1680
ttgcacacat tggttgtagt catgtctcaa agttttcaag catatgtcac tatcccaagc   1740
aaatttggga acatgacttg cttacgctat ctgagattgg aggggaatat ttgtggaaaa   1800
ctgccaaata gtattgtcaa gctcacacgt ctagagacca tagacattga tcgacgtagc   1860
ctcattcaac ctccttctgg tgtttgggag tctaaacatt tgagacatct ttgttataga   1920
gattatggac aagcatgtaa cagttgcttt tctataagct cattttaccc aaatatttac   1980
tcattgcatc ctaacaatct acaaaccttg atgtggatac ctgataaatt ttttgaaccg   2040
aggttgttgc accgattgat caatttaaga aaactgggta tactgggagt gtccaattct   2100
accgttaaga tgttatcaat atttagccct gtgcttaagg cgctgaggt tctgaagctc   2160 agtttttcca gtgacccgag tgaacaaata aagttgtcat cgtatccaca tattgctaag   2220
```

-continued

```
ttgcatttga atgttaacag aacaatggcc ttgaactctc aatcatttcc tccaaatctc      2280
atcaagctta ctctagccta ctttagtgta gaccgttata tactggcagt acttaagaca      2340
tttcccaaat taagaaaact taaaatgttc atctgcaagt ataatgaaga aaagatggat      2400
ctctcgggcg aggcaaatgg ttatagcttt ccgcaacttg aagttttgca tattcatagc      2460
ccgatggggt tgtctgaagt aacgtgcacg gatgatgtca gtatgcccaa attgaaaaag      2520
ctgttactta caggattcca ttgccgaatc agtttatcgg aacggcttaa aaagctgagt      2580
aaatga                                                                  2586

<210> SEQ ID NO 35
<211> LENGTH: 2586
<212> TYPE: DNA
<213> ORGANISM: artificial
<220> FEATURE:
<223> OTHER INFORMATION: mutant

<400> SEQUENCE: 35
atggctgaaa ttcttcttac atcagtaatc aataaatctg tagaaatagc tggaaattta        60
ctgattcaag aaggaaagcg tttatattgg ttgaaagagg atatcgattg gctccagaga       120
gaaatgagac acattcgatc ttatgttgac aacgcaaagg ccaaggaagc tggaggtgat       180
tcaagggtca aaaacttatt gaaagatatt caagaattgg caggtgatgt ggaggatctc       240
ttagatgact tccttccaaa aattcaacaa tccaataagt tcaattattg ccttaagagg       300
agttcttttg cagatgagtt tgctatggag attgagaaga taaagagaag ggttgttgac       360
attgaccgaa taaggaaaac ttacaacatc atagatacag ataacaataa tgatgattgt       420
gttctgctgg atcggagaag attattccta catgctgatg aaacagagat catcggtttg       480
gatgatgact tcaatatgct acaagccaaa ttacttaatc aagatttgca ttatggagtt       540
gtttccatag ttggcatgcc cggtctgggg aaaacaactc ttgccaagaa actttatagg       600
ctcattcgtg atcaatttga gtgttctgga ctggtctacg tttcacaaca gccaagagcg       660
agtgaaatct tacttgacat tgccaaacaa attggactga cggaacgaaa aatgaaggaa       720
aatttggagg acaacctgcg atcactcttg aaaataaaaa ggtatgttat cctcctagat       780
gacatttggg atgtggaaat ttgggatgat ctgaaacttg tccttcctga atgtgattca       840
aaagtcggca gtagaatgat aatcacgtct cgaaatagta atgtaggcag atacatagga       900
ggggaatcct ccctccatgc attgcaaccc ctagaatccg agaaaagctt tgaactcttt       960
accaagaaaa tctttaattt tgatgataat aatagttggg ccaatgcttc acctgacttg      1020
gtgaatattg gtagaaatat agttgggaga tgtggaggta taccgctagc catagtggtg      1080
actgcaggca tgtgtaaggg caagagaaaga acagaacatg cgtggaacag agtacttgag      1140
agtatgggcc ataaagttca agatggatgt gctaaggtat tggctctcag ttacaatgat      1200
ttacctattg cctcaaggcc atgtttcttg tactttggcc tttaccccga ggaccatgaa      1260
attcgtgctt ttgatttgat aaatatgtgg attgctgaga agtttatagt agtaaatagt      1320
ggtaataggc gagaggctga ggatttggcg gaggacgtcc taaatgattt ggtttctaga      1380
aacttgattc aacttgccaa aaggacatat aatggaagaa tttcaagttg tcgcatacat      1440
gacttgttac atagtttgtg tgtggacttg gctaaggaaa gtaacttctt tcacaccgcg      1500
catgatgcat ttggtgatcc cggcaatgtt gctaggctcc gaaggattac attctactct      1560
gacaatgtca tgattgagtt cttccgttca aatcctaagc ttgagaagct tcgtgtactt      1620
```

-continued

```
ttctgtttcg caaaagaccc ttccatattt tctcatatgg cttattttga cttcaaattg      1680
ttgcacacat tggttgtagt catgtctcaa agttttcaag catatgtcac tatcccaagc      1740
aaatttggga acatgacttg cttacgctat ctgagattgg aggggaatat ttgtggaaaa      1800
ctgccaaata gtattgtcaa gctcacacgt ctagagacca tagacattga tcgacgtagc      1860
ctcattcaac ctccttctgg tgtttgggag tctaaacatt tgagacatct ttgttataga      1920
gattatggac aagcatgtaa cagttgcttt tctataagct cattttaccc aaatatttac      1980
tcattgcatc ctaacaatct acaaaccttg atgtggatac ctgataaatt ttttgaaccg      2040
aggttgttgc accgattgat caatttaaga aaactgggta tactgggagt gtccaattct      2100
accgttaaga tgttatcaat atttagccct gtgcttaagg cgctggaggt tctgaagctc      2160 agttttttcca gtgacccgag tgaacaaata aagttgtcat cgtatccaca tattgctaag      2220
ttgcatttga atgttaacag aacaatggcc ttgaactctc aatcatttcc tccaaatctc      2280
atcaagctta ctctagccta ctttagtgta gaccgttata tactggcagt acttaagaca      2340
tttcccaaat taagaaaact taaaatgttc atctgcaagt ataatgaaga aaagatggat      2400
ctctcgggcg aggcaaatgg ttatagcttt ccgcaacttg aagttttgca tattcatagc      2460
ccgtatgggt tgtctgaagt aacgtgcacg gatgatgtca gtatgcccaa attgaaaaag      2520
ctgttactta caggattcca ttgccgaatc agtttatcgg aacggcttaa aaagctgagt      2580
aaatga                                                                 2586
```

```
<210> SEQ ID NO 36
<211> LENGTH: 2586
<212> TYPE: DNA
<213> ORGANISM: artificial
<220> FEATURE:
<223> OTHER INFORMATION: mutant

<400> SEQUENCE: 36
```

```
atggctgaaa ttcttcttac atcagtaatc aataaatctg tagaaatagc tggaaattta       60
ctgattcaag aaggaaagcg tttatattgg ttgaaagagg atatcgattg gctccagaga      120
gaaatgagac acattcgatc ttatgttgac aacgcaaagg ccaaggaagc tggaggtgat      180
tcaagggtca aaaacttatt gaaagatatt caagaattgg caggtgatgt ggaggatctc      240
ttagatgact tccttccaaa aattcaacaa tccaataagt tcaattattg ccttaagagg      300
agttcttttg cagatgagtt tgctatggag attgagaaga taaagagaag ggttgttgac      360
attgaccgaa taaggaaaac ttacaacatc atagatacag ataacaataa tgatgattgt      420
gttctgctgg atcggagaag attattccta catgctgatg aaacagagat catcggtttg      480
gatgatgact tcaatatgct acaagccaaa ttacttaatc aagatttgca ttatggagtt      540
gtttccatag ttggcatgcc cggtctgggg aaaacaactc ttgccaagaa actttatagg      600
ctcattcgtg atcaatttga gtgttctgga ctggtctacg tttcacaaca gccaagagcg      660
agtgaaatct tacttgacat tgccaaacaa attggactga cggaacagaa aatgaaggaa      720
aatttggagg acaacctgcg atcactcttg aaaataaaaa ggtatgttat cctcctagat      780
gacatttggg atgtggaaat ttgggatgat ctgaaacttg tccttcctga atgtgattca      840
aaagtcggca gtagaatgat aatcacgtct cgaaatagta atgtaggcag atacatagga      900
ggggaatcct ccctccatgc attgcaaccc ctagaatccg agaaaagctt tgaactcttt      960
accaagaaaa tctttaattt tgatgataat aatagttggg ccaatgcttc acctgacttg     1020
gtgaatattg gtagaaatat agttgggaga tgtggaggta taccgctagc catagtggtg     1080
```

-continued

```
actgcaggca tgttaagggc aagagaaaga acagaacatg cgtggaacag agtacttgag      1140
agtatgggcc ataaagttca agatggatgt gctaaggtat tggctctcag ttacaatgat      1200
ttacctattg cctcaaggcc atgtttcttg tactttggcc tttaccccga ggaccatgaa      1260
attcgtgctt ttgatttgat aaatatgtgg attgctgaga agtttatagt agtaaatagt      1320
ggtaataggc gagaggctga ggatttggcg gaggacgtcc taaatgattt ggtttctaga      1380
aacttgattc aacttgccaa aaggacatat aatggaagaa tttcaagttg tcgcatacat      1440
gacttgttac atagtttgtg tgtggacttg gctaaggaaa gtaacttctt tcacaccgcg      1500
catgatgcat ttggtgatcc cggcaatgtt gctaggctcc gaaggattac attctactct      1560
gacaatgtca tgattgagtt cttccgttca aatcctaagc ttgagaagct tcgtgtactt      1620
ttctgtttcg caaaagaccc ttccatattt tctcatatgg cttatttga cttcaaattg       1680 ttgcacacat tggttgtagt catgtctcaa agttttcaag catatgtcac tatcccaagc      1740
aaatttggga acatgacttg cttacgctat ctgagattgg aggggaatat ttgtggaaaa      1800
ctgccaaata gtattgtcaa gctcacacgt ctagagacca tagacattga tcgacgtagc      1860
ctcattcaac ctccttctgg tgtttgggag tctaaacatt tgagacatct ttgttataga      1920
gattatggac aagcatgtaa cagttgcttt tctataagct cattttaccc aaatatttac      1980
tcattgcatc ctaacaatct acaaaccttg atgtggatac ctgataaatt ttttgaaccg       2040
aggttgttgc accgattgat caatttaaga aaactgggta tactgggagt gtccaattct      2100
accgttaaga tgttatcaat atttagccct gtgcttaagg cgctggaggt tctgaagctc      2160 agttttttcca gtgacccgag tgaacaaata aagttgtcat cgtatccaca tattgctaag      2220
ttgcatttga atgttaacag aacaatggcc ttgaactctc aatcatttcc tccaaatctc      2280
atcaagctta ctctagccta ctttagtgta gaccgttata tactggcagt acttaagaca      2340
tttcccaaat taagaaaact taaaatgttc atctgcaagt ataatgaaga aaagatggat      2400
ctctcgggcg aggcaaatgg ttatagcttt ccgcaacttg aagttttgca tattcatagc      2460
ccgtgggggt tgtctgaagt aacgtgcacg gatgatgtca gtatgcccaa attgaaaaag      2520
ctgttactta caggattcca ttgccgaatc agtttatcgg aacggcttaa aaagctgagt      2580
aaatga                                                                 2586
```

```
<210> SEQ ID NO 37
<211> LENGTH: 18
<212> TYPE: DNA
<213> ORGANISM: artificial
<220> FEATURE:
<223> OTHER INFORMATION: primer

<400> SEQUENCE: 37
cctgccgaga aagtatcc                                                      18

<210> SEQ ID NO 38
<211> LENGTH: 18
<212> TYPE: DNA
<213> ORGANISM: artificial
<220> FEATURE:
<223> OTHER INFORMATION: primer

<400> SEQUENCE: 38
gccaacgcta tgtcctga                                                      18

<210> SEQ ID NO 39
```

-continued

```
<211> LENGTH: 21
<212> TYPE: DNA
<213> ORGANISM: artificial
<220> FEATURE:
<223> OTHER INFORMATION: primer

<400> SEQUENCE: 39
ttcctccaaa tctcatcaag c                                          21

<210> SEQ ID NO 40
<211> LENGTH: 22
<212> TYPE: DNA
<213> ORGANISM: artificial
<220> FEATURE:
<223> OTHER INFORMATION: primer

<400> SEQUENCE: 40
caacaagcca agagaaaaca ca                                         22

<210> SEQ ID NO 41
<211> LENGTH: 11668
<212> TYPE: DNA
<213> ORGANISM: artificial
<220> FEATURE:
<223> OTHER INFORMATION: plasmid

<400> SEQUENCE: 41
atggctgaaa ttcttcttac atcagtaatc aataaatctg tagaaatagc tggaaattta    60
ctgattcaag aaggaaagcg tttatattgg ttgaaagagg atatcgattg gctccagaga   120
gaaatgagac acattcgatc ttatgttgac aacgcaaagg ccaaggaagc tggaggtgat   180
tcaagggtca aaaacttatt gaaagatatt caagaattgg caggtgatgt ggaggatctc   240
ttagatgact tccttccaaa aattcaacaa tccaataagt tcaattattg ccttaagagg   300
agttcttttg cagatgagtt tgctatggag attgagaaga taaagagaag ggttgttgac   360
attgaccgaa taaggaaaac ttacaacatc atagatacag ataacaataa tgatgattgt   420
gttctgctgg atcggagaag attattccta catgctgatg aaacagagat catcggtttg   480
gatgatgact tcaatatgct acaagccaaa ttacttaatc aagatttgca ttatggagtt   540
gtttccatag ttggcatgcc cggtctgggg aaaacaactc ttgccaagaa actttatagg   600
ctcattcgtg atcaatttga gtgttctgga ctggtctacg tttcacaaca gccaagagcg   660
agtgaaatct tacttgacat tgccaaacaa attggactga cggaacagaa aatgaaggaa   720
aatttggagg acaacctgcg atcactcttg aaaataaaaa ggtatgttat cctcctagat   780
gacatttggg atgtggaaat ttgggatgat ctgaaacttg tccttcctga atgtgattca   840
aaagtcggca gtagaatgat aatcacgtct cgaaatagta atgtaggcag atacatagga   900
ggggaatcct ccctccatgc attgcaaccc ctagaatccg agaaaagctt tgaactcttt   960
accaagaaaa tctttaattt tgatgataat aatagttggg ccaatgcttc acctgacttg  1020
gtgaatattg gtagaaatat agttgggaga tgtggaggta taccgctagc catagtggtg  1080
actgcaggca tgttaagggc aagagaaaga acagaacatg cgtggaacag agtacttgag  1140
agtatgggcc ataaagttca agatggatgt gctaaggtat tggctctcag ttacaatgat  1200
ttacctattg cctcaaggcc atgtttcttg tactttggcc tttaccccga ggaccatgaa  1260
attcgtgctt ttgatttgat aaatatgtgg attgctgaga gtttatagt agtaaatagt  1320 ggtaataggc gagaggctga ggatttggcg gaggacgtcc taaatgattt ggtttctaga  1380
aacttgattc aacttgccaa aaggacatat aatggaagaa tttcaagttg tcgcatacat  1440
```

-continued

```
gacttgttac atagtttgtg tgtggacttg gctaaggaaa gtaacttctt tcacaccgcg      1500
catgatgcat ttggtgatcc cggcaatgtt gctaggctcc gaaggattac attctactct      1560
gacaatgtca tgattgagtt cttccgttca aatcctaagc ttgagaagct tcgtgtactt      1620
ttctgtttcg caaaagaccc ttccatattt tctcatatgg cttattttga cttcaaattg      1680
ttgcacacat tggttgtagt catgtctcaa agttttcaag catatgtcac tatcccaagc      1740
aaatttggga acatgacttg cttacgctat ctgagattgg aggggaatat ttgtggaaaa      1800
ctgccaaata gtattgtcaa gctcacacgt ctagagacca tagacattga tcgacgtagc      1860
ctcattcaac ctccttctgg tgtttgggag tctaaacatt tgagacatct ttgttataga      1920
gattatggac aagcatgtaa cagttgcttt tctataagct cattttaccc aaatatttac      1980
tcattgcatc ctaacaatct acaaaccttg atgtggatac ctgataaatt ttttgaaccg      2040
aggttgttgc accgattgat caatttaaga aaactgggta tactgggagt gtccaattct      2100
accgttaaga tgttatcaat atttagccct gtgcttaagg cgctggaggt tctgaagctc      2160 agttttttcca gtgacccgag tgaacaaata aagttgtcat cgtatccaca tattgctaag      2220
ttgcatttga atgttaacag aacaatggcc ttgaactctc aatcatttcc tccaaatctc      2280
atcaagctta ctctagccta ctttagtgta gaccgttata tactggcagt acttaagaca      2340
tttcccaaat taagaaaact taaaatgttc atctgcaagt ataatgaaga aaagatggat      2400
ctctcgggcg aggcaaatgg ttatagcttt ccgcaacttg aagttttgca tattcatagc      2460
ccgaatgggt tgtctgaagt aacgtgcacg gatgatgtca gtatgcccaa attgaaaaag      2520
ctgttactta caggattcca ttgccgaatc agtttatcgg aacggcttaa aaagctgagt      2580
aaatgaacct agggtgggat atgaagatga agatgaaata tttggtgtgt caaataaaaa      2640
gcttgtgtgc ttaagtttgt gttttttttct tggcttgttg tgttatgaat ttgtggcttt      2700
ttctaatatt aaatgaatgt aagatctcat tataatgaat aaacaaatgt ttctataatc      2760
cattgtgaat gttttgttgg atctcttctg cagcatataa ctactgtatg tgctatggta      2820
tggactatgg aatatgatta aagataaggt gatatcgaat tcctgcggta cccgccttca      2880
gtttaaacta tcagtgtttg acaggatata ttggcgggta aacctaagag aaaagagcgt      2940
ttattagaat aacggatatt taaaagggcg tgaaaaggtt tatccgttcg tccatttgta      3000
tgtgcatgcc aaccacaggg ttcccctcgg gatcaaagta ctttgatcca acccctccgc      3060
tgctatagtg cagtcggctt ctgacgttca gtgcagccgt cttctgaaaa cgacatgtcg      3120
cacaagtcct aagttacgcg acaggctgcc gccctgccct tttcctggcg ttttcttgtc      3180
gcgtgtttta gtcgcataaa gtagaatact tgcgactaga accggagaca ttacgccatg      3240
aacaagagcg ccgccgctgg cctgctgggc tatgcccgcg tcagcaccga cgaccaggac      3300
ttgaccaacc aacgggccga actgcacgcg gccggctgca ccaagctgtt ttccgagaag      3360
atcaccggca ccaggcgcga ccgcccggag ctggccagga tgcttgacca cctacgccct      3420
ggcgacgttg tgacagtgac caggctagac cgcctggccc gcagcacccg cgacctactg      3480
gacattgccg agcgcatcca ggaggccggc gcgggcctgc gtagcctggc agagccgtgg      3540
gccgacacca ccacgccggc cggccgcatg gtgttgaccg tgttcgccgg cattgccgag      3600
ttcgagcgtt ccctaatcat cgaccgcacc cggagcgggc gcgaggccgc caaggcccga      3660
ggcgtgaagt ttggcccccg ccctaccctc accccggcac agatcgcgca cgcccgcgag      3720
ctgatcgacc aggaaggccg caccgtgaaa gaggcggctg cactgcttgg cgtgcatcgc      3780
```

-continued

```
tcgaccctgt accgcgcact tgagcgcagc gaggaagtga cgcccaccga ggccaggcgg    3840
cgcggtgcct tccgtgagga cgcattgacc gaggccgacg ccctggcggc cgccgagaat    3900
gaacgccaag aggaacaagc atgaaaccgc accaggacgg ccaggacgaa ccgttttca     3960 ttaccgaaga gatcgaggcg gagatgatcg cggccgggta cgtgttcgag ccgcccgcgc    4020
acgtctcaac cgtgcggctg catgaaatcc tggccggttt gtctgatgcc aagctggcgg    4080
cctggccggc cagcttggcc gctgaagaaa ccgagcgccg ccgtctaaaa aggtgatgtg    4140
tatttgagta aaacagcttg cgtcatgcgg tcgctgcgta tatgatgcga tgagtaaata    4200
aacaaatacg caaggggaac gcatgaaggt tatcgctgta cttaaccaga aaggcgggtc    4260
aggcaagacg accatcgcaa cccatctagc ccgcgccctg caactcgccg gggccgatgt    4320
tctgttagtc gattccgatc cccagggcag tgcccgcgat tgggcggccg tgcgggaaga    4380
tcaaccgcta accgttgtcg gcatcgaccg cccgacgatt gaccgcgacg tgaaggccat    4440
cggccggcgc gacttcgtag tgatcgacgg agcgcccag gcggcggact tggctgtgtc    4500
cgcgatcaag gcagccgact tcgtgctgat tccggtgcag ccaagccctt acgacatatg    4560
ggccaccgcc gacctggtgg agctggttaa gcagcgcatt gaggtcacgg atggaaggct    4620
acaagcggcc tttgtcgtgt cgcgggcgat caaaggcacg cgcatcggcg gtgaggttgc    4680
cgaggcgctg gccgggtacg agctgcccat tcttgagtcc cgtatcacgc agcgcgtgag    4740
ctacccaggc actgccgccg ccggcacaac cgttcttgaa tcagaacccg agggcgacgc    4800
tgcccgcgag gtccaggcgc tggccgctga aattaaatca aaactcattt gagttaatga    4860
ggtaaagaga aaatgagcaa aagcacaaac acgctaagtg ccggccgtcc gagcgcacgc    4920
agcagcaagg ctgcaacgtt ggccagcctg gcagacacgc cagccatgaa gcgggtcaac    4980
tttcagttgc cggcggagga tcacaccaag ctgaagatgt acgcggtacg ccaaggcaag    5040
accattaccg agctgctatc tgaatacatc gcgcagctac cagagtaaat gagcaaatga    5100
ataaatgagt agatgaattt tagcggctaa aggaggcggc atggaaaatc aagaacaacc    5160
aggcaccgac gccgtggaat gccccatgtg tggaggaacg ggcggttggc caggcgtaag    5220
cggctgggtt gtctgccggc cctgcaatgg cactggaacc cccaagcccg aggaatcggc    5280
gtgacggtcg caaaccatcc ggcccggtac aaatcggcgc ggcgctgggt gatgacctgg    5340
tggagaagtt gaaggccgcg caggccgccc agcggcaacg catcgaggca gaagcacgcc    5400
ccggtgaatc gtggcaagcg gccgctgatc gaatccgcaa agaatcccgg caaccgccgg    5460
cagccggtgc gccgtcgatt aggaagccgc ccaaggcga cgagcaacca gattttttcg    5520
ttccgatgct ctatgacgtg ggcacccgcg atagtcgcag catcatggac gtggccgttt    5580
tccgtctgtc gaagcgtgac cgacgagctg gcgaggtgat ccgctacgag cttccagacg    5640
ggcacgtaga ggtttccgca gggccggccg gcatggccag tgtgtgggat tacgacctgg    5700
tactgatggc ggtttcccat ctaaccgaat ccatgaaccg ataccgggaa gggaagggag    5760
acaagcccgg ccgcgtgttc cgtccacacg ttgcggacgt actcaagttc tgccggcgag    5820
ccgatggcgg aaagcagaaa gacgacctgg tagaaacctg cattcggtta aacaccacgc    5880
acgttgccat gcagcgtacg aagaaggcca agaacggccg cctggtgacg gtatccgagg    5940
gtgaagcctt gattagccgc tacaagatcg taaagagcga aaccgggcgg ccggagtaca    6000
tcgagatcga gctagctgat tggatgtacc gcgagatcac agaaggcaag aacccggacg    6060
tgctgacggt tcaccccgat tactttttga tcgatcccgg catcggccgt tttctctacc    6120
gcctggcacg ccgcgccgca ggcaaggcag aagccagatg gttgttcaag acgatctacg    6180
```

-continued

```
aacgcagtgg cagcgccgga gagttcaaga agttctgttt caccgtgcgc aagctgatcg   6240
ggtcaaatga cctgccggag tacgatttga aggaggaggc ggggcaggct ggcccgatcc   6300
tagtcatgcg ctaccgcaac ctgatcgagg gcgaagcatc cgccggttcc taatgtacgg   6360
agcagatgct agggcaaatt gccctagcag gggaaaaagg tcgaaaaggt cactttcctg   6420
tggatagcac gtacattggg aacccaaagc cgtacattgg gaaccggaac ccgtacattg   6480
ggaacccaaa gccgtacatt gggaaccggt cacacatgta agtgactgat ataaaagaga   6540
aaaaaggcga tttttccgcc taaaactctt taaaacttat taaaactctt aaaacccgcc   6600
tggcctgtgc ataactgtct ggccagcgca cagccgaaga gctgcaaaaa gcgcctaccc   6660
ttcggtcgct gcgctcccta cgccccgccg cttcgcgtcg gcctatcgcg gccgctggcc   6720
gctcaaaaat ggctggccta cggccaggca atctaccagg gcgcggacaa gccgcgccgt   6780
cgccactcga ccgccggcgc ccacatcaag gcaccctgcc tcgcgcgttt cggtgatgac   6840
ggtgaaaacc tctgacacat gcagctcccg gagacggtca cagcttgtct gtaagcggat   6900
gccgggagca gacaagcccg tcagggcgcg tcagcgggtg ttggcgggtg tcggggcgca   6960
gccatgaccc agtcacgtag cgatagcgga gtgtatactg gcttaactat gcggcatcag   7020
agcagattgt actgagagtg caccatatgc ggtgtgaaat accgcacaga tgcgtaagga   7080
gaaaataccg catcaggcgc tcttccgctt cctcgctcac tgactcgctg cgctcggtcg   7140
ttcggctgcg gcgagcggta tcagctcact caaaggcggt aatacggtta tccacagaat   7200
caggggataa cgcaggaaag aacatgtgag caaaaggcca gcaaaaggcc aggaaccgta   7260
aaaaggccgc gttgctggcg tttttccata ggctccgccc ccctgacgag catcacaaaa   7320
atcgacgctc aagtcagagg tggcgaaacc cgacaggact ataaagatac caggcgtttc   7380
cccctggaag ctccctcgtg cgctctcctg ttccgaccct gccgcttacc ggatacctgt   7440
ccgcctttct cccttcggga agcgtggcgc tttctcatag ctcacgctgt aggtatctca   7500
gttcggtgta ggtcgttcgc tccaagctgg gctgtgtgca cgaacccccc gttcagcccg   7560
accgctgcgc cttatccggt aactatcgtc ttgagtccaa cccggtaaga cacgacttat   7620
cgccactggc agcagccact ggtaacagga ttagcagagc gaggtatgta ggcggtgcta   7680
cagagttctt gaagtggtgg cctaactacg gctacactag aaggacagta tttggtatct   7740
gcgctctgct gaagccagtt accttcggaa aaagagttgg tagctcttga tccggcaaac   7800
aaaccaccgc tggtagcggt ggtttttttg tttgcaagca gcagattacg cgcagaaaaa   7860
aaggatctca agaagatcct ttgatctttt ctacggggtc tgacgctcag tggaacgaaa   7920
actcacgtta agggattttg gtcatgcatg atatatctcc caatttgtgt agggcttatt   7980
atgcacgctt aaaaataata aaagcagact tgacctgata gtttggctgt gagcaattat   8040
gtgcttagtg catctaatcg cttgagttaa cgccggcgaa gcggcgtcgg cttgaacgaa   8100
tttctagcta gacaaggtac taaaacaatt catccagtaa aatataatat tttattttct   8160
cccaatcagg cttgatcccc agtaagtcaa aaaatagctc gacatactgt tcttccccga   8220
tatcctccct gatcgaccgg acgcagaagg caatgtcata ccacttgtcc gccctgccgc   8280
ttctcccaag atcaataaag ccacttactt tgccatcttt cacaaagatg ttgctgtctc   8340
ccaggtcgcc gtgggaaaag acaagttcct cttcgggctt ttccgtcttt aaaaaatcat   8400
acagctcgcg cggatcttta aatggagtgt cttcttccca gttttcgcaa tccacatcgg   8460
ccagatcgtt attcagtaag taatccaatt cggctaagcg gctgtctaag ctattcgtat   8520
```

-continued

```
agggacaatc cgatatgtcg atggagtgaa agagcctgat gcactccgca tacagctcga   8580
taatcttttc agggctttgt tcatcttcat actcttccga gcaaaggacg ccatcggcct   8640
cactcatgag cagattgctc cagccatcat gccgttcaaa gtgcaggacc tttggaacag   8700
gcagctttcc ttccagccat agcatcatgt ccttttcccg ttccacatca taggtggtcc   8760
ctttataccg gctgtccgtc atttttaaat ataggttttc attttctccc accagcttat   8820
ataccttagc aggagacatt ccttccgtat cttтttacgca gcggtatttt tcgatcagtt   8880
ttttcaattc cggtgatatt ctcattttag ccataacaag aagccatgaa aaccgccact   8940
gcgccgttac caccgctgcg ttcggtcaag gttctggacc agttgcgtga cggcagttac   9000
gctacttgca ttacagctta cgaaccgaac gaggcttatg tccactgggt tcgtgcccga   9060
attgatcaca ggcagcaacg ctctgtcatc gttacaatca acatgctacc ctccgcgaga   9120
tcatccgtgt ttcaaacccg gcagcttagt tgccgttctt ccgaatagca tcggtaacat   9180
gagcaaagtc tgccgcctta caacggctct cccgctgacg ccgtcccgga ctgatgggct   9240
gcctgtatcg agtggtgatt ttgtgccgag ctgccggtcg gggagctgtt ggctggctgg   9300
tggcaggata tattgtggtg taaacaaatt gacgcttaga caacttaata acacattgcg   9360
gacgttttta atgtactgaa ttaacgccga attgaattat cagcttgcat gcagctctcc   9420
catatggtcg actagaggcc tgccgtttтta cgtttggaac tgacagaacc gcaacgttga   9480
aggagccact cagccgcggg tttctggagt ttaatgagct aagcacatac gtcagaaacc   9540
attattgcgc gttcaaaagt cgcctaaggt cactatcagc tagcaaatat ttcttgtcaa   9600
aaatgctcca ctgacgttcc ataaattccc ctcggtatcc aattagagtc tcatattcac   9660
tctcaactcg atcgaggcat gattgaacaa gatggattgc acgcaggttc tccggccgct   9720
tgggtggaga ggctattcgg ctatgactgg gcacaacaga caatcggctg ctctgatgcc   9780
gccgtgttcc ggctgtcagc gcaggggcgc ccggttcttt ttgtcaagac cgacctgtcc   9840
ggtgccctga atgaactcca agacgaggca gcgcggctat cgtggctggc cacgacgggc   9900
gttccttgcg cagctgtgct cgacgttgtc actgaagcgg gaagggactg gctgctattg   9960
ggcgaagtgc cggggcagga tctcctgtca tctcaccttg ctcctgccga gaaagtatcc   10020
atcatggctg atgcaatgcg gcggctgcat acgcttgatc cggctacctg cccattcgac   10080
caccaagcga aacatcgcat cgagcgagca cgtactcgga tggaagccgg tcttgtcgat   10140
caggatgatc tggacgaaga gcatcagggg ctcgcgccag ccgaactgtt cgccaggctc   10200
aaggcgcgga tgcccgacgg cgaggatctc gtcgtgaccc acggcgatgc ctgcttgccg   10260
aatatcatgg tggaaaatgg ccgcttttct ggattcatcg actgtggccg ctgggtgtg   10320 gcggaccgct atcaggacat agcgttggct acccgtgata ttgctgaaga gcttggcggc   10380
gaatgggctg accgcttcct cgtgctttac ggtatcgccg ctcccgattc gcagcgcatc   10440
gccttctatc gccttcttga cgagttcttc tgagcgggac tctggggttc ggactctagc   10500
tagagtcaag cagatcgttc aaacatttgg caataaagtt tcttaagatt gaatcctgtt   10560
gccggtcttg cgatgattat catataattt ctgttgaatt acgttaagca tgtaataatt   10620
aacatgtaat gcatgacgtt atttatgaga tgggttttta tgattagagt cccgcaatta   10680
tacatttaat acgcgataga aaacaaaata tagcgcgcaa actaggataa attatcgcgc   10740
gcggtgtcat ctatgttact agatctgcag gtcaacatgg tggagcacga cactctcgtc   10800
tactccaaga atatcaaaga tacagtctca gaagaccaaa gggctattga cttttttcaa   10860
caaagggtaa tatcgggaaa cctcctcgga ttccattgcc cagctatctg tcacttcatc   10920
```

-continued

```
aaaaggacag tagaaaagga aggtggcacc tacaaatgcc atcattgcga taaaggaaag    10980
gctatcgttc aagatgcctc tgccgacagt ggtcccaaag atggaccccc acccacgagg    11040
agcatcgtgg aaaaagaaga cgttccaacc acgtcttcaa agcaagtgga ttgatgtgat    11100
aacatggtgg agcacgacac tctcgtctac tccaagaata tcaaagatac agtctcagaa    11160
gaccaaaggg ctattgagac ttttcaacaa agggtaatat cgggaaacct cctcggattc    11220
cattgcccag ctatctgtca cttcatcaaa aggacagtag aaaaggaagg tggcacctac    11280
aaatgccatc attgcgataa aggaaaggct atcgttcaag atgcctctgc cgacagtggt    11340
cccaaagatg gaccccacc cacgaggagc atcgtggaaa aagaagacgt tccaaccacg    11400
tcttcaaagc aagtggattg atgtgatatc tccactgacg taagggatga cgcacaatcc    11460
cactatcctt cgcaagacct tcctctatat aaggaagttc atttcatttg agaggacct    11520 cgagaattct caacacaaca tatacaaaac aaacgaatct caagcaatca agcattctac    11580
ttctattgca gcaatttaaa tcatttcttt taaagcaaaa gcaattttct gaaaattttc    11640
accatttacg aacgatagtt aattaacc                                       11668
```

<210> SEQ ID NO 42
<211> LENGTH: 11670
<212> TYPE: DNA
<213> ORGANISM: artificial
<220> FEATURE:
<223> OTHER INFORMATION: plasmid

<400> SEQUENCE: 42

```
acaaattgac gcttagacaa cttaataaca cattgcggac gttttttaatg tactgaatta     60 acgccgaatt gaattatcag cttgcatgca gctctcccat atggtcgact agaggcctgc    120
cgttttacgt ttggaactga cagaaccgca acgttgaagg agccactcag ccgcgggttt    180
ctggagttta atgagctaag cacatacgtc agaaaccatt attgcgcgtt caaaagtcgc    240
ctaaggtcac tatcagctag caaatatttc ttgtcaaaaa tgctccactg acgttccata    300
aattcccctc ggtatccaat tagagtctca tattcactct caactcgatc gaggcatgat    360
tgaacaagat ggattgcacg caggttctcc ggccgcttgg gtggagaggc tattcggcta    420
tgactgggca caacagacaa tcggctgctc tgatgccgcc gtgttccggc tgtcagcgca    480
ggggcgcccg gttcttttttg tcaagaccga cctgtccggt gccctgaatg aactccaaga    540
cgaggcagcg cggctatcgt ggctggccac gacgggcgtt ccttgcgcag ctgtgctcga    600
cgttgtcact gaagcgggaa gggactggct gctattgggc gaagtgccgg ggcaggatct    660
cctgtcatct caccttgctc ctgccgagaa agtatccatc atggctgatg caatgcggcg    720
gctgcatacg cttgatccgg ctacctgccc attcgaccac caagcgaaac atcgcatcga    780
gcgagcacgt actcggatgg aagccggtct tgtcgatcag gatgatctgg acgaagagca    840
tcaggggctc gcgccagccg aactgttcgc caggctcaag gcgcggatgc ccgacggcga    900
ggatctcgtc gtgacccacg gcgatgcctg cttgccgaat atcatggtgg aaaatggccg    960 ctttttctgga ttcatcgact gtggccggct gggtgtggcg gaccgctatc aggacatagc    1020
gttggctacc cgtgatattg ctgaagagct tggcggcgaa tgggctgacc gcttcctcgt    1080
gctttacggt atcgccgctc ccgattcgca gcgcatcgcc ttctatcgcc ttcttgacga    1140
gttcttctga gcgggactct ggggttcgga ctctagctag agtcaagcag atcgttcaaa    1200
catttggcaa taaagtttct taagattgaa tcctgttgcc ggtcttgcga tgattatcat    1260
```

```
ataatttctg ttgaattacg ttaagcatgt aataattaac atgtaatgca tgacgttatt  1320
tatgagatgg gttttttatga ttagagtccc gcaattatac atttaatacg cgatagaaaa  1380
caaaatatag cgcgcaaact aggataaatt atcgcgcgcg gtgtcatcta tgttactaga  1440
tctgcaggtc aacatggtgg agcacgacac tctcgtctac tccaagaata tcaaagatac  1500
agtctcagaa gaccaaaggg ctattgagac ttttcaacaa agggtaatat cgggaaacct  1560
cctcggattc cattgcccag ctatctgtca cttcatcaaa aggacagtag aaaaggaagg  1620
tggcacctac aaatgccatc attgcgataa aggaaaggct atcgttcaag atgcctctgc  1680
cgacagtggt cccaaagatg dacccccacc cacgaggagc atcgtggaaa aagaagacgt  1740
tccaaccacg tcttcaaagc aagtggattg atgtgataac atggtggagc acgacactct  1800
cgtctactcc aagaatatca aagatacagt ctcagaagac caaagggcta ttgagacttt  1860
tcaacaaagg gtaatatcgg gaaacctcct cggattccat tgcccagcta tctgtcactt  1920
catcaaaagg acagtagaaa aggaaggtgg cacctacaaa tgccatcatt gcgataaagg  1980
aaaggctatc gttcaagatg cctctgccga cagtggtccc aaagatggac ccccacccac  2040
gaggagcatc gtggaaaaag aagacgttcc aaccacgtct tcaaagcaag tggattgatg  2100
tgatatctcc actgacgtaa gggatgacgc acaatcccac tatccttcgc aagaccttcc  2160
tctatataag gaagttcatt tcatttggag aggacctcga gaattctcaa cacaacatat  2220 acaaacaaa cgaatctcaa gcaatcaagc attctacttc tattgcagca atttaaatca  2280
tttcttttaa agcaaaagca attttctgaa aattttcacc atttacgaac gatagttaat  2340
taaccatggc tgaaattctt cttacatcag taatcaataa atctgtagaa atagctggaa  2400
atttactgat tcaagaagga aagcgtttat attggttgaa agaggatatc gattggctcc  2460
agagagaaat gagacacatt cgatcttatg ttgacaacgc aaaggccaag gaagctggag  2520
gtgattcaag ggtcaaaaac ttattgaaag atattcaaga attggcaggt gatgtggagg  2580
atctcttaga tgacttcctt ccaaaaattc aacaatccaa taagttcaat tattgcctta  2640
agaggagttc ttttgcagat gagtttgcta tggagattga gaagataaag agaagggttg  2700
ttgacattga ccgaataagg aaaacttaca acatcataga tacagataac aataatgatg  2760
attgtgttct gctggatcgg agaagattat tcctacatgc tgatgaaaca gagatcatcg  2820
gtttggatga tgacttcaat atgctacaag ccaaattact taatcaagat ttgcattatg  2880
gagttgtttc catagttggc atgcccggtc tggggaaaac aactcttgcc aagaaacttt  2940
ataggctcat tcgtgatcaa tttgagtgtt ctggactggt ctacgtttca caacagccaa  3000
gagcgagtga aatcttactt gacattgcca aacaaattgg actgacggaa cagaaaatga  3060
aggaaaattt ggaggacaac ctgcgatcac tcttgaaaat aaaaaggtat gttatcctcc  3120
tagatgacat ttgggatgtg gaaatttggg atgatctgaa acttgtcctt cctgaatgtg  3180
attcaaaagt cggcagtaga atgataatca cgtctcgaaa tagtaatgta ggcagataca  3240
taggagggga atcctccctc catgcattgc aaccctaga atccgagaaa agctttgaac  3300
tctttaccaa gaaaatcttt aattttgatg ataataatag ttgggccaat gcttcacctg  3360
acttggtgaa tattggtaga aatatagttg ggagatgtgg aggtataccg ctagccatag  3420
tggtgactgc aggcatgtta agggcaagag aaagaacaga acatgcgtgg aacagagtac  3480
ttgagagtat gggccataaa gttcaagatg gatgtgctaa ggtattggct ctcagttaca  3540
atgatttacc tattgcctca aggccatgtt tcttgtactt tggcctttac cccgaggacc  3600
atgaaattcg tgcttttgat ttgataaata tgtgggattgc tgagaagttt atagtagtaa  3660
```

-continued

```
atagtggtaa taggcgagag gctgaggatt tggcggagga cgtcctaaat gatttggttt   3720
ctagaaactt gattcaactt gccaaaagga catataatgg aagaatttca agttgtcgca   3780
tacatgactt gttacatagt ttgtgtgtgg acttggctaa ggaaagtaac ttctttcaca   3840
ccgcgcatga tgcatttggt gatcccggca atgttgctag gctccgaagg attacattct   3900
actctgacaa tgtcatgatt gagttcttcc gttcaaatcc taagcttgag aagcttcgtg   3960
tacttttctg tttcgcaaaa gacccttcca tattttctca tatggcttat tttgacttca   4020
aattgttgca cacattggtt gtagtcatgt ctcaaagttt tcaagcatat gtcactatcc   4080
caagcaaatt tgggaacatg acttgcttac gctatctgag attggagggg aatatttgtg   4140
gaaaactgcc aaatagtatt gtcaagctca cacgtctaga aaccatagac attgatcgac   4200
gtagcctcat tcaacctcct tctggtgttt gggagtctaa acatttgaga catctttgtt   4260
atagagatta tggacaagca tgtaacagtt gcttttctat aagctcatta tacccaaata   4320
tttactcatt gcatcctaac aatctacaaa ccttgatgtg gatacctgat aaattttttg   4380
aaccgaggtt gttgcaccga ttgatcaatt taagaaaact gggtatactg ggagtgtcca   4440
attctaccgt taagatgtta tcaatattta gccctgtgct taaggcgctg gaggttctga   4500
agctcagttt ttccagtgac ccgagtgaac aaataaagtt gtcatcgtat ccacatattg   4560
ctaagttgca tttgaatgtt aacagaacaa tggccttgaa ctctcaatca tttcctccaa   4620
atctcatcaa gcttactcta gcctacttta gtgtagaccg ttatatactg gcagtactta   4680
agacatttcc caaattaaga aaacttaaaa tgttcatctg caagtataat gaagaaaaga   4740
tggatctctc gggcgaggca aatggttata gctttccgca acttgaagtt ttgcatattc   4800
atagcccgaa tgggttgtct gaagtaacgt gcacggatga tgtcagtatg cccaaattga   4860
aaaagctgtt acttacagga ttccatcgcc gaatcagttt atcggaacgg cttaaaaagc   4920
tgagtaaatg aagcttctag ggtgggatat gaagatgaag atgaaatatt tggtgtgtca   4980
aataaaaagc ttgtgtgctt aagtttgtgt tttctcttgg cttgttgtgt tatgaatttg   5040 tggcttttc taatattaaa tgaatgtaag atctcattat aatgaataaa caaatgtttc   5100
tataatccat tgtgaatgtt ttgttggatc tcttctgcag catataacta ctgtatgtgc   5160
tatggtatgg actatggaat atgattaaag ataaggtgat atcgaattcc tgcggtaccc   5220
gccttcagtt taaactatca gtgtttgaca ggatatattg gcgggtaaac ctaagagaaa   5280
agagcgttta ttgaataac ggatatttaa aagggcgtga aaaggtttat ccgttcgtcc   5340
atttgtatgt gcatgccaac cacagggttc ccctcgggat caaagtactt tgatccaacc   5400
cctccgctgc tatagtgcag tcggcttctg acgttcagtg cagccgtctt ctgaaaacga   5460
catgtcgcac aagtcctaag ttacgcgaca ggctgccgcc ctgccctttt cctggcgttt   5520
tcttgtcgcg tgtttttagtc gcataaagta gaatacttgc gactagaacc ggagacatta   5580
cgccatgaac aagagcgccg ccgctggcct gctgggctat gcccgcgtca gcaccgacga   5640
ccaggacttg accaaccaac gggccgaact gcacgcggcc ggctgcacca agctgttttc   5700
cgagaagatc accggcacca ggcgcgaccg cccggagctg gccaggatgc ttgaccacct   5760
acgccctggc gacgttgtga cagtgaccag gctagaccgc ctggcccgca gcacccgcga   5820
cctactggac attgccgagc gcatccagga ggccggcgcg ggcctgcgta gcctggcaga   5880
gccgtgggcc gacaccacca cgccggccgg ccgcatggtg ttgaccgtgt cgcggcat   5940 tgccgagttc gagcgttccc taatcatcga ccgcacccgg agcgggcgcg aggccgccaa   6000
```

-continued

```
ggcccgaggc gtgaagtttg gcccccgccc taccctcacc ccggcacaga tcgcgcacgc    6060
ccgcgagctg atcgaccagg aaggccgcac cgtgaaagag gcggctgcac tgcttggcgt    6120
gcatcgctcg accctgtacc gcgcacttga gcgcagcgag gaagtgacgc ccaccgaggc    6180
caggcggcgc ggtgccttcc gtgaggacgc attgaccgag gccgacgccc tggcggccgc    6240
cgagaatgaa cgccaagagg aacaagcatg aaaccgcacc aggacggcca ggacgaaccg    6300
tttttcatta ccgaagagat cgaggcggag atgatcgcgg ccgggtacgt gttcgagccg    6360
cccgcgcacg tctcaaccgt gcggctgcat gaaatcctgg ccggtttgtc tgatgccaag    6420
ctggcggcct ggccggccag cttggccgct gaagaaaccg agcgccgccg tctaaaaagg    6480
tgatgtgtat ttgagtaaaa cagcttgcgt catgcggtcg ctgcgtatat gatgcgatga    6540
gtaaataaac aaatacgcaa ggggaacgca tgaaggttat cgctgtactt aaccagaaag    6600
gcgggtcagg caagacgacc atcgcaaccc atctagcccg cgccctgcaa ctcgccgggg    6660
ccgatgttct gttagtcgat tccgatcccc agggcagtgc ccgcgattgg gcggccgtgc    6720
gggaagatca accgctaacc gttgtcggca tcgaccgccc gacgattgac cgcgacgtga    6780
aggccatcgg ccggcgcgac ttcgtagtga tcgacggagc gccccaggcg gcggacttgg    6840
ctgtgtccgc gatcaaggca gccgacttcg tgctgattcc ggtgcagcca agcccttacg    6900
acatatgggc caccgccgac ctggtggagc tggttaagca gcgcattgag gtcacggatg    6960
gaaggctaca agcggccttt gtcgtgtcgc gggcgatcaa aggcacgcgc atcggcggtg    7020
aggttgccga ggcgctggcc gggtacgagc tgcccattct tgagtcccgt atcacgcagc    7080
gcgtgagcta cccaggcact gccgccgccg gcacaaccgt tcttgaatca gaacccgagg    7140
gcgacgctgc ccgcgaggtc caggcgctgg ccgctgaaat taaatcaaaa ctcatttgag    7200
ttaatgaggt aaagagaaaa tgagcaaaag cacaaacacg ctaagtgccg gccgtccgag    7260
cgcacgcagc agcaaggctg caacgttggc cagcctggca gacacgccag ccatgaagcg    7320
ggtcaacttt cagttgccgg cggaggatca caccaagctg aagatgtacg cggtacgcca    7380
aggcaagacc attaccgagc tgctatctga atacatcgcg cagctaccag agtaaatgag    7440
caaatgaata aatgagtaga tgaattttag cggctaaagg aggcggcatg gaaaatcaag    7500
aacaaccagg caccgacgcc gtggaatgcc ccatgtgtgg aggaacgggc ggttggccag    7560
gcgtaagcgg ctgggttgtc tgccggccct gcaatggcac tggaacccccc aagcccgagg    7620 aatcggcgtg acggtcgcaa accatccggc ccggtacaaa tcggcgcggc gctgggtgat    7680
gacctggtgg agaagttgaa ggccgcgcag gccgcccagc ggcaacgcat cgaggcagaa    7740
gcacgccccg gtgaatcgtg gcaagcggcc gctgatcgaa tccgcaaaga atcccggcaa    7800
ccgccggcag ccggtgcgcc gtcgattagg aagccgccca agggcgacga gcaaccagat    7860
tttttcgttc cgatgctcta tgacgtgggc acccgcgata gtcgcagcat catggacgtg    7920 gccgtttttcc gtctgtcgaa gcgtgaccga cgagctggcg aggtgatccg ctacgagctt    7980
ccagacgggc acgtagaggt ttccgcaggg ccggccggca tggccagtgt gtgggattac    8040
gacctggtac tgatggcggt ttcccatcta accgaatcca tgaaccgata ccgggaaggg    8100
aagggagaca gcccggccg cgtgttccgt ccacacgttg cggacgtact caagttctgc    8160
cggcgagccg atggcggaaa gcagaaagac gacctggtag aaacctgcat tcggttaaac    8220
accacgcacg ttgccatgca gcgtacgaag aaggccaaga acggccgcct ggtgacggta    8280
tccgagggtg aagccttgat tagccgctac aagatcgtaa agagcgaaac cgggcggccg    8340
gagtacatcg agatcgagct agctgattgg atgtaccgcg agatcacaga aggcaagaac    8400
```

-continued

```
ccggacgtgc tgacggttca ccccgattac tttttgatcg atcccggcat cggccgtttt   8460
ctctaccgcc tggcacgccg cgccgcaggc aaggcagaag ccagatggtt gttcaagacg   8520
atctacgaac gcagtggcag cgccggagag ttcaagaagt tctgtttcac cgtgcgcaag   8580
ctgatcgggt caaatgacct gccggagtac gatttgaagg aggaggcggg gcaggctggc   8640
ccgatcctag tcatgcgcta ccgcaacctg atcgagggcg aagcatccgc cggttcctaa   8700
tgtacggagc agatgctagg gcaaattgcc ctagcagggg aaaaaggtcg aaaaggtcac   8760
tttcctgtgg atagcacgta cattgggaac ccaaagccgt acattgggaa ccggaacccg   8820
tacattggga acccaaagcc gtacattggg aaccggtcac acatgtaagt gactgatata   8880
aaagagaaaa aaggcgattt ttccgcctaa aactctttaa aacttattaa aactcttaaa   8940
acccgcctgg cctgtgcata actgtctggc cagcgcacag ccgaagagct gcaaaaagcg   9000
cctacccttc ggtcgctgcg ctccctacgc cccgccgctt cgcgtcggcc tatcgcggcc   9060
gctggccgct caaaaatggc tggcctacgg ccaggcaatc taccagggcg cggacaagcc   9120
gcgccgtcgc cactcgaccg ccggcgccca catcaaggca ccctgcctcg cgcgtttcgg   9180
tgatgacggt gaaaacctct gacacatgca gctcccggag acggtcacag cttgtctgta   9240
agcggatgcc gggagcagac aagcccgtca gggcgcgtca gcgggtgttg gcgggtgtcg   9300
gggcgcagcc atgacccagt cacgtagcga tagcggagtg tatactggct taactatgcg   9360
gcatcagagc agattgtact gagagtgcac catatgcggt gtgaaatacc gcacagatgc   9420
gtaaggagaa ataccgcat caggcgctct tccgcttcct cgctcactga ctcgctgcgc   9480
tcggtcgttc ggctgcggcg agcggtatca gctcactcaa aggcggtaat acggttatcc   9540
acagaatcag gggataacgc aggaaagaac atgtgagcaa aaggccagca aaaggccagg   9600
aaccgtaaaa aggccgcgtt gctggcgttt ttccataggc tccgcccccc tgacgagcat   9660
cacaaaaatc gacgctcaag tcagaggtgg cgaaacccga caggactata aagataccag   9720
gcgtttcccc ctggaagctc cctcgtgcgc tctcctgttc cgaccctgcc gcttaccgga   9780
tacctgtccg cctttctccc ttcgggaagc gtggcgcttt ctcatagctc acgctgtagg   9840
tatctcagtt cggtgtaggt cgttcgctcc aagctgggct gtgtgcacga accccccgtt   9900
cagcccgacc gctgcgcctt atccggtaac tatcgtcttg agtccaaccc ggtaagacac   9960
gacttatcgc cactggcagc agccactggt aacaggatta gcagagcgag gtatgtaggc   10020
ggtgctacag agttcttgaa gtggtggcct aactacggct acactagaag gacagtattt   10080
ggtatctgcg ctctgctgaa gccagttacc ttcggaaaaa gagttggtag ctcttgatcc   10140
ggcaaacaaa ccaccgctgg tagcggtggt ttttttgttt gcaagcagca gattacgcgc   10200
agaaaaaaag gatctcaaga agatcctttg atctttctta cggggtctga cgctcagtgg   10260
aacgaaaact cacgttaagg gattttggtc atgcatgata tatctcccaa tttgtgtagg   10320
gcttattatg cacgcttaaa aataataaaa gcagacttga cctgatagtt tggctgtgag   10380
caattatgtg cttagtgcat ctaatcgctt gagttaacgc cggcgaagcg gcgtcggctt   10440
gaacgaattt ctagctagac aaggtactaa aacaattcat ccagtaaaat ataatatttt   10500
attttctccc aatcaggctt gatccccagt aagtcaaaaa atagctcgac atactgttct   10560
tccccgatat cctccctgat cgaccggacg cagaaggcaa tgtcatacca cttgtccgcc   10620
ctgccgcttc tcccaagatc aataaagcca cttactttgc catctttcac aaagatgttg   10680
ctgtctccca ggtcgccgtg ggaaaagaca agttcctctt cgggcttttc cgtctttaaa   10740
```

-continued

```
aaatcataca gctcgcgcgg atctttaaat ggagtgtctt cttcccagtt ttcgcaatcc    10800
acatcggcca gatcgttatt cagtaagtaa tccaattcgg ctaagcggct gtctaagcta    10860
ttcgtatagg gacaatccga tatgtcgatg gagtgaaaga gcctgatgca ctccgcatac    10920
agctcgataa tcttttcagg gctttgttca tcttcatact cttccgagca aaggacgcca    10980
tcggcctcac tcatgagcag attgctccag ccatcatgcc gttcaaagtg caggaccttt    11040
ggaacaggca gctttccttc cagccatagc atcatgtcct tttcccgttc cacatcatag    11100
gtggtccctt tataccggct gtccgtcatt tttaaatata ggttttcatt ttctcccacc    11160
agcttatata ccttagcagg agacattcct tccgtatctt ttacgcagcg gtattttctcg    11220 atcagttttt tcaattccgg tgatattctc attttagcca taacaagaag ccatgaaaac    11280
cgccactgcg ccgttaccac cgctgcgttc ggtcaaggtt ctggaccagt tgcgtgacgc    11340
cagttacgct acttgcatta cagcttacga accgaacgag gcttatgtcc actgggttcg    11400
tgcccgaatt gatcacaggc agcaacgctc tgtcatcgtt acaatcaaca tgctaccctc    11460
cgcgagatca tccgtgtttc aaacccggca gcttagttgc cgttcttccg aatagcatcg    11520
gtaacatgag caaagtctgc cgccttacaa cggctctccc gctgacgccg tcccggactg    11580
atgggctgcc tgtatcgagt ggtgattttg tgccgagctg ccggtcgggg agctgttggc    11640
tggctggtgg caggatatat tgtggtgtaa                                     11670
```

<210> SEQ ID NO 43
<211> LENGTH: 11670
<212> TYPE: DNA
<213> ORGANISM: artificial
<220> FEATURE:
<223> OTHER INFORMATION: plasmid

<400> SEQUENCE: 43

```
acaaattgac gcttagacaa cttaataaca cattgcggac gttttttaatg tactgaatta      60 acgccgaatt gaattatcag cttgcatgca gctctcccat atggtcgact agaggcctgc     120
cgttttacgt ttggaactga cagaaccgca acgttgaagg agccactcag ccgcgggttt     180
ctggagttta atgagctaag cacatacgtc agaaaccatt attgcgcgtt caaaagtcgc     240
ctaaggtcac tatcagctag caaatatttc ttgtcaaaaa tgctccactg acgttccata     300
aattcccctc ggtatccaat tagagtctca tattcactct caactcgatc gaggcatgat     360
tgaacaagat ggattgcacg caggttctcc ggccgcttgg gtggagaggc tattcggcta     420
tgactgggca caacagacaa tcggctgctc tgatgccgcc gtgttccggc tgtcagcgca     480
ggggcgcccg gttctttttg tcaagaccga cctgtccggt gccctgaatg aactccaaga     540
cgaggcagcg cggctatcgt ggctggccac gacgggcgtt ccttgcgcag ctgtgctcga     600
cgttgtcact gaagcgggaa gggactggct gctattgggc gaagtgccgg ggcaggatct     660
cctgtcatct caccttgctc ctgccgagaa agtatccatc atggctgatg caatgcggcg     720
gctgcatacg cttgatccgg ctacctgccc attcgaccac caagcgaaac atcgcatcga     780
gcgagcacgt actcggatgg aagccggtct tgtcgatcag gatgatctgg acgaagagca     840 tcagggggctc gcgccagccg aactgttcgc caggctcaag gcgcggatgc ccgacggcga     900
ggatctcgtc gtgacccacg gcgatgcctg cttgccgaat atcatggtgg aaaatggccg     960
cttttctgga ttcatcgact gtggccggct gggtgtggcg gaccgctatc aggacatagc    1020
gttggctacc cgtgatattg ctgaagagct tggcggcgaa tgggctgacc gcttcctcgt    1080
gctttacggt atcgccgctc ccgattcgca gcgcatcgcc ttctatcgcc ttcttgacga    1140
```

-continued

```
gttcttctga gcgggactct ggggttcgga ctctagctag agtcaagcag atcgttcaaa    1200
catttggcaa taaagtttct taagattgaa tcctgttgcc ggtcttgcga tgattatcat    1260
ataatttctg ttgaattacg ttaagcatgt aataattaac atgtaatgca tgacgttatt    1320
tatgagatgg gtttttatga ttagagtccc gcaattatac atttaatacg cgatagaaaa    1380
caaaatatag cgcgcaaact aggataaatt atcgcgcgcg gtgtcatcta tgttactaga    1440
tctgcaggtc aacatggtgg agcacgacac tctcgtctac tccaagaata tcaaagatac    1500
agtctcagaa gaccaaaggg ctattgagac ttttcaacaa agggtaatat cgggaaacct    1560
cctcggattc cattgcccag ctatctgtca cttcatcaaa aggacagtag aaaaggaagg    1620
tggcacctac aaatgccatc attgcgataa aggaaaggct atcgttcaag atgcctctgc    1680
cgacagtggt cccaaagatg dacccccacc cacgaggagc atcgtggaaa aagaagacgt    1740
tccaaccacg tcttcaaagc aagtggattg atgtgataac atggtggagc acgacactct    1800
cgtctactcc aagaatatca aagatacagt ctcagaagac caaagggcta ttgagacttt    1860
tcaacaaagg gtaatatcgg gaaacctcct cggattccat tgcccagcta tctgtcactt    1920
catcaaaagg acagtagaaa aggaaggtgg cacctacaaa tgccatcatt gcgataaagg    1980
aaaggctatc gttcaagatg cctctgccga cagtggtccc aaagatggac ccccacccac    2040
gaggagcatc gtgaaaaag aagacgttcc aaccacgtct tcaaagcaag tggattgatg    2100
tgatatctcc actgacgtaa gggatgacgc acaatcccac tatccttcgc aagaccttcc    2160
tctatataag gaagttcatt tcatttggag aggacctcga gaattctcaa cacaacatat    2220
acaaaacaaa cgaatctcaa gcaatcaagc attctacttc tattgcagca atttaaatca    2280
tttcttttaa agcaaaagca attttctgaa aattttcacc atttacgaac gatagttaat    2340
taaccatggc tgaaattctt cttacatcag taatcaataa atctgtagaa atagctggaa    2400
atttactgat tcaagaagga aagcgtttat attggttgaa agaggatatc gattggctcc    2460
agagagaaat gagacacatt cgatcttatg ttgacaacgc aaaggccaag gaagctggag    2520
gtgattcaag ggtcaaaaac ttattgaaag atattcaaga attggcaggt gatgtggagg    2580
atctcttaga tgacttcctt ccaaaaattc aacaatccaa taagttcaat tattgcctta    2640
agaggagttc ttttgcagat gagtttgcta tggagattga gaagataaag agaagggttg    2700
ttgacattga ccgaataagg aaaacttaca acatcataga tacagataac aataatgatg    2760
attgtgttct gctggatcgg agaagattat tcctacatgc tgatgaaaca gagatcatcg    2820
gtttggatga tgacttcaat atgctacaag ccaaattact taatcaagat ttgcattatg    2880
gagttgtttc catagttggc atgcccggtc tggggaaaac aactcttgcc aagaaacttt    2940
ataggctcat tcgtgatcaa tttgagtgtt ctggactggt ctacgtttca caacagccaa    3000
gagcgagtga atcttacctt gacattgcca aacaaattgg actgacggaa cagaaaatga    3060
aggaaaattt ggaggacaac ctgcgatcac tcttgaaaat aaaaaggtat gttatcctcc    3120
tagatgacat ttgggatgtg gaaatttggg atgatctgaa acttgtcctt cctgaatgtg    3180
attcaaaagt cggcagtaga atgataatca cgtctcgaaa tagtaatgta ggcagataca    3240
taggagggga atcctccctc catgcattgc aacccctaga atccgagaaa agctttgaac    3300 tcttaccaa gaaaatcttt aattttgatg ataataatag ttgggccaat gcttcacctg    3360
acttggtgaa tattggtaga aatatagttg ggagatgtgg aggtataccg ctagccatag    3420
tggtgactgc aggcatgtta agggcaagag aaagaacaga acatgcgtgg aacagagtac    3480
```

-continued

```
ttgagagtat gggccataaa gttcaagatg gatgtgctaa ggtattggct ctcagttaca    3540
atgatttacc tattgcctca aggccatgtt tcttgtactt tggcctttac cccgaggacc    3600
atgaaattcg tgcttttgat ttgataaata tgtggattgc tgagaagttt atagtagtaa    3660
atagtggtaa taggcgagag gctgaggatt tggcggagga cgtcctaaat gatttggttt    3720
ctagaaactt gattcaactt gccaaaagga catataatgg aagaatttca agttgtcgca    3780
tacatgactt gttacatagt ttgtgtgtgg acttggctaa ggaaagtaac ttctttcaca    3840
ccgcgcatga tgcatttggt gatcccggca atgttgctag gctccgaagg attacattct    3900
actctgacaa tgtcatgatt gagttcttcc gttcaaatcc taagcttgag aagcttcgtg    3960
tacttttctg tttcgcaaaa gacccttcca tattttctca tatggcttat tttgacttca    4020
aattgttgca cacattggtt gtagtcatgt ctcaaagttt tcaagcatat gtcactatcc    4080
caagcaaatt tgggaacatg acttgcttac gctatctgag attggagggg aatatttgtg    4140
gaaaactgcc aaatagtatt gtcaagctca cacgtctaga aaccatagac attgatcgac    4200
gtagcctcat tcaacctcct tctggtgttt gggagtctaa acatttgaga catctttgtt    4260
atagagatta tggacaagca tgtaacagtt gcttttctat aagctcattt tacccaaata    4320
tttactcatt gcatcctaac aatctacaaa ccttgatgtg gatacctgat aaattttttg    4380
aaccgaggtt gttgcaccga ttgatcaatt taagaaaact gggtatactg ggagtgtcca    4440
attctaccgt taagatgtta tcaatattta gccctgtgct taaggcgctg gaggttctga    4500
agctcagttt ttccagtgac ccgagtgaac aaataaagtt gtcatcgtat ccacatattg    4560
ctaagttgca tttgaatgtt aacagaacaa tggccttgaa ctctcaatca tttcctccaa    4620
atctcatcaa gcttactcta gcctactta gtgtagaccg ttatatactg gcagtactta    4680
agacatttcc caaattaaga aaacttaaaa tgttcatctg caagtataat gaagaaaaga    4740
tggatctctc gggcgaggca aatggttata gctttccgca acttgaagtt ttgcatattc    4800
atagcccgaa tgggttgtct gaagtaacgt gcacggatga tgtcagtatg cccaaattga    4860
aaaagctgtt acttacagga ttccatcgcc gaatcagttt atcggaacgg cttaaaaagc    4920
tgagtaaatg aagcttctag ggtgggatat gaagatgaag atgaaatatt tggtgtgtca    4980
aataaaaagc ttgtgtgctt aagtttgtgt tttctcttgg cttgttgtgt tatgaatttg    5040 tggcttttc taatattaaa tgaatgtaag atctcattat aatgaataaa caaatgtttc    5100
tataatccat tgtgaatgtt ttgttggatc tcttctgcag catataacta ctgtatgtgc    5160
tatggtatgg actatggaat atgattaaag ataaggtgat atcgaattcc tgcggtaccc    5220
gccttcagtt taaactatca gtgtttgaca ggatatattg gcgggtaaac ctaagagaaa    5280
agagcgttta ttagaataac ggatatttaa aagggcgtga aaaggtttat ccgttcgtcc    5340
atttgtatgt gcatgccaac cacagggttc ccctcgggat caaagtactt tgatccaacc    5400
cctccgctgc tatagtgcag tcggcttctg acgttcagtg cagccgtctt ctgaaaacga    5460
catgtcgcac aagtcctaag ttacgcgaca ggctgccgcc ctgccctttt cctggcgttt    5520
tcttgtcgcg tgttttagtc gcataaagta gaatacttgc gactagaacc ggagacatta    5580
cgccatgaac aagagcgccg ccgctggcct gctgggctat gcccgcgtca gcaccgacga    5640
ccaggacttg accaaccaac gggccgaact gcacgcggcc ggctgcacca agctgttttc    5700
cgagaagatc accggcacca ggcgcgaccg cccggagctg gccaggatgc ttgaccacct    5760
acgccctggc gacgttgtga cagtgaccag gctagaccgc ctggcccgca gcacccgcga    5820
cctactggac attgccgagc gcatccagga ggccggcgcg ggcctgcgta gcctggcaga    5880
```

-continued

```
gccgtgggcc  gacaccacca  cgccggccgg  ccgcatggtg  ttgaccgtgt  tcgccggcat      5940
tgccgagttc  gagcgttccc  taatcatcga  ccgcacccgg  agcgggcgcg  aggccgccaa      6000
ggcccgaggc  gtgaagtttg  gcccccgccc  taccctcacc  ccggcacaga  tcgcgcacgc      6060
ccgcgagctg  atcgaccagg  aaggccgcac  cgtgaaagag  gcggctgcac  tgcttggcgt      6120
gcatcgctcg  accctgtacc  gcgcacttga  gcgcagcgag  gaagtgacgc  ccaccgaggc      6180
caggcggcgc  ggtgccttcc  gtgaggacgc  attgaccgag  gccgacgccc  tggcggccgc      6240
cgagaatgaa  cgccaagagg  aacaagcatg  aaaccgcacc  aggacggcca  ggacgaaccg      6300
tttttcatta  ccgaagagat  cgaggcggag  atgatcgcgg  ccgggtacgt  gttcgagccg      6360
cccgcgcacg  tctcaaccgt  gcggctgcat  gaaatcctgg  ccggtttgtc  tgatgccaag      6420
ctggcggcct  ggccggccag  cttggccgct  gaagaaaccg  agcgccgccg  tctaaaaagg      6480
tgatgtgtat  ttgagtaaaa  cagcttgcgt  catgcggtcg  ctgcgtatat  gatgcgatga      6540
gtaaataaac  aaatacgcaa  ggggaacgca  tgaaggttat  cgctgtactt  aaccagaaag      6600
gcgggtcagg  caagacgacc  atcgcaaccc  atctagcccg  cgccctgcaa  ctcgccgggg      6660
ccgatgttct  gttagtcgat  tccgatcccc  agggcagtgc  ccgcgattgg  gcggccgtgc      6720
gggaagatca  accgctaacc  gttgtcggca  tcgaccgccc  gacgattgac  cgcgacgtga      6780
aggccatcgg  ccggcgcgac  ttcgtagtga  tcgacggagc  gccccaggcg  gcggacttgg      6840
ctgtgtccgc  gatcaaggca  gccgacttcg  tgctgattcc  ggtgcagcca  agcccttacg      6900
acatatgggc  caccgccgac  ctggtggagc  tggttaagca  gcgcattgag  gtcacggatg      6960
gaaggctaca  agcggccttt  gtcgtgtcgc  gggcgatcaa  aggcacgcgc  atcggcggtg      7020
aggttgccga  ggcgctggcc  gggtacgagc  tgcccattct  tgagtcccgt  atcacgcagc      7080
gcgtgagcta  cccaggcact  gccgccgccg  gcacaaccgt  tcttgaatca  gaacccgagg      7140
gcgacgctgc  ccgcgaggtc  caggcgctgg  ccgctgaaat  taaatcaaaa  ctcatttgag      7200
ttaatgaggt  aaagagaaaa  tgagcaaaag  cacaaacacg  ctaagtgccg  gccgtccgag      7260
cgcacgcagc  agcaaggctg  caacgttggc  cagcctggca  gacacgccag  ccatgaagcg      7320
ggtcaacttt  cagttgccgg  cggaggatca  caccaagctg  aagatgtacg  cggtacgcca      7380
aggcaagacc  attaccgagc  tgctatctga  atacatcgcg  cagctaccag  agtaaatgag      7440
caaatgaata  aatgagtaga  tgaattttag  cggctaaagg  aggcggcatg  gaaaatcaag      7500
aacaaccagg  caccgacgcc  gtggaatgcc  ccatgtgtgg  aggaacgggc  ggttggccag      7560
gcgtaagcgg  ctgggttgtc  tgccggccct  gcaatggcac  tggaaccccc  aagcccgagg      7620
aatcggcgtg  acggtcgcaa  accatccggc  ccggtacaaa  tcggcgcggc  gctgggtgat      7680
gacctggtgg  agaagttgaa  ggccgcgcag  gccgcccagc  ggcaacgcat  cgaggcagaa      7740
gcacgccccg  gtgaatcgtg  gcaagcggcc  gctgatcgaa  tccgcaaaga  atcccggcaa      7800
ccgccggcag  ccggtgcgcc  gtcgattagg  aagccgccca  agggcgacga  gcaaccagat      7860
tttttcgttc  cgatgctcta  tgacgtgggc  acccgcgata  gtcgcagcat  catggacgtg      7920
gccgttttcc  gtctgtcgaa  gcgtgaccga  cgagctggcg  aggtgatccg  ctacgagctt      7980
ccagacgggc  acgtagaggt  ttccgcaggg  ccggccggca  tggccagtgt  gtgggattac      8040
gacctggtac  tgatggcggt  ttcccatcta  accgaatcca  tgaaccgata  ccgggaaggg      8100
aagggagaca  gcccggccg   cgtgttccgt  ccacacgttg  cggacgtact  caagttctgc      8160
cggcgagccg  atggcggaaa  gcagaaagac  gacctggtag  aaacctgcat  tcggttaaac      8220
```

```
accacgcacg ttgccatgca gcgtacgaag aaggccaaga acggccgcct ggtgacggta      8280
tccgagggtg aagccttgat tagccgctac aagatcgtaa agagcgaaac cgggcggccg      8340
gagtacatcg agatcgagct agctgattgg atgtaccgcg agatcacaga aggcaagaac      8400
ccggacgtgc tgacggttca ccccgattac tttttgatcg atcccggcat cggccgtttt      8460
ctctaccgcc tggcacgccg cgccgcaggc aaggcagaag ccagatggtt gttcaagacg      8520
atctacgaac gcagtggcag cgccggagag ttcaagaagt tctgtttcac cgtgcgcaag      8580
ctgatcgggt caaatgacct gccggagtac gatttgaagg aggaggcggg gcaggctggc      8640
ccgatcctag tcatgcgcta ccgcaacctg atcgagggcg aagcatccgc cggttcctaa      8700
tgtacggagc agatgctagg gcaaattgcc ctagcagggg aaaaaggtcg aaaaggtcac      8760
tttcctgtgg atagcacgta cattgggaac ccaaagccgt acattgggaa ccggaacccg      8820
tacattggga acccaaagcc gtacattggg aaccggtcac acatgtaagt gactgatata      8880
aaagagaaaa aaggcgattt ttccgcctaa aactctttaa aacttattaa aactcttaaa      8940
acccgcctgg cctgtgcata actgtctggc cagcgcacag ccgaagagct gcaaaaagcg      9000
cctacccttc ggtcgctgcg ctccctacgc cccgccgctt cgcgtcggcc tatcgcggcc      9060
gctggccgct caaaaatggc tggcctacgg ccaggcaatc taccagggcg cggacaagcc      9120
gcgccgtcgc cactcgaccg ccggcgccca catcaaggca ccctgcctcg cgcgtttcgg      9180
tgatgacggt gaaaacctct gacacatgca gctcccggag acggtcacag cttgtctgta      9240
agcggatgcc gggagcagac aagcccgtca gggcgcgtca gcgggtgttg gcgggtgtcg      9300
gggcgcagcc atgacccagt cacgtagcga tagcggagtg tatactggct taactatgcg      9360
gcatcagagc agattgtact gagagtgcac catatgcggt gtgaaatacc gcacagatgc      9420
gtaaggagaa aataccgcat caggcgctct tccgcttcct cgctcactga ctcgctgcgc      9480
tcggtcgttc ggctgcggcg agcggtatca gctcactcaa aggcggtaat acggttatcc      9540
acagaatcag gggataacgc aggaaagaac atgtgagcaa aaggccagca aaaggccagg      9600
aaccgtaaaa aggccgcgtt gctggcgttt ttccataggc tccgcccccc tgacgagcat     9660
cacaaaaatc gacgctcaag tcagaggtgg cgaaacccga caggactata aagataccag      9720
gcgtttcccc ctggaagctc cctcgtgcgc tctcctgttc cgaccctgcc gcttaccgga      9780
tacctgtccg cctttctccc ttcgggaagc gtggcgcttt ctcatagctc acgctgtagg      9840
tatctcagtt cggtgtaggt cgttcgctcc aagctgggct gtgtgcacga accccccgtt      9900
cagcccgacc gctgcgcctt atccggtaac tatcgtcttg agtccaaccc ggtaagacac      9960
gacttatcgc cactggcagc agccactggt aacaggatta gcagagcgag gtatgtaggc     10020
ggtgctacag agttcttgaa gtggtggcct aactacggct acactagaag gacagtattt     10080
ggtatctgcg ctctgctgaa gccagttacc ttcggaaaaa gagttggtag ctcttgatcc     10140
ggcaaacaaa ccaccgctgg tagcggtggt ttttttgttt gcaagcagca gattacgcgc     10200
agaaaaaaag gatctcaaga agatcctttg atctttcta cggggtctga cgctcagtgg     10260
aacgaaaact cacgttaagg gattttggtc atgcatgata tatctcccaa tttgtgtagg     10320
gcttattatg cacgcttaaa aataataaaa gcagacttga cctgatagtt tggctgtgag     10380
caattatgtg cttagtgcat ctaatcgctt gagttaacgc cggcgaagcg gcgtcggctt     10440
gaacgaattt ctagctagac aaggtactaa aacaattcat ccagtaaaat ataatatttt     10500
attttctccc aatcaggctt gatccccagt aagtcaaaaa atagctcgac atactgttct     10560
tccccgatat cctccctgat cgaccggacg cagaaggcaa tgtcatacca cttgtccgcc     10620
```

```
ctgccgcttc tcccaagatc aataaagcca cttactttgc catctttcac aaagatgttg   10680
ctgtctccca ggtcgccgtg ggaaaagaca agttcctctt cgggcttttc cgtctttaaa   10740
aaatcataca gctcgcgcgg atctttaaat ggagtgtctt cttcccagtt ttcgcaatcc   10800
acatcggcca gatcgttatt cagtaagtaa tccaattcgg ctaagcggct gtctaagcta   10860
ttcgtatagg gacaatccga tatgtcgatg gagtgaaaga gcctgatgca ctccgcatac   10920
agctcgataa tcttttcagg gctttgttca tcttcatact cttccgagca aaggacgcca   10980
tcggcctcac tcatgagcag attgctccag ccatcatgcc gttcaaagtg caggaccttt   11040
ggaacaggca gctttccttc cagccatagc atcatgtcct tttcccgttc cacatcatag   11100
gtggtccctt tataccggct gtccgtcatt tttaaatata ggttttcatt ttctcccacc   11160
agcttatata ccttagcagg agacattcct tccgtatctt ttacgcagcg gtattttcg    11220 atcagttttt tcaattccgg tgatattctc attttagcca taacaagaag ccatgaaaac   11280
cgccactgcg ccgttaccac cgctgcgttc ggtcaaggtt ctggaccagt tgcgtgacgg   11340
cagttacgct acttgcatta cagcttacga accgaacgag gcttatgtcc actgggttcg   11400
tgcccgaatt gatcacaggc agcaacgctc tgtcatcgtt acaatcaaca tgctaccctc   11460
cgcgagatca tccgtgtttc aaacccggca gcttagttgc cgttcttccg aatagcatcg   11520
gtaacatgag caaagtctgc cgccttacaa cggctctccc gctgacgccg tcccggactg   11580
atgggctgcc tgtatcgagt ggtgattttg tgccgagctg ccggtcgggg agctgttggc   11640
tggctggtgg caggatatat tgtggtgtaa                                    11670
```

```
<210> SEQ ID NO 44
<211> LENGTH: 20
<212> TYPE: DNA
<213> ORGANISM: artificial
<220> FEATURE:
<223> OTHER INFORMATION: primer

<400> SEQUENCE: 44
agatttccct ggcttttgga                                                  20

<210> SEQ ID NO 45
<211> LENGTH: 21
<212> TYPE: DNA
<213> ORGANISM: artificial
<220> FEATURE:
<223> OTHER INFORMATION: primer

<400> SEQUENCE: 45
ctctttctga tatcaagcac t                                                21

<210> SEQ ID NO 46
<211> LENGTH: 22
<212> TYPE: DNA
<213> ORGANISM: artificial
<220> FEATURE:
<223> OTHER INFORMATION: probe

<400> SEQUENCE: 46
caaggagaga ctgctaaatc gg                                               22
```

TOMATO PLANTS RESISTANT TO ToBRFV, TMV, ToMV AND ToMMV AND CORRESPONDING RESISTANCE GENES

The present invention relates to resistance in plants of *Solanum lycopersicum*, also known as *Lycopersicum esculentum*, to tobamoviruses, especially to the Tomato Brown Rugose Fruit virus (ToBRFV, previously abbreviated TBRFV), and preferably also to Tobacco Mosaic Virus (TMV), Tomato Mosaic Virus (ToMV) and/or Tomato Mottle Mosaic Virus (ToMMV). More specifically, the present invention relates to tomato plants and fruits comprising a resistance gene that leads to resistance to at least ToBRFV and preferably to at least one additional tobamovirus. According to the invention, the resistance gene conferring resistance to these tobamoviruses is a variant of the Tm-2 and Tm-2-2 gene alleles. The resistance gene can be present homozygously or heterozygously in the genome of a *S. lycopersicum* plant. The invention further relates to this resistance gene, parts thereof, to encoded polypeptides and proteins and to the use of these sequences and proteins to obtain resistant plants. The invention also relates to the seeds and progeny of such plants, to propagation material for obtaining such plants, and to different uses of these plants.

BACKGROUND OF THE INVENTION

All cultivated and commercial forms of tomato belong to a species most frequently referred to as *Lycopersicon esculentum* Miller. *Lycopersicon* is a relatively small genus within the extremely large and diverse family Solanaceae which is considered to consist of around 90 genera, including pepper, tobacco and eggplant. The genus *Lycopersicon* has been divided into two subgenera, the *esculentum* complex which contains those species that can easily be crossed with the commercial tomato and the *peruvianum* complex which contains those species which are crossed with considerable difficulty. Due to its value as a crop, *L. esculentum* Miller has become widely disseminated all over the world.

Tomato is grown for its fruit, widely used as a fresh market or processed product. As a crop, tomato is grown commercially wherever environmental conditions permit the production of an economically viable yield. The majority of fresh market tomatoes are harvested by hand at vine ripe and mature green stage of ripeness. Fresh market tomatoes are available year round. Processing tomato are mostly mechanically harvested and used in many forms, as canned tomatoes, tomato juice, tomato sauce, puree, paste or even catsup.

Tomato is a normally simple diploid species with twelve pairs of differentiated chromosomes. However, polyploidy tomato is also part of the present invention. The cultivated tomato is self-fertile and almost exclusively self-pollinating. The tomato flowers are hermaphrodites. Commercial cultivars were initially open pollinated. As hybrid vigor has been identified in tomatoes, hybrids are replacing the open pollinated varieties by gaining more and more popularity amongst farmers with better yield and uniformity of plant characteristics. Due to its wide dissemination and high value, tomato has been intensively bred. This explains why such a wide array of tomato is now available. The shape may range from small to large, and there are cherry, plum, pear, blocky, round, and beefsteak types.

Tomatoes may be grouped by the amount of time it takes for the plants to mature fruit for harvest and, in general the cultivars are considered to be early, midseason or late-maturing. Tomatoes can also be grouped by the plant's growth habit; determinate, semi-determinate or indeterminate. Determinate plants tend to grow their foliage first, then set flowers that mature into fruit if pollination is successful. All of the fruits tend to ripen on a plant at about the same time. Indeterminate tomatoes start out by growing some foliage, then continue to produce foliage and flowers throughout the growing season. These plants will tend to have tomato fruit in different stages of maturity at any given time. The semi-determinate tomatoes have a phenotype between determinate and indeterminate, they are typical determinate types except that grow larger than determinate varieties. More recent developments in tomato breeding have led to a wider array of fruit color. In addition to the standard red ripe color, tomatoes can be creamy white, lime green, pink, yellow, golden, orange or purple. Hybrid commercial tomato seed can be produced by hand pollination. Pollen of the male parent is harvested and manually applied to the stigmatic surface of the female inbred. Prior to and after hand pollination, flowers are covered so that insects do not bring foreign pollen and create a mix or impurity. Flowers are tagged to identify pollinated fruit from which seed will be harvested.

A variety of pathogens affect the productivity of tomato plants, including virus, fungi, bacteria, nematodes and insects. Tomatoes are inter alia susceptible to many viruses and virus resistance is therefore of major agricultural importance.

Tobamoviruses are among the most important plant viruses causing severe damages in agriculture, especially to vegetable and ornamental crops around the world. Tobamoviruses are easily transmitted by mechanical means, as well as through seed transmission. Tobamoviruses are generally characterized by a rod-shaped particle of about 300 nm encapsidating a single stranded, positive RNA genome encoding four proteins. In tomatoes, tobacco mosaic virus (TMV) and tomato mosaic virus (ToMV) are feared by growers worldwide as they can severely damage crop production, for example through irregular ripening (fruits having yellowish patches on the surface and brownish spots beneath the surface). Several genes have however been identified by plants breeders over the years and TMV and/or ToMV resistant tomato varieties are nowadays available.

Another tobamovirus, namely the Tomato mottle mosaic virus (ToMMV), has been recently described infecting tomato plants in several countries worldwide, reducing annual yield and quality of tomato production.

Tobamoviruses belong to the a-like supergroup of viruses. They have a proteinaceous rod, made up of copies of the coat protein (CP), which envelops the linear RNA(+) genome. After infection of the plant cell, the RNA genome is uncoated and transcribed, producing the RNA-dependent RNA polymerase (RdRP), the movement protein (MP) and the coat protein (CP). Infection of neighboring cells as well as long-distance transport of the virus are dependent on the movement protein (MP). Resistance against pathogens like tobamoviruses requires the presence of resistance (R) genes, whose polypeptide products, R proteins, recognize products of the tobamoviruses and, subsequently, are able to trigger a defense response, generally hypersensitive response.

For the last decades, all modern indeterminate tomato varieties and many of the determinate tomato varieties indeed contain the Tm-2 gene or preferably the Tm-2$^2$ (also known as Tm-2-2) allele of this gene, as resistance gene. These genes, introgressed from *S. peruvianum*, indeed give them immunity to almost all known races of Tobamoviruses which affected commercial tomatoes (ToMV and TMV)

before 2014. The resistance gene Tm-2-2 appears to also mostly confer resistance to ToMMV (Nagai et al, 2019; Sui et al, 2017).

The Tm-2 (SEQ ID No:2) and the Tm-2-2 (SEQ ID No:3) resistance genes are considered to be allelic and share the movement protein (MP) of ToMV as the matching aviru-lence (Avr) protein. The TM-2 and TM-2-2 proteins (SEQ ID No:7 and 8 respectively) have the characteristics of the nucleotide binding site/leucine-rich repeat type of R proteins (NBS-LRR proteins, also known as NLR proteins) and differ considerably from the polypeptide (SEQ ID No:6) encoded by the tm-2 allele (SEQ ID No:1) isolated from susceptible *L. esculentum* lines (Lanfermeijer et al. 2003). Tm-2 and Tm-2-2 mediated resistance requires that these NLR pro-teins recognize a tobamovirus movement protein (MP) (Calder and Palukaitis 1992; Meshi et al. 1989; Weber and Pfitzner 1998; Weber et al. 1993).

The differences between the products of the tm2 and Tm-2 genes are concentrated in the leucine-rich repeat (LRR) domain, as well as the difference between the Tm-2 and Tm-2-2 genes (Lanfermeijer et al. 2005).

During 2014-2015, a severe outbreak of virus affected tomato productions areas in the middle east, such as in Jordan and in Israel. Most of the tomato varieties affected were considered TMV and/or ToMV resistant, but were still severely affected and showed typical TMV/ToMV like symptoms: while the foliar ones were quite similar to the TMV/ToMV symptoms, the fruit symptoms were much more frequent and severe than the usual symptoms from such viruses with fruits lesions and deformations. The fruit quality was very poor and rather unmarketable. Salem et al, 2015 sequenced this new Tobamovirus species, and pro-posed to name this Jordanian virus: Tomato Brown Rugose Fruit virus (previously TBRFV and now ToBRFV). The comparison to other Tobamoviruses sequences showed that it is indeed a Tobamovirus, but not TMV or ToMV. The resistance to TMV and/or ToMV does not confer resistance to this new virus ToBRFV; i.e plants comprising either the Tm-2 or the Tm-2-2 resistance gene are still susceptible to ToBRFV.

Luria et al, 2017 have concomitantly isolated and sequenced the complete genome of the Israeli tobamovirus infecting tomato in Israel, they have shown a very high sequence identity between the Israeli and the Jordanian viruses (more than 99% sequence identity) and have con-cluded to two different isolates of tomato brown rugose fruit virus.

Recently, the virus was identified in Europe, especially in Sicily, Germany, the Netherlands and France, and in Mexico, and therefore now it is considered as a major global threat to tomato crop. Identification of a resistance gene against this new tobamovirus has thus become important and urgent for tomato breeders.

Identification of tomato plants which display resistance to ToBRFV and localization and identification of genetic deter-minants, also referred to hereafter as QTLs (Quantitative Trait Locus) that lead to resistance to the Tomato Brown Rugose Fruit virus have recently been described in WO2018/219941. Two QTLs, namely QTL1 and QTL2, on chromosome 6 and 9 respectively, confer independently or in combination an improved tolerance or resistance in the fruits of a tomato plant infected or likely to be infected by the ToBRFV, when present homozygously into a *S. lycoper-sicum* background. A third QTL, QTL3, on chromosome 11, confers an improved tolerance or resistance in the leaves of a tomato plant infected or likely to be infected by the ToBRFV, when present homozygously.

Whereas these QTLs, either alone or in combination, provide tolerance or resistance to ToBRFV, this tolerance/resistance appears quantitative and polygenic, and plants are not free of virus. Moreover, these QTLs are described as providing resistance when present homozygously. Insofar as QTL2, on chromosome 9, is present at the same locus as the Tm-2-2 gene, in a region which is generally transmitted "en bloc" without recombination, such a QTL on chromosome 9 is therefore likely to be difficult to combine with the Tm-2-2 gene which remains mandatory for commercial plants. WO2020/148021 recently described a resistance gene, on chromosome 8, conferring resistance to ToBRFV; this gene codes for a NBS-LRR protein (Nucleotide-binding site Leucine-rich repeat). The resistance gene disclosed in this document is thus to be combined with the Tm-2-2 resistance gene in order to provide resistance simultaneously to ToBRFV, TMV and ToMV.

Since Tobamovirus particles are very stable and highly infectious, their prevention is generally very difficult. There-fore, one of the most effective ways of combating tobamo-viruses infections is the introduction of genetic resistance gene. There is thus an urgent need to identify improved resistance genes against several tobamoviruses simultane-ously, including this new Tobamovirus ToBRFV, failing that would result in entire regions in which tomato crop could not be produced anymore.

Plant NLR proteins have been extensively reviewed. (Baggs et al. 2017; Kapos et al. 2019). NLRs are proteins that upon recognition of an 'effector protein' trigger a resistance response in plants. NLRs have been grouped into two major subclasses according to their N-terminal domain. The two major subclasses are CNLs and TNLs for proteins that contain either a coiled coil (C) or a toll/interleukin 1 receptor (TIR) domain, respectively at their N-terminus. In addition to the N-terminal domain NLRs also have a nucleo-tide binding (NB) domain and a Leucine Rich Repeat (LRR) domain. Each of the common domains (NB, LRR, CC and TIR) are proposed to play a role in activation of the NLR Protein (Wang et al. 2020). The LRR domain in particular is usually associated with effector protein recognition. As a result, allelic diversity in the LRR domain is often associated with specificity of effector protein binding and LRR domain diversity appears to be under positive selection (Mondragon-Palomino et al. 2002). The LRR domain can also act as an auto-inhibitory domain preventing auto-activation and downstream signaling. The NB domain binds ATP and can switch between an active or inactive form. The CC and TIR domains are generally thought to be involved in signaling. There are also reports where transferring part of a LRR domain between two NLR proteins could confer new speci-ficity to an NLR protein (Slootweg et al. 2017).

In the case of the NLR proteins TM2/TM-2-2 it has been demonstrated that a single amino acid (AA) change in the LRR domain is responsible for expanding the diversity of tobamovirus Movement proteins (MP) recognized by the protein (Kobayashi et al. 2011).

The present inventors have unexpectedly found that, contrary to the teaching of the prior art, resistance to TMV, ToMV and ToBRFV can be conferred by a single resistance protein, encoded by a single resistant gene, without requir-ing the combination of different resistance genes and pro-teins. They have moreover found that such a protein con-ferring resistance to ToBRFV can be obtained by modifying the recognition domain, namely the LRR domain, of a NLR protein conferring resistance to TMV and ToMV, namely by modifying the LRR domain of a TM-2-2 protein.

SUMMARY

The present invention is directed to a variant LRR domain, deriving from the LRR domain of the TM-2-2 protein, such that a NBS-LRR protein comprising said mutant LRR domain recognizes and/or binds the Movement Proteins of several different tobamoviruses, including at least ToBRFV, and preferably also TMV, ToMV and/or ToMMV, most preferably TMV, ToMV and ToMMV.

The invention is also directed to polypeptides comprising such a mutant LRR domain, as well as nucleotide sequences encoding said domains and polypeptides.

The invention also concerns a Resistance gene, encoding a mutant or allelic variant of the TM-2-2 protein (SEQ ID No:8), conferring to tomatoes resistance against several tobamoviruses, including at least against ToBRFV.

The newly discovered resistance protein or LRR domain confers resistance against ToBRFV, preferably in addition to resistance against ToMV and TMV, thanks to at least one substitution in the LRR domain of the TM-2-2 protein, at position 822, 825 or 848, namely the substitution of the asparagine (N) 822 by a cysteine (C), a phenylalanine (F), a methionine (M), a tyrosine (Y) or a tryptophan (VW), the substitution of the serine (S) 825 by a histidine (H), a lysine (K) or a threonine (T), the substitution of the cysteine (C) 848 by an arginine (R), or a combination of these substitutions. Additional substitutions, and preferably the substitution of the phenylalanine (F) at position 655 by a leucine (L), may improve the resistance conferred by the substitution at position 848, 822 and/or 825, especially substitution at position 848.

The present invention also provides plants, especially *S. lycopersicum* plants that display resistance to ToBRFV, including commercial plants, lines and hybrids, as well as methods that produce or identify plants, especially *S. lycopersicum* plants or populations (germplasm) that display resistance to ToBRFV. The present invention also discloses molecular genetic markers, linked to the newly discovered resistance gene. Plants obtained through the methods and uses of such molecular markers are also provided.

The invention also provides several methods, including methods for identifying ToBRFV resistant plants, methods for improving the yield of tomato production in an environment infested by different tobamoviruses including ToBRFV, methods for protecting a tomato field from tobamoviruses infestation including ToBRFV and methods for identifying, detecting and/or selecting mutants of the Tm-2-2 or Tm-2 gene conferring resistance against at least ToBRFV.

Definitions

The term "Resistance" is as defined by the ISF (International Seed Federation) Vegetable and Ornamental Crops Section for describing the reaction of plants to pests or pathogens, and abiotic stresses for the Vegetable Seed Industry. Specifically, by resistance, it is meant the ability of a plant variety to restrict the growth and development of a specified pest or pathogen and/or the damage they cause when compared to susceptible plant varieties under similar environmental conditions and pest or pathogen pressure. Resistant varieties may exhibit some disease symptoms or damage under heavy pest or pathogen pressure. Two levels of resistance are defined:

High Resistance: plants that highly restrict the growth and/or development of the specified pest and/or the damage it causes under normal pest pressure when compared to susceptible plants. These plants may, however, exhibit some symptoms or damage under heavy pest pressure.

Intermediate Resistance: plants that highly restrict the growth and/or development of the specified pest and/or the damage it causes but may exhibit a greater range of symptoms or damage compared to high resistance plants. Intermediate resistant plants will still show less severe symptoms or damage than susceptible plants when grown under similar environmental conditions and/or pest pressure.

The term "Tolerance" is normally used to describe the ability of a plant to endure abiotic stresses without serious consequences for growth, appearance and yield.

In the literature and patents, this term is however also used to indicate a phenotype of a plant wherein at least some of the disease-symptoms remain absent upon exposure of said plant to an infective dose of virus, whereby the presence of a systemic or local infection, virus multiplication, at least the presence of viral genomic sequences in cells of said plant and/or genomic integration thereof can be established, at least under some culture conditions. Tolerant plants are therefore resistant for symptom expression but symptomless carriers of the virus. Sometimes, viral sequences may be present or even multiply in plants without causing disease symptoms. It is to be understood that a tolerant plant, although it is infected by the virus, is generally able to restrict at least moderately the growth and development of the virus. For this reason, tolerant plants according to this definition are best characterized by Intermediate Resistant plants.

Symptoms on leaves of ToBRFV infection generally include mosaic, distortion of the leaflets and in many cases also shoestrings like symptoms. Symptoms on fruits of ToBRFV infection generally include typical yellow lesions (discoloration) and deformation of the fruits. In many cases there are also "chocolate spots" on the fruits.

Susceptibility: The inability of a plant to restrict the growth and development of a specified pest or pathogen; a susceptible plant displays the detrimental symptoms linked to the virus infection, namely the foliar damages and fruit damages in case of ToBRFV infection.

A *S. lycopersicum* plant susceptible to Tomato Brown Rugose Fruit virus, is for example the commercially available variety Candela as mentioned in the 2015 Salem et al. publication.

As used herein, the term "offspring" or "progeny" refers to any plant resulting as progeny from a vegetative or sexual reproduction from one or more parent plants or descendants thereof. For instance, an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (a true-breeding parent is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "genotype" refers to the genetic makeup of an individual cell, cell culture, tissue, organism (e.g., a plant), or group of organisms.

As used herein, the term "grafting" is the operation by which a rootstock is grafted with a scion. The primary motive for grafting is to avoid damages by soil-born pest and pathogens when genetic or chemical approaches for disease management are not available. Grafting a susceptible scion onto a resistant rootstock can provide a resistant cultivar without the need to breed the resistance into the cultivar. In addition, grafting may enhance tolerance to abiotic stress, increase yield and result in more efficient water and nutrient uses.

As used herein, the term "heterozygote" refers to a diploid or polyploid individual cell or plant having different alleles (forms of a given gene, genetic determinant or sequences) present at least at one locus.

As used herein, the term "heterozygous" refers to the presence of different alleles (forms of a given gene, genetic determinant or sequences) at a particular locus.

As used herein, the term "homozygote" refers to an individual cell or plant having the same alleles at one or more loci on all homologous chromosomes.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "locus" (plural: "loci") refers to any site that has been defined genetically, this can be a single position (nucleotide) or a chromosomal region. A locus may be a gene, a genetic determinant, a part of a gene, or a DNA sequence, and may be occupied by different sequences. A locus may also be defined by a SNP (Single Nucleotide Polymorphism), by several SNPs, or by two flanking SNPs.

As used herein, the term "rootstock" is the lower part of a plant capable of receiving a scion in a grafting process.

As used herein, the term "scion" is the higher part of a plant capable of being grafted onto a rootstock in a grafting process.

The invention encompasses plants of different ploidy levels, essentially diploid plants, but also triploid plants, tetraploid plants, etc.

DETAILED DESCRIPTION OF THE INVENTION

The present inventors have identified variants of the LRR domain of the TM-2-2 protein, such that a NBS-LRR protein comprising said variants of the LRR domain recognizes and/or binds the Movement Proteins (MP) of several tobamoviruses, including at least ToBRFV (Tomato Brown Rugose Fruit Virus) and preferably also MP of TMV (Tobacco Mosaic Virus) and/or ToMV (Tomato Mosaic Virus), and preferably also ToMMV (Tomato Mottle Mosaic Virus).

The present invention is thus directed to variants of the Leucine-Rich Repeat of the TM-2-2 protein, namely variants of SEQ ID No:11, wherein said variants have at least 90% sequence identity with SEQ ID No:11 and said variants confer, if incorporated into a NBS-LRR protein, the capacity to recognize and/or bind at least the Movement Protein of the ToBRFV (SEQ ID No:15); and preferably also the MP of the ToMV (SEQ ID No:14) and/or of the TMV (SEQ ID No:13), and still preferably also the MP of ToMMV (SEQ ID No:16). By way of contrast, the LRR domain of TM-2-2, i.e. SEQ ID No:11, confers the capacity to bind MP of ToMV and TMV, but does not confer significant binding to or recognition of MP of ToBRFV. Variants of the LRR domain of TM-2-2 of the invention are interchangeably referred to as LRR variants or mutants, or LRR domain variants or mutants, or LRR variant domains of the invention.

Substitution of the LRR domain of TM-2-2, i.e. SEQ ID No:11, by a LRR variant of the invention, confers to the thus obtained protein recognition of the ToBRFV MP, i.e. results in a protein recognizing ToBRFV MP.

A NBS-LRR protein is said to recognize the ToBRFV MP if said protein binds, directly or indirectly, the ToBRFV MP; the direct or indirect binding may be at the LRR domain level, or may involve the whole protein. Such a recognition can be tested by the assay disclosed in the examples.

The inventors have moreover demonstrated that the variation conferring recognition of ToBRFV MP lies in the substitution of at least one of the amino acids at position 822, 825 and 848 of the TM-2-2 protein (SEQ ID No:8), and more specifically in at least one of the substitutions consisting in:

the substitution of the cysteine (C) at position 848 of the TM-2-2 protein (SEQ ID No:8), corresponding to position 372 of SEQ ID No:11 (LRR domain of TM-2-2, corresponding to amino acids 477 to 861 of TM-2-2 protein), by an arginine (R), the substitution of the asparagine (N) at position 822 of the TM-2-2 protein (SEQ ID No:8), corresponding to position 346 of SEQ ID No:11 (LRR domain of TM-2-2), by a cysteine (C), a phenylalanine (F), a methionine (M), a tyrosine (Y) or a tryptophan (VW), and the substitution of the serine (S) at position 825 of the TM-2-2 protein (SEQ ID No:8), corresponding to position 349 of SEQ ID No:11 (LRR domain of TM-2-2), by a histidine (H), a lysine (K) or a threonine (T).

The LRR variants according to the invention are thus characterized by the presence of an arginine at the position corresponding to cysteine 848 in the TM-2-2 protein, and/or by a cysteine, a phenylalanine, a methionine, a tyrosine or a tryptophan at the position corresponding to asparagine 822 in the TM-2-2 protein and/or by a histidine, a lysine or a threonine at the position corresponding to serine 825 of the TM-2-2 protein. An LRR variant of the invention may comprise one of the described substitutions, at only one position from 822, 825 and 848, or at two or at all of them. Preferably, an LRR variant of the invention does not comprise simultaneously a C848R and a N822Y substitution.

According to a preferred embodiment, only one of the 822, 825 and 848 positions is substituted.

The inventors have moreover shown that a mutation or substitution at position 655 in the LRR variants of the invention may improve the recognition of ToBRFV MP, preferably the substitution of phenylalanine (F) by Leucine (L). Without being bound by theory, it is expected that a mutation at position 655 improves the presentation of the domain of the LRR variants interacting with the ToBRFV MP. Preferred LRR variants of the invention thus also comprise a mutation at position 655, more preferably a F655L mutation. Position 655, with respect to the whole TM2-2 protein, corresponds to position 179 of SEQ ID No:11 (LRR domain of TM-2-2).

The variants of the invention are also characterized by the presence of a tyrosine (Y), a phenylalanine (F) or a tryptophan (W) at the position corresponding to tyrosine 767 in the TM-2-2 protein, i.e. presence of Y, F or W at the position in the LRR variant corresponding to position 291 of the TM-2-2 LRR (SEQ ID No:11). Indeed, as demonstrated by the inventors in the experimental section, said tyrosine, naturally occurring in the TM-2-2 LRR/protein, can be substituted by F or W without loss of function. This position has moreover been demonstrated in Kobayashi et al, as providing the durable resistance to ToMV.

In the following, the numbering of the amino acids is with respect to the position of said amino acids in the full-length TM-2-2 protein (SEQ ID No:8).

The ability of a given LRR domain to confer to NBS-LRR proteins; and especially to a TM-2-2 protein, the capacity to recognize and/or bind at least the Movement Protein of the Tomato Brown Rugose Fruit Virus (ToBRFV), can be tested easily with the transient expression assay disclosed in the experimental section, namely by transient expression in *N. benthamiana* of a NBS-LRR protein comprising the LRR domain to be tested, in presence of the ToBRFV MP, and by screening for hypersensitive response. Preferably, the NBS-LRR protein is the TM-2-2 protein, in which the naturally occurring LRR domain is substituted by the LRR variant to be tested.

Preferably, a LRR domain mutant of the invention is such that substitution of the LRR domain of TM-2-2, i.e. SEQ ID No:11, by the LRR variant of the invention, retains the capacity to recognize the MP of ToMV, TMV and/or ToMMV, and preferably at least TMV and ToMV.

A variant LRR domain of the invention exhibits at least 90% sequence identity, at the amino acid level, with SEQ ID No: 11, which corresponds to the sequence of the LRR domain of TM-2-2.

Sequence identity between two amino acid sequences is as defined usually in the domain of the invention. A suitable program for defining sequence identity is for example Clustal Omega.

According to preferred embodiments of the invention, the LRR variant has preferably at least 95% sequence identity with SEQ ID No:11, preferably at least 96%, at least 97% or at least 98%. According to still further embodiments, the LRR variant has 99% sequence identity with SEQ ID No:11 or more.

Irrespective of the percentage of sequence identity with the wild-type LRR domain of TM-2-2, a variant according to the invention comprises Y, F or W at the position corresponding to position 767 of the TM-2-2 protein and one or more of:

R at the position corresponding to cysteine 848 of the TM-2-2 protein,

C, F, M, Y or W at the position corresponding to asparagine 822 of the TM-2-2 protein, and H, K or T at the position corresponding to serine 825 of the TM-2-2 protein.

A variant preferably also comprises leucine (L) at the position corresponding to position 655 of the TM-2-2 protein, in addition to the above-mentioned variations.

Variations to the LRR domain of TM-2-2 in the vicinity of amino acids 822, 825 and 848 in the tridimensional structure of the LRR domain are preferably to be limited; amino acids close to positions 822, 825 and 848 are positions 823, 826, 827, 830, 847, 849, 850, 851, 857 and 858. As demonstrated in the examples, some variations at these positions are however acceptable, such as the K857Q substitution.

Variations or mutations between a LRR variant of the invention and SEQ ID No.11 concern thus preferably amino acids which are not those in the vicinity of amino acids 346, 349 and 372 (corresponding to amino acid 822, 825 and 848 in the TM-2-2 protein).

Variations or mutations are preferably conservative amino-acids substitutions, preferably preserving the 3D structure of the LRR domain.

Namely a basic amino acid like lysine or arginine is preferably substituted by another basic amino acid; an acidic amino acid like aspartic acid or glutamic acid is preferably substituted by another acidic amino acid. A small apolar amino acid like glycine, alanine, proline, cysteine or valine is preferably substituted by another small apolar amino acid. A large apolar amino acid like leucine, isoleucine, phenylalanine, methionine or tryptophan is preferably substituted by another large apolar amino acid. A small polar amino acid like serine or threonine is preferably substituted by another small polar amino acid. A large polar amino acid like asparagine or glutamine is preferably substituted by another large polar amino acid. An aromatic amino acid like tyrosine, phenylalanine or tryptophan is preferably substituted aby another aromatic amino acid.

Potential variations or mutations according to the invention may concern amino acids corresponding to position 655 of TM-2-2, or position 857 and/or 769, as demonstrated in the experimental section. According to a preferred embodiment, a LRR domain variant according to the invention exhibits 20 mutations or less with respect to the LRR domain of TM-2-2, preferably 15 or less, and more preferably 10 mutations or less. Said mutations are preferably conservative mutations; they are preferably to be found in portions of the LRR domain which are not in the vicinity of cysteine 848, asparagine 822 and serine 825 substitutions.

Potential LRR variants according to the invention comprise: leucine (L) at position 655, arginine (R) at position 848 and tyrosine (Y) at position 767, or leucine (L) at position 655, arginine (R) at position 848 and phenylalanine (F) at position 767, or leucine (L) at position 655, arginine (R) at position 848 and tryptophan (WW) at position 767, or arginine (R) at position 848 and tyrosine (Y) at position 767, as well as all the LRR variants illustrated in the examples.

The present invention is also directed to a nucleotide sequence encoding a LRR domain mutant as defined above. In view of the degeneracy of the genetic code, very different nucleotide sequences can be envisaged, coding for a LRR domain variant of the invention, namely coding for a variant of SEQ ID No: 11, characterized essentially by an arginine at the position corresponding to cysteine 848 of the TM-2-2 protein, and/or by a cysteine, a phenylalanine, a methionine, a tyrosine or a tryptophan at the position corresponding to asparagine 822 and/or by a histidine, a lysine or a threonine at the position corresponding to serine 825, wherein said variant of SEQ ID No:11 has a tyrosine, a phenylalanine or a tryptophan at position 767, and potentially a leucine at position 655. The sequence can be isolated or not.

A suitable nucleotide sequence is for example a sequence corresponding to SEQ ID No:12, namely the wild type sequence encoding Tm-2-2 LRR, in which at least the codon corresponding to cysteine at position 848 of TM-2-2 has been substituted by a codon corresponding to arginine, or at least the codon corresponding to asparagine at position 822 of TM-2-2 has been substituted by a codon corresponding to cysteine, phenylalanine, methionine, tyrosine or tryptophan, or at least the codon corresponding to serine at position 825 of TM-2-2 has been substituted by a codon corresponding to histidine, lysine or threonine. Suitable nucleotide sequences are for example nucleotides 1429 to 2586 (or 2583 in excluding the stop codon) of SEQ ID No: 4, or 5. Other suitable nucleotide sequences deriving from SEQ ID No:12, in which at least one of the following codons has been substituted:

the codon TGC encoding the cysteine at position 848 of TM-2-2, i.e. the nucleotides at positions 1114-1116 of SEQ ID No:12, has been substituted by a codon encoding an arginine, i.e. by AGA, AGG, CGG, CGA, CGC or CTG, the codon AAT encoding the asparagine at position 822 of TM-2-2, i.e. the nucleotides at positions 1036-1038 of SEQ ID No:12, has been substituted by a codon encoding a cysteine, i.e. by TGT or TGC, by a codon encoding a phenylalanine, i.e. by TTT or TTC, by a codon encoding a methionine, i.e by ATG, by a codon encoding a tyrosine, i.e. by TAT or TAC, or by a codon encoding a tryptophan, i.e. by TGG, and the codon TCT encoding the serine at position 825 of TM-2-2, i.e. the nucleotides at positions 1045-1047 of SEQ ID No:12, has been substituted by a codon encoding a histidine, i.e. by CAT or CAC, by a codon encoding a lysine, i.e. by AAA or AAG, or by a codon encoding a threonine, i.e. by ACC, ACT, ACG or ACA.

In addition, the codon TAC encoding the tyrosine at position 767 of TM-2-2, i.e. the nucleotides at positions 871-873 of SEQ ID No.:12, may be substituted by a codon encoding a phenylalanine, i.e. by TTT or TTC or by a codon encoding a tryptophan, i.e. by TGG.

The codon encoding the phenylalanine at position 655 of TM-2-2, i.e. the nucleotides at positions 535-537 of SEQ ID No.:12, may be substituted by a codon encoding a leucine, i.e. by CTT, CTC, CTA, CTG, TTA or TTG.

The present invention also concerns sequences deriving from SEQ ID No:12 having at least 70% sequence identity with said sequence, preferably at least 75%, at least 80%, at least 85%, at least 90% or at least 95% sequence identity. Irrespective of the percentage of sequence identity with SEQ ID No:12, a sequence according to the invention encodes a LRR domain variant of the invention as defined above. Given the degeneracy of the genetic code, a sequence encoding a LRR domain variant of the invention may nevertheless have less than 70% sequence identity with SEQ ID No:12, and is also in the scope of the present invention.

According to a further aspect, the invention is also directed to polypeptides and proteins comprising a mutant LRR domain of the invention, especially polypeptides and proteins, recognizing or binding the Movement Protein (MP) of at least ToBRFV, and preferably also of other tobamoviruses including at least ToMV or TMV, and preferably also ToMMV.

According to a preferred embodiment of the present invention, a protein comprising a mutant or variant LRR domain of interest is a member of the NLR class of protein (NBS-LRR), and more preferably is a coiled-coil NLR (CC-NBS-LRR). As demonstrated in Slootweg et al, LRR exchange between NBS-LRR proteins may indeed modify the target of the NBS-LRR protein. The LRR domain mutant of the invention can thus be substituted to the wild-type LRR of any NBS-LRR thus creating a chimeric NBS-LRR specifically targeting the MP of ToBRFV, and preferably also the MP of ToMV, TMV and/or ToMMV.

The present invention thus also encompasses such chimeric NBS-LRR proteins, comprising the NBS portion of a NBS-LRR protein, and the LRR domain mutant according to the invention. As indicated above, such a NBS-LRR protein is preferably a CC-NBS-LRR.

Such a NBS-LRR protein of the invention preferably comprises the NBS portion of the TM-2-2 protein, corresponding to amino acids 1 to 476 of SEQ ID No:8, fused to a LRR domain mutant of the invention. Such a protein may advantageously have the sequence SEQ ID No:9 (TM2-14-25), SEQ ID No:10 (TM2-467), SEQ ID No:17 (TM2-4), SEQ ID No:18 (TM2-5), SEQ ID No:19 (TM2-825H), SEQ ID No:20 TM2-825K), SEQ ID No:21 (TM2-825T), SEQ ID No:22 (TM1-822C), SEQ ID No:23 (TM2-822F), SEQ ID No:24 (TM2-822M), SEQ ID No:25 (TM2-822Y) or SEQ ID No:26 (TM2-822-W). These proteins of the invention are thus TM-2-2 protein variants, differing from the TM-2-2 protein only in the LRR domain.

Alternative NBS-LRR proteins of the invention comprise the NBS portion of SEQ ID No:6 and 7 (corresponding to the proteins encoded by tm2 and Tm2 genes) fused to a LRR domain mutant of the invention.

The invention is also directed to TM-2-2 protein variants, having at least 90% amino acid identity with the sequence of the TM-2-2 protein (SEQ ID No:8), interacting with and/or recognizing or targeting the MP of ToBRFV and comprising a tyrosine, a phenylalanine or a tryptophan at the position corresponding to Y767 of SEQ ID No:8, and comprising at least one of an arginine at position corresponding to C848 of SEQ ID No:8, a histidine, a lysine or a threonine at the position corresponding to S825 and a cysteine, a phenylalanine, a methionine, a tyrosine or a tryptophan at the position corresponding to N822, i.e. comprising at least one of the following variations: N822C, N822F, N822M, N822Y, N822W, S825H, S825K, S825T and C848R. Such variants may also comprise a leucine at the position corresponding to F655 of SEQ ID No:8. The variations within the TM-2-2 protein may be present in the NBS domain or in the LRR domain of the protein. They are preferably to be found mainly in the NBS domain. For variations in the LRR domain, the requirements for the variations or mutations are as described previously in connection with the LRR mutants of the invention. The variations or mutations are preferably conservative mutations. The variants are isolated or not.

According to a preferred embodiment, only one of the 822, 825 and 848 positions is substituted. According to alternative embodiments, two of said positions, or all these positions are substituted. Preferably, the variant does not comprise simultaneously C848R and N822Y substitutions.

The TM-2-2 protein variants according to the invention have preferably at least 90% amino acid identity globally with the sequence of the TM-2-2 protein, with at least 95% sequence identity at the LRR domain level. According to additional embodiments, the global percentage of sequence identity of the TM-2-2 protein variants of the invention is at least 95% with SEQ ID No:8, with preferably a greater sequence identity at the LRR domain level. Preferably, the sequence identity between a TM-2-2 protein and SEQ ID No:8 is at least 96%, at least 97%, at least 98% or even at least 99%.

According to a preferred embodiment, a TM-2-2 protein variant according to the invention exhibits 60 mutations or less with respect to the TM-2-2 protein, preferably 50 or less, and more preferably 20 mutations or less. Said mutations are preferably conservative mutations; they are preferably to be found in majority in the domains of the protein which are not the LRR domain.

A TM-2-2 protein variant according to the invention triggers a hypersensitive response (HR) in presence of the MP of ToBRFV, and preferably also in presence of MP of other tobamoviruses, including at least one of TMV, ToMV and ToMMV. A TM-2-2 protein variant according to the invention thus confers resistance against ToBRFV infection in tomatoes, and preferably also resistance against additional tobamoviruses, including TMV, ToMV and/ToMMV.

It is noted in this regard that detection of a hypersensitive response in a transient expression assay in a surrogate plant like *N. benthamiana* equates detection of resistance in tomato. There is indeed a perfect correlation between the ability of a NBS-LRR protein to trigger a robust HR response in *N. benthamiana* leaves (in the presence of a tobamovirus MP) and virus resistance in tomato. This point has been confirmed by the inventors in the experimental section.

According to still another embodiment, the invention is also directed to a nucleotide sequence encoding a polypeptide or protein as disclosed above, especially encoding a protein comprising a LRR domain mutant of the invention, a chimeric NBS-LRR as described or a TM-2-2 protein variant of the invention. A nucleotide sequence according to the invention encompasses at least DNA, single-stranded DNA, RNA, double stranded RNA, and mixture of DNA and RNA. The sequence can be isolated or not.

A suitable nucleotide sequence is for example SEQ ID No:4 or 5; these sequences are derived from the wild type sequence Tm-2-2 encoding TM-2-2, in which at least the codon corresponding to cysteine at position 848 of TM-2-2 has been substituted by a codon corresponding to arginine. The present invention is thus also directed to mutated Tm-2-2 genes, as for example SEQ ID No:4 (Tm2-14-25) or SEQ ID No:5 (Tm2-467). The invention is also directed to a sequence deriving from SEQ ID No:3, corresponding to the wild type sequence Tm-2-2 encoding TM-2-2, in which at least one of the following codons has been substituted:

the codon TGC encoding the cysteine at position 848 of TM-2-2, i.e. the nucleotides at positions 2542-2544 of SEQ ID No:3, has been substituted by a codon encoding an arginine, i.e. by AGA, AGG, CGG, CGA, CGC or CTG, the codon AAT encoding the asparagine at position 822 of TM-2-2, i.e. the nucleotides at positions 2464-2466 of SEQ ID No:3, has been substituted by a codon encoding a cysteine, i.e. by TGT or TGC, by a codon encoding a phenylalanine, i.e. by TTT or TTC, by a codon encoding a methionine, i.e by ATG, by a codon encoding a tyrosine, i.e. by TAT or TAC, or by a codon encoding a tryptophan, i.e. by TGG, and/or the codon TCT encoding the serine at position 825 of TM-2-2, i.e. the nucleotides at positions 2473-2475 of SEQ ID No:3, has been substituted by a codon encoding a histidine, i.e. by CAT or CAC, by a codon encoding a lysine, i.e. by AAA or AAG, or by a codon encoding a threonine, i.e. by ACC, ACT, ACG or ACA.

The codon TAC encoding the tyrosine at position 767 of TM-2-2, i.e. the nucleotides at positions 2299-2301 of SEQ ID No:3 may also be substituted by a codon encoding a phenylalanine, i.e. by TTT or TTC, or by a codon encoding a tryptophan, i.e. by TGG.

The codon TTT encoding the phenylalanine at position 655 of TM-2-2, i.e. the nucleotides at positions 1963-1965 of SEQ ID No:3 may also be substituted by a codon encoding a leucine, i.e. by CTT, CTC, CTA, CTG, TTA or TTG.

According to specific embodiments, a substituted sequence deriving from SEQ ID No:3 as described above is chosen from SEQ ID No:27 (encoding TM2-4), SEQ ID No:28 (encoding TM2-5), SEQ ID No:29 (encoding TM2-825H), SEQ ID No:30 (encoding TM2-825K), SEQ ID No:31 (encoding TM2-825T), SEQ ID No:32 (encoding TM1-822C), SEQ ID No:33 (encoding TM2-822F), SEQ ID No:34 (encoding TM2-822M), SEQ ID No:35 (encoding TM2-822Y) or SEQ ID No:36 (encoding TM2-822-W).

The invention also concerns sequences deriving from SEQ ID No:3, 4, 5, 27, 28, 29, 30, 31, 32, 33, 34, 35 or 36, or from the substituted sequences described above, having at least 70% sequence identity with said sequences, preferably at least 75%, at least 80%, at least 85%, at least 90% or at least 95% sequence identity. Irrespective of the percentage of sequence identity with SEQ ID No:3, 4, 5, 27, 28, 29, 30, 31, 32, 33, 34, 35 or 36, or with the substituted sequences described above, such a sequence encodes a protein, polypeptide or TM-2-2 variant according to the invention. Given the degeneracy of the genetic code, a sequence encoding such a polypeptide, protein or variant of the invention may nevertheless have less than 70% sequence identity with SEQ ID No:3, 4, 5, 27, 28, 29, 30, 31, 32, 33, 34, 35 or 36, or with the substituted sequences described above, but is also in the scope of the present invention.

Potential additional variations are especially substitution of Y767 by F or W. Additional mutations or variations have already been explicated in the preceding aspects of the invention are applied mutatis mutandis to this aspect.

The invention according to another aspect also relates to a Resistance gene, encoding a NBS-LRR protein which is a mutant or allele of the TM-2-2 protein, conferring to plants, especially tomatoes, resistance against at least ToBRFV, and preferably against at least one or more of TMV, ToMV and ToMMV. Preferably, such a resistance gene confers resistance against at least ToBRFV, TMV and ToMV, and even preferably against ToBRFV, TMV, ToMV and ToMMV. The mutant or allele of the TM-2-2 protein is a variant of the TM-2-2 protein as disclosed above, comprising at least one of the substitutions C848R at position 848 of the TM-2-2 protein, N822C, N822F, N822M, N822Y and N822W at position 822 of the TM-2-2 protein and S825H, S825K and S825T at position 825 of the TM-2-2 protein.

The mutant or allele of the TM-2-2 protein may comprise one of the described substitutions, at only one position from 822, 825 and 848, or at two or at all of them. Preferably, a mutant or allele of the TM-2-2 protein of the invention does not comprise simultaneously a C848R and a N822Y substitution.

The mutant or allele of the TM-2-2 protein may further comprise a F655L substitution.

The newly discovered resistance protein and the resistance gene encoding said protein, confer resistance against ToBRFV, preferably in addition to resistance against ToMV and TMV, thanks to the substitution of the cysteine 848, the asparagine 822 and/or the serine 825 in the LRR domain of the TM-2-2 protein, by an arginine for C848, by a cysteine, a phenylalanine, a methionine, a tyrosine or a tryptophan for N822 and a histidine, a lysine or a threonine for S825.

According to still another aspect, the invention is also directed to a nucleic acid construct comprising a sequence encoding a polypeptide or protein according to the invention or comprising a nucleotide sequence encoding a TM-2-2 variant or comprising a resistance gene according to the invention.

Such a sequence, encoding a polypeptide or protein according to the invention, or comprising a nucleotide sequence encoding a TM-2-2 variant or comprising a resistance gene is interchangeably referred to as a nucleotide sequence or resistance gene, or variant Tm-2-2 gene or mutated Tm-2-2 gene of the invention, in the following.

Such a sequence encoding the protein, polypeptide or variant of interest is preferably under the control of a promoter, which is a constitutive or inducible promoter.

Preferably, the promoter is a promoter which is active in plant cells. According to an embodiment, the promoter is not the wild-type promoter of Tm-2, Tm-2-2 or tm-2 gene. Preferably the promoter for the Tm-2-2 variant gene is the native promoter of Tm-2, Tm-2-2 or tm-2.

A nucleic acid construct according to the invention can thus be a vector, a plasmid or a T-DNA plasmid. Presence of a construct of the invention in a cell thus may give rise to the expression of a protein, polypeptide TM-2-2 variant or Resistance protein according to the invention and as defined above.

The invention also encompasses expression vector or construct suitable for expression of a polypeptide, protein, TM-2-2 variant or resistance protein according to the invention, preferably expression in a plant cell.

According to a further embodiment, the invention is also directed to the use of a sequence as defined, encoding a TM-2-2 variant of the invention, or a construct comprising such a sequence for conferring resistance against at least ToBRFV to a *S. lycopersicum* plant or for obtaining transgenic *S. lycopersicum* plants resistant against ToBRFV. Indeed, as demonstrated in the example, the TM-2-2 variant recognizes the ToBRFV MP thus triggering a HR response associated with ToBRFV resistance. A TM-2-2 variant of the invention may also recognize at least the movement proteins of TMV, ToMV and/or ToMMV, thus conferring resistance against these tobamoviruses. The invention thus also encompasses the use of said sequence for conferring resistance against ToBRFV and against at least one of TMV, ToMV and ToMMV, to a *S. lycopersicum* plant and also uses for obtaining transgenic *S. lycopersicum* plants exhibiting these resistances.

According to a further aspect, the invention also concerns a cell comprising a nucleotide sequence or resistance gene according to the invention or a DNA construct as disclosed above.

The cell is preferably a plant cell, preferably from the Solanaceae family, for example from the *Solanum* genus, and even more preferably a cell of *S. lycopersicum* plant, or a cell of the *Capsicum* or *Nicotiana* genus. The cell comprises, in its genome and preferably in its nuclear genome, a nucleotide sequence or resistance gene or DNA construct according to the present invention. The presence of these sequences confers the phenotype of interest, namely expression of a protein interacting with at least the ToBRFV MP triggering HR response in suitable conditions. The presence of these sequences can be revealed by any techniques well known to the skilled reader, based on the sequence.

Particularly preferred types of cells are cells of the *Solanum, Nicotiana* or *Capsicum* genus, and more preferably *S. lycopersicum* cells.

Cells according to the invention can be any type of cell, especially of *S. lycopersicum* cell, inter alia an isolated cell and/or a cell capable of regenerating a whole plant, especially a *S. lycopersicum* plant bearing the nucleotide sequence or resistance gene of the invention. A cell can thus be a regenerable cell or a non regenerable cell.

The nucleotide sequence or resistance gene of interest can be present homozygously or heterozygously in a cell of the invention. Preferably, a cell according to the invention comprises the resistance gene, or the nucleotide sequence as defined above, at the heterozygous state.

The present invention is also directed to a tissue culture of non-regenerable or regenerable cells as defined above according to the present invention; preferably, the regenerable cells are derived from embryos, protoplasts, meristematic cells, callus, pollen, leaves, anthers, stems, petioles, roots, root tips, fruits, seeds, flowers, cotyledons, and/or hypocotyls of the invention, and the cells contain the nucleotide sequences or resistance gene in their genome conferring the resistance against at least ToBRFV. Preferably, such sequences or resistance gene also provide resistance against TMV and/or ToMV, and preferably also against ToMMV.

The invention is also directed to any plant part, especially a *S. lycopersicum* plant part, particularly seeds, explants, reproductive material, scion, cutting, seed, fruit, root, rootstock, pollen, ovule, embryo, protoplast, leaf, anther, stem, petiole or flowers, wherein said plant part comprises at least one cell as described above.

The invention also provides a protoplast comprising the nucleotide sequences or resistance gene of the invention.

According to another aspect, the invention is directed to a plant, and more preferably to a *S. lycopersicum* plant comprising in its genome a nucleotide sequence or a resistance gene as defined above, encoding a protein or peptide of the invention. Such a nucleotide sequence or resistance gene thus encodes for a variant of the TM-2-2 protein, comprising (1) at least one of a C848R mutation at position 848, a N822C, N822F, N822M, N822Y or N822W mutation at position 822, and a S825H, S825K or S825T mutation at position 825, and (2) Y, F or W at position 767, and conferring resistance against at least ToBRFV, and preferably also against one or more of TMV, ToMV and ToMMV, and more preferably against TMV, ToMV and ToMMV, in addition to ToBRFV. Preferably the nucleotide sequence or resistance gene encodes a variant of the TM-2-2 protein further comprising leucine at position 655.

The invention thus also encompasses a *S. lycopersicum* plant resistant against at least ToBRFV, comprising a mutated Tm-2-2 gene encoding a variant of the TM-2-2 protein (SEQ ID No:8) according to the invention namely having at least 90% sequence identity with SEQ ID No:8, comprising a tyrosine, phenylalanine or tryptophan at the position corresponding to position 767 of SEQ ID No:8, and comprising at least one of the mutations/variations:

an arginine at the position corresponding to position 848 of SEQ ID No:8, instead of the cysteine present in the wild type TM-2-2 sequence;

a cysteine, a phenylalanine, a methionine, a tyrosine or a tryptophan at the position corresponding to position 822 of SEQ ID No:8, instead of the asparagine present in the wild type TM-2-2 sequence, and a histidine, a lysine or a threonine at the position corresponding to position 825 of SEQ ID No:8, instead of the serine present in the wild type TM-2-2 sequence.

The mutated Tm-2-2 gene is a resistance gene according to the invention.

It may advantageously also comprise a leucine at the position corresponding to position 655 of SEQ ID No:8, instead of the phenylalanine present in the wild-type TM-2-2 sequence.

The resistance gene or nucleotide sequence of the invention is preferably stably present in the nuclear genome of the cells of the plant. It can be either stably integrated into the nuclear genome, for example after transformation, or it can result from a mutagenesis process such as Tilling as detailed in the experimental section of the application. The presence of these sequences conferring at least resistance against ToBRFV may also result from introgression from a resistant parent. These sequences conferring resistance against tobamoviruses, including at least ToBRFV, are preferably but not necessarily, to be found on chromosome 9, at the locus of the tm-2 or the Tm-2 gene. Other positions in the genome, for example resulting from random integration, are also suitable and encompassed by the present invention.

The resistance phenotype can be tested and scored as described in the experimental section, especially in example 1.4, by natural infection or by artificial inoculation, at the first leaves level, or at the fruit level.

The sequences or resistance gene conferring resistance against at least ToBRFV can be present homozygously or heterozygously in the genome of a plant according to the invention, especially a *S. lycopersicum* plant. These sequences can also be present as multiple copies.

The resistance gene or mutated Tm-2-2 gene according to this aspect of the invention is as defined in connection with the other aspects of the invention and thus encodes a variant of TM-2-2 protein, which may be SEQ ID No:9, SEQ ID No:10, SEQ ID No:17, SEQ ID No:18, SEQ ID No:19, SEQ ID No:20, SEQ ID No:21, SEQ ID No:22, SEQ ID No:23, SEQ ID No:24, SEQ ID No:25 or SEQ ID No:26. Suitable resistance genes or mutated Tm-2-2 genes are for example those having SEQ ID No:4 or SEQ ID No:5, SEQ ID No:27, SEQ ID No:28, SEQ ID No:29, SEQ ID No:30, SEQ ID No:31, SEQ ID No:32, SEQ ID No:33, SEQ ID No:34, SEQ ID No:35, SEQ ID No:36, or the substituted sequences described above, or sequences derived from SEQ ID No:4 or SEQ ID No:5 or from the substituted sequences described above further to the degeneracy of the genetic code.

The invention is also directed to tissue of a plant of the invention; the tissue can be an undifferentiated tissue, or a differentiated tissue. Such a tissue comprises one or more cells comprising the resistance gene or mutated Tm-2-2 gene of the invention.

The invention is also directed to propagation material, capable of producing a resistant plant according to the invention, especially a resistant tomato plant, comprising the resistance gene or mutated Tm-2-2 gene as defined above. The invention is particularly directed to seeds of such a resistant plant, comprising the resistance gene or mutated Tm-2-2 gene, especially *S. lycopersicum* seeds and seed which can be grown into a *S. lycopersicum* plant according to the invention.

The seed of such *S. lycopersicum* are preferably coated or pelleted with individual or combined active species such as plant nutrients, enhancing microorganisms, or products for disinfecting the environment of the seeds and plants. Such species and chemicals may be a product that promotes the growth of plants, for example hormones, or that increases their resistance to environmental stresses, for example defense stimulators, or that stabilizes the pH of the substrate and its immediate surroundings, or alternatively a nutrient.

They may also be a product for protecting against agents that are unfavorable toward the growth of young plants, including herein viruses and pathogenic microorganisms, for example a fungicidal, bactericidal, hematicidal, insecticidal or herbicidal product, which acts by contact, ingestion or gaseous diffusion; it is, for example, any suitable essential oil, for example extract of thyme. All these products reinforce the resistance reactions of the plant, and/or disinfect or regulate the environment of said plant. They may also be a live biological material, for example a nonpathogenic microorganism, for example at least one fungus, or a bacterium, or a virus, if necessary with a medium ensuring its viability; and this microorganism, for example of the *pseudomonas, bacillus, trichoderma, clonostachys, fusarium, rhizoctonia,* etc. type stimulates the growth of the plant, or protects it against pathogens.

A plant, cell or seed of the invention may be heterozygous or homozygous for the resistance gene or mutated Tm-2-2 gene of the invention conferring ToBRFV resistance. The resistance imparted by this gene is expected to be dominant, such that plants having heterozygously the resistance gene or mutated Tm-2-2 gene of the invention are also resistant to ToBRFV. The present invention thus also encompasses plant, cell or seed having heterozygously in their genome the resistance gene or mutated Tm-2-2 gene of the invention as defined above.

Preferably, a *S. lycopersicum* plant according to the invention is a commercial plant or line. Such a commercial plant or line preferably also exhibits one or more of the following additional features: nematode resistance trait (Mi-1 or Mi-j), *Fusarium* resistance, *Verticillium* resistance, and/or TYLCV resistance.

Other resistances or tolerances are also envisaged according to the invention.

Moreover, the commercial plant of the invention gives rise to fruits in suitable conditions, which are at least 10 grams, preferably 25 grams at full maturity, preferably at least 100 g at full maturity and or even more preferably at least 150 g or at least 200 g at full maturity. The number of fruits per plant is moreover essentially unaffected by the presence of the resistance gene or mutated Tm-2-2 gene of the invention, i.e. the productivity of a plant according to the invention is not inferior by more than 20% to a plant having the same genotype but devoid of said resistance gene or mutated Tm-2-2 gene.

According to still another embodiment, a plant of the invention is a determinate, indeterminate or semi-indeterminate plant, or seed or cell thereof, i.e. corresponding to determinate, indeterminate or semi-indeterminate growth habit.

By determinate, it is meant tomato plants which tend to grow their foliage first, then set flowers that mature into fruit if pollination is successful. All of the fruits tend to ripen on a plant at about the same time. Indeterminate tomatoes start out by growing some foliage, then continue to produce foliage and flowers throughout the growing season. These plants will tend to have tomato fruit in different stages of maturity at any given time. The semi-determinate tomatoes have a phenotype between determinate and indeterminate, they are typical determinate types except that grow larger than determinate varieties.

A plant, cell or seed according to the present invention may advantageously also comprise the Tm-1 gene. The Tm-1 gene is as defined inter alia in the publication Ishibashi et al, 2007; preferably 'Tm-1 gene' refers to a genetic sequence encoding a protein having the Tm-1 activity reported in the article, namely the ability to inhibit the viral replication of a wild-type ToMV strain Tm-1 sensitive, for example the strain ToMV-L disclosed in this article.

The invention thus also encompasses tomato plant, cell or seed comprising the Tm-1 gene, either homozygously or heterozygously, in addition to the resistance gene or mutated Tm-2-2 gene of the invention.

According to still another embodiment, a plant of the invention is used as a scion or as a rootstock in a grafting process. Grafting is a process that has been used for many years in crops such as *cucurbitacea*, but only more recently for tomato. Grafting may be used to provide a certain level of resistance to telluric pathogens such as *Phytophthora* or to certain nematodes. Grating is therefore intended to prevent contact between the plant or variety to be cultivated and the infested soil. The variety of interest used as the graft or scion, optionally an F1 hybrid, is grafted onto the resistant plant used as the rootstock. The resistant rootstock remains healthy and provides, from the soils, the normal supply for the graft that it isolates from the diseases.

As detailed above, the invention is directed to *S. lycopersicum* plants, exhibiting the ToBRFV resistance, preferably also TMV, ToMV and/or ToMMV resistance, as well as to seeds giving rise to those plants, and cells of these plants or seeds, or other plant parts, comprising the resistance gene or mutated Tm-2-2 gene in their genome, and to progeny of such a plant of the invention comprising said resistance gene or mutated Tm-2-2 gene.

Progeny encompasses the first, the second, and all further descendants from a cross with a plant according to the invention, wherein a cross comprises a cross with itself or a cross with another plant.

It is noted that the seeds or plants of the invention may be obtained by different processes, and are not exclusively obtained by means of an essentially biological process. The resistance gene or the mutated Tm-2-2 gene can indeed be introduced, incorporated or obtained "in cellulo" by different techniques. Plants, cells or seeds according to the invention may thus be transgenic, or non-transgenic, they are preferably obtained by technical processes which are not essentially biological processes, as detailed in other sections of this description and in the examples. According to a preferred embodiment, the plants, cells or seeds according to the invention are not exclusively obtained by means of an essentially biological process.

A mutated Tm-2-2 gene, encoding a TM-2-2 variant as disclosed, may advantageously be obtained by gene editing techniques, base-editing or prime editing techniques, such a mutagenesis, especially targeted mutagenesis such a TILL-ING, or by other gene editing techniques such as CRISPR/Cas system, or by custom-made endonucleases, or by base-editing or prime editing with Cas9, Cas12a or other Cas proteins.

These techniques are well known to the skilled reader. Examples of these techniques are illustrated in the experimental section of the application.

In specific embodiments of the invention, the mutations in the Tm-2-2 gene are induced by means of genetic engineering. The genetic engineering means which can be used include the use of all such techniques called New Breeding Techniques which are various new technologies developed and/or used to create new characteristics in plants through genetic variation, the aim being targeted mutagenesis, targeted introduction of new genes or gene silencing (RdDM). Example of such new breeding techniques are targeted sequence changes facilitated through the use of Zinc finger nuclease (ZFN) technology (ZFN-1, ZFN-2 and ZFN-3, see U.S. Pat. No. 9,145,565), Oligonucleotide directed mutagenesis (ODM), Cisgenesis and intragenesis, Grafting (on GM rootstock), Reverse breeding, Agro-infiltration (agro-infiltration "sensu stricto", agro-inoculation, floral dip), Transcription Activator-Like Effector Nucleases (TALENs, see U.S. Pat. Nos. 8,586,363 and 9,181,535), the CRISPR/Cas system (see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641), engineered meganuclease re-engineered homing endonucleases, DNA guided genome editing (Gao et al., Nature Biotechnology (2016)), and Synthetic genomics. A major part of targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, or transgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. A complete description of each of these techniques can be found in the report made by the Joint Research Center (JRC) Institute for Prospective Technological Studies of the European Commission in 2011 and titled "New plant breeding techniques—State-of-the-art and prospects for commercial development".

A resistance gene as defined may also be introduced into a plant, cell or seed of the invention by transformation, especially *Agrobacterium* transformation, thus producing transgenic plants, cells or seeds. This technique is also illustrated in the example section of the application.

The application is directed to plants, seed or cells comprising the resistance gene or the mutated Tm-2-2 gene as already defined irrespective of the mode of provision of these sequences; and thus is directed to transgenic and non-transgenic plants.

In a further aspect, the invention is also directed to different methods for obtaining, breeding or producing plants, especially *S. lycopersicum* plant resistant against ToBRFV, and preferably also resistant against ToMV, TMV and/or ToMMV, more preferably resistant against ToMV, TMV and ToMMV.

The invention thus encompasses methods of producing a plant, especially *S. lycopersicum* plant resistant to ToBRFV, and preferably also resistant to ToMV, TMV and/or ToMMV comprising the following steps:

a) treating M0 seeds of a plant, preferably a tomato plant to be modified with a mutagenic agent to obtain M1 seeds;

b) growing plants from the thus obtained M1 seeds to obtain M1 plants;

c) producing M2 seeds by self-fertilisation of M1 plants; and d) optionally repeating step b) and c) n times to obtain M1+n seeds.

The M1 or M2 seeds are grown into plants and submitted to ToBRFV infection or to screening to identify variations in the Tm-2-2 gene.

In this method, the M1 seeds of step a) can be obtained via chemical mutagenesis such as EMS mutagenesis or by other chemical mutagenic agents or physical means, such as irradiation, which is for example selected ionizing radiations (X-Ray, gamma rays, alpha particles . . . ), heavy-ion beam irradiation, ultraviolet radiations, radioactive decay or fast neutrons irradiation.

Another method for producing a *S. lycopersicum* plant resistant against at least ToBRFV, and preferably also against one or more of TMV, ToMV and ToMMV, comprises the introduction into a plant already comprising a tm2, Tm-2 or Tm-2-2 gene on chromosome 9, of mutations into said tm2, Tm-2 or Tm-2-2 gene, in order to create a mutated Tm-2-2 gene according to the invention, namely encoding a TM-2-2 variant comprising at least one of the C848R, N822C, N822F, N822M, N822Y, N822W, S825H, S825K and S825T mutations with respect to TM-2-2 and comprising F, Y or W at position 767, and potentially also comprising the F655L mutation.

When the starting material is a *S. lycopersicum* plant comprising a Tm-2-2 gene, the method advantageously comprises the introduction of at least one mutation in said Tm-2-2 gene, preferably by mutagenesis, by TILLING or by genome editing, base-editing or prime editing, in particular by mutagenesis induced by a physical agent or a chemical agent, inter alia by a technique selected from ethyl methanesulfonate (EMS) mutagenesis, N-methyl-N-nitrosourea (MNU) mutagenesis, or Sodium Azide (NaN3, SA) mutagenesis, oligonucleotide directed mutagenesis (ODM), Zinc finger nuclease (ZFN) technology, Transcription Activator-Like Effector Nucleases (TALENs), the CRISPR/Cas system, Cas9, Cas12a, or other Cas proteins, engineered meganuclease, re-engineered homing endonucleases and DNA guided genome editing, wherein said at least one mutation gives rise to the C848R, N822C, N822F, N822M, N822Y, N822W, S825H, S825K or S825T substitution in the protein encoded by the Tm-2-2 gene. The method may comprise the introduction of further mutations in the Tm-2-2 gene, for example for giving rise to the Y767F or Y767W substitution in the protein encoded by the Tm-2-2 gene.

Additional mutations may also be introduced, provided the recognition of the ToBRFV MP is not lost, and preferably also the recognition of the TMV, ToMV and ToMMV MPs is also not lost.

The invention also encompasses different methods for obtaining transgenic plants according to the invention, especially transgenic *S. lycopersicum* plants resistant against al least ToBRFV and preferably also resistant against ToMV, TMV and/or ToMMV, by introducing a resistance gene or mutated Tm-2-2 gene according to the invention. These methods may comprise the following steps:

Obtaining a DNA construct as defined in a preceding aspect of the invention, i.e. comprising a resistance gene or mutated Tm-2-2 gene, encoding a TM-2-2 variant according to the invention, Introducing said construct into a cell, especially into a *S. lycopersicum* cell, Regenerating a transgenic plant and Optionally propagating the obtained plant.

According to another aspect, the present invention is also directed to the use of a tomato seed or plant of the invention, preferably comprising homozygously the resistance gene or mutated Tm-2-2 gene of the invention, as a breeding partner in a breeding program for obtaining *S. lycopersicum* plants having the ToBRFV resistance phenotype, and preferably having ToBRFV, ToMV, TMV and ToMMV resistances. Indeed, such a breeding partner harbors homozygously in its genome the resistance gene or mutated Tm-2-2 gene conferring the phenotype of interest. By crossing this plant with a tomato plant, especially a line, it is thus possible to transfer the resistance gene or mutated Tm-2-2 gene of the present invention conferring the desired phenotype, to the progeny. A plant according to the invention can thus be used as a breeding partner for introgressing the resistance gene or mutated Tm-2-2 gene into a *S. lycopersicum* plant or germplasm. Although a plant or seed bearing heterozygously the resistant gene of interest, can also be used as a breeding partner as detailed above, the segregation of the phenotype is likely to render the breeding program more complex.

The invention thus also concerns a method for breeding a *S. lycopersicum* plant resistant against at least ToBRFV and preferably also to TMV, ToMV and/or ToMMV, most preferably to all of them, comprising:

(a) Crossing a *S. lycopersicum* plant comprising a resistance gene or mutated Tm-2-2 gene according to the invention with an initial *S. lycopersicum* plant devoid of resistance gene or mutated gene, (b) Selecting in the progeny thus obtained, a plant bearing the resistance gene or mutated gene, (c) Optionally self-pollinating one or several times the plant obtained at step (b) and selecting in the progeny thus obtained a plant bearing the resistance gene or mutated gene.

The selection can be made by any appropriate means well known to the skilled person, inter alia by using markers specific to the resistance gene or mutated gene.

The invention is also directed to a method of producing a *S. lycopersicum* plant resistant to at least ToBRFV, and preferably also to TMV, ToMV and/or ToMMV, most preferably to all of them, comprising obtaining a part of a plant according to the invention, thus comprising a resistance gene or mutated Tm-2-2 gene as already defined, and vegetatively propagating said plant part to generate a plant from said plant part.

In all the methods and processes according to the invention, the *S. lycopersicum* plant is determinate, indeterminate or semi-determinate.

As already disclosed, the tomato plants according to the invention are preferably also resistant to nematodes, TYLCV, *Fusarium* and/or *Verticillium*.

The present invention is also directed to a *S. lycopersicum* plant and seed obtained or obtainable by any of the methods and processes disclosed above. Such a plant is indeed a *S. lycopersicum* plant expressing a TM-2-2 variant of the invention conferring resistance against tobamoviruses, especially against ToBRFV, and preferably also to at least one of TMV, ToMV and ToMMV.

According to still another aspect, the invention is also directed to a method for genotyping a plant, preferably a *S. lycopersicum* plant or tomato germplasm, for the presence of a resistance gene or mutated Tm-2-2 gene according to the invention associated with resistance against ToBRFV infection, wherein the method comprises the determination or detection in the genome of the tested plant of a nucleic acid comprising or corresponding to at least one of the C848R, N822C, N822F, N822M, N822Y, N822W, S825H, S825K and S825T mutations in the Tm-2-2 gene. Preferably, the method comprises the step of identifying in a sample of the plant to be tested specific sequences associated with one of these mutations conferring resistance to ToBRFV. Similarly, the invention is also directed to a method for identifying, detecting and/or selecting *S. lycopersicum* plants resistant to ToBRFV in plants resistant to TMV and ToMV, said method comprising the detection of a mutant allele of the Tm-2-2 gene in the genome of said plants, wherein said mutant allele comprises at least one mutation chosen from the mutations giving rise to a C848R amino acid substitution at position 848 of the TM-2-2 protein, the mutations giving rise to a N822C, N822F, N822M, N822Y or N822W amino acid substitution at position 822 of the TM-2-2 protein and the mutations giving rise to a S825H, S825K and S825T amino acid substitution at position 825 of the TM-2-2 protein.

In view of the ability of the resistant plants of the invention to restrict the damages caused by different tobamoviruses infection, including ToBRFV infection, they are advantageously grown in an environment infested or likely to be infested or infected by ToBRFV, and potentially also by TMV, ToMV and/or ToMMV; in these conditions, the resistant plants of the invention produce more marketable tomatoes than susceptible plants. The invention is thus also directed to a method for improving the yield of tomato plants in an environment infested by ToBRFV, and also potentially by TMV, ToMV and/or ToMMV, comprising growing tomato plants comprising in their genome the resistance gene or mutated Tm-2-2 gene as defined according to the previous aspects of the invention, and conferring to said plants resistance to at least ToBRFV.

Preferably, the method comprises a first step of choosing or selecting a tomato plant comprising said resistance gene or mutated Tm-2-2 gene of interest. The method can also be defined as a method of increasing the productivity of a tomato field, tunnel or glasshouse, or as a method of reducing the intensity or number of chemical or fungicide applications in the production of tomatoes.

The invention is also directed to a method for reducing the loss on tomato production in condition of ToBRFV infestation or infection, or more generally in condition of ToMV, TMV and/or ToBRFV infestation, comprising growing a tomato plant as defined above.

These methods are particularly valuable for a population of tomato plants, either in a field, in tunnels or in glasshouses.

Alternatively, said methods for improving the yield or reducing the loss on tomato production may comprise a first step of identifying tomato plants resistant to ToBRFV, preferably also to ToMV, TMV and ToMMV, and comprising in their genome the resistance gene or mutated Tm-2-2 gene of the invention, that confers to said plants at least ToBRFV resistance, and then growing said resistant plants in an environment infested or likely to be infested by the virus.

The resistant plants of the invention are also able to restrict the growth of ToBRFV, thus limiting the infection of further plants and the propagation of the virus. Accordingly, the invention is also directed to a method of protecting a field, tunnel or glasshouse, or any other type of plantation, from ToBRFV infection, or of at least limiting the level of infection by ToBRFV of said field, tunnel or glasshouse or of limiting the spread of ToBRFV in a field, tunnel or glasshouse, especially in a tomato field. Such a method preferably comprises the step of growing a resistant plant of the invention, i.e. a plant comprising in its genome the resistance gene or mutated Tm-2-2 gene, conferring to said plant ToBRFV resistance.

The invention also concerns the use of a plant resistant to ToBRFV for controlling ToBRFV infection or infestation in a field, tunnel or glasshouse, or other plantation; such a plant is a plant of the invention, comprising in its genome the resistance gene or mutated Tm-2-2 gene as defined above. This use or method is also a method for disinfecting a field, tunnel or glasshouse by decreasing its viral population.

In still a further aspect, the invention also relates to a method of producing tomatoes comprising:
   a) growing a *S. lycopersicum* plant of the invention, comprising the resistance gene or mutated Tm-2-2 gene as defined previously;
   b) allowing said plant to set fruit; and
   c) harvesting fruit of said plant, preferably at maturity and/or before maturity.

All the preferred embodiments regarding the resistance gene or mutated Tm-2-2 gene are already disclosed in the context of the previous aspects of the invention. The method may advantageously comprise a further step of processing said tomatoes into a tomato processed food.

The invention also concerns a process for the production of tomatoes in a transgenic tomato plant, comprising introducing into a *S. lycopersicum* plant a nucleic acid molecule coding for a TM-2-2 variant according to the invention. The process may further comprise a step of regenerating a transgenic plant, and allowing the plant to set fruit. The process may also comprise a step of harvesting fruit(s) of said transgenic plant.

According to still another embodiment, the invention is also directed to a method for identifying, detecting and/or selecting mutants of the Tm-2-2 gene conferring resistance against at least ToBRFV, and preferably also against at least one of TMV, ToMV and ToMMV, comprising:
   Expressing transiently or constitutively in a surrogate plant host, preferably in a Solanaceae plant, even more preferably in a *Nicotiana* species or a *Capsicum* species, the mutated Tm-2-2 gene to be tested in presence of the movement protein (MP) of ToBRFV, and
   Detecting an interaction between the protein expressed from the mutated gene and the ToBRFV MP protein, and preferably detecting hypersensitive response.

Preferred *Nicotiana* and *Capsicum* species are *Nicotiana benthamiana, Nicotiana tabacum* and *Capsicum annuum*. This method is illustrated in the experimental section of the application, in *Nicotiana benthamiana* and *Nicotiana tabacum* plants. In case resistance against some or all of TMV, ToMV and ToMMV, is also needed, the method can be simultaneously carried out in replacing the ToBRFV MP by the MP of these viruses. Preferably, the mutated Tm-2-2 gene or mutant of the Tm-2-2 gene is as defined in connection with the preceding aspects of the invention, namely with at least one of the C848R, N822C, N822F, N822M, N822Y, N822W, S825H, S825K and S825T substitutions, and with Y, F or W at the position 767, and potentially also with L at the position 655. By this method, further mutations of the Tm-2-2 gene can be easily and rapidly tested. As already stressed, detection of hypersensitive response in this assay is a surrogate for detection of resistance against said tobamoviruses in tomato comprising the mutated Tm-2-2 gene to be tested.

Similarly, in order to identify, detect or select mutants of the TM-2-2 protein conferring resistance against ToBRFV, the method is carried out by transiently or constitutively expressing a nucleotide sequence encoding the mutant of the TM-2-2 protein to be tested.

Sequences:
   SEQ ID No:1: nucleotide sequence of tm2.
   SEQ ID No:2: nucleotide sequence of Tm-2.
   SEQ ID No:3: nucleotide sequence of Tm-2-2.
   SEQ ID No:4: nucleotide sequence of Tm2-14-25.
   SEQ ID No:5: nucleotide sequence of Tm2-467.
   SEQ ID No:6: amino acid sequence of protein encoded by tm2.
   SEQ ID No:7: amino acid sequence of TM-2 encoded by Tm-2.
   SEQ ID No:8: amino acid sequence of TM-2-2 encoded by Tm-2-2.
   SEQ ID No:9: amino acid sequence of TM2-14-25 encoded by Tm2-14-25.
   SEQ ID No:10: amino acid sequence of TM2-467 encoded by Tm2-467.

SEQ ID No:11: amino acid sequence of LRR domain of
   TM-2-2
SEQ ID No:12: nucleotide sequence encoding the LRR
   domain of TM-2-2
SEQ ID No:13: amino acid sequence of Movement Pro-
   tein of TMV.
SEQ ID No:14: amino acid sequence of Movement Pro-
   tein of ToMV.
SEQ ID No:15: amino acid sequence of Movement Pro-
   tein of ToBRFV.
SEQ ID No:16: amino acid sequence of Movement Pro-
   tein of ToMMV.
SEQ ID No:17: amino acid sequence of TM2-4.
SEQ ID No:18: amino acid sequence of TM2-5.
SEQ ID No:19: amino acid sequence of TM2-825H.
SEQ ID No:20: amino acid sequence of TM2-825K.
SEQ ID No:21: amino acid sequence of TM2-825T.
SEQ ID No:22: amino acid sequence of TM2-822C.
SEQ ID No:23: amino acid sequence of TM2-822-F.
SEQ ID No:24: amino acid sequence of TM2-822-M.
SEQ ID No:25: amino acid sequence of TM2-822-Y.
SEQ ID No:26: amino acid sequence of TM2-822-W.
SEQ ID No:27: nucleotide sequence of TM2-4.
SEQ ID No:28: nucleotide sequence of TM2-5.
SEQ ID No:29: nucleotide sequence of TM2-825H.
SEQ ID No:30: nucleotide sequence of TM2-825K.
SEQ ID No:31: nucleotide sequence of TM2-825T.
SEQ ID No:32: nucleotide sequence of TM2-822C.
SEQ ID No:33: nucleotide sequence of TM2-822-F.
SEQ ID No:34: nucleotide sequence of TM2-822-M.
SEQ ID No:35: nucleotide sequence of TM2-822-Y.
SEQ ID No:36: nucleotide sequence of TM2-822-W.
SEQ ID No:37: nucleotide sequence of primer npt2F.
SEQ ID No:38: nucleotide sequence of primer npt2R.
SEQ ID No:39: nucleotide sequence of primer tm2-2-F2.
SEQ ID No:40: nucleotide sequence of primer thsp-R.
SEQ ID No:41: nucleotide sequence of binary plasmid
   pJL469.
SEQ ID No:42: nucleotide sequence of binary plasmid
   pJL470.
SEQ ID No:43: nucleotide sequence of binary plasmid
   pJL471.
SEQ ID No:44: nucleotide sequence of primer LM_T-
   BRFV-1-F.
SEQ ID No:45: nucleotide sequence of primer LM_T-
   BRFV-1-R.
SEQ ID No:44: nucleotide sequence of probe LM_T-
   BRFV-1-probe.

LEGEND OF THE FIGURES

FIG. 1: Transient expression in *N. benthamiana* of dif-
ferent TM-2-2 variants in presence or absence of movement
proteins of TMV or ToBRFV. Photo taken about 5 days post
infiltration.

Figure 2:
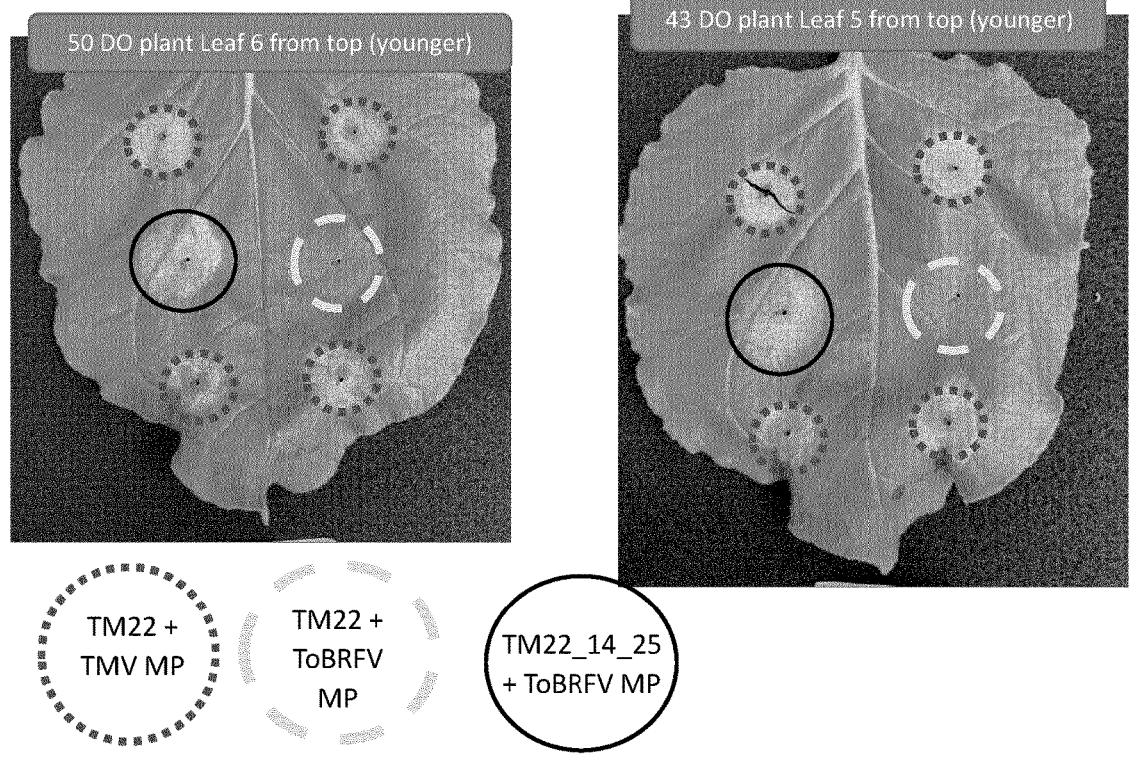

FIG. 2: Transient expression in *N. benthamiana* of dif-
ferent TM-2-2 variants in presence or absence of movement
proteins of TMV or ToBRFV. Leaves of 2 different ages of
*N. benthamiana* plants were infiltrated. About 50 day old
plant (Left) or 43 day old plant (Right) were infiltrated with
*Agrobacterium* cultures to transiently express different
TM-2-2 protein variants in the presence or absence of
movement proteins of TMV or ToBRFV. Photographs taken
approximately 5 days after infiltration.

26

FIG. 3: plasmids for transformation of tomato

Figure 3A:
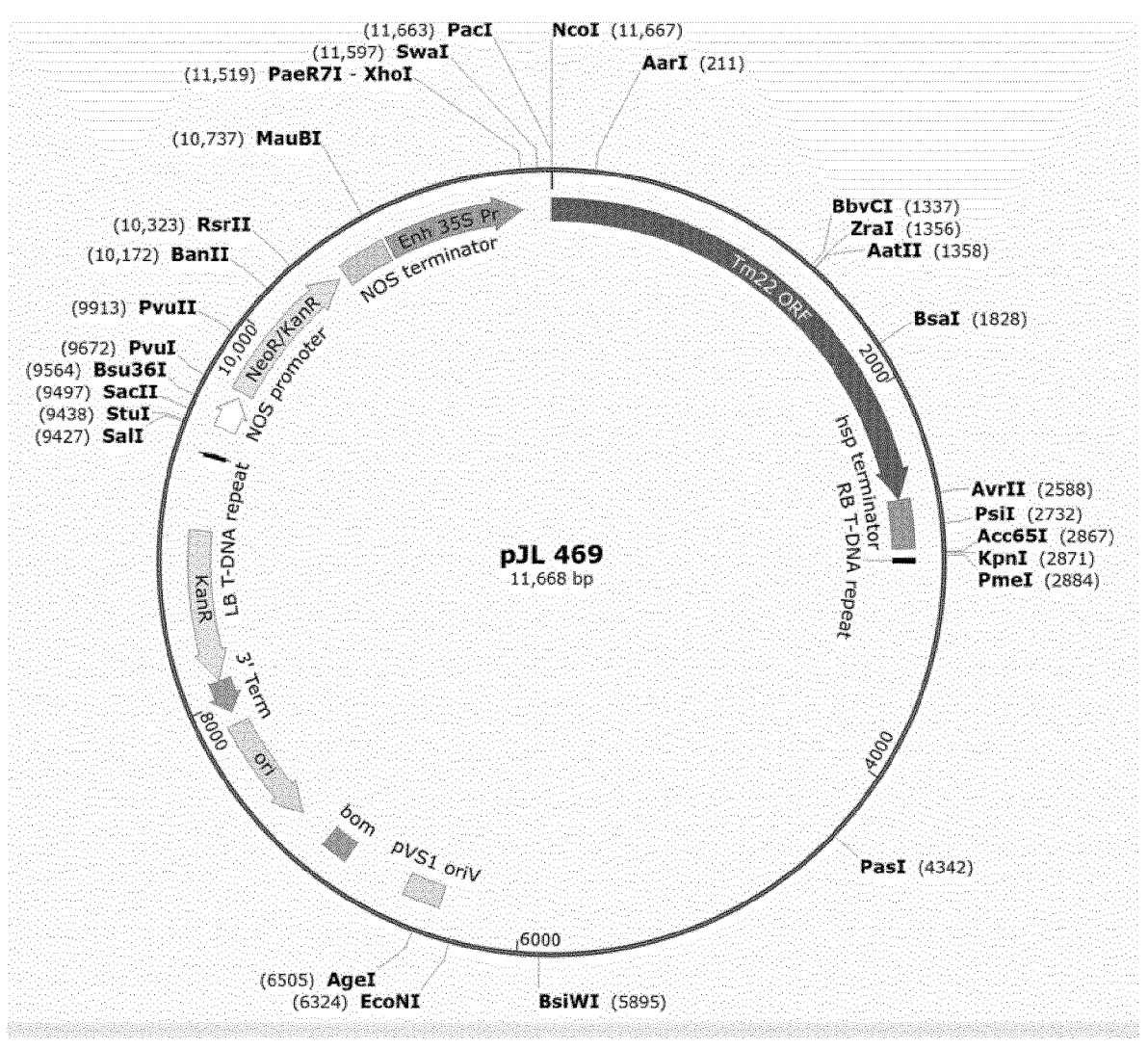

FIG. 3A: binary plasmids pJL469 (SEQ ID NO:41)

Figure 3B:
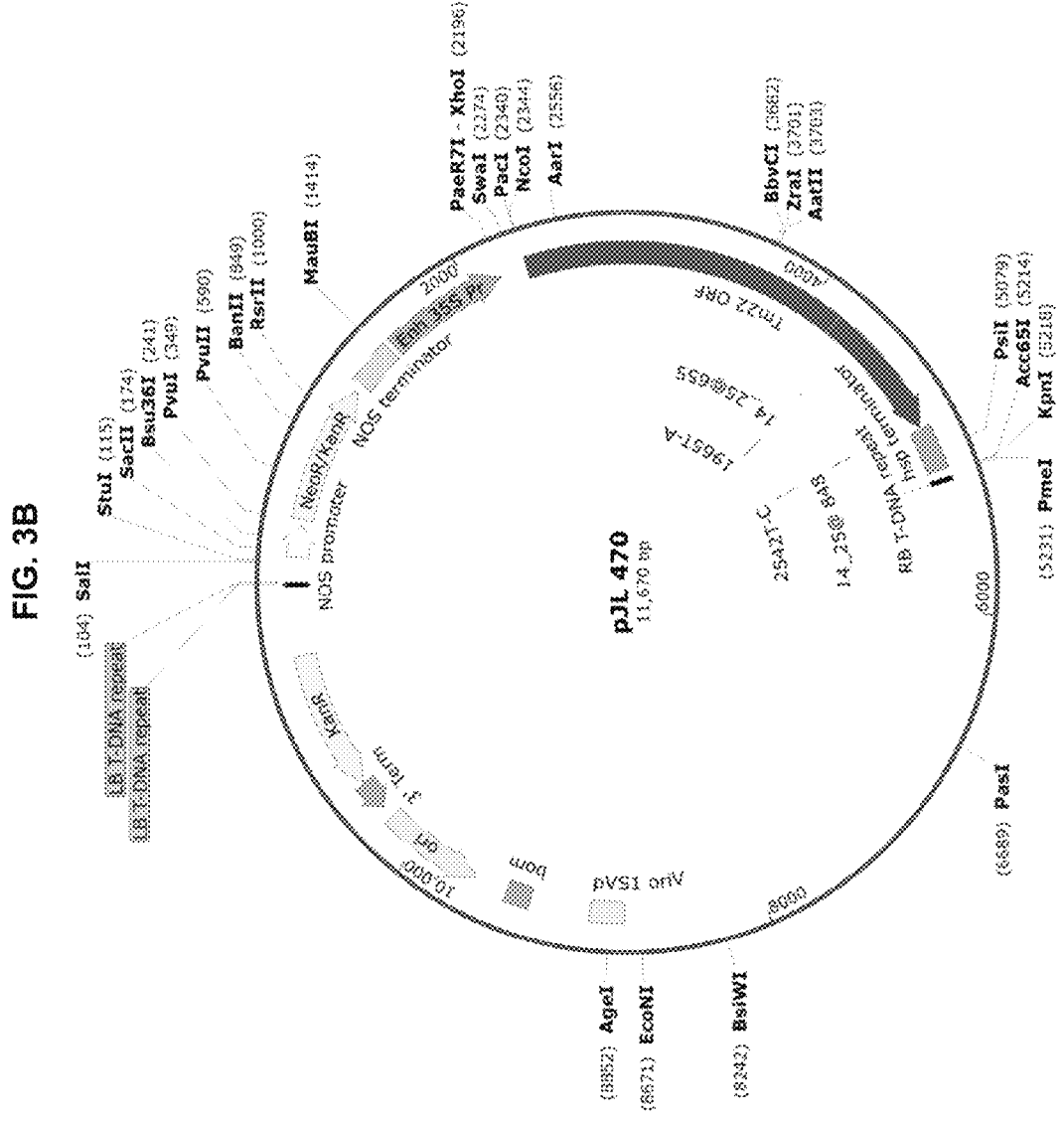
Figure 3C:
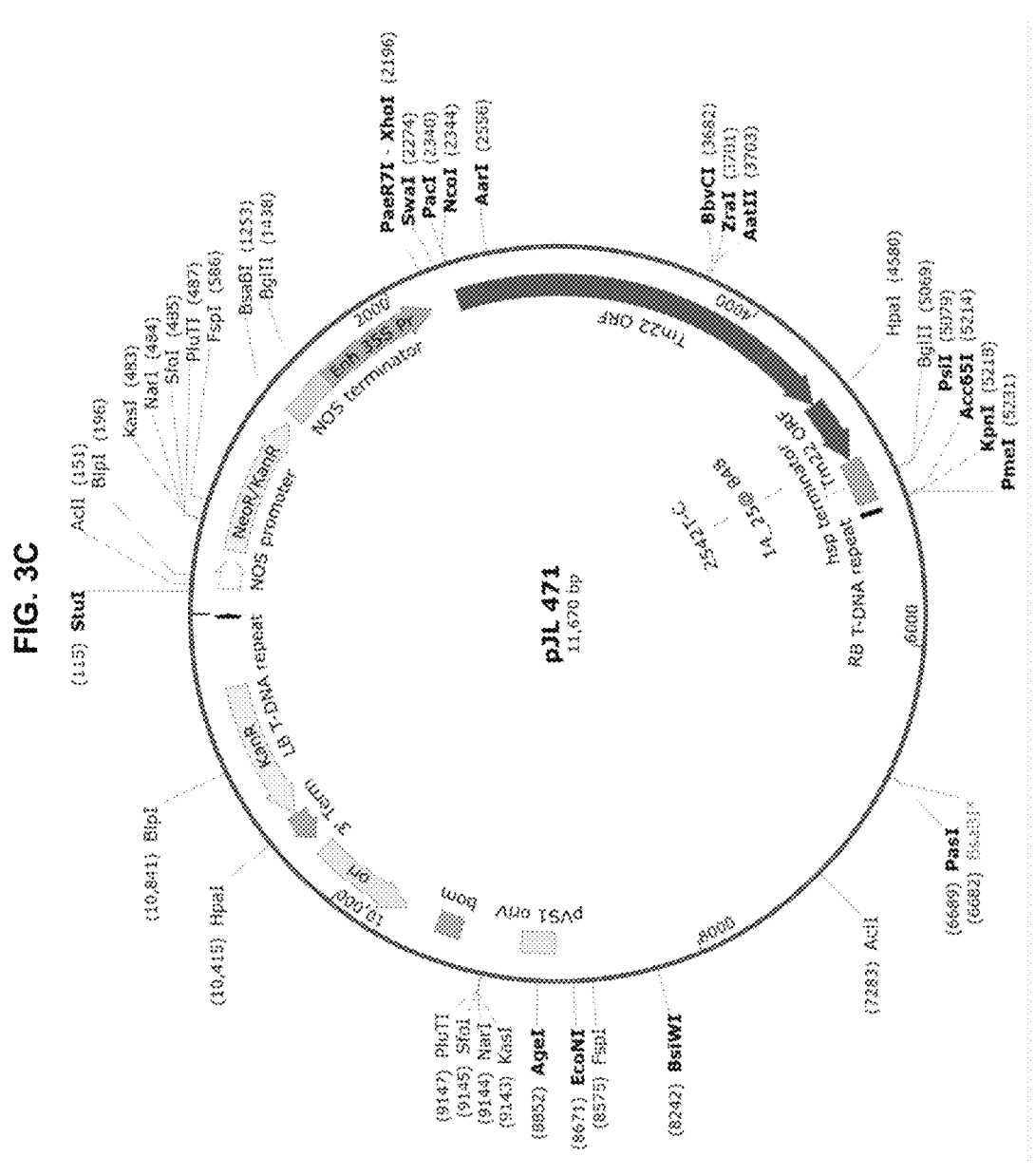

FIG. 3B: binary plasmids pJL470 (SEQ ID NO:42),

FIG. 3C: binary plasmids pJL471 (SEQ ID NO:43).

FIG. 4: Alignment of proteins of genes Tm2-2, Tm-2-14-
25 and Tm2-467.

FIG. 5: Transient expression in *N. benthamiana* and *N.
tabacum* of different TM-2-2 variants in presence or absence
of movement proteins of ToBRFV. TM22 848R variants
with different amino acids at AA 767 were transiently
expressed in presence (+MP) of absence of movement
protein of ToBRFV. The various amino acids at position 767
are labeled on the Figure using the standard single amino
acid code to identify variant. Photo taken 2 days after
agroinfiltration.

Figure 5A:
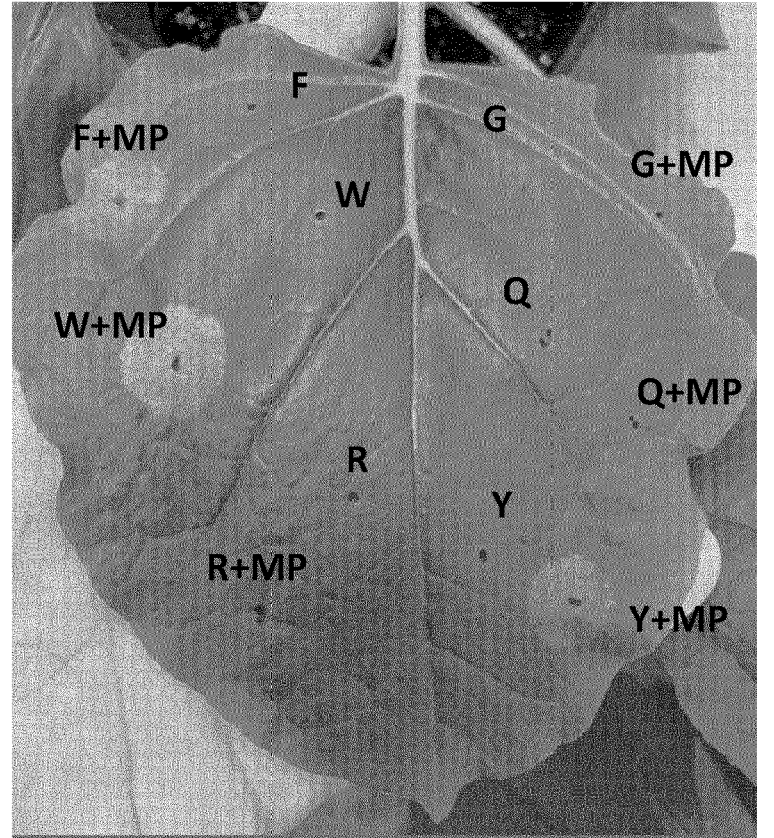

FIG. 5A: *N. benthamiana*

Figure 5B:
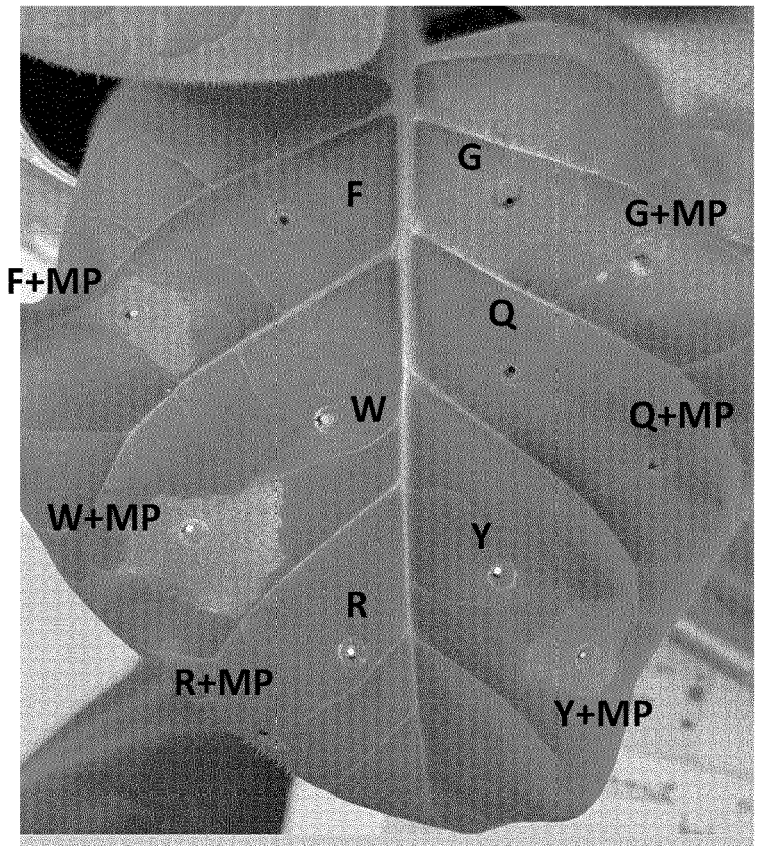

FIG. 5B: *N. tabacum*

EXAMPLES

The TM-2-2 protein (product of the Tm-2-2 gene) is a
nucleotide binding leucine rich repeat protein (NLR) and
confers resistance to TMV and ToMV by binding the move-
ment protein (MP) produced from either virus, and signaling
an effective immune response against the invading virus.
The result of binding between TM-2-2 and tobamovirus MP
can be observed as a hypersensitive response (tissue necro-
sis) in a transient expression assay in *N. benthamiana*.

The NLR proteins TM-2 and TM-2-2 differ by only 4
amino acids (Lanfermeijer et al. 2005). These differences are
associated with different spectrums of resistance. For
example the TM-2-2 variant can confer resistance to a
broader range of TMV and ToMV isolates than TM-2
(Lanfermeijer et al. 2005; Lanfermeirjer 2004). One amino
acid change in particular, amino acid 767 in the LRR
domain, was demonstrated to be responsible for the more
durable and broader host range of resistance in the TM-2-2
protein (Kobayashi et al. 2011). TM-2 and TM-2-2 proteins
however provide no resistance against ToBRFV.

The present inventors have thus hypothesized that muta-
tions in the TM-2 and TM-2-2 proteins could retain the
capacity to recognize ToMV and TMV MP while conferring
the capacity to also recognize ToBRFV MP.

Using the transient expression assay in *N. benthamiana* in
order to test the capacity to recognize tobamovirus MP, the
inventors have been able to test efficiently a high number of
variants. They have unexpectedly isolated variants of the
TM-2-2 protein which efficiently recognize the movement
protein (MP) of ToBRFV, triggering a hypersensitive
response when co-expressed along with the ToBRFV MP
(effector). Furthermore these variants also bind and respond
to the ToMV and TMV MP.

The DNA sequences of these variants have been obtained,
as well as sequences of further variants also recognizing
ToBRFV MP in addition to TMV and ToMV MP (examples
2, 3, 4 and 5).

By TILLING, plants comprising TM-2-2 mutants as
described can be obtained (example 6), as well as by
*Agrobacterium* transformation (example 7).

Example 1: Material and Methods 1.1. Sequences of the Tm-2 Gene Alleles and of the MP Proteins Referred to in this Section:

TABLE 1

List of some tm2 gene alleles.

| Gene Name | SEQ # | Protein | Phenotype induced and comments |
|---|---|---|---|
| tm2 | AF536199 SEQ ID No: 1 | SEQ ID No: 6 | TMV-U1 (S), ToMV-GeRo (S); ToBRFV (S); No HR with ToBRFV MP in *N. benthamiana* test |
| Tm-2 | AF536200 SEQ ID No: 2 Plasmid pJL398 | TM-2 SEQ ID No: 7 | TMV-U1 (R); ToMV-GeRo (S); ToBRFV (S); No HR with ToBRFV MP in *N. benthamiana* test |
| Tm-2² | AF536201 SEQ ID No: 3 Plasmid pJL366 | TM-2-2 SEQ ID No: 8 | TMV_U1 (R); ToMV-GeRo (R); ToBRFV (S); No HR with ToBRFV MP in *N. benthamiana* test |
| Tm-2¹⁴⁻²⁵ | SEQ ID No: 4 | SEQ ID No: 9 | HR with TMV, ToMV and ToBRFV MP in N. benthamiana test |
| Tm2⁻⁴⁶⁷ | SEQ ID No: 5 Plasmid pJL467 | SEQ ID No: 10 | HR with ToBRFV MP in *N. benthamiana* test |
| Tm2-4 | SEQ ID No: 27 Plasmid 517_6 | TM2-4 SEQ ID No: 17 | HR with ToBRFV MP in *N. benthamiana* test |
| Tm2-5 | SEQ ID No: 28 Plasmid pJL_517_7 | TM2-5 SEQ ID No: 18 | HR with ToBRFV MP in *N. benthamiana* test |
| Tm2-825H | SEQ ID No: 29 Plasmid 564_25 | TM2-825H SEQ ID No: 19 | HR with ToBRFV MP in *N. benthamiana* test |
| Tm2-825K | SEQ ID No: 30 Plasmid 565_10 | TM2-825K SEQ ID No: 20 | HR with ToBRFV MP in *N. benthamiana* test |
| Tm2-825T | SEQ ID No: 31 Plasmid 565_5 | TM2-825T SEQ ID No: 21 | HR with ToBRFV MP in *N. benthamiana* test |
| Tm2-822C | SEQ ID No: 32 Plasmid 607_5 | TM2-822C SEQ ID No: 22 | HR with ToBRFV MP in *N. benthamiana* test |
| Tm2-822F | SEQ ID No: 33 Plasmid 607_11 | TM2-822F SEQ ID No: 23 | HR with ToBRFV MP in *N. benthamiana* test |
| Tm2-822M | SEQ ID No: 34 Plasmid 608_18 | TM2-822M SEQ ID No: 24 | HR with ToBRFV MP in *N. benthamiana* test |
| Tm2-822Y | SEQ ID No: 35 Plasmid 607_12 | TM2-822Y SEQ ID No: 25 | HR with ToBRFV MP in *N. benthamiana* test |
| Tm2-822W | SEQ ID No: 36 Plasmid 606_1 | TM2-822W SEQ ID No: 26 | HR with ToBRFV MP in *N. benthamiana* test |

TMV-U1 = Tobacco Mosaic virus U1 strain
ToMV = Tomato Mosaic Virus GeRo Strain
ToBRFV = Tomato Brown Rugose Fruit virus
HR = hypersensitive response
R = resistant;
S = Susceptible

TABLE 2

Amino acid sequences of selected Tobamovirus MPs referred to in the examples.

| MP Source | AA seq | Plasmid name |
|---|---|---|
| TMV (AF546184.1 Flavum strain) | SEQ ID No: 13 | pJL 380 |
| ToMV (X02144.1 OM strain) | SEQ ID No: 14 | pJL 481 |
| ToBRFV (MS549394.1 Ca1A isolate) | SEQ ID No: 15 | pJL 379 |
| ToMMV (KX898033) | SEQ ID No: 16 | |

1.2. Mutagenesis:

To find TM-2-2 protein variants that trigger HR in the presence of ToBRFV MP (MP_Rugose in the following), two different approaches were deployed, namely random and site-directed mutagenesis, each designed to create variation in the LRR domain of TM-2-2.

Using the Takara Diversify PCR Random Mutagenesis Kit and PCR conditions that generated, on average, 4 changes per 1000 basepairs, the last around 750 nucleotides of the TM-2-2 gene were amplified by the PCR. The resulting PCR product was cloned into a Tm-2-2 gene expression plasmid, replacing the wt 3'~750 nts of the Tm-2-2 gene.

When it is desirable to introduce variation at specific locations in the Tm-2-2 gene site directed mutagenesis can be used. This is accomplished by the synthesis of portions of the Tm-2-2 gene with sequence variation at specific codons of interest. For example a synthetic oligonucleotide that can be used as a primer in the PCR can be designed for amplification of part of the Tm-2-2 gene, yet still designed to have one or more non-wild type nucleotides at specific locations. Following the PCR with such an oligonucleotide primer, the PCR product can be cloned into the appropriate location of the Tm-2-2 gene. In this manner it is possible to introduce nucleotide diversity at specific locations in a gene.

1.3. Transient Expression in *N. benthamiana* and Evaluation of Necrosis:

Transient expression in *N. benthamiana* and *N. tabacum* was carried out essentially as described in Ma et al, and in Kobayashi et al.

The products of the ligation reaction disclosed in example 1.2 were transformed into *Agrobacterium tumefaciens* (GV3101) and plated on LB plates with 50 ug/ml Kanamycin and 25 ug/ml Gentamycin to select for transformed *Agrobacterium.*

Approximately 860 different *Agrobacterium* colonies were selected from the transformation. Each colony grown in liquid culture and used to prepare an *Agrobacterium* suspension for agroinfiltration using standard procedures commonly used in plant biology (Tomita et al. 2019). Prior to infiltration into *N. benthamiana* leaves, cultures were mixed 1:1 with a suspension of *Agrobacterium* that had been transformed with the tobamovirus MP expression plasmid, for example the ToBRFV MP expression plasmid pJL 379.

Infiltrated plants were kept under either LED or fluorescent lights (18 hr light, 6 hr dark) at between 22 and 25 C. With an error rate of approximately 4 changes per kb it was estimated that approximately 2500 nucleotides changes were sampled (750 bp/clone×860 clones×4 errors/1000 bp=~2580 nt changes). In initial characterization of this library by sequencing the inventors estimated about 75% of the nucleotide changes would result in amino acid changes. If 75% of all the nucleotide mutations in the clones screened generated amino acid changes this would be approximately 1900 AA changes to the TM-2-2 protein were screened (0.75×2580=1935)

Approximately 6 days post infiltration infiltrated leaves were observed and the degree of necrosis (Hypersensitive Response, HR) in infiltrated zones were measured. Typically a scale from 0 to 4 was used to estimate the percentage of infiltrated zone showing necrosis. Details of the scale are as follows: 0=0% HR, 1=~25% HR, 2=~50% HR, 3=~75% HR, 4=100% HR. As a control, plants were also infiltrated with a 1:1 mix of *Agrobacterium* carrying the wt Tm-2-2 expression plasmid (pJL 366) and Rugose MP expression plasmid (pJL 379).

1.4. Protocol for Evaluation of Tobamovirus Resistance:

Several Tobamovirus isolates were used to perform Bioassay: ToBRFV isolates (inter alia Jordan_2015), ToMV, TMV or other tobamovirus.

Virus isolates are maintained by frozen storage of infectious juice coming from 14 days old infected tomato leaves grinded in water (inoculum proportion: 1 g leaves for 4 ml of water). Bioassay are carried out by sap-inoculation of tomato plantlets at two-leaf stage (i.e. 14-16 days after seeding) by rubbing the cotyledons with the index finger. At least 18 plantlets (separated in 2 or 3 repetitions) per tomato lines/accessions/genotypes were tested for tobamovirus resistance.

Phenotypic evaluation of plant is carried out by plant by plant scoring, without contacting the plants. The presence of local lesions on the inoculated organs is carried out between 7 and 10 DPI. If at least one plant per genotype exhibits local lesions on inoculated organs, the genotype is considered as potentially interesting. The tobamoviruses indeed, do not generally trigger necrosis on susceptible plants.

Systemic symptoms evaluations are carried out at 14, 21 and 28 DPI, the last evaluation being optional. Symptoms are visually assessed according the following scale: 9: No visible symptoms/7: small phenotypic difference but not clearly attributable to a disease symptom/5: mild symptoms (mosaic and/or light vein banding)/3: strong symptoms (strong mosaic and/or pronounced vein banding and/or small leaves deformation)/1: very strong symptoms (leaves deformation and/or mosaic and/or highly pronounced vein banding).

After 14 and/or 28 days of test, the plants without symptoms are tested by ELISA and/or quantitative PCR to evaluate the presence of tobamovirus in plant.

1.5. TILLING (Targeting Induced Local Lesions IN Genomes):

Tilling method is applied according to the usual protocols.

All DNA reactive chemical agents (mutagens) can be used for inducing lesions in the DNA and are not limited to EMS.

Physical DNA reactive agents (mutagens) can also be used, such as:

Ionizing radiations (X-Ray, gamma rays, alpha particles . . . ) heavy-ion beam irradiation Ultraviolet radiations Radioactive decay The physical or chemical mutagen is applied on M0 seed. The M1 plants, heterozygous for all mutations introduced by the mutagen are then selfed, giving rise to the seeds M2. A portion of these seeds are stored. A sampling is then conducted on at least 8 plants M2 for sequencing. The theoretical ratios are ½ of the plants will be heterozygous for a given mutation, ¼ will be homozygous for the mutation and ¼ will be homozygous for the absence of said mutation.

Alternatively, the screening for suitable mutations can also be conducted on M1 plants.

In the present case, insofar as the expected mutation in the Tm-2-2 gene is highly specific, it is important to test a very large population of mutants.

Example 2: Identification of a Tm2 Gene Allele that Recognizes ToBRFV MP

Background

Tomato Brown Rugose Fruit Virus (ToBRFV) is a serious pathogen of tomatoes and peppers. It is related to other tobamoviruses such as Tobacco Mosaic Virus (TMV) and Tomato Mosaic Virus (ToMV).

Genetic Resistance against TMV and ToMV maps to the Tm-2-2 gene. The TM-2-2 protein, product of the Tm-2 gene, is a resistance (R) protein of the nucleotide binding leucine rich repeat (NLR) class, also known as NBS-LRR class. There are two commonly use alleles of the Tm-2 gene in commercial tomato germplasm, namely Tm-2 and Tm-2-2. The different alleles confer resistance to different tobamoviruses (see Table 1). The Tm-2-2 allele in particular is widely deployed in commercial tomato germplasm because it confers durable genetic resistance to two tobamoviruses (TMV and ToMV) which are significant disease threats to tomato. However ToBRFV can infect plants that carry the Tm-2 or Tm-2-2 genes and there are no identified Tm-2 alleles that confer resistance to ToBRFV. Moreover, there are no known resistance genes that provide effective resistance simultaneously against ToBRFV, TMV and ToMV.

The TM-2-2 protein confers resistance to TMV and ToMV by binding the movement protein (MP) produced from either virus, and signaling an effective immune response against the invading virus by triggering a hypersensitive response (HR) in tomato, resulting in cell death. The result of binding between TM-2-2 and tobamovirus MP, namely the HR response, can be also observed by transiently expressing TM-2-2 protein and either TMV or ToMV MP in leaves of *N. benthamiana* plants, following the protocol disclosed in Kobayashi et al, 2011.

Transient expression of TM-2-2 and either TMV or ToMV MP in *N. benthamiana* leaves (by the Agroinfiltration technique) indeed results in a hypersensitive reaction and extensive tissue necrosis in just a few days. In contrast transient expression of TM-2-2 and ToBRFV MP (MP_Rugose) in *N. benthamiana* leaves usually results in no, or occasionally very mild, necrosis.

The HR response assay in *N. benthamiana* has previously been used to identify specific amino acids in the NLR protein which are critical for recognizing tobamovirus MPs (Kobayashi et al, 2011). There is a perfect correlation between the ability of a TM2 NLR protein to trigger a robust HR response in *N. benthamiana* leaves (in the presence of a tobamovirus MP) and virus resistance in tomato. Moreover, transient expression of proteins by Agroinfiltration is a well established technique in plant biology.

In view of this perfect correlation, this assay in *N. benthamiana* can be used as a surrogate for resistance in tomato.

However, whereas the prior uses of this assay or method aimed at identifying the specific amino acids in the NLR protein which are critical for recognizing tobamovirus MPs, by detecting the mutations giving rise to loss of function, the inventors have for the first time used this method to test mutants likely to provide a gain of function, i.e. the capacity to recognize further tobamovirus MPs.

The inventors have first generated a library of mutants of the Tm-2-2 gene using error prone PCR methods. This library of variants was then transiently expressed along with the ToBRFV MP in leaves of *N. benthamiana* plants (see Material and Methods in examples 1.2 and 1.3). After screening more than 860 transformed *agrobacterium* cultures, corresponding in average to 2.25 amino-acid modifications per variant, the inventors identified one colony (LP 14-25) showing a repeatable and noticeably increased HR response (as compared to the control) when co-expressed with ToBRFV MP. The inventors have moreover checked that this variant, triggering a robust HR response in the presence of ToBRFV MP, has not lost its ability to trigger also a robust HR response in the presence of TMV or ToMV MP (See FIGS. 1 and 2 and table 3).

TABLE 3

HR response of various TM2 protein variants to tobamovirus movement proteins.

| Protein | TMV_U1 MP SEQ ID No: 13 | ToBRFV MP SEQ ID No: 15 |
|---|---|---|
| tm2 | − | − |
| Tm-2-2 | + | − |
| Tm2-14-25 | + | + |
| Tm2-467 | + | + |

− = no HR response when proteins are co-expressed in *N. benthamiana* leaves.
+ = strong HR response when proteins are co-expressed in *N. benthamiana* leaves.

Detailed analysis of this variant revealed that it was different from the TM-2-2 protein at 2 amino acids (F655L and C848R). This new variant is called Tm2-14-25 (see Table 1).

Through additional analysis, using standard molecular techniques, including site-directed mutagenesis, the inventors mapped the ability to recognize ToBRFV MP to a single amino acid change (C848R). The inventors identify this new Tm-2 allele as Tm2-467 (see Table 1 and Table 4).

This experiment revealed that C848R change to TM-2-2 was both involved and sufficient for detection and response to MP-Rugose (ToBRFV MP).

TABLE 4 reports the HR response of different variants:

| Construct Name | AA changes to TM-2-2 | HR when expressed with MP Rugose |
|---|---|---|
| LP_14-25 | F655L, C848R | 4 |
| pJL 466 | F655L | <1 |

TABLE 4-continued reports the HR response of different variants:

| Construct Name | AA changes to TM-2-2 | HR when expressed with MP Rugose |
|---|---|---|
| pJL 467 | C848R | 4 |
| pJL 366 | None (wt TM-2-2) | <1 |

An alignment of the proteins TM2-2, TM2-14-25 and TM2-467 (protein products of the Tm-2-2, Tm2-14-25 and Tm2-467 genes, respectively) is presented in FIG. 4.

Since both TM2-14-25 and TM2-467 proteins recognize ToBRFV MP it is apparent that the amino acid change they share is responsible for the ability to robustly recognize ToBRFV MP (as compared to TM-2-2 protein). It is also observed that the protein can have additional mutations (such as the change unique to TM2-14-25) and still recognizes ToBRFV MP. Both TM2-14-25 and TM2-467 proteins still recognize TMV and ToMV MPs.

Either TM2_14-25 or TM2-467 protein sequences can confer improved resistance to ToBRFV in tomato, while simultaneously conferring resistance against TMV and ToMV.

Example 3: Additional Mutants

As detailed in the preceding example, the inventors have shown that a single amino acid change in the TM-2-2 protein is sufficient for triggering a robust HR response in the presence of ToBRFV MP, without loss of resistance against TMV and ToMV.

In order to better characterize this mutation, and additional mutations likely to improve the resistance, other amino acid variations were created, using a site-directed approach. Selected codons in the LRR domain were changed to encode for non-wild type amino acids. Functional screening of the protein variants was performed by agroinfiltration and transient expression in *N. benthamiana* in the presence of MP_rugose (as described above). In some cases, selected amino acid changes were screened in a TM-2-2 protein background that also had the 848R change discussed in example 2. Results of some of the screens are shown in Tables 5-11.

Position 848

TABLE 5

Tests for mutants at position 848

| Construct Name | AA at 848 | HR when expressed with MP Rugose |
|---|---|---|
| pJL 366 | C (wt) | <1 |
| pJL 468_A | A | <1 |
| pJL 468_D | D | <1 |
| pJL 468_E | E | <1 |
| pJL 468_H | H | <1 |
| pJL 468_K | K | ~1 |
| pJL 468_L | L | <1 |
| pJL 468_M | M | <1 |
| pJL 468_N | N | <1 |
| pJL 468_P | P | <1 |
| pJL 468_Q | Q | <1 |
| pJL 468_R | R | 4 |
| pJL 468_S | S | ~1 |
| pJL 468_T | T | ~1 |

Conclusion: None of the amino acid variations at position 848 creates a TM-2-2 variant that elicits a similar let alone a stronger hypersensitive response in the presence of MP_Rugose than C848R.

Position 857

The impact of AA variation at position 857 was also tested, this position being near position 848 and in the vicinity of amino acid 848 in the 3D structure of the TM-2-2 protein. The results are presented in table 6.

TABLE 6

| | Tests for mutants at position 857, with or without C848R variation. | | |
|---|---|---|---|
| Construct Name | AA 848 | AA 857 | HR to MP Rugose |
| pJL 366 | C (wt) | K (wt) | <1 |
| pLP 14-25 | R | K | 3 |
| pJL 480Q | R | Q | 3 |
| pJL 480E | R | E | <1 |
| pJL 480T | R | T | <1 |
| pJL 480R | R | R | <1 |
| pJL 480I | R | I | <1 |

Conclusion: several AA changes at position 857, with AA 848 as R, reduce the HR response to MP Rugose. Other AA changes near 848R can however preserve the response to MP Rugose.

Variations at position 857 are thus allowable but to a limited extent. Acceptable variations can be easily tested.

Position 767

The impact of AA variation at position 767 (only) was also tested (without variation at position 848). The amino acid at this position has been demonstrated by Kobayasi et al as being decisive for the differences between TM-2 and TM-2-2 resistances. The results are presented in table 7.

TABLE 7

| Construct Name | AA 767 | HR to MP Rugose |
|---|---|---|
| pJL 366 | Y (wt) | <1 |
| L11_10 | I | 0 |
| L11_11 | C | 0 |
| L11_15 | L | 0 |
| L11_16 | G | 0 |
| L11_19 | N | 0 |
| L11_20 | V | 0 |
| L11_1 | R | <1 |

Conclusion: Of 7 different AA variants at position 767 tested, none improved the ability to detect and respond to MP Rugose, in the absence of the C848R mutation.

Position 769

The impact of AA variation at position 767 (only) was also tested (without variation at position 848). The results are presented in table 8.

TABLE 8

| Construct Name | AA 769 | HR to MP Rugose |
|---|---|---|
| pJL 366 | S (wt) | <1 |
| L12_11 | G | <1 |
| L12_12 | R | <1 |
| L12_4 | F | <1 |
| L12_16 | E | <1 |
| L12_3 | V | <1 |
| L12_A | A | 0 |

Conclusion: Testing TM22 variants with 6 different (non wt) AA at position 769 did not reveal any variants that are better at binding and responding to MP Rugose, than the C848R variant.

Position 767 in the TM-2-2 848R Background

The impact of AA variation at position 767, in addition to the C848R variation, was also tested. The results are presented in table 9.

TABLE 9

| Construct Name | AA 767 | AA 769 | AA 848 | HR to MP Rugose |
|---|---|---|---|---|
| pJL 511_1 | S | A | R | 0 |
| pJL 511_2 | S | S (wt) | R | 0 |
| pJL 511_3 | Y | A | R | 4 |
| pJL 511_5 | Y (wt) | S (wt) | R | 4 |
| pJL 511_8 | D | A | R | 0 |
| pJL 511_12 | D | S (wt) | R | 0 |

Conclusion: Detection of MP Rugose is dependent upon the AAs at both positions 767 and 848.

The TM-2-2 variant with AA 848 as R and 767 as Y can detect and respond to MP_Rugose. However changing AA 767 to S or D dramatically reduces the ability of the protein to respond to MP_Rugose. This indicates that both residues 767 and 848 are important for binding MP_Rugose.

Further investigations by the inventors have demonstrated that position 767 can however be substituted by W and F without significantly reducing the ability of the protein to respond to MP_Rugose, and even enhancing this ability (see example 4).

Position 822

The impact of AA variation at position 822 was also tested, in the context of the C848R variation, this position 822 being proposed to be in the vicinity of amino acid 848 in the 3D structure of the TM-2-2 protein. The results are presented in table 10.

TABLE 10

| Construct Name | AA 822 | AA 848 | HR to MP Rugose |
|---|---|---|---|
| pJL 366 | N (wt) | C (wt) | <1 |
| pLP 14-25 | N | R | 4 |
| pJL 476_S | S | R | 4 |
| pJL 476_I | I | R | 0 |
| pJL 476_F | F | R | 2 |
| pJL 476_C | C | R | 2 |
| pJL 476_T | T | R | <1 |
| pJL 477_H | H | R | <1 |
| pJL 477_D | D | R | <1 |
| pJL 476_K | K | R | 0 |
| pJL 476_R | R | R | 0 |

Conclusions: Various amino acids at position 822, can reduce ability of TM22 848R to bind and respond to MP_rugose but other variations are allowable. Amino acids N and S are preferred at position 822 when 848 is R.

Further investigations by the inventors have demonstrated that position 822 can however be substituted by C, F, M, Y and W and provide the ability of the protein to respond to MP_Rugose even in the absence of the C848R mutation (see example 5).

In summary, in the process of identifying this mutant and further mutants comprising mutations allowing this gain of function, more than 1000 different variants were screened, using a combination of site directed and random mutagenesis. It is to be noted that some members of the libraries of mutants obtained by random mutagenesis were screened in HR assay without being sequenced. Table 11 below details the different variants which were screened for response to ToBRFV MP, with mention of the tested mutation if known.

TABLE 11

| LINE ID | Library type | AA position targeted | Strategy | Approx # screened before sequencing | specific AA tested |
|---|---|---|---|---|---|
| | | | Overview of variants of TM22 screened for response to MP_Rugose | | |
| 1 | site directed | 767 | Degenerate codons/synthetic oligos | | YICLGNVRSD |
| 2 | site directed | 769 | Degenerate codons/synthetic oligos | | SGRFEVA |
| 3 | random | 611-861 | error prone pcr | 860 | unknown |
| 4 | site directed | 822 | Degenerate codons/synthetic oligos | | NSIFCTYHDKR |
| 5 | site directed | 825 | Degenerate codons/synthetic oligos | | AITPCFYNRS |
| 6 | site directed | 827 | Degenerate codons/synthetic oligos | 96 | VGLQHFSM |
| 7 | site directed | 848 | Degenerate codons/synthetic oligos | | ADEHKLMNPQRST |
| 8 | site directed | 851 | Degenerate codons/synthetic oligos | | ACEFGHKLNPQRSTVW |
| 9 | site directed | 857 | Degenerate codons/synthetic oligos | | KQETRI |
| | | | TOTAL | 956 | 81 |

In Summary, 767Y and 848R in TM-2-2 appear as critical residues for binding and responding to MP_Rugose according to these tests (further modifications appear however to be permissive, see example 4). Other amino acid changes at other locations of the LRR domain can often lead to mild or sometimes significant, decreases in MP_Rugose binding, but not all; suitable amino acid changes can easily be tested by the assay described in the present invention.

The amino acids in the vicinity of amino acid 848 in the 3D structure of TM-2-2 are likely to be less prone to mutations without loss of binding to the ToBRFV.

In other experiments libraries of variants at a single codon were screened. An example of one such experiment, at codon 827, and its results are shown below:

Degenerate Codon Libraries at Codon 827 in TM-2-2 848R Gene Background

| Library Name | Degenerate codon | Possible AA (#) | # isolates screened | HR response to MP Rugose |
|---|---|---|---|---|
| Library 1 | HWK | K, N, M, I, Q, H, L, Y, F (9) | 41 | NONE better than TM22 848R |
| Library 2 | KVS | D, E, A, G, S, C, W, Y (7) | 41 | NONE better than TM22 848R |
| Library 3 | MSA | T, R, P, L | 14 | NONE better than TM22 848R |

Degenerate Codon Libraries Screened at Codon 827 in TM22 (848C) Gene Background

| Library | Codon | AA possible (#) | # isolates screened | HR to MP Rugose |
|---|---|---|---|---|
| Library 4 | HWK | K, N, M, I, Q, H, L, Y, F (9) | 41 | NONE better than TM22 848R |
| Library 5 | KVS | D, E, A, G, S, C, W, Y (7) | 41 | NONE better than TM22 848R |
| Library 6 | MSA | T, R, P, L | 14 | NONE better than TM22 848R |

The results obtained with libraries 1-6, similar to results obtained at other positions, demonstrate that the variation at position 848 is very important and that variations of other codons in the LRR region of TM-2-2 do not produce variants that have an improved recognition and response to MP_rugose. In any event, the mutation at position 848 appears necessary for the MP_rugose recognition.

Example 4: Further Modification at Position 767 and Validation in Different *Nicotiana* Species Further modifications at position 767 of the TM-2-2 protein variant comprising the C848R substitution have been tested in different *Nicotiana* species.

Specifically, plants (*N. benthamiana* and *N. tabacum*) were infiltrated with *Agrobacterium* cultures containing plasmids with T-DNAs for expression of a TM-2-2 protein variant alone, or co-expression of a TM-2-2 protein variant and MP_Rugose.

The results are presented on FIG. 5. Letter by spots on leaf denote the amino acid at position 767 in TM-2-2 848R variant background. TM-2-2 variants were expressed alone (Letter only) or co-expressed with Rugose MP (+MP).

Plants have been photographed ~48 hours post infiltration.

Results show that TM-2-2 767Y 848R (TM2-467); 767F 848R (TM2-4), and 767W 848R (TM2-5) all trigger an HR response in presence of MP_Rugose in either *N. benthamiana* (FIG. 5A) or *N. tabacum* cv *Xanthi* (FIG. 5B). The 767W and Y variants appear to be more 'responsive' to MP rugose than the 767F variant in this assay. In contrast TM-2-2 variants with R, Q or G amino acids at position 767 did not trigger HR in presence of MP_Rugose.

Example 5: Identification of Further Tm2 Gene Alleles that Recognize ToBRFV MP In view of the importance of the C848R mutation, further mutants have been tested wherein amino acids in the vicinity of C848, in the 3D-structure, are mutated. Namely the 20 different amino acids have been tested at position 822 and at position 825 of the TM-2-2 protein, in the absence of the C848R mutation.

Plants (*N. benthamiana*) were infiltrated with *Agrobacterium* cultures containing plasmids with T-DNAs for expression of a TM-2-2 protein variant alone, or co-expression of a TM-2-2 protein variant and MP_Rugose.

The variants giving rise to an intense hypersensitive response are reported in table 12, with the details of the alleles at positions 767, 822, 825 and 848. All other variants at positions 822 and 825, in combination with C848 (wt) and Y767 (wt), do not give rise to HR to MP Rugose.

In conclusion, in addition to the C848R mutation of the TM2-2 protein, the N822C, N822F, N822M, N822Y, N822W, S825H, S825K and S825T mutations of the TM2-2 protein are also sufficient for conferring resistance to ToBRFV, as can be deduced from the HR response to MP_Rugose.

Example 6: Providing Non-Transgenic Plants Carrying the New Variants of Tm2 Recognizing the ToBRFV MP by TILLING (Targeted Induced Local Lesions in Genomes) Strategy In Mutagenized Population:

A large variant tomato population is created using a physical or chemical mutagen agent, well known to the skilled person, that induced all kind of random mutations in genomic sequence by nucleotide substitution. The parental line used for the population is a line which preferably carries the Tm2$^2$ gene at homozygous level. This line is resistant to ToMV, TMV and susceptible to ToBRFV.

A massive screening of the population is done at M1 or M2 step (protocol detailed in example 1.5) to identify variations in the Tm2 gene (Solyc09 g018220) using well known screening methods, which are preferably molecular assay based or sequenced based.

Plants carrying variations in Tm2 gene are selfed for seed production. The following generation (M2 or M3) are genotyped for the targeted variation and heterozygous or homozygous plants (fixation of the variation) are used for phenotyping and for introgression in Elite line by MABC (marker-assisted backcrossing) or other classical breeding method. Several backcrosses are performed to remove other variations in the genetic background.

Plants carrying the variation are phenotyped for ToBRFV and other tobamovirus resistance using the protocol detailed in example 1.4.

Example 7: Provision of Transgenic Plants Carrying the New Variants of Tm2 Recognizing the ToBRFV MP Anabelle tomato line is used for *Agrobacterium* transformation with Tm2-2 variants as identified in the previous sections of the results.

Seeds are surface-sterilized for 20 min in 2% sodium hypochlorite containing 2 drops of Tween20 under agitation then washed 3 times with sterile distilled water.

Seeds are then cultivated in plastic jars with MS medium (M0222, Duchefa) pH 5.9 containing 20 g/l sucrose and 0.8% microagar and placed at 25° C. under light (3000-4000 lux, 16 h photoperiod).

TABLE 12 further variants at position 822 and 825 and results of the HR to MP Rugose test

| Name of the allele | Position 767 | Position 822 | Position 825 | Position 848 | HR to MP Rugose | Nb of AA changes wrt TM2-2 (SEQ ID No. 8) | Plasmid name |
|---|---|---|---|---|---|---|---|
| TM2-825H | Y (wt) | N (wt) | H | C (wt) | ++ | 1 | 564__25 |
| TM2-825K | Y (wt) | N (wt) | K | C (wt) | ++ | 1 | 565__10 |
| TM2-825T | Y (wt) | N (wt) | T | C (wt) | ++ | 1 | 565__5 |
| TM2__822C | Y (wt) | C | S (wt) | C (wt) | ++ | 1 | 607__5 |
| TM2__822F | Y (wt) | F | S (wt) | C (wt) | ++ | 1 | 607__11 |
| TM2__822M | Y (wt) | M | S (wt) | C (wt) | ++ | 1 | 608__18 |
| TM2__822Y | Y (wt) | Y | S (wt) | C (wt) | ++ | 1 | 607__12 |
| TM2__822W | Y (wt) | W | S (wt) | C (wt) | ++ | 1 | 606__1 |

39

Explants are excised from cotyledons of 10 days seedlings. Using a sterile forceps and razorblade, both ends of each cotyledon are removed and cotyledons are then cut into 2 pieces. Explants are placed onto 10 cm diameter Petri dishes containing CC medium (MS medium pH5.9 containing 20 g/l sucrose and 0.8% microagar supplemented with 2 mg/l NAA, 1 mg/l BAP, 160 mg/l glucuronic acid and 40 mg/l acetosyringone) and placed at 25° C. under light (3000-4000 lux, 16 h photoperiod) for one day.

*Agrobacterium tumefaciens* strains A1224, A1225 and A1250 were obtained by electroporation of the binary plasmids pJL470, pJL471 and pJL469, respectively (see FIGS. 3A, 3B and 3C), into *Agrobacterium tumefaciens* strain GV3101.

A single colony of *Agrobacterium tumefaciens* containing T-DNA plasmid was cultivated in 15 ml LB broth containing rifampicin 10 μg/ml and kanamycin 50 μg/ml in a shaker (200 rpm) at 28° C. for 20 h. Bacteria are pelleted by centrifugation of the overnight suspension for 20 mn at 1000 g and resuspended in sterile CC liquid medium (MS medium pH5.9 containing 20 g/l sucrose supplemented with 2 mg/l NAA, 1 mg/l BAP, 160 mg/l glucuronic acid and 40 mg/l acetosyringone) to an OD600 nm of 0.1

In a sterile beaker, cotyledonary explants are soaked in the *Agrobacterium* suspension for 15 min under slow agitation (100 rpm). With sterile forceps, explants are blotted on a sterile filter paper then transferred to solid CC medium (MS medium pH5.9 containing 20 g/l sucrose and 0.8% microagar supplemented with 2 mg/l NAA, 1 mg/l BAP, 160 mg/l glucuronic acid and 40 mg/l acetosyringone). Plates are placed at 25° C. under light (3000-4000 lux, 16 h photoperiod) for 48 hr Explants are rinsed two times with 100 ml of liquid MS medium pH 5.9 containing 20 g/l sucrose and supplemented of 100 mg/l amoxicillin 20 mg/l clavulanic acid then blotted onto a sterile paper then transferred to solid selection medium (MS medium containing 20 g/l sucrose and 0.8% microagar supplemented with 1 mg/l zeatin, 100 mg/l amoxicillin 20 mg/l clavulanic acid and 100 mg/l kanamycin) (10 explants/Petri dish). Petri dishes are placed at 25° C. under light (3000-4000 lux, 16 h photoperiod). and medium is refreshed every 2 weeks until shoot regeneration.

Shoots and plantlets are isolated and placed in plastic jars containing rooting medium (MS medium pH5.9 containing 20 g/l sucrose and 0.8% microagar supplemented with 0.5 mg/l IAA, 100 mg/l amoxicillin 20 mg/l clavulanic acid and 100 mg/l kanamycin). Jars are placed at 25° C. under light (3000-4000 lux, 16 h photoperiod).

Well rooted plantlets are transferred to soil. Agar is carefully removed by rinsing roots with water and plants are put in trays with soil and transferred to greenhouse.

Two weeks after acclimatization, plants are sampled and a piece of young leaf is analyzed by flow cytometry to select diploid plants. Genomic DNA is extracted from a young leaf disk and a PCR amplification of nptII gene is performed, using the primers:

```
Forward primer: npt2F
                    (SEQ ID NO: 37)
CCTGCCGAGAAAGTATCC
and
```

40

```
-continued
Reverse primer: npt2R
                    (SEQ ID NO: 38)
GCCAACGCTATGTCCTGA
``` to screen the transformants.

Transformants could be also characterized by PCR amplification with the following primers:

```
Forward primer: tm2-2-F2
                    (SEQ ID NO: 39)
TTCCTCCAAATCTCATCAAGC,
and Reverse primer: thsp-R
                    (SEQ ID NO: 40)
CAACAAGCCAAGAgAAAACACA.
```

The plants obtained by this protocol have been tested in order to confirm the resistance to ToBRFV, as well as resistance to TMV, ToMV and ToMMV.

Molecular quantification of ToBRFV sequence in infected plants has also been carried out by quantitative PCR (qPCR) with TaqMan probes, to also confirm the reduction of virus replication.

The protocol for the molecular quantification of ToBRFV by qPCR is as follows:

The young wrapper leaf at head grown are sampled (3 to 4 leaves per plant). The leaves are ground in liquid nitrogen and an aliquot of 100 mg is kept for RNA extraction. For each sample, 100 mg of grounded leaves are used for RNA extraction RNA extraction is performed using the «Maxwell® 16 LEV Plant RNA Kit» from Promega® and the Maxwell® extraction robot (Promega®). Extracted RNA are stored at −20° C.

qPCR for virus quantification is performed using the TaqMan universal Master Mix (ThermoFisher Scientific®) with Kit Gotaq Probe OneStep RTqPCR system A6120 Promega, following the manufacturer instructions.

Primers and probes used are disclosed in the table below:

| primer | Sequence | SEQ ID NO |
|---|---|---|
| LM_TBRFV-1-F | AGATTTCCCTG GCTTTTGGA | SEQ ID NO: 44 |
| LM_TBRFV-1-R | CTCTTTCTGAT ATCAAGCACT | SEQ ID NO: 45 |
| LM_TBRFV-1-probe | CAAGGAGAGAC TGCTAAATCGG | SEQ ID NO: 46 |

The amplified fragment is 187 bp.

Mix:

Kit TaqMan universal Master Mix, Applied Biosystem ThermoFisher Scientific.

| Product | Initial concentration | Final concentration | μL/well |
|---|---|---|---|
| Water (nuclease free) | | Qsp 20 μL | 7.1 |
| Primer Reverse LM_TBRFV-1-R | 10 μM | 0.5 μM (200 nM-1 μM) | 1 |
| Primer Forward LM_TBRFV-1-F | 10 μM | 0.5 μM (200 nM-1 μM) | 1 |
| Probe LM_TBRFV-1-probe | 5 μM | 0.25 μM (100-300 nM) | 0.5 |
| Gotaq Probe qPCR master mix | 2X | 1X | 10 |
| GoScript RT Mix for 1 step RT-qPCR | 50X | 1X | 0.4 |

The total volume of the mix is 20 μL; 2 μL of RNA are added; such that the final volume is 22 μL.

Thermocycler:

Reverse transcription: 15 minutes at 45° C.;

Inactivation of Reverse transcription and Activation: 2 minutes at 95° C.;

40 cycles comprising:

Denaturation: 15 seconds at 95° C.,

Annealing primers: 15 seconds at 54° C.; and

Annealing probes: 30 seconds at 48° C.

For each sample, 3 replicates are performed. Standard dilution curves are used for the relative quantification.

A melting curve is performed at the end of the protocol in the StepOne® to ensure the specificity of the detection/quantification The Ct of each sample is reported on the standard curve to calculate the relative quantity of virus in each sample.

Results

Anabelle tomato line, which is susceptible to ToMV, TMV, ToBRFV and ToMMV is used for *Agrobacterium* transformation with Tm2-2 variants as identified in the previous sections of the results. Infection by ToBRFV was carried out as disclosed on point 1.4, on transformants (presence of the T-DNA is checked as disclosed above) and on different controls (untransformed Anabelle). The phenotype of the plants is then scored at 14 DPI and 21 DPI. Presence of viral DNA is quantified by qPCR at 28 DPI, giving rise to a Ct value. The Ct or threshold cycle value is the cycle number at which the fluorescence generated within a reaction crosses the fluorescence threshold, corresponding to a fluorescent signal significantly above the background fluorescence. At the threshold cycle (Ct), a detectable amount of the amplified product has been generated during the early exponential phase of the reaction. The threshold cycle is inversely proportional to the original relative expression level of the gene of interest, i.e. the higher the Ct value, the higher the resistance level (it means the virus multiplication in plant is lower). The value of the susceptible plants transformed by a T-DNA providing an unmutated sequence of Tm2-2 can be used as control. A difference of Ct of 3.32 means a difference of 10 fold regarding virus quantity in the sample.

The test is reproduced twice (test 1 and test 2).

The results are detailed in the following table 13.

In this table, REP means the repetition number, "Plt nb" means the number of the plant. When "present" is indicated in the column "T-DNA genotype", this means that the presence of the T-DNA has been checked by PCR, as disclosed above.

The results reported in this table clearly show that the resistance observed in the surrogate assay with transient expression in *N. benthamiana* is indeed representative of the resistance in tomato plants comprising the resistance gene.

These results moreover demonstrate that the mutant TM-2-2 gene, with at least the C848R mutation provides resistance against ToBRFV infection, and that the presence of the F655L mutation may improve the resistance.

The results regarding the resistance evaluated by visual symptoms (AUDPC Area under the disease progress curve at 0, 14 and 21 DPI) and the resistance evaluated by qPCR Ct (corresponding to viral presence) can be summarized in the following table depending on the genotype. The visual symptoms are evaluated with respect to a susceptible control, wherein "+" means less symptoms than the control, and "–" means no improvement. The Ct evaluated by qPCR is also evaluated with respect to a susceptible control, wherein "+" means less viral sequences detected and "–" means no improvement.

| genotype | description | Visual symptoms | qPCR Ct |
|---|---|---|---|
| TM-2-2 | Negative control (transformed) | Control | control |
| TM-2-2 with mutation C848R | Single mutation | + | + |
| TM-2-2 with mutations C848R and F665L | Double mutation | + | ++ |
| Anabelle | Susceptible control (untransformed) | – | – |
| Resistance source | Resistant control (untransformed | + | Not tested |

The inventors have then checked the resistance to other tobamoviruses, especially ToMV race 0, TMV and ToMMV of the plants transformed with T-DNA comprising the Tm2-2 variant with the double mutation (C848R and F655L). The results are reported in table 14 and clearly show that the plants comprising the T-DNA (i.e. marked as "present" in the last column) are resistant to all these tobamoviruses, in addition to ToBRFV as shown in table 13 (same mutant code).

These results entirely confirm the results presented in the preceding examples, namely that mutants of the TM-2-2 gene may provide resistance against ToBRFV infection to tomato plants, whilst simultaneously providing resistance against ToMV, TMV and ToMMV.

TABLE 13 results of ToBRFV infection of initially susceptible plants, transformed with different T-DNA, or untransformed.

| Test nb | DESCRIPTION | Mutant plant code | REP | Plt Nb | T-DNA GENOTYPE | SCORING 14 DPI | SCORING 21 DPI | ct 28 DPI |
|---|---|---|---|---|---|---|---|---|
| 1 | Susceptible variety transformed with Tm2-14-25 | 52T-SL-ANA-A1224-1099-3745 | 1 | 9 | PRESENT | 9 | 7 | 24.19 |
| 1 | Susceptible variety transformed with Tm2-14-25 | 52T-SL-ANA-A1224-1099-3745 | 3 | 7 | PRESENT | 7 | 7 | 21.94 |
| 1 | Susceptible variety transformed with Tm2-467 | 7T-SL-ANA-A1225-990-3331 | 1 | 7 | PRESENT | 9 | 7 | 14.54 |
| 1 | Susceptible variety transformed with Tm2-467 | 7T-SL-ANA-A1225-990-3331 | 2 | 5 | PRESENT | 9 | 7 | 14.09 |
| 1 | Susceptible variety transformed with Tm2-467 | 7T-SL-ANA-A1225-983-3421 | 3 | 9 | PRESENT | 7 | 7 | 7.58 |
| 1 | Susceptible variety without Tm2$^2$ | na | 1 | 1 | | 5 | 1 | |
| 1 | Susceptible variety without Tm2$^2$ | na | 1 | 2 | | 5 | 1 | |
| 1 | Susceptible variety without Tm2$^2$ | na | 1 | 3 | | 5 | 1 | |
| 1 | Susceptible variety without Tm2$^2$ | na | 1 | 4 | | 3 | 1 | |
| 1 | Susceptible variety without Tm2$^2$ | na | 1 | 5 | | 3 | 1 | |
| 1 | Susceptible variety without Tm2$^2$ | na | 1 | 6 | | 5 | 1 | |
| 1 | Susceptible variety without Tm2$^2$ | na | 1 | 7 | | 5 | 3 | |
| 1 | Susceptible variety without Tm2$^2$ | na | 1 | 8 | | 5 | 1 | |
| 1 | Susceptible variety with Tm2$^2$ (without mutation) | 54T-SL-ANA-A1250-1074-3521 | 1 | 1 | PRESENT | 5 | 1 | |
| 1 | Susceptible variety with Tm2$^2$ (without mutation) | 54T-SL-ANA-A1250-1074-3521 | 1 | 4 | PRESENT | 5 | 3 | |
| 1 | Susceptible variety with Tm2$^2$ (without mutation) | 54T-SL-ANA-A1250-1074-3521 | 1 | 6 | PRESENT | 5 | 1 | 10.73 |
| 1 | Susceptible variety with Tm2$^2$ (without mutation) | 54T-SL-ANA-A1250-1074-3521 | 1 | 8 | PRESENT | 7 | 3 | |
| 1 | Susceptible variety with Tm2$^2$ (without mutation) | 54T-SL-ANA-A1250-1074-3521 | 1 | 9 | PRESENT | 5 | 3 | |
| 1 | Susceptible variety with Tm2$^2$ (without mutation) | 54T-SL-ANA-A1250-1074-3521 | 2 | 1 | PRESENT | 5 | 5 | |
| 1 | Susceptible variety with Tm2$^2$ (without mutation) | 54T-SL-ANA-A1250-1074-3521 | 2 | 2 | PRESENT | 7 | 1 | |
| 1 | Susceptible variety with Tm2$^2$ (without mutation) | 54T-SL-ANA-A1250-1074-3521 | 2 | 4 | PRESENT | 9 | 3 | |
| 1 | Susceptible variety with Tm2$^2$ (without mutation) | 54T-SL-ANA-A1250-1074-3521 | 2 | 6 | PRESENT | 5 | 3 | |
| 1 | Susceptible variety with Tm2$^2$ (without mutation) | 54T-SL-ANA-A1250-1074-3521 | 2 | 7 | PRESENT | 7 | 1 | 10.83 |
| 1 | Susceptible variety with Tm2$^2$ (without mutation) | 54T-SL-ANA-A1250-1074-3521 | 2 | 9 | PRESENT | 5 | 1 | |
| 1 | Susceptible variety with Tm2$^2$ (without mutation) | 54T-SL-ANA-A1250-1074-3521 | 3 | 3 | PRESENT | 5 | 3 | |
| 1 | Susceptible variety with Tm2$^2$ (without mutation) | 54T-SL-ANA-A1250-1074-3521 | 3 | 5 | PRESENT | 5 | 5 | 11.05 |
| 1 | Susceptible variety with Tm2$^2$ (without mutation) | 54T-SL-ANA-A1250-1074-3521 | 3 | 6 | PRESENT | 7 | 3 | |
| 1 | Susceptible variety with Tm2$^2$ (without mutation) | 54T-SL-ANA-A1250-1074-3521 | 3 | 7 | PRESENT | 5 | 5 | 7.06 |
| 1 | Susceptible variety with Tm2$^2$ (without mutation) | 54T-SL-ANA-A1250-1074-3521 | 3 | 8 | PRESENT | 5 | 3 | |
| 2 | Susceptible variety without Tm2$^2$ | | 1 | P2 | | 3 | 3 | |
| 2 | Susceptible variety without Tm2$^2$ | | 1 | P3 | | 3 | 3 | |
| 2 | Susceptible variety without Tm2$^2$ | | 1 | P5 | | 3 | 3 | |
| 2 | Susceptible variety without Tm2$^2$ | | 1 | P6 | | 3 | 3 | |
| 2 | Susceptible variety without Tm2$^2$ | | 1 | P7 | | 3 | 3 | |
| 2 | Susceptible variety without Tm2$^2$ | | 1 | P8 | | 3 | 3 | |
| 2 | Susceptible variety transformed with Tm2-14-25 | 52T-SL-ANA-A1224-1099-3745 | 2 | P14 | PRESENT | 9 | 7 | 21.16 |
| 2 | Susceptible variety transformed with Tm2-14-25 | 52T-SL-ANA-A1224-1099-3745 | 2 | P15 | PRESENT | 7 | 7 | 26.83 |
| 2 | Susceptible variety transformed with Tm2-14-25 | 52T-SL-ANA-A1224-1099-3582 | 2 | P3 | PRESENT | 9 | 7 | 25.74 |
| 2 | Susceptible variety transformed with Tm2-14-25 | 52T-SL-ANA-A1224-1099-3582 | 2 | P9 | PRESENT | 9 | 7 | 27.57 |
| 2 | Susceptible variety transformed with Tm2-14-25 | | 1 | P2 | PRESENT | 5 | 7 | 22.35 |

TABLE 14 resistance of the transformants, transformed with Tm2-14-25 (double mutants) to ToMV, TMV and ToMMV. R stands for "resistant" and S for "susceptible".

| Mutant plant code | Plant Nb | Strain | Score | T-DNA |
|---|---|---|---|---|
| 52T-SL-ANA-A1224-1099-3745 | 2 | ToMV race0 | S | |
| 52T-SL-ANA-A1224-1099-3745 | 3 | ToMV race0 | S | |
| 52T-SL-ANA-A1224-1099-3745 | 4 | ToMV race0 | S | |
| 52T-SL-ANA-A1224-1099-3745 | 5 | ToMV race0 | S | |
| 52T-SL-ANA-A1224-1099-3745 | 7 | ToMV race0 | S | |
| 52T-SL-ANA-A1224-1099-3745 | 9 | ToMV race0 | S | |
| 52T-SL-ANA-A1224-1099-3745 | 10 | ToMV race0 | S | |
| 52T-SL-ANA-A1224-1099-3745 | 12 | ToMV race0 | S | |
| 52T-SL-ANA-A1224-1099-3745 | 14 | ToMV race0 | R | Present |
| 52T-SL-ANA-A1224-1099-3745 | 15 | ToMV race0 | S | |
| 52T-SL-ANA-A1224-1099-3745 | 17 | ToMV race0 | R | Present |
| 52T-SL-ANA-A1224-1099-3745 | 19 | ToMV race0 | S | |
| 52T-SL-ANA-A1224-1099-3745 | 20 | ToMV race0 | S | |
| 52T-SL-ANA-A1224-1099-3745 | 25 | ToMV race0 | R | Present |
| 52T-SL-ANA-A1224-1099-3745 | 28 | ToMV race0 | S | |
| 52T-SL-ANA-A1224-1099-3745 | 29 | ToMV race0 | S | |
| 52T-SL-ANA-A1224-1099-3745 | 30 | ToMV race0 | R | Present |
| 52T-SL-ANA-A1224-1099-3745 | 31 | ToMV race0 | S | |
| 52T-SL-ANA-A1224-1099-3745 | 32 | ToMV race0 | S | |
| 52T-SL-ANA-A1224-1099-3745 | 33 | ToMV race0 | S | |
| 52T-SL-ANA-A1224-1099-3745 | 34 | ToMV race0 | S | |
| 52T-SL-ANA-A1224-1099-3745 | 36 | ToMV race0 | S | |
| 52T-SL-ANA-A1224-1099-3745 | 39 | ToMV race0 | R | Present |
| 52T-SL-ANA-A1224-1099-3745 | 41 | ToMV race0 | S | |

TABLE 14-continued resistance of the transformants, transformed with Tm2-14-25 (double mutants) to ToMV, TMV and ToMMV. R stands for "resistant" and S for "susceptible".

| Mutant plant code | Plant Nb | Strain | Score | T-DNA |
|---|---|---|---|---|
| 52T-SL-ANA-A1224-1099-3745 | 42 | ToMV race0 | S | |
| 52T-SL-ANA-A1224-1099-3745 | 44 | ToMV race0 | S | |
| 52T-SL-ANA-A1224-1099-3745 | 47 | ToMV race0 | S | |
| 52T-SL-ANA-A1224-1099-3745 | 49 | ToMV race0 | S | |
| 52T-SL-ANA-A1224-1099-3745 | 51 | ToMV race0 | S | |
| 52T-SL-ANA-A1224-1099-3745 | 53 | ToMV race0 | S | |
| 52T-SL-ANA-A1224-1099-3745 | 54 | ToMV race0 | S | |
| 52T-SL-ANA-A1224-1099-3745 | 3 | TMV | S | |
| 52T-SL-ANA-A1224-1099-3745 | 5 | TMV | S | |
| 52T-SL-ANA-A1224-1099-3745 | 6 | TMV | S | |
| 52T-SL-ANA-A1224-1099-3745 | 8 | TMV | S | |
| 52T-SL-ANA-A1224-1099-3745 | 9 | TMV | S | |
| 52T-SL-ANA-A1224-1099-3745 | 14 | TMV | R | Present |
| 52T-SL-ANA-A1224-1099-3745 | 15 | TMV | S | |
| 52T-SL-ANA-A1224-1099-3745 | 16 | TMV | R | Present |
| 52T-SL-ANA-A1224-1099-3745 | 18 | TMV | S | |
| 52T-SL-ANA-A1224-1099-3745 | 19 | TMV | S | |
| 52T-SL-ANA-A1224-1099-3745 | 20 | TMV | S | |
| 52T-SL-ANA-A1224-1099-3745 | 21 | TMV | S | |
| 52T-SL-ANA-A1224-1099-3745 | 22 | TMV | S | |
| 52T-SL-ANA-A1224-1099-3745 | 23 | TMV | S | |
| 52T-SL-ANA-A1224-1099-3745 | 24 | TMV | R | Present |
| 52T-SL-ANA-A1224-1099-3745 | 25 | TMV | S | |
| 52T-SL-ANA-A1224-1099-3745 | 28 | TMV | S | |
| 52T-SL-ANA-A1224-1099-3745 | 32 | TMV | S | |
| 52T-SL-ANA-A1224-1099-3745 | 34 | TMV | R | Present |
| 52T-SL-ANA-A1224-1099-3745 | 36 | TMV | S | |
| 52T-SL-ANA-A1224-1099-3745 | 38 | TMV | S | |
| 52T-SL-ANA-A1224-1099-3745 | 39 | TMV | S | |
| 52T-SL-ANA-A1224-1099-3745 | 40 | TMV | R | Present |
| 52T-SL-ANA-A1224-1099-3745 | 42 | TMV | R | Present |
| 52T-SL-ANA-A1224-1099-3745 | 46 | TMV | R | Present |
| 52T-SL-ANA-A1224-1099-3745 | 47 | TMV | S | |
| 52T-SL-ANA-A1224-1099-3745 | 51 | TMV | S | |
| 52T-SL-ANA-A1224-1099-3745 | 52 | TMV | R | Present |
| 52T-SL-ANA-A1224-1099-3745 | 53 | TMV | S | |
| 52T-SL-ANA-A1224-1099-3745 | 54 | TMV | R | Present |
| 52T-SL-ANA-A1224-1099-3745 | 2 | ToMMV | R | Present |
| 52T-SL-ANA-A1224-1099-3745 | 3 | ToMMV | R | Present |
| 52T-SL-ANA-A1224-1099-3745 | 4 | ToMMV | S | |
| 52T-SL-ANA-A1224-1099-3745 | 5 | ToMMV | S | |
| 52T-SL-ANA-A1224-1099-3745 | 6 | ToMMV | S | |
| 52T-SL-ANA-A1224-1099-3745 | 8 | ToMMV | R | Present |
| 52T-SL-ANA-A1224-1099-3745 | 10 | ToMMV | R | Present |
| 52T-SL-ANA-A1224-1099-3745 | 11 | ToMMV | S | |
| 52T-SL-ANA-A1224-1099-3745 | 12 | ToMMV | S | |
| 52T-SL-ANA-A1224-1099-3745 | 13 | ToMMV | S | |
| 52T-SL-ANA-A1224-1099-3745 | 14 | ToMMV | R | Present |
| 52T-SL-ANA-A1224-1099-3745 | 15 | ToMMV | S | |
| 52T-SL-ANA-A1224-1099-3745 | 17 | ToMMV | R | Present |
| 52T-SL-ANA-A1224-1099-3745 | 18 | ToMMV | S | |
| 52T-SL-ANA-A1224-1099-3745 | 19 | ToMMV | S | |
| 52T-SL-ANA-A1224-1099-3745 | 20 | ToMMV | S | |
| 52T-SL-ANA-A1224-1099-3745 | 21 | ToMMV | S | |
| 52T-SL-ANA-A1224-1099-3745 | 23 | ToMMV | S | |
| 52T-SL-ANA-A1224-1099-3745 | 24 | ToMMV | S | |
| 52T-SL-ANA-A1224-1099-3745 | 26 | ToMMV | S | |
| 52T-SL-ANA-A1224-1099-3745 | 29 | ToMMV | S | |
| 52T-SL-ANA-A1224-1099-3745 | 30 | ToMMV | S | |
| 52T-SL-ANA-A1224-1099-3745 | 31 | ToMMV | S | |
| 52T-SL-ANA-A1224-1099-3745 | 32 | ToMMV | S | |
| 52T-SL-ANA-A1224-1099-3745 | 34 | ToMMV | S | |
| 52T-SL-ANA-A1224-1099-3745 | 36 | ToMMV | S | |
| 52T-SL-ANA-A1224-1099-3745 | 37 | ToMMV | R | Present |
| 52T-SL-ANA-A1224-1099-3745 | 39 | ToMMV | S | |
| 52T-SL-ANA-A1224-1099-3745 | 40 | ToMMV | S | |
| 52T-SL-ANA-A1224-1099-3745 | 41 | ToMMV | S | |
| 52T-SL-ANA-A1224-1099-3745 | 42 | ToMMV | S | |
| 52T-SL-ANA-A1224-1099-3745 | 44 | ToMMV | S | |
| 52T-SL-ANA-A1224-1099-3745 | 45 | ToMMV | S | |
| 52T-SL-ANA-A1224-1099-3745 | 49 | ToMMV | R | Present |
| 52T-SL-ANA-A1224-1099-3745 | 50 | ToMMV | S | |
| 52T-SL-ANA-A1224-1099-3745 | 52 | ToMMV | S | |
| 52T-SL-ANA-A1224-1099-3745 | 53 | ToMMV | S | |

BIBLIOGRAPHY

Baggs, E., Dagdas, G., and Krasileva, K. V. 2017. NLR diversity, helpers and integrated domains: making sense of the NLR IDentity. Curr Opin Plant Biol 38:59-67.

Calder, V. L., and Palukaitis, P. 1992. Nucleotide sequence analysis of the movement genes of resistance breaking strains of tomato mosaic virus. J Gen Virol 73 (Pt 1):165-168.

Ishibashi et al, 2007. An inhibitor of viral RNA replication is encoded by a plant resistance gene. PNAS 104 (34) 13833-13838.

Kapos, P., Devendrakumar, K. T., and Li, X. 2019. Plant NLRs: From discovery to application. Plant Sci 279:3-18.

Kobayashi, M., Yamamoto-Katou, A., Katou, S., Hirai, K., Meshi, T., Ohashi, Y., and Mitsuhara, I. 2011. Identification of an amino acid residue required for differential recognition of a viral movement protein by the Tomato mosaic virus resistance gene Tm-2(2). J Plant Physiol 168:1142-1145.

Lanfermeijer, F. C., Warmink, J., and Hille, J. 2005. The products of the broken Tm-2 and the durable Tm-2(2) resistance genes from tomato differ in four amino acids. J Exp Bot 56:2925-2933.

Lanfermeijer, F. C., Dijkhuis, J., Sturre, M. J., de Haan, P., and Hille, J. 2003. Cloning and characterization of the durable tomato mosaic virus resistance gene Tm-2(2) from *Lycopersicon esculentum*. Plant Mol Biol 52:1037-1049.

Lanfermeirjer, F., Jiang, G, Ferwerda, M A, Kijkhuis, J, de Haan, P, Yang, R, Hille, J. 2004. The durable resistance gene Tm-22 from tomato confers resistance against ToMV in tobacco and preserves its viral specificity. Plant Science 167:687-692.

Luria N. et al. 2017. A New Israeli Tobamovirus Isolate Infects Tomato Plants Harboring Tm-2$^2$ Resistance Genes. PLoS One; 12(1): e0170429.

Ma, L., Lukasik, E, Gawehns F, Takken F L W. 2012. The use of agroinfiltration for transient expression of plant resistance and fungal effector proteins in *Nicotiana benthamiana* leaves. Methods Mol Biol 835:61-74.

Meshi, T., Motoyoshi, F., Maeda, T., Yoshiwoka, S., Watanabe, H., and Okada, Y. 1989. Mutations in the tobacco mosaic virus 30-kD protein gene overcome Tm-2 resistance in tomato. Plant Cell 1:515-522.

Mondragon-Palomino, M., Meyers, B. C., Michelmore, R. W., and Gaut, B. S. 2002. Patterns of positive selection in the complete NBS-LRR gene family of *Arabidopsis thaliana*. Genome Res 12:1305-1315.

Nagai, A., Duarte M. L. L., Chaves A. L R., Peres L. E P., dos Santos D. Y. A. C. 2019. Tomato mottle mosaic virus in Brazil and its relationship with Tm-2$^2$ gene. Eur J Plant Pathol 155, 353-359.

Salem N. et al, 2015. A new tobamovirus infecting tomato crops in Jordan. Arch. Virol. 161 (2), 503-506.

Segretin, M. E., Pais, M., Franceschetti, M., Chaparro-Garcia, A., Bos, J. I. B., Banfield, M. J., and Kamoun, S. 2014. Single Amino Acid Mutations in the Potato Immune Receptor R3a Expand Response to *Phytophthora* Effectors. Molecular Plant-Microbe Interactions® 27:624-637.

Slootweg, E., Koropacka, K., Roosien, J., Dees, R., Overmars, H., Lankhorst, R. K., van Schaik, C., Pomp, R., Bouwman, L., Helder, J., Schots, A., Bakker, J., Smant, G., and Goverse, A. 2017. Sequence Exchange between Homologous NB-LRR Genes Converts Virus Resistance into Nematode Resistance, and Vice Versa. Plant Physiol 175:498-510.

Sui, X. et al, 2017. Molecular and Biological Characterization of Tomato mottle mosaic virus and Development of RT-PCR Detection. Plant Disease 101, 704-711.

Tomita, R., Sekine, K. T., Tateda, C., and Kobayashi, K. 2019. Identification and Functional Analysis of NB-LRR-Type Virus Resistance Genes: Overview and Functional Analysis of Candidate Genes. Methods Mol Biol 2028: 1-10.

Wang, J., Chen, T., Han, M., Qian, L., Li, J., Wu, M., Han, T., Cao, J., Nagalakshmi, U., Rathjen, J. P., Hong, Y., and Liu, Y. 2020. Plant NLR immune receptor Tm-22 activation requires NB-ARC domain-mediated self-association of CC domain. PLoS Pathog 16:e1008475.

Weber, H., and Pfitzner, A. J. 1998. Tm-2(2) resistance in tomato requires recognition of the carboxy terminus of the movement protein of tomato mosaic virus. Mol Plant Microbe Interact 11:498-503.

Weber, H., Schultze, S., and Pfitzner, A. J. 1993. Two amino acid substitutions in the tomato mosaic virus 30-kilodalton movement protein confer the ability to overcome the Tm-2(2) resistance gene in the tomato. J Virol 67:6432-6438.

Weber, H., Ohnesorge, S., Silber, M. V., and Pfitzner, A. J. 2004. The Tomato mosaic virus 30 kDa movement protein interacts differentially with the resistance genes Tm-2 and Tm-2(2). Arch Virol 149:1499-1514.

The invention claimed is:

1. A TM-2-2 protein variant, which confers resistance against at least ToBRFV infection in tomatoes, and
    wherein said TM-2-2 protein variant comprises
    a tyrosine (Y), a phenylalanine (F) or a tryptophan (W) at the position corresponding to tyrosine 767 of SEQ ID No:8, and one of the following substitutions:
    a) an arginine (R) at the position corresponding to cysteine 848 of the TM-2-2 protein (SEQ ID No:8), an asparagine or a serine at the position corresponding to asparagine 822 of the TM-2-2 protein (SEQ ID No:8) and a serine at the position corresponding to serine 825 of the TM-2-2 protein (SEQ ID No:8);
    b) a cysteine (C), a phenylalanine (F), a methionine (M), a tyrosine (Y) or a tryptophan (W) at the position corresponding to asparagine 822 of the TM-2-2 protein (SEQ ID No:8), a cysteine at the position corresponding to cysteine 848 of the TM-2-2 protein (SEQ ID No:8) and a serine at the position corresponding to serine 825 of the TM-2-2 protein (SEQ ID No:8), and
    c) a histidine (H), a lysine (K) or a threonine (T) at the position corresponding to serine 825 of the TM-2-2 protein (SEQ ID No:8), a cysteine at the position corresponding to cysteine 848 of the TM-2-2 protein (SEQ ID No:8) and an asparagine at the position corresponding to asparagine 822 of the TM-2-2 protein (SEQ ID No:8).

2. The TM-2-2 protein variant according to claim 1, further comprising a leucine at the position corresponding to phenylalanine 655 of the TM-2-2 protein (SEQ ID NO:8).

3. A resistance gene encoding the TM-2-2 protein variant according to claim 1, conferring resistance to ToBRFV infection in tomato plants.

4. A nucleic acid construct comprising a sequence encoding the TM-2-2 protein variant according to claim 1.

5. A plant cell, comprising the resistance gene according to claim 3 within its genomic DNA, homozygously or heterozygously.

6. The cell according to claim 5 or a tissue culture of said cells, wherein the cells are derived from embryos, protoplasts, meristematic cells, callus, pollen, leaves, anthers, stems, petioles, roots, root tips, seeds, flowers, cotyledons, and/or hypocotyls, and contain in their genome said resistance gene.

7. A plant resistant against ToBRFV,
    wherein said plant comprises in its genome the resistance gene according to claim 3, homozygously or heterozygously.

8. A *S. lycopersicum* plant resistant to ToBRFV, comprising a mutated Tm-2-2 gene encoding a variant of the TM-2-2 protein (SEQ ID No:8),
    wherein the tyrosine (Y) at the position corresponding to position 767 of SEQ ID No:8 is not mutated or is substituted by a phenylalanine (F) or a tryptophan (W) and
    wherein said TM-2-2 protein variant comprises one of the following substitutions:
    a) the cysteine (C) at the position corresponding to position 848 of SEQ ID No:8 is substituted by an arginine (R), an asparagine or a serine is present at the position corresponding to asparagine 822 of the TM-2-2 protein (SEQ ID No:8) and a serine is present at the position corresponding to serine 825 of the TM-2-2 protein (SEQ ID No:8),
    b) the asparagine (N) at the position corresponding to position 822 of SEQ ID No:8 is substituted by a cysteine (C), a phenylalanine (F), a methionine (M), a tyrosine (Y) or a tryptophan (W), a cysteine is present at the position corresponding to cysteine 848 of the TM-2-2 protein (SEQ ID No:8) and a serine is present at the position corresponding to serine 825 of the TM-2-2 protein (SEQ ID No:8), and
    c) the serine (S) at the position corresponding to position 825 of SEQ ID No:8 is substituted by a histidine (H), a lysine (K) or a threonine (T), a cysteine is present at the position corresponding to cysteine 848 of the TM-2-2 protein (SEQ ID No:8) and an asparagine is present at the position corresponding to asparagine 822 of the TM-2-2 protein (SEQ ID No:8).

9. The *S. lycopersicum* plant according to claim 8, wherein said mutated Tm-2-2 gene encodes a variant of the TM-2-2 protein further comprising a leucine at the position corresponding to phenylalanine 655 of the TM-2-2 protein (SEQ ID NO:8).

10. The *S. lycopersicum* plant according to claim 8, wherein said mutated Tm-2-2 gene encodes a variant of TM-2-2 protein, having SEQ ID No:9, SEQ ID No:10, SEQ ID No:17, SEQ ID No:18, SEQ ID No:19, SEQ ID No:20, SEQ ID No:21, SEQ ID No:22, SEQ ID No:23, SEQ ID No:24, SEQ ID No:25 or SEQ ID No:26.

11. The *S. lycopersicum* plant according to claim 8, wherein said mutated Tm-2-2 gene is obtained by gene editing, base-editing or prime-editing techniques.

12. A plant part of the *S. lycopersicum* plant resistant to ToBRFV, comprising a mutated Tm-2-2 gene encoding the variant of the TM-2-2 protein (SEQ ID No:8),
    wherein the tyrosine (Y) at the position corresponding to position 767 of SEQ ID No:8 is not mutated or is substituted by the phenylalanine (F) or the tryptophan (W) and
    wherein said TM-2-2 protein variant comprises one of the following substitutions:
    a) the cysteine (C) at the position corresponding to position 848 of SEQ ID No:8 is substituted by an arginine (R), an asparagine or a serine is present at the position corresponding to asparagine 822 of the TM-2-2 protein (SEQ ID No:8) and a serine is present at the position corresponding to serine 825 of the TM-2-2 protein (SEQ ID No:8),
    b) the asparagine (N) at the position corresponding to position 822 of SEQ ID No:8 is substituted by the cysteine (C), the phenylalanine (F), the methionine (M), the tyrosine (Y) or the tryptophan (W), a cysteine is present at the position corresponding to cysteine 848 of the TM-2-2 protein (SEQ ID No:8) and a serine is present at the position corresponding to serine 825 of the TM-2-2 protein (SEQ ID No:8), and
    c) the serine (S) at the position corresponding to position 825 of SEQ ID No:8 is substituted by the histidine (H), the lysine (K) or the threonine (T), a cysteine is present at the position corresponding to cysteine 848 of the TM-2-2 protein (SEQ ID No:8) and an asparagine is present at the position corresponding to asparagine 822 of the TM-2-2 protein (SEQ ID No:8), wherein said plant part comprises at least one cell according to claim 5.

13. A *S. lycopersicum* seed, which comprises at least one cell according to claim 5.

14. A method for obtaining transgenic *S. lycopersicum* plants resistant to ToBRFV, comprising:
    obtaining a construct comprising a sequence encoding the TM-2-2 protein variant according to claim 1, introducing said construct into a *S. lycopersicum* cell, regenerating a transgenic plant;

optionally propagating the obtained plant.

15. A method for breeding a *S. lycopersicum* plant resistant to ToBRFV, and optionally to at least one of TMV, ToMV, and/or ToMMV, comprising:

crossing a *S. lycopersicum* plant comprising the resistance gene according to claim 3 with an initial *S. lycopersicum* plant devoid of resistance gene, selecting in the progeny thus obtained, a plant bearing the resistance gene, optionally self-pollinating one or several times the plant obtained at step (b) and selecting in the progeny thus obtained a plant bearing the resistance gene.

16. A method of producing a *S. lycopersicum* plant resistant to ToBRFV, and optionally to at least one of TMV, ToMV, and/or ToMMV, comprising:

obtaining a part of the plant according claim 8, vegetatively propagating said plant part to generate a plant from said plant part.

17. A method for improving the yield of tomato plants or for reducing the loss on tomato production in an environment infested or likely to be infested by ToBRFV comprising growing tomato plants comprising in their genome the resistance gene according to claim 3.

18. A method for reducing the loss on tomato production in condition of ToMV, TMV, ToMMV and/or ToBRFV infestation, comprising growing a tomato plant comprising in its genome the resistance gene according to claim 3.

19. A method of producing tomatoes comprising:

growing the *S. lycopersicum* plant according to claim 8;

allowing said plant to set fruit; and harvesting fruit of said plant.

* * * * *